(12) United States Patent
Lau

(10) Patent No.: US 10,688,093 B2
(45) Date of Patent: Jun. 23, 2020

(54) METHODS, COMPOSITIONS, AND USES OF NOVEL FYN KINASE INHIBITORS

(71) Applicant: Warren C. Lau, Houston, TX (US)

(72) Inventor: Warren C. Lau, Houston, TX (US)

( * ) Notice: Subject to any disclaimer, the term of this patent is extended or adjusted under 35 U.S.C. 154(b) by 0 days.

(21) Appl. No.: 15/758,274

(22) PCT Filed: Sep. 8, 2016

(86) PCT No.: PCT/US2016/050776
§ 371 (c)(1),
(2) Date: Mar. 7, 2018

(87) PCT Pub. No.: WO2017/044623
PCT Pub. Date: Mar. 16, 2017

(65) Prior Publication Data
US 2018/0250297 A1 Sep. 6, 2018

Related U.S. Application Data

(60) Provisional application No. 62/216,349, filed on Sep. 9, 2015.

(51) Int. Cl.
| | | |
|---|---|---|
| A61K 31/497 | (2006.01) |
| A61K 31/4965 | (2006.01) |
| A61K 31/4985 | (2006.01) |
| A61K 31/44 | (2006.01) |
| A61K 31/4436 | (2006.01) |
| A61K 31/444 | (2006.01) |
| A61K 31/496 | (2006.01) |
| A61K 31/5025 | (2006.01) |
| A61K 31/519 | (2006.01) |
| A61K 31/5377 | (2006.01) |

(52) U.S. Cl.
CPC ............ *A61K 31/497* (2013.01); *A61K 31/44* (2013.01); *A61K 31/444* (2013.01); *A61K 31/4436* (2013.01); *A61K 31/496* (2013.01); *A61K 31/4965* (2013.01); *A61K 31/4985* (2013.01); *A61K 31/5025* (2013.01); *A61K 31/519* (2013.01); *A61K 31/5377* (2013.01)

(58) Field of Classification Search
CPC .............. A61K 31/497; A61K 31/4965; A61K 31/4985
See application file for complete search history.

(56) References Cited

U.S. PATENT DOCUMENTS

| | | |
|---|---|---|
| 2003/0199511 A1 | 10/2003 | Li et al. |
| 2008/0249058 A1 | 10/2008 | Roberson et al. |
| 2013/0040949 A1 | 2/2013 | Gray et al. |

FOREIGN PATENT DOCUMENTS

| | | | |
|---|---|---|---|
| EP | 2818471 A1 * | 12/2014 | ........... C07D 471/04 |
| WO | 2011/119199 A1 | 9/2011 | |

OTHER PUBLICATIONS

International Search Report of PCT/US2016/050776 dated Jan. 19, 2017.
Written Opinion of PCT/US2016/050776 dated Jan. 19, 2017.
Yamada, E., et al., "Fyn-dependent regulation of energy expenditure and body weight is mediated by tyrosine phosphorylation of LKB1," Cell Metab., vol. 11, No. 2, pp. 113-124 (Feb. 3, 2010).

* cited by examiner

*Primary Examiner* — Samira J Jean-Louis
(74) *Attorney, Agent, or Firm* — Polsinelli PC

(57) ABSTRACT

The present invention provides methods for inhibiting Fyn kinase, using 5-3-pyridin-2-amine, 6-3-imidazo[1,2-a] pyrazine, 6-3-imidazo[1,2-b] pyridazine, N-(5-imidazo [2,1-b] [1,3,4] thiadiazol-2-yl)-amine, 4-3-1H-pyrazolo[3,4-b] pyridine, and N-(3-imidazo [1,2-b] pyridazin-6-yl) amine compounds and methods of treatment, prevention, inhibition or amelioration of diseases and conditions associated with Fyn kinase using such compounds.

5 Claims, No Drawings

METHODS, COMPOSITIONS, AND USES OF NOVEL FYN KINASE INHIBITORS

CROSS REFERENCE TO RELATED APPLICATIONS

The present application is the 35 U.S.C. 371 National Stage of International Application Number PCT/US2016/050776, filed Sep. 8, 2016, which claims priority from U.S. Provisional Patent Application No. 62/216,349 filed Sep. 9, 2015, the contents of each of which are incorporated herein by reference.

FIELD OF THE INVENTION

The present invention relates to methods for inhibiting, regulating or modulating the activity of Fyn kinase, using compounds or pharmaceutical compositions containing such compounds and methods of treatment using the compounds or compositions to treat diabetes, pre-diabetes, metabolic conditions, immune disorders, cancer and neurodegenerative disorders such as Multiple Sclerosis. Alzheimer's and Parkinson's disease.

BACKGROUND OF THE INVENTION

Fyn kinase, a cytoplasmic Src family tyrosine kinase, plays an important role in many physiologic processes and is ubiquitous in human cells. Fyn kinase is primarily found on the cytoplasmic face of the plasma membrane where it phosphorylates tyrosine residues of a number of different enzymes involved in the signaling pathways associated with various cell-surface receptors. Fyn kinase is involved in cellular development, apoptosis, and homeostatic regulation, as well as in the development of many different kinds of pathologies. Fyn kinase represents an attractive target for drug therapies designed to control cellular metabolism for management of diabetes, pre-diabetes and general weight loss applications, as an anti-cancer therapeutic and as potential target for the control or prevention of Multiple Sclerosis, Alzheimer's and Parkinson's disease.

Fyn knockout mice exhibit increased lipid utilization and increased energy expenditure. Wild-type mice treated with the highly selective Src family kinase inhibitor SU6656, exhibit similar increases in lipid utilization and energy utilization, whereas the Fyn knockout strains show no increase in either parameter upon treatment with SU6656 (WO 2011/119199). Both the Fyn knockout and SU6656 treated mice have significantly reduced fat mass relative to untreated or genetically matched Fyn-competent control mice. Treatment with SU6656 appears to reduce adiposity and promote weight loss, likely through a Fyn-kinase-dependent mechanism.

Fyn kinases ability to regulate fatty acid oxidation and increase energy expenditure is thought to result from its affect on sequestration of LKB1 to the nucleus of skeletal muscle cells. Fyn kinase phosphorylates LKB1 present in the cytoplasm of such cells and the phosphorylated LKB1 is preferentially localized to the nucleus where it has little or no access to AMPK, which is found almost exclusively in the cytoplasm. Thus, LKB1 phosphorylated by Fyn kinase cannot activate AMPK (AMP-dependent protein kinase). Activated AMPK serves as a cellular energy sensor directly regulated by alterations in the intracellular AMP/ATP ratio that occurs during prolonged fasting and re-feeding. At high AMP/ATP ratios activation of AMPK results in phosphorylation and inhibition of Acetyl CoA Carboxylase, thereby increasing fatty acid oxidation and decreasing fatty acid biosynthesis. Specific inhibition of Fyn kinase allows LKB1 to constitutively activate AMPK. In this model inhibition of Fyn kinase results in increased cytoplasmic localization of LKB1, resulting in increased levels of activated AMPK.

AMPK also regulates glucose metabolism in liver. Hepatic glucose production that is not regulated by insulin is known to play an important role in development of Type 2 diabetes. The asymptomatic insulin resistance phase of Type 2 diabetes is generally followed by defects in insulin secretion that result in severe hyperglycemia if left untreated. Chronic high glucose levels have been shown to result in the death of pancreatic n-cells and loss of insulin production altogether. Activated AMPK reduces insulin secretion and is thought to have a pro-apoptotic effect on pancreatic β-cells.

Like many Src family kinases, Fyn plays a role in regulating several physiological processes including cellular growth, proliferation, morphogenesis and motility. Fyn has also been recognized as a potential oncogene and has been shown to be capable of inducing the fully tumorigenic phenotype. Fyn interacts with a number of cancer related pathways. Fyn is a mediator of growth-factor induced anti-apoptotic activity of Akt/PKB, and regulates Rac and Rho GTPases and activates the ERK/MAPK pathways. Fyn also plays a key role in the regulation of matrix formation and degradation, which is important for matrix remodeling and cellular adherence.

In addition to metabolic and oncogenic regulation, Fyn is recognized as playing a key role in T-cell development as well as dendritic maturation of cells within the central nervous system. Further, inhibition of Fyn kinase is viewed as an attractive therapeutic target for treatment of Multiple Sclerosis. Alzheimer's and Parkinson's disease. It is the object of this disclosure to describe pharmaceutically effective inhibitors of Fyn kinase with enhanced specificity for therapeutic treatment of one or more of the pathologies in which Fyn kinase plays a role.

Structurally, Fyn kinase is relatively well characterized despite the lack of a complete high-resolution structure. The enzyme comprises 537 amino acids in a single polypeptide chain organized into 4 domains, with a molecular weight of 59 kilodaltons. The N-terminal membrane anchoring domain (SH4) possesses myristylated or palmitylated residues essential for proper enzyme trafficking and localization to the cytoplasmic membrane, immediately adjacent to this are the SH3 and SH2 domains, which play critical roles in the interaction of Fyn kinase with its protein targets, followed by a flexible linker connecting the C-terminal tyrosine kinase domain (SH1). Although a complete high-resolution structure of the entire Fyn kinase protein is not available, such structures are available for each of the SH2, 3 and 4 domains, individually.

The SH2 domain of Fyn kinase binds phosphotyrosine-containing sequences and functions as a target recognition domain. The SH3 domain promiscuously complexes with polyproline peptides and plays a role in mediating protein-protein interactions between Fyn kinase and other polypeptides. Interaction between the SH3 and SH2 domains enhances the specificity of ligand binding and regulates the activity of the kinase (SH4) domain.

The well conserved SH4 domain contains two potential inhibitor binding sites, the first, sensitive to non-specific competitive inhibitors of ATP such as staurosporine, represents the actual ATP binding site of the kinase domain, whereas the second site, immediately adjacent to the ATP binding pocket, is oriented towards the SH2 domain. This second site may be occupied in such a way that ATP binding at the first site is not directly blocked. However, free access to the second site is blocked by the presence of ATP at the first site, and hence, inhibitors targeted to the second site display pseudo-competitive kinetics with respect to the availability of ATP. Although the ATP binding site is highly conserved among Src kinases, the amino acids comprising the hydrophobic pocket typical of the second site are less conserved and may represent the best target for Fyn-specific inhibitors. Regardless, the SH1 domain is essential for the activity of Fyn kinase on any of its protein targets, and has been targeted for the development of potent Fyn kinase inhibitors.

Existing Fyn kinase inhibitors all suffer from a lack of specificity and although many Fyn kinase inhibitors have been isolated, most significantly cross-react with other Src family enzymes. Some of the best known Fyn kinase inhibitors include: phenolic compounds such as rosmarinic acid, (−)-epigallocatechin gallate and myricetin; the pyrazolol[3,4-d] pyrimidines PP1, PP2, and various derivatives thereof; as well as other fused pyrimidine compounds such as benzyl 21-methoxy-5,7,19-trioxa-2,13,24,26-tetraazapentacyclo [18.6.2.0$^{3,11}$0.0$^{4,8}$0.0$^{23,27}$]octacosa-1(26),3(11),4(8),9,20, 22,24,27-octaene-13-carboxylate (Janssen Pharmaceuticals, U.S. Pat. No. 8,492,377) and CT5263 and CT5102 (CellTech). The structure of a few of these compounds and their associated IC50 (when known) and log P values are presented in Table 1.

TABLE 1

Known Fyn kinase inhibitors.

| Structure | IUPAC name | IC50 FYN (µM) | logP (consensus) | Common name |
|---|---|---|---|---|
| | (2R)-3-(3,4-dihydroxy-phenyl)-2-{[(2E)-3-(3,4-dihydroxyphenyl)prop-2-enoyl]oxy} propanoic acid | 1.3 | 3.00 | rosmarinic acid |
| | (2R,3R)-5,7-dihydroxy-2-(3,4,5-trihydroxy-phenyl)-3,4-dihydro-2H-1-benzopyran-3-yl 3,4,5 | unknown | 3.08 | (−)-epigallo-catechin gallate |
| | 5,7-dihydroxy-2-(3,4,5-trihydroxyphenyl)-4H-chromen-4-one | unknown | 0.65 | myricetin |

TABLE 1-continued

Known Fyn kinase inhibitors.

| Structure | IUPAC name | IC50 FYN (μM) | logP (consensus) | Common name |
|---|---|---|---|---|
| 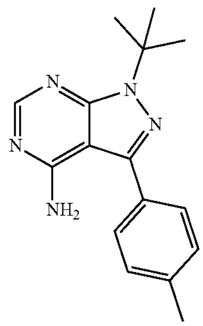 [SMILES: Cc1ccc(-c2nn(C(C)(C)C)c3ncnc(N)c23)cc1] | 1-tert-butyl-3-(4-methylphenyl)-1H-pyrazolo[3,4-d]pyrimidin-4-amine | 0.006 | 3.23 | PP1 (Pfizer) |
| 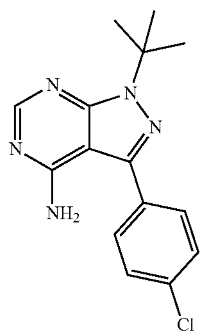 [SMILES: CC(C)(C)n1nc(-c2ccc(Cl)cc2)c2c(N)ncnc21] | 1-tert-butyl-3-(4-chlorophenyl)-1H-pyrazolo[3,4-d]pyrimidin-4-amine | 0.006 | 3.32 | PP2 (Pfizer) |
| | N-(4-{4-amino-1-[(1r,4r)-4-(4-methyl-piperazin-1-yl)cyclo-hexyl]-1H-pyrazolo[3,4-d]pyrimidin-3-yl}-2-methoxy-phenyl)-1-methyl-1H-indole-2-carboxamide | 0.330 | 3.81 | A-420983 (Abbott) |
| | benzyl-21-methoxy-5,7,19-trioxa-2,13,24,26-tetraazapenta-cyclo[18,6.2.0$^3$,$^{11}$.0$^{4,8}$.0$^{23,27}$]octacosa-1(26),3(11),4(8),9,20,22,24,27-octaene-13-carboxylate | 0.00669 | 5.13 | Compound B50 (U.S. Pat. No. 8,492,377) (Janssen Pharmaceuticals) |

TABLE 1-continued

Known Fyn kinase inhibitors.

| Structure | IUPAC name | IC50 FYN (µM) | logP (con-sensus) | Common name |
|---|---|---|---|---|
| 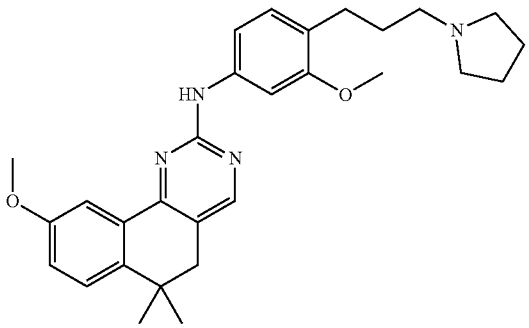 [SMILES: COc1ccc2c(c1)-c1nc(Nc3ccc(CCCN4CCCC4)c(OC)c3)ncc1CC2(C)C] | 9-methoxy-N-{3-methoxy-4-[3-(pyrrolidin-1-yl)propyl]phenyl}-6,6-dimethyl-5H,6H-benzo[h]quinazolin-2-amine | 0.008 | 6.12 | CT5263 (CellTech) |
|  | N-{4-[2-(dimethyl-amino)ethoxy]-3,5-dimethyl phenyl}-9-methoxy-5H,6H-benzo[h]quinazolin-2-amine | 0.008 | 5.49 | CT5102 (CellTech) |

SUMMARY OF THE INVENTION

Among its many embodiments, the present invention comprises methods for inhibiting Fyn kinase using 5-[R2]-3-[R1] pyridin-2-amine compounds or pharmaceutical compositions comprising such compounds and methods of treatment, prevention, inhibition or amelioration of one or more of the diseases or conditions associated with Fyn kinase.

In one aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being 5-[R2]-3-[R1] pyridin-2-amine, wherein R1 and R2 are each individually selected from the group consisting of H, alkyl, alkenyl, alkylene, alkynyl, aryl, arylalkyl, alkylaryl, arylalkenyl, cycloalkyl, cycloalkylalkyl, cycloalkenyl, cycloalkenylalkyl, heteroaryl, heteroarylalkyl, heterocyclyl, heterocyclylalkyl, heterocyclenyl, wherein each of the alkyl, alkenyl, alkylene, alkynyl, alkynylalkyl, aryl, arylalkyl, alkylaryl, arylalkenyl, cycloalkyl, cycloalkylalkyl, cycloalkenyl, cycloalkenylalkyl, heterocyclic moieties can be substituted with one or more moieties which can be the same or different, each moiety being independently selected from the group consisting of acyl, alcohol, alkyl, aryl, aroyl, alkoxy, aryloxy, arylalkyloxy, alkylthio, arylthio, aralkylthio, alkoxycarbonyl, aryloxycarbonyl, aralkoxycarbonyl, alkylsulfonyl, arylsulfonyl, cyano, hydroxyalkyl, amide, amine, thiol, thiophene, pyrrole, furan, alkylsulfate, arylsulfate, alkylphosphate and arylphosphate.

In another aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being one of the 5-[R2]-3-[R1] pyridin-2-amine derivatives of Tables 3 and 4.

In another aspect, the present invention provides a method of treating, or slowing progression of a disease associated with Fyn kinase, the method comprising administering a therapeutically effective amount of at least one compound, or a pharmaceutically acceptable salt or solvate of the compound to a patient in need thereof, the compound being at least one of the 5-[R2]-3-[R1] pyridin-2-amines described above, or a pharmaceutically acceptable salt or solvate thereof.

In another embodiment, the present invention comprises methods for inhibiting Fyn kinase using 4-[R2]-3-[R1] imidazo[1,2-a] pyrazine compounds or pharmaceutical compositions comprising such compounds and methods of treatment, prevention, inhibition or amelioration of one or more of the diseases or conditions associated with Fyn kinase.

In one aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being 6-[R2]-3-[R1] imidazo[1,2-a] pyrazine, wherein R1 and R2 are each individually selected from the group consisting of H, alkyl, alkenyl, alkylene, alkynyl, aryl, arylalkyl, alkylaryl, arylalkenyl, cycloalkyl, cycloalkylalkyl, cycloalkenyl, cycloalkenylalkyl, heteroaryl, heteroarylalkyl, heterocyclyl, heterocyclylalkyl, heterocyclenyl, wherein each of the alkyl, alkenyl, alkylene, alkynyl, alkynylalkyl, aryl, arylalkyl, alkylaryl, arylalkenyl, cycloalkyl, cycloalkylalkyl, cycloalkenyl, cycloalkenylalkyl, heterocyclic moieties can be substituted with one or more moieties which can be the same or different, each moiety being independently selected from the group consisting of acyl, alcohol, alkyl, aryl, aroyl, alkoxy, aryloxy, arylalkyloxy, alkylthio, arylthio, aralkylthio, alkoxycarbonyl, aryloxycarbonyl, aralkoxycarbonyl, alkylsulfonyl, arylsulfonyl, cyano, hydroxyalkyl, amide, amine, thiol, thiophene, pyrrole, furan, alkylsulfate, arylsulfate, alkylphosphate and arylphosphate.

In another aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being one of the 6-[R2]-3-[R1] imidazo[1,2-a] pyrazine derivatives of Tables 3 and 4.

In another aspect, the present invention provides a method of treating, or slowing progression of a disease associated with Fyn kinase, the method comprising administering a therapeutically effective amount of at least one compound, or a pharmaceutically acceptable salt or solvate of the compound to a patient in need thereof, the compound being at least one of the 6-[R2]-3-[R1] imidazo[1,2-a] pyridines described above, or a pharmaceutically acceptable salt or solvate thereof.

In another embodiment, the present invention comprises methods for inhibiting Fyn kinase using 6-[R2]-3-[R1] imidazo[1,2-b] pyridazine compounds or pharmaceutical compositions comprising such compounds and methods of treatment, prevention, inhibition or amelioration of one or more of the diseases or conditions associated with Fyn kinase.

In one aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being 6-[R2]-3-[R1] imidazo [1,2-b] pyridazine, wherein R1 and R2 are each individually selected from the group consisting of H, alkyl, alkenyl, alkylene, alkynyl, aryl, arylalkyl, alkylaryl, arylalkenyl, cycloalkyl, cycloalkylalkyl, cycloalkenyl, cycloalkenylalkyl, heteroaryl, heteroarylalkyl, heterocyclyl, heterocyclylalkyl, heterocyclenyl, wherein each of the alkyl, alkenyl, alkylene, alkynyl, alkynylalkyl, aryl, arylalkyl, alkylaryl, arylalkenyl, cycloalkyl, cycloalkylalkyl, cycloalkenyl, cycloalkenylalkyl, heterocyclic moieties can be substituted with one or more moieties which can be the same or different, each moiety being independently selected from the group consisting of acyl, alcohol, alkyl, aryl, aroyl, alkoxy, aryloxy, arylalkyloxy, alkylthio, arylthio, aralkylthio, alkoxycarbonyl, aryloxycarbonyl, aralkoxycarbonyl, alkylsulfonyl, arylsulfonyl, cyano, hydroxyalkyl, amide, amine, thiol, thiophene, pyrrole, furan, alkylsulfate, arylsulfate, alkylphosphate and arylphosphate.

In another aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being one of the 6-[R2]-3-[R1] imidazo [1,2-b] pyridazine derivatives of Tables 3 and 4.

In another aspect, the present invention provides a method of treating, or slowing progression of a disease associated with Fyn kinase, the method comprising administering a therapeutically effective amount of at least one compound, or a pharmaceutically acceptable salt or solvate of the compound to a patient in need thereof, the compound being at least one of the 6-[R2]-3-[R1] imidazo [1,2-b] pyridoxines described above, or a pharmaceutically acceptable salt or solvate thereof.

In another embodiments, the present invention comprises methods for inhibiting Fyn kinase using N-(5-[R2] imidazo [2,1-b][1,3,4] thiadiazol-2-yl)[R1]-amine compounds or pharmaceutical compositions comprising such compounds and methods of treatment, prevention, inhibition or amelioration of one or more of the diseases or conditions associated with Fyn kinase.

In one aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being N-(5-[R2]imidazo[2,1-b][1,3,4] thiadiazol-2-yl)[R1]-amine, wherein R1 and R2 are each individually selected from the group consisting of H, alkyl, alkenyl, alkylene, alkynyl, aryl, arylalkyl, alkylaryl, arylalkenyl, cycloalkyl, cycloalkylalkyl, cycloalkenyl, cycloalkenylalkyl, heteroaryl, heteroarylalkyl, heterocyclyl, heterocyclylalkyl, heterocyclenyl, wherein each of the alkyl, alkenyl, alkylene, alkynyl, alkynylalkyl, aryl, arylalkyl, alkylaryl, arylalkenyl, cycloalkyl, cycloalkylalkyl, cycloalkenyl, cycloalkenylalkyl, heterocyclic moieties can be substituted with one or more moieties which can be the same or different, each moiety being independently selected from the group consisting of acyl, alcohol, alkyl, aryl, aroyl, alkoxy, aryloxy, arylalkyloxy, alkylthio, arylthio, aralkylthio, alkoxycarbonyl, aryloxycarbonyl, aralkoxycarbonyl, alkylsulfonyl, arylsulfonyl, cyano, hydroxyalkyl, amide, amine, thiol, thiophene, pyrrole, furan, alkylsulfate, arylsulfate, alkylphosphate and arylphosphate.

In another aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being one of the N-(5-[R2]imidazo[2,1-b][1,3,4] thiadiazol-2-yl)[R1]-amine derivatives of Tables 3 and 4.

In another aspect, the present invention provides a method of treating, or slowing progression of a disease associated with Fyn kinase, the method comprising administering a therapeutically effective amount of at least one compound, or a pharmaceutically acceptable salt or solvate of the compound to a patient in need thereof, the compound being at least one of the N-(5-[R2] imidazo [2,1-b] [1,3,4] thiadiazol-2-yl) [R1]-amines described above, or a pharmaceutically acceptable salt or solvate thereof.

In another embodiment, the present invention comprises methods for inhibiting Fyn kinase using 4-[R2]-3-[R1]-1H-pyrazolo[3,4-b] pyridine compounds or pharmaceutical compositions comprising such compounds and methods of treatment, prevention, inhibition or amelioration of one or more of the diseases or conditions associated with Fyn kinase.

In one aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being 4-[R2]-3-[R1]-1H-pyrazolo[3,4-b] pyridine, wherein R1 and R2 are each individually selected from the group consisting of H, alkyl, alkenyl, alkylene, alkynyl, aryl, arylalkyl, alkylaryl, arylalkenyl, cycloalkyl, cycloalkylalkyl, cycloalkenyl, cycloalkenylalkyl, heteroaryl, heteroarylalkyl, heterocyclyl, heterocyclylalkyl, heterocyclenyl, wherein each of the alkyl, alkenyl, alkylene, alkynyl, alkynylalkyl, aryl, arylalkyl, alkylaryl, arylalkenyl, cycloalkyl, cycloalkylalkyl, cycloalkenyl, cycloalkenylalkyl, heterocyclic moieties can be substituted with one or more moieties which can be the same or different, each moiety being independently selected from the group consisting of acyl, alcohol, alkyl, aryl, aroyl, alkoxy, aryloxy, arylalkyloxy, alkylthio, arylthio, aralkylthio, alkoxycarbonyl, aryloxycarbonyl, aralkoxycarbonyl, alkylsulfonyl, arylsulfonyl, cyano, hydroxyalkyl, amide, amine, thiol, thiophene, pyrrole, furan, alkylsulfate, arylsulfate, alkylphosphate and arylphosphate.

In another aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being one of the 4-[R2]-3-[R1]-1H-pyrazolo[3,4-b] pyridine derivatives of Tables 3 and 4.

In another aspect, the present invention provides a method of treating, or slowing progression of a disease associated with Fyn kinase, the method comprising administering a therapeutically effective amount of at least one compound, or a pharmaceutically acceptable salt or solvate of the compound to a patient in need thereof, the compound being at least one of the 4-[R2]-3-[R1]-1H-pyrazolo[3,4-b] pyridines described above, or a pharmaceutically acceptable salt or solvate thereof.

In another embodiment, the present invention comprises methods for inhibiting Fyn kinase using N-(3-[R2] imidazo [1,2-b] pyridazin-6-yl) [R1] amine compounds or pharmaceutical compositions comprising such compounds and methods of treatment, prevention, inhibition or amelioration of one or more of the diseases or conditions associated with Fyn kinase.

In one aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being N-(3-[R2] imidazo [1,2-b] pyridazin-6-yl) [R1] amine, wherein R1 and R2 are each individually selected from the group consisting of H, alkyl, alkenyl, alkylene, alkynyl, aryl, arylalkyl, alkylaryl, arylalkenyl, cycloalkyl, cycloalkylalkyl, cycloalkenyl, cycloalkenylalkyl, heteroaryl, heteroarylalkyl, heterocyclyl, heterocyclylalkyl, heterocyclenyl, wherein each of the alkyl, alkenyl, alkylene, alkynyl, alkynylalkyl, aryl, arylalkyl, alkylaryl, arylalkenyl, cycloalkyl, cycloalkylalkyl, cycloalkenyl, cycloalkenylalkyl, heterocyclic moieties can be substituted with one or more moieties which can be the same or different, each moiety being independently selected from the group consisting of acyl, alcohol, alkyl, aryl, aroyl, alkoxy, aryloxy, arylalkyloxy, alkylthio, arylthio, aralkylthio, alkoxycarbonyl, aryloxycarbonyl, aralkoxycarbonyl, alkylsulfonyl, arylsulfonyl, cyano, hydroxyalkyl, amide, amine, thiol, thiophene, pyrrole, furan, alkylsulfate, arylsulfate, alkylphosphate and arylphosphate.

In another aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being one of the N-(3-[R2] imidazo [1,2-b] pyridazin-6-yl) [R1] amine derivatives of Tables 3 and 4.

In another aspect, the present invention provides a method of treating, or slowing progression of a disease associated with Fyn kinase, the method comprising administering a therapeutically effective amount of at least one compound, or a pharmaceutically acceptable salt or solvate of the compound to a patient in need thereof, the compound being at least one of the N-(3-[R2] imidazo [1,2-b] pyridazin-6-yl) [R1] amine described above, or a pharmaceutically acceptable salt or solvate thereof.

In another aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound selected from the group consisting of N-[3-[6-(2-furylmethylamino)pyrazin-2-yl]phenyl]acetamide, 4-[6-[1-(hydroxymethyl)propylamino]pyrazin-2-yl]phenol, 2-[[6-(5-isopropyl-2-methoxy-phenyl)pyrazin-2-yl]amino]butan-1-ol, 6-(3-aminophenyl)-N-benzyl-pyrazin-2-amine, 2-[[6-(4-aminophenyl)pyrazin-2-yl]amino]butan-1-ol, N-[3-(dimethylamino)propyl]-3-[6-(4-methoxyphenyl)pyrazin-2-yl]benzamide, 2-methoxy-4-[6-(4-methoxyphenyl)pyrazin-2-yl]phenol, N-[3-[6-(4-methoxyphenyl)pyrazin-2-yl]phenyl]acetamide, N-[3-[6-(3-hydroxyphenyl)pyrazin-2-yl]phenyl]acetamide, 3-[5-(3-furylmethylamino)-3-pyridyl]phenol, N-[3-[5-(3,4,5-trimethoxyanilino)-3-pyridyl]phenyl]acetamide, 3-[(3-methoxyphenyl)methyl]-5-(3,4,5-trimethoxyphenyl)-1H-imidazo[4,5-b]pyrazin-2-one, N,N-dimethyl-3-[2-oxo-3-[(1S)-1-phenylethyl]-1H-imidazo[4,5-b]pyrazin-5-yl]benzamide, 5-[3-(dimethylamino)phenyl]-N-(4-morpholinophenyl)imidazo[1,2-a]pyrazin-8-amine, 3-[5-[(6-methoxy-3-pyridyl)amino]pyrazolo[1,5-a]pyrimidin-3-yl]phenol, 3-(3-methoxyphenyl)-N-(6-methoxy-3-pyridyl)pyrazolo[1,5-a]pyrimidin-5-amine, 1-[3-[5-[(6-methoxy-3-pyridyl)amino]pyrazolo[1,5-a]pyrimidin-3-yl]phenyl]ethanone, N-[5-[[[3-(3-hydroxyphenyl)pyrazolo[1,5-a]pyrimidin-5-yl]amino]-2-methyl-phenyl]methanesulfonamide, 3-(3,4-dimethoxyphenyl)-N-(3-pyridylmethyl)pyrazolo[1,5-a]pyrimidin-5-amine, N-(3-pyridylmethyl)-3-(3,4,5-trimethoxyphenyl)pyrazolo[1,5-a]pyrimidin-5-amine, N-(4-isopropylphenyl)-3-(4-methoxyphenyl)pyrazolo[1,5-a]pyrimidin-5-amine, 3-(5-methoxy-3-pyridyl)-N-(4-morpholinophenyl)pyrazolo[1,5-a]pyrimidin-5-amine, 3-(3-aminophenyl)-N-(3-pyridylmethyl)pyrazolo[1,5-a]pyrimidin-5-amine, 3-(2-methoxyphenyl)-N-(3-pyridylmethyl)pyrazolo[1,5-a]pyrimidin-5-amine, (E)-3-[3-[5-(3-pyridylmethylamino)pyrazolo[1,5-a]pyrimidin-3-yl]phenyl]prop-2-enoic acid, N-[3-(dimethylamino)propyl]-4-[6-(2-fluoro-3-methoxy-phenyl)-1H-pyrazolo[3,4-b]pyridin-3-yl]benzamide, 6-(1H-indol-5-yl)-N-methyl-pyrazin-2-amine, N-ethyl-2-(3,4,5-trimethoxyanilino)-7,8-dihydro-5H-pyrido[4,3-d]pyrimidine-6-carboxamide, 6-propyl-N-(3,4,5-trimethoxyphenyl)-7,8-dihydro-5H-pyrido[4,3-d]pyrimidin-2-amine, [2-[3-(dimethylamino)anilino]-5,7-dihydropyrrolo[3,4-d]pyrimidin-6-yl]-(2-methoxyphenyl)methanone, N-[3-(4-fluorophenyl)-6-[4-(morpholine-4-carbonyl)phenyl]imidazo[1,2-a]pyridin-8-yl]formamide, N-[3-(3-acetylphenyl)-6-[4-(morpholine-4-carbonyl)phenyl]imidazo[1,2-a]pyridin-8-yl]formamide, N-[3-(3-chloro-4-fluoro-phenyl)-6-[3-(methanesulfonamido)phenyl]imidazo[1,2-a]pyridin-8-yl]formamide, N-[3-(4-fluorophenyl)-6-(1-methylpyrazol-4-yl)imidazo[1,2-a]pyridin-8-yl]formamide, 1-methyl-N-[4-(4-methylpiperazin-1-yl)phenyl]-2-[3-(trifluoromethyl)phenyl]pyrrolo[3,2-c]pyridin-6-amine, 1-methyl-N-pyrimidin-4-yl-2-[3-(trifluoromethyl)phenyl]pyrrolo[3,2-c]pyridin-6-amine, 2-(3-fluorophenyl)-1-methyl-N-[4-(4-methylpiperazin-1-yl)phenyl]pyrrolo[3,2-c]pyridin-6-amine, 2-(3-fluorophenyl)-1-methyl-N-pyrimidin-4-yl-pyrrolo[3,2-c]pyridin-6-amine, 1-benzyl-N-[4-(4- methylpiperazin-1-yl)phenyl]-2-(3-pyridyl)pyrrolo[3,2-c]pyridin-6-amine, 2-(1H-pyrazol-4-yl)-N-(2-pyridyl)-1H-pyrrolo[3,2-c]pyridin-6-amine, N-(4-methylsulfonylphenyl)-2-(1H-pyrazol-4-yl)-1H-pyrrolo[3,2-c]pyridin-6-amine, 1-benzyl-2-(3-pyridyl)-N-pyrimidin-4-yl-pyrrolo[3,2-c]pyridin-6-amine, N-(3-methoxyphenyl)-2-(1H-pyrazol-4-yl)-1H-pyrrolo[3,2-c]pyridin-6-amine, N-(3,4-dimethoxyphenyl)-2-(1H-pyrazol-4-yl)-1H-pyrrolo[3,2-c]pyridin-6-amine, 1-benzyl-N-[4-(4-methylpiperazin-1-yl)phenyl]-2-phenyl-pyrrolo[3,2-c]pyridin-6-amine, N-[3-[8-acetamido-3-(3,4-dimethoxyphenyl)imidazo[1,2-a]pyridin-6-yl]phenyl]acetamide, N-[3-(3-acetylphenyl)-6-(3-methoxyphenyl)imidazo[1,2-a]pyridin-8-yl]acetamide, N-[3-(3-acetylphenyl)-6-(2,4-dimethoxyphenyl)imidazo[1,2-a]pyridin-8-yl]acetamide, N-[3-(3-acetylphenyl)-6-(2-methoxyphenyl)imidazo[1,2-a]pyridin-8-yl]acetamide, N-[6-(4-aminophenyl)-3-(4-fluorophenyl)imidazo[1,2-a]pyridin-8-yl]acetamide, N-[3-(3-acetylphenyl)-6-[4-(morpholine-4-carbonyl)phenyl]imidazo[1,2-a]pyridin-8-yl]acetamide, N,N-dimethyl-4-[4-[4-(4-methylpiperazin-1-yl)anilino]-1H-pyrrolo[3,2-c]pyridin-2-yl]benzamide, 4-[2-(3,5-dimethoxyphenyl)-1H-pyrrolo[3,2-c]pyridin-4-yl]morpholine, N-[4-[[2-(2-methoxyphenyl)-1H-pyrrolo[3,2-c]pyridin-4-yl]amino]phenyl]acetamide, 2-(2-methoxyphenyl)-1-methyl-N-[3-(trifluoromethyl)phenyl]pyrrolo[3,2-c]pyridin-4-amine, 6-(3-chlorophenyl)-3-(3,4-dimethoxyphenyl)pyrazolo[1,5-a]pyrimidin-7-amine, 5-amino-4-(1H-benzimidazol-2-yl)-1-(1,3-benzodioxol-5-yl)-2H-pyrrol-3-one, 8-(2,5-dimethoxyphenyl)-7-(4-fluorophenyl)-1-methyl-3H-imidazo[1,2-g]purine-2,4-dione, methyl 2-amino-1-(3-hydroxyphenyl)pyrrolo[3,2-b]quinoxaline-3-carboxylate, 2-(3,4-dimethoxyphenyl)-6-hydroxy-chromen-4-one, 2-amino-1-(3-methoxyphenyl)pyrrolo[3,2-b]quinoxaline-3-carboxamide.

In another aspect, the present invention provides a method of treating, or slowing progression of a disease associated with Fyn kinase, the method comprising administering a therapeutically effective amount of at least one compound, or a pharmaceutically acceptable salt or solvate of the compound to a patient in need thereof, wherein the compound is selected from the group consisting of N-[3-[6-(2-furylmethylamino)pyrazin-2-yl]phenyl]acetamide, 4-[6-[1-(hydroxymethyl)propylamino]pyrazin-2-yl]phenol, 2-[[6-(5-isopropyl-2-methoxy-phenyl)pyrazin-2-yl]amino]butan-1-ol, 6-(3-aminophenyl)-N-benzyl-pyrazin-2-amine, 2-[[6-(4-aminophenyl)pyrazin-2-yl]amino]butan-1-ol, N-[3-(dimethylamino)propyl]-3-[6-(4-methoxyphenyl)pyrazin-2-yl]benzamide, 2-methoxy-4-[6-(4-methoxyphenyl)pyrazin-2-yl]phenol, N-[3-[6-(4-methoxyphenyl)pyrazin-2-yl]phenyl]acetamide, N-[3-[6-(3-hydroxyphenyl)pyrazin-2-yl]phenyl]acetamide, 3-[5-(3-furylmethylamino)-3-pyridyl]phenol, N-[3-[5-(3,4,5-trimethoxyanilino)-3-pyridyl]phenyl]acetamide, 3-[(3-methoxyphenyl)methyl]-5-(3,4,5-trimethoxyphenyl)-1H-imidazo[4,5-b]pyrazin-2-one, N,N-dimethyl-3-[2-oxo-3-[(1S)-1-phenylethyl]-1H-imidazo[4,5-b]pyrazin-5-yl]benzamide, 5-[3-(dimethylamino)phenyl]-N-(4-morpholinophenyl)imidazo[1,2-a]pyrazin-8-amine, 3-[5-[(6-methoxy-3-pyridyl)amino]pyrazolo[1,5-a]pyrimidin-3-yl]phenol, 3-(3-methoxyphenyl)-N-(6-methoxy-3-pyridyl)pyrazolo[1,5-a]pyrimidin-5-amine, 1-[3-[5-[(6-methoxy-3-pyridyl)amino]pyrazolo[1,5-a]pyrimidin-3-yl]phenyl]ethanone, N-[5[[3-(3-hydroxyphenyl)pyrazolo[1,5-a]pyrimidin-5-yl]amino]-2-methyl-phenyl]methanesulfonamide, 3-(3,4-dimethoxyphenyl)-N-(3-pyridylmethyl)pyrazolo[1,5-a]pyrimidin-5-amine, N-(3-pyridylmethyl)-3-(3,4,5-trimethoxyphenyl)pyrazolo[1,5-a]pyrimidin-5-amine, N-(4-isopropylphenyl)-3-(4-methoxyphenyl) pyrazolo[1,5-a]pyrimidin-5-amine, 3-(5-methoxy-3-pyridyl)-N-(4-morpholinophenyl)pyrazolo[1,5-a]pyrimidin-5-amine, 3-(3-aminophenyl)-N-(3-pyridylmethyl)pyrazolo[1,5-a]pyrimidin-5-amine, 3-(2-methoxyphenyl)-N-(3-pyridylmethyl)pyrazolo[1,5-a]pyrimidin-5-amine, (E)-3-[3-[5-(3-pyridylmethylamino)pyrazolo[1,5-a]pyrimidin-3-yl]phenyl]prop-2-enoic acid, N-[3-(dimethylamino)propyl]-4-[6-(2-fluoro-3-methoxy-phenyl)-1H-pyrazolo[3,4-b]pyridin-3-yl]benzamide, 6-(1H-indol-5-yl)-N-methyl-pyrazin-2-amine, N-ethyl-2-(3,4,5-trimethoxyanilino)-7,8-dihydro-5H-pyrido[4,3-d]pyrimidine-6-carboxamide, 6-propyl-N-(3,4,5-trimethoxyphenyl)-7,8-dihydro-5H-pyrido[4,3-d]pyrimidin-2-amine, [2-[3-(dimethylamino)anilino]-5,7-dihydropyrrolo[3,4-d]pyrimidin-6-yl]-(2-methoxyphenyl)methanone, N-[3-(4-fluorophenyl)-6-[4-(morpholine-4-carbonyl)phenyl]imidazo[1,2-a]pyridin-8-yl]formamide, N-[3-(3-acetylphenyl)-6-[4-(morpholine-4-carbonyl)phenyl]imidazo[1,2-a]pyridin-8-yl]formamide, N-[3-(3-chloro-4-fluoro-phenyl)-6-[3-(methanesulfonamido)phenyl]imidazo[1,2-a]pyridin-8-yl]formamide, N-[3-(4-fluorophenyl)-6-(1-methylpyrazol-4-yl)imidazo[1,2-a]pyridin-8-yl]formamide, 1-methyl-N-[4-(4-methylpiperazin-1-yl)phenyl]-2-[3-(trifluoromethyl)phenyl]pyrrolo[3,2-c]pyridin-6-amine, 1-methyl-N-pyrimidin-4-yl-2-[3-(trifluoromethyl)phenyl]pyrrolo[3,2-c]pyridin-6-amine, 2-(3-fluorophenyl)-1-methyl-N-[4-(4-methylpiperazin-1-yl)phenyl]pyrrolo[3,2-c]pyridin-6-amine, 2-(3-fluorophenyl)-1-methyl-N-pyrimidin-4-yl-pyrrolo[3,2-c]pyridin-6-amine, 1-benzyl-N-[4-(4-methylpiperazin-1-yl)phenyl]-2-(3-pyridyl)pyrrolo[3,2-c]pyridin-6-amine, 2-(1 H-pyrazol-4-yl)-N-(2-pyridyl)-1H-pyrrolo[3,2-c]pyridin-6-amine, N-(4-methylsulfonylphenyl)-2-(1H-pyrazol-4-yl)-1H-pyrrolo[3,2-c]pyridin-6-amine, 1-benzyl-2-(3-pyridyl)-N-pyrimidin-4-yl-pyrrolo[3,2-c]pyridin-6-amine, N-(3-methoxyphenyl)-2-(1H-pyrazol-4-yl)-1H-pyrrolo[3,2-c]pyridin-6-amine, N-(3,4-dimethoxyphenyl)-2-(1H-pyrazol-4-yl)-1H-pyrrolo[3,2-c]pyridin-6-amine, 1-benzyl-N-[4-(4-methylpiperazin-1-yl)phenyl]-2-phenyl-pyrrolo[3,2-c]pyridin-6-amine, N-[3-[8-acetamido-3-(3,4-dimethoxyphenyl)imidazo[1,2-a]pyridin-6-yl]phenyl]acetamide, N-[3-(3-acetylphenyl)-6-(3-methoxyphenyl)imidazo[1,2-a]pyridin-8-yl]acetamide, N-[3-(3-acetylphenyl)-6-(2,4-dimethoxyphenyl)imidazo[1,2-a]pyridin-8-yl]acetamide, N-[3-(3-acetylphenyl)-6-(2-methoxyphenyl)imidazo[1,2-a]pyridin-8-yl]acetamide, N-[6-(4-aminophenyl)-3-(4-fluorophenyl)imidazo[1,2-a]pyridin-8-yl]acetamide, N-[3-(3-acetylphenyl)-6-[4-(morpholine-4-carbonyl)phenyl]imidazo[1,2-a]pyridin-8-yl]acetamide, N,N-dimethyl-4-[4-[4-(4-methylpiperazin-1-yl)anilino]-1H-pyrrolo[3,2-c]pyridin-2-yl]benzamide, 4-[2-(3,5-dimethoxyphenyl)-1H-pyrrolo[3,2-c]pyridin-4-yl]morpholine, N-[4-[[2-(2-methoxyphenyl)-1H-pyrrolo[3,2-c]pyridin-4-yl]amino]phenyl]acetamide, 2-(2-methoxyphenyl)-1-methyl-N-[3-(trifluoromethyl)phenyl]pyrrolo[3,2-c]pyridin-4-amine, 6-(3-chlorophenyl)-3-(3,4-dimethoxyphenyl)pyrazolo[1,5-a]pyrimidin-7-amine, 5-amino-4-(1 H-benzimidazol-2-yl)-1-(1,3-benzodioxol-5-yl)-2H-pyrrol-3-one, 8-(2,5-dimethoxyphenyl)-7-(4-fluorophenyl)-1-methyl-3H-imidazo[1,2-g]purine-2,4-dione, methyl 2-amino-1-(3-hydroxyphenyl)pyrrolo[3,2-b]quinoxaline-3-carboxylate, 2-(3,4-dimethoxyphenyl)-6-hydroxy-chromen-4-one, 2-amino-1-(3-methoxyphenyl)pyrrolo[3,2-b]quinoxaline-3-carboxamide.

In another aspect, the present invention provides a method of inhibiting Fyn kinase in a patient, the method comprising administering a therapeutically effective amount of at least one compound, or a pharmaceutically acceptable salt or solvate of the compound to a patient in need thereof, the compound being any one of those listed in Tables 3 and 4.

In another aspect, the present invention provides a method of treating, or slowing progression of a disease associated with Fyn kinase, the method comprising administering a therapeutically effective amount of at least one compound, or a pharmaceutically acceptable salt or solvate of the compound to a patient in need thereof, of at least one compound described above, or a pharmaceutically acceptable salt or solvate thereof. Without limitation, the Fyn kinase inhibitors described here may be utilized to treat Types I and II diabetes, pre-diabetes and may prove effective in facilitating overall weight control, extend longevity and improve physical and mental well-being. In addition, such Fyn kinase inhibitors may improve exercise tolerance and increase the human body's ability to endure physical stress, as well as improve recovery from exercise and physical stress.

Fyn kinase inhibitors may be effective cancer therapeutics and may, when administered prophylactically, reduce the occurrence of various cancers in an individual. Due to its central role in intracellular regulatory phosphorylation cascades, Fyn kinase can play diverse roles in many common cancers. In breast cancers Fyn kinase regulates phosphorylation of ERB receptors and has been directly implicated in the genesis of tamoxifen and trastuzumab resistant breast cancers. Fyn kinase is also implicated in many forms of prostate cancer and Fyn expression is unusually high in prostate cancer cells. In liver cancers, and hepatocellular cancers generally, Fyn expression also appears to be significantly elevated. Mutant pancreatic cancer cells transfected with highly expressed kinase-dead Fyn genes have been shown to have decreased liver metastases activity in mouse models, suggesting a model by which Fyn kinase activity regulates cell proliferation and apoptosis. Esophageal and gastric cancers also exhibit high levels of Fyn kinase and such cancers are thought to be particularly sensitive to the epidermal growth factor receptor signaling pathway in which Fyn plays a key role. Fyn also plays a role in cervical and ovarian cancers. Elevated levels of Fyn kinase observed in many such cancers appears to be the result of overexpression of NRDG1, which when suppressed by shRNA treatment results in concomitant decrease in Fyn expression and a subsequent decrease in cell adhesion, migration and invasion activity.

Existing Fyn kinase inhibitors are also known to mitigate and lessen the severity of neurodegenerative diseases such as Multiple Sclerosis, Alzheimer's and Parkinson's and the Fyn kinase inhibitors described here may exhibit improved therapeutic efficacy in such treatments. The Fyn kinase inhibitors described here may also be effective in improving recovery from head or spinal trauma as well as promoting overall neurological health.

The invention described here relate to pharmacophores identified by analysis of specific chemical, physical and biological properties of a large set of chemical combinations based on a limited set of pharmacores. Such pharmacophores define the relevant parameters necessary to specifically modulate Fyn kinase activity and to provide therapeutic treatment for physiologic and pathologic conditions amenable to treatment by regulation of Fyn kinase activity in patients in need of such treatment.

Definitions

As used herein and throughout this disclosure, the following terms are to be understood to have the following meaning.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Alcohol" means a functional group of the general formula R—OH, wherein R represents and alkane, alkene or any other carbon-containing group.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)2, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more 20 lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and -5(alkyl). Non-limiting examples of suitable alkenyl groups include ethenyl, propenyl, n-butenyl, 3-methylbut-2-enyl, n-pentenyl, octenyl and decenyl.

"Alkoxy" means an alkyl-O-group. Non-limiting examples of suitable alkoxy groups include methoxy, ethoxy, n-propoxy, isopropoxy and n-butoxy. The bond to the parent moiety is through the ether oxygen.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Alkylphosphate" means a compound of the general formula ROP(O)3-, wherein the R represents any alkyl group.

"Alkylsulfate" means a compound of the general formula ROS(O)3-, wherein the R represents any alkyl group.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Aroyl" means an aryl-C(O)-group. The bond to the parent moiety is through the carbonyl. Non-limiting examples of suitable groups include benzoyl and 1-naphthoyl.

"Arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. A non-limiting example of a suitable alkylaryl group is tolyl. The bond to the parent moiety is through the aryl.

"Alkylthio" means an alkyl-S-group. Non-limiting examples of suitable alkylthio groups include methylthio and ethylthio. The bond to the parent moiety is through the sulfur.

"Arylphosphate" means a compound of the general formula ROP(O)3-, wherein the R represents any aryl group.

"Arylsulfate" means a compound of the general formula ROS(O)3-, wherein the R represents any aryl group.

"Arylthio" means an aryl-S-group. Non-limiting examples of suitable arylthio groups include phenylthio and naphthylthio. The bond to the parent moiety is through the sulfur.

"Alkoxycarbonyl" means an alkyl-O—CO-group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)-group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(02)-group. Preferred groups are those in which the alkyl group is lower alkyl. The bond to the parent moiety is through the sulfonyl.

"Amide" means a functional group comprising (R1)C(O)N(R2)(R3) wherein the R groups refer to H or organic groups and the carbon and nitrogen atoms are covalently linked. Other amides include "sulfonamides" of the general formula (R1)S(O2)N(R2)(R3), wherein the sulfur and nitrogen atoms are covalently linked; and "phosphoramides" of the general formula (R1)(R2)O(O)N(R3)(R4), wherein the phosphate and the nitrogen are covalently linked. A non-limiting example of an amide is acetamide.

"Amine" means a functional group comprising: NI-12 (R1), a "primary amine"; NH(R1)(R2), a "secondary amine": N(R1)(R2)(R3), a "tertiary amine", wherein the bond to the parent moiety runs through the nitrogen.

"Arylsulfonyl" means an aryl-S(02)-group. The bond to the parent moiety is through the sulfonyl.

"Aralkylthio" means an aralkyl-S-group in which the aralkyl group is as previously described. Non-limiting example of a suitable aralkylthio group is benzylthio. The bond to the parent moiety is through the sulfur.

"Arylalkenyl" means an alkenyl-aryl-group. Preferred arylalkenyls comprise a lower alkenyl group. A non-limiting example of a suitable arylalkenyl group is phenylacetylene.

"Aryloxy" means an aryl-O-group. Non-limiting examples of suitable aryloxy groups include phenoxy and naphthoxy. The bond to the parent moiety is through the ether oxygen.

"Aralkyloxy" means an aralkyl-O-group in which the aralkyl group is as previously described. Non-limiting examples of suitable aralkyloxy groups include benzyloxy and 1- or 2-naphthalenemethoxy. The bond to the parent moiety is through the ether oxygen.

"Composition" is intended to encompass a product comprising the specified ingredients in the specified amounts, as well as any product which results, directly or indirectly, from combination of the specified ingredients in the specified amounts.

"Cyano" means a —CN group in which the bond to the parent moiety is through the carbon.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

"Furan" is a heterocyclic aromatic compound of the formula C4H4O. Compounds comprising such structures may be referred to as "furans."

"Halogen" or "halo" means fluorine, chlorine, bromine, or iodine. Preferred are fluorine, chlorine and bromine.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least one of a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2, 1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Heteroarylalkyl" means a heteroaryl moiety as defined above linked via an alkyl moiety (defined above) to a parent core. Non-limiting examples of suitable heteroarylalkyls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to 30 about 1 0 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

"Heterocyclylalkyl" means a heterocyclyl moiety as defined above linked via an alkyl moiety (defined above) to a parent core. Non-limiting examples of suitable heterocylalkyls include piperidinylmethyl, piperazinylmethyl and the like.

"Heterocyclenyl" means a non-aromatic monocyclic or multicyclic ring system comprising about 3 to about 1 0 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, dihydroimidazole, dihydrooxazole, dihydrooxadiazole, dihydrothiazole, 3,4-dihydro-2H-pyran, dihydrofuranyl, fluorodihydrofuranyl, 7oxabicyclo[2.2.1]heptenyl, dihydrothiophenyl, dihydrothiopyranyl, and the like.

"Hydroxyalkyl" means a HO-alkyl- group in which alkyl is as previously defined.

Preferred hydroxyalkyls contain lower alkyl. Non-limiting examples of suitable hydroxyalkyl groups include hydroxymethyl and 2-hydroxyethyl.

"Patient" or "Subject" includes both human and animals.

"Pharmacore" means a specific chemical structure to which combinations of additional chemical constituents may be added. The combination of pharmacore and additional chemical groups represents the "pharmacophore."

"Pharmacophore" is the ensemble of steric and electronic features of a pharmacore and any additional chemical constituents necessary to ensure supramolecular interactions with a specific biological target structure to trigger or block its biological response. A pharmacophore does not necessarily represent a real molecule or association of functional groups, although it may, but embodies the concept that accounts for the common molecular interaction capacities of a group of compounds towards their target structure. The pharmacophore can be considered the largest common denominator shared by a set of active molecules.

"Physiologic function" is the physiological activity of an organ, body part, or pathway within an animal.

"Purified", "in purified form", "isolated", or "in isolated and purified form" for a compound refers to the physical state of said compound after being isolated from a synthetic process or natural source or combination thereof. Thus, the term "purified", "in purified form", "isolated", or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

"Pyrrole" is a heterocyclic aromatic compound of the formula C4H4N. Compounds comprising such structures may be referred to as "pyrroles."

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH2, —C(=NH)—NH2, —C(=NH)—NH(alkyl), Y1 Y2N-, Y1Y2N-alkyl-, Y1Y2NC(O)—, Y1Y2NSOr and —S02NY1Y2, wherein Y1 and Y2 can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are methylene dioxy, ethylenedioxy, —C(CH3) 2- and the like.

"Substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent. The term "optionally substituted" means optional substitution with the specified groups, radicals or moieties.

"Thiol" means a functional group of the general formula R—SH, wherein R represents and alkane, alkene or any other carbon-containing group, may also be referred to as a "mercaptan" or "sulfhydryl" group.

"Thiophene" is a heterocyclic aromatic compound of the formula C4H4S, may also be referred to as thiofuran.

Any carbon as well as heteroatom with unsatisfied valences in the text, examples and Tables herein is assumed to have the sufficient number of hydrogen atom(s) to satisfy the valences.

The compounds described herein may contain asymmetric or chiral centers, and, therefore, exist in different stereoisomeric forms. It is intended that all stereoisomeric forms of these compounds as well as mixtures thereof, including racemic mixtures, form part of the present invention. In addition, the present invention embraces all geometric and positional isomers. For example, if a compound incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of chiral HPLC column.

The compounds herein may in some cases form salts which are also within the scope of this invention. Reference to a compound herein is understood to include reference to salts thereof, unless otherwise indicated. The term "salt(s)", as employed herein, denotes acidic salts formed with inorganic and/or organic acids, as well as basic salts formed with inorganic and/or organic bases.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is water. One or more compounds of the invention may also exist as, or optionally be converted to, a solvate. Preparation of solvates is generally known.

The compounds of this invention may exist in unsolvated as well as solvated forms with pharmaceutically acceptable solvents such as water, ethanol, and the like, and it is intended that the invention embrace both solvated and unsolvated forms.

It is also possible that the compounds herein may exist in different tautomeric forms, and all such forms are embraced within the scope of the invention, for example, all keto-enol and imine-enamine forms of the compounds are included in the invention.

DETAILED DESCRIPTION OF THE INVENTION

Identifying FYN Kinase Inhibitors.

Individual compounds within a chemical library consisting of 600 potential kinase inhibitors were assayed with the ADP-Glo™ Kinase Assay kit (V9102, Promega UK Ltd. Southhampton, Hampshire, UK) to identify the most potent FYN kinase inhibitors within the collection. The chemical library was comprised of the SoftFocus ATP-competitive hinge binding compounds described by Harris, C. J., Hill, R. D., Sheppard, D. W., et al., The Design and Application of Target-Focused Compound Libraries. Combinatorial Chemistry and High Throughput Screening 14:521-31 (2011). The specific pharmacore chemistries included SFK52 comprising 6-[R2]-3-[R1]imidazo[1,2-b] pyridazine compounds, SFK33 comprising N-(3-[R2] imidazo [1,2-b] pyridazin-6-yl) [R1] amine compounds, SFK49 comprising N-(5-[R2] imidazo [2,1-b][1,3,4] thiadiazol-2-yl)[R1]-amine compounds, SFK 40 comprising 5-[R2]-3-[R1] pyridin-2-amine compounds, SFK43 comprising 6-[R2]-3-[R1]imidazo[1,2-a]pyrazine compounds, and SFK63. The scaffold structure of each pharmacore is shown in Table 2. The chemical structures of the initial 600 potential kinase inhibitors are presented in Table 3, with those chosen for additional analysis presented in Table 4. Comparison of the compounds presented in Table 1 and those of Tables 2, 3 and 4, illustrate the novelty of the chemical structures claimed herein.

FYN kinase (10 micrograms) was from the FYN A Kinase Enzyme System (V3571, Promega UK Ltd.), a full-length recombinant human FYN A containing an N-terminal GST tag of about 85 kDa, expressed by baculovirus in S19 insect cells, supplied at a concentration of 0.1 microgram/microliter in 5×reaction buffer. The FYN substrate, a 12 amino acid peptide of the sequence EFGTYGTLSKKK, containing a single tyrosine phosphorylation site, was custom synthesized (Peptide Synthetics, Peptide Protein Research, Fareham, UK) and supplied as a 4 mg/ml aqueous solution. All other reagents were obtained from Sigma (Sigma-Aldrich, Gillingham, Dorset, UK), with the exception of UltraPure ATP (V9102, Promega UK Ltd.) and the ATP-competitive broad spectrum protein kinase inhibitor staurosporine (569397, Merck Millipore, Watford, Hertfordshire, UK), or as otherwise indicated.

The assay procedure determines the IC50 of each potential FYN kinase inhibitor by measuring the enzyme catalyzed ATP-dependent phosphorylation of the FYN substrate peptide. The ADP-Glo™ Kinase Assay is specifically designed to quantify kinase activity by measuring the ADP produced in the reaction The reaction buffer comprises 40 mM Tris.HCl (pH 7.5), 20 mM $MgCl_2$, 0.1 mg/ml BSA and 5 microM DTT. Individual compounds within the chemical library were dissolved in DMSO at known concentrations. Briefly, 2.5 microliters of reaction buffer containing 3 picograms of FYN kinase and serial dilutions of each potential FYN kinase inhibitor (9 3-fold dilutions of a 10 micromolar top sample) are placed into each well of a 384 well microtiter plate and incubated at room temperature for 30 minutes. An additional 2.5 microliters of reaction buffer containing 100 picograms of the FYN substrate and 12.5 picomoles of ATP are then added to each well and the reaction carried out for 90 minutes at room temperature. The reactions are terminated by addition of 5 microliters of the ADP-Glo™ Reagent component of the ADP-Glo™ Kinase Assay kit to each well. The ADP-Glo™ Reagent comprises an ATP-dependent adenylate cyclase, an inorganic pyrophosphatase and an excess of staurosporine. The adenylate cyclase converts the remaining ATP to cAMP and pyrophospahte, the pyrophosphatase converts the pyrophosphate to phosphate and the staurosporine inhibits the activity of the FYN kinase, the net effect is to remove all residual ATP while preserving the ADP produced by FYN kinase. The terminated reactions are incubated for 40 minutes at room temperature, prior to addition of the Kinase Detection Reagent component of the ADP-Glo™ Kinase Assay kit to each well. The Kinase Detection Reagent comprises pyruvate kinase, phosphoenol pyruvate (PEP), luciferin and luciferase. The pyruvate kinase converts PEP to pyruvate and in the process generates ATP from the residual ADP present in the terminated reaction. The ATP is then consumed by the luciferase catalyzed, light emitting conversion of luciferin to oxyluciferin producing AMP, pyrophosphate and $CO_2$. The emitted light was measured on an Envion Luminometer to determine the relative activity of the FYN kinase in each well. A 10 point dose-response curve for each potential FYN kinase inhibitor dilution series was used to determine the IC50, of each compound. Details of the analysis, including assay procedures and representative dilution schema for measuring kinase inhibitors are presented in the Technical Manual accompanying the ADP-Glo™ Kinase Assay kit (Doc. TM313. Promega Corp.) as well as U.S. Pat. Nos. 8,183,007 and 8,802,411, the contents of which are incorporated herein, in their entirety.

The results of screening candidate libraries are presented in Table 3, which lists the structure of each compound, the standard IUPAC name of the compound, the observed IC50 and the calculated lipophilicity of the compound. The most potent FYN kinase inhibitors, generally those with the most favorable combination of IC50 and drugability were resynthesized and subjected to further testing and expansion. In general, the best candidate compounds exhibit an IC50 of less than 200 nM and and drugability as measured by LLE (Ligand-lipophilicity efficiency) of greater than 2.5. LLE= (pIC50-c Log P) where pIC50 is the negative log of the observed IC50 and c Log P is a calculated consensus measure of the lipophilicity of the compound. In practice, this means a c Log P of less than 3.5, based on an average IC50 of less than or equal to 1 µM, represents a favorable level of drugability (LLE>2.5). Candidate compounds selected for additional testing and expansion are listed in Table 4.

Cell Based Assay(s) of FYN Kinase Inhibitors

Test compounds exhibiting superior IC50 and LLE profiles are further tested for their ability to stimulate T cell proliferation and to inhibit production of Interleukin 2 by stimulated T-cells.

T-cell proliferation is analyzed by staining with carboxyfluorescein diacetate succinimidyl ester (CFSE) at a final concentration 5 µM (Molecular Probes, Invitrogen) according to the manufacturer's instructions. Briefly, cells are resuspended in warm PBS containing 5 µM CFSE and incubated at 37° C. for 10 minutes. Subsequently, cells are washed twice and resuspended in culture media containing 10% FBS before the experimental treatments are initiated. Cells may be analyzed by flow cytometry after 5 days in culture. Alternatively, a 96-well plate is coated with a monoclonal antibody to CD3 (G19-4), the antibody is allowed to bind, and then the plate is washed. Normal human peripheral blood T cells are added to the wells, along with test compound and anti-CD28 antibody to provide co-stimulation. After 3 days, [$^3$H]thymidine is added to the cells and incubated for 6 hours. The cells are harvested and counted in a liquid scintillation counter to measure proliferation.

To measure the ability of test compounds to block IL-2 production by Fyn mediated tyrosine phosphorylation induced by anti-CD3 and IL-2 stimulated T-cell proliferation, human T-cells, such as Jurkat cells are preincubated with various concentrations of test compound in serum-free medium at 37° C. for 10 min and then stimulated with plastic-immobilized anti-CD3 mAbs. Cells are cultured in complete media supplemented with 5% fetal bovine serum for 24 h in the presence of 10 µg/ml of anti-human CD25 mAbs to prevent IL-2 autocrine consumption. The supernatants are then harvested and centrifuged, and the IL-2 in the supernatant measured in a bioassay using a murine IL-2-dependent cell line, such as CTLL-4, as described by Trevillyan, et al., J. Immunol. 145:3223-30 (1990). To avoid the influence of residual test compound in the supernatants on proliferation of CTLL-4 cells, the test compound is removed by extensive dialysis against phosphate-buffered saline (0.1 M, pH 7.4). A control supernatant harvested from anti-CD3-stimulated Jurkat cells lacking Lck is spiked with 200 EM test compound is included along with the test compound dilution series to ascertain that all test compound is removed by the dialysis procedure. This "dialysis control" supernatant stimulates CTLL-4 proliferation as well as the positive control supernatant without added test compound, indicating the dialysis procedure has removed the test compound. Alternatively, IL-2 can be directly measured with an in vitro cytokine assays using labeled anti-IL2 mAbs, such as CisBio's Human IL2 Assay Kit (CisBio US. Bedford. Mass.) without requiring prior removal of test compound.

One of skill in the art will recognize that other assays may be devised to measure the efficacy of Fyn kinase inhibition by test compounds and that such assays are conventional in the art and known to those of ordinary skill.

TABLE 2

Representative scaffold structures of SoftFocus library pharmacores

| Structure | Name | Formula |
|---|---|---|
| (R2, R1 pyridine with NH2) | 5-[R2]-3-[R1]pyridin-2-amine | Formula I (SFK40 pharmacore) |
| (imidazo[1,2-a]pyrazine) | 6-[R2]-3-[R1]imidazo[1,2-a]pyrazine | Formula II (SFK43 pharmacore) |
| (imidazo[1,2-b]pyridazine) | 6-[R2]-3-[R1]imidazo[1,2-b]pyridazine | Formula III (SFK52 pharmacore) |
| (imidazo[2,1-b][1,3,4]thiadiazole) | N-(5-[R2]imidazo[2,1-b][1,3,4]thiadiazol-2-yl)[R1]amine | Formula IV (SFK49 pharmacore) |
| (pyrazolo[3,4-b]pyridine) | 4-[R2]-3-[R1]-1H-pyrazolo[3,4-b]pyridine | Formula V (SFK63 pharmacore) |
| (imidazo[1,2-b]pyridazin-6-yl amine) | N-(3-[R2]imidazo[1,2-b]pyridazin-6-yl)[R1]amine | Formula VI (SFK33 pharmacore) |

TABLE 3

Primary screen- initial compounds.

| | Structure | | IUPAC name | IC50 FYN (µM) | logP (consensus) | Compound ID. |
|---|---|---|---|---|---|---|
| | (structure 1) | 1 | N-[3-[6-(2-furyl-methylamino)pyrazin-2-yl]phenyl]acetamide | 11.18502 | 1.66 | 035_0144_0081 |
| | (structure 2) | 2 | 4-[6-[1-(hydroxymethyl)propylamino]pyrazin-2-yl]phenol | 15.34591 | 1.58 | 035_0153_0080 |

TABLE 3-continued

Primary screen- initial compounds.

| Structure | | IUPAC name | IC50 FYN (μM) | logP (consensus) | Compound ID. |
|---|---|---|---|---|---|
| 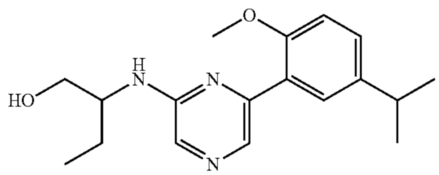 [SMILES: CCC(CO)Nc1cncc(-c2cc(C(C)C)ccc2OC)n1] | 3 | 2-[[6-(5-isopropyl-2-methoxyphenyl)pyrazin-2-yl]amino]butan-1-ol | 11.79042 | 2.97 | 035_0153_0286 |
| 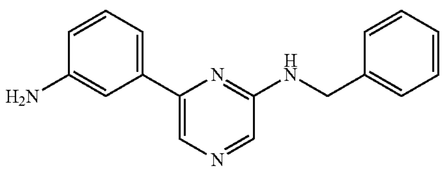 [SMILES: Nc1cccc(-c2cncc(NCc3ccccc3)n2)c1] | 4 | 6-(3-aminophenyl)-N-benzyl-pyrazin-2-amine | 6.67663 | 2.53 | 035_0232_0005 |
| 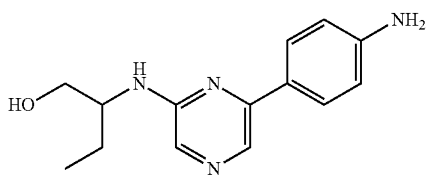 [SMILES: CCC(CO)Nc1cncc(-c2ccc(N)cc2)n1] | 5 | 2-[[6-(4-aminophenyl)pyrazin-2-yl]amino]butan-1-ol | 21.05663 | 1.06 | 035_0153_0333 |
| 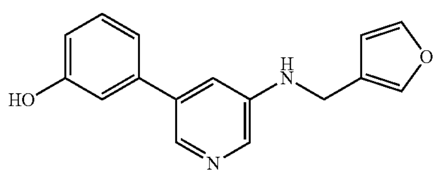 [SMILES: Oc1cccc(-c2cncc(NCc3ccoc3)c2)c1] | 6 | 3-[5-(3-furylmethylamino)-3-pyridyl]phenol | 10.89609 | 2.44 | 081_0284_2069 |
| 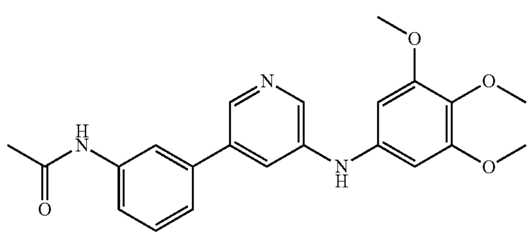 [SMILES: COc1cc(Nc2cncc(-c3cccc(NC(C)=O)c3)c2)cc(OC)c1OC] | 7 | N-[3-[5-(3,4,5-trimethoxyanilino)-3-pyridyl]phenyl]acetamide | 0.3913 | 2.61 | 081_0087_0081 |
| 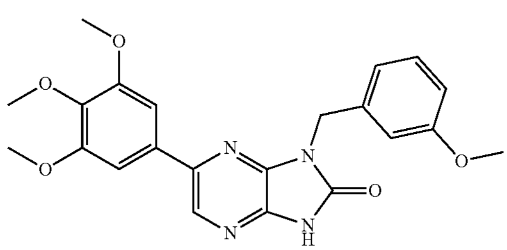 | 8 | 3-[(3-methoxyphenyl)methyl]-5-(3,4,5-trimethoxyphenyl)-1H-imidazo[4,5-b]pyrazin-2-one | 23.44 | 3.07 | 170_4313_0087 |
| 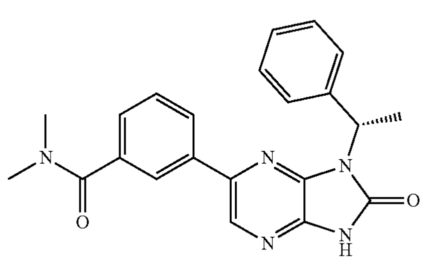 [SMILES: C[C@@H](c1ccccc1)n1c(=O)[nH]c2ncc(-c3cccc(C(=O)N(C)C)c3)nc21] | 9 | N,N-dimethyl-3-[2-oxo-3-[(1S)-1-phenylethyl]-1H-imidazo[4,5-b]pyrazin-5-yl]benzamide | 1.77669 | 3.42 | 170_0148_0349 |

TABLE 3-continued

Primary screen- initial compounds.

| Structure | | IUPAC name | IC50 FYN (μM) | logP (consensus) | Compound ID. |
|---|---|---|---|---|---|
| 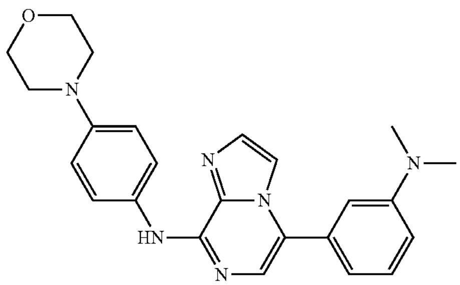 [SMILES: CN(C)c1cccc(-c2cnc(Nc3ccc(N4CCOCC4)cc3)c3nccn23)c1] | 10 | 5-[3-(dimethyl-amino)phenyl]-N-(4-morpholino-phenyl)imidazo[1,2-a]pyrazin-8-amine | 2.70242 | 3.14 | 184_0088_0135 |
| 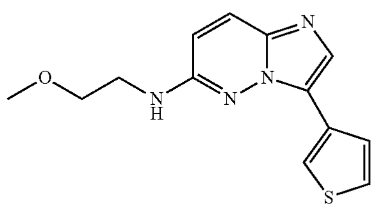 [SMILES: COCCNc1ccc2ncc(-c3ccsc3)n2n1] | 11 | N-(2-methoxy-ethyl)-3-(3-thienyl)imidazo[1,2-b]pyridazin-6-amine | 5.2312 | 2.02 | 229_0033_0074 |
| 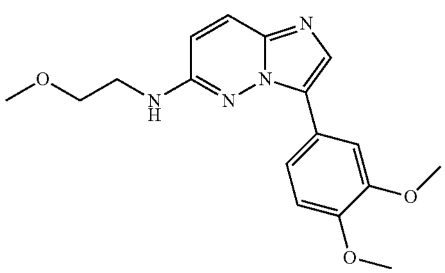 | 12 | 3-(3,4-dimethoxy-phenyl)-N-(2-methoxyethyl)imidazo[1,2-b]pyridazin-6-amine | 1.54534 | 1.93 | 229_0033_0079 |
| 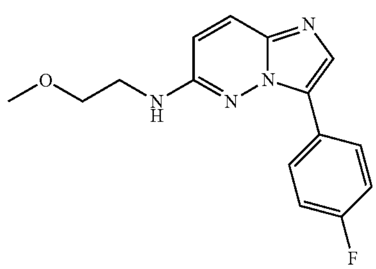 [SMILES: COCCNc1ccc2ncc(-c3ccc(F)cc3)n2n1] | 13 | 3-(4-fluoro-phenyl)-N-(2-methoxyethyl)imidazo[1,2-b]pyridazin-6-amine | 4.00393 | 2.38 | 229_0033_0339 |
| 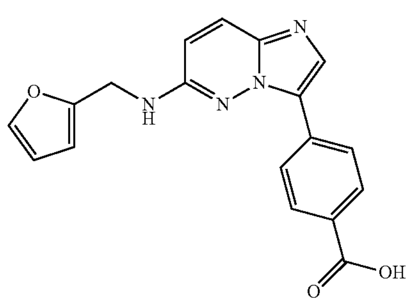 [SMILES: O=C(O)c1ccc(-c2cnc3ccc(NCc4ccco4)nn23)cc1] | 14 | 4-[6-(2-furylmethyl-amino)imidazo[1,2-b]pyridazin-3-yl]benzoic acid | 3.879 | 2.73 | 229_0144_0140 |

TABLE 3-continued

Primary screen- initial compounds.

| Structure | | IUPAC name | IC50 FYN (μM) | logP (consensus) | Compound ID. |
|---|---|---|---|---|---|
| 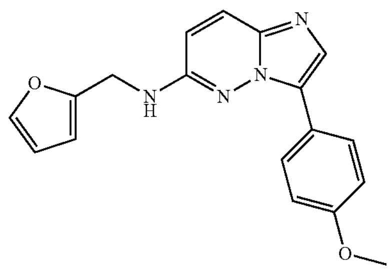 | 15 | N-(2-furyl-methyl)-3-(4-methoxyphenyl)imidazo[1,2-b]pyridazin-6-amine | 3.67644 | 2.91 | 229_0144_0280 |
| 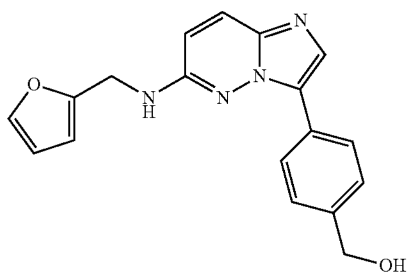 [SMILES: OCc1ccc(-c2cnc3ccc(NCc4ccco4)nn23)cc1] | 16 | [4-[6-(2-furyl-methylamino)imidazo[1,2-b]pyridazin-3-yl]phenyl]methanol | 2.20497 | 2.30 | 229_0144_0285 |
| 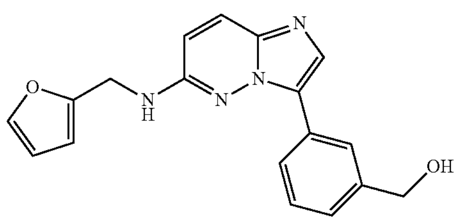 [SMILES: OCc1cccc(-c2cnc3ccc(NCc4ccco4)nn23)c1] | 17 | [3-[6-(2-furyl-methylamino)imidazo[1,2-b]pyridazin-3-yl]phenyl]methanol | 3.85557 | 2.30 | 229_0144_0291 |
| 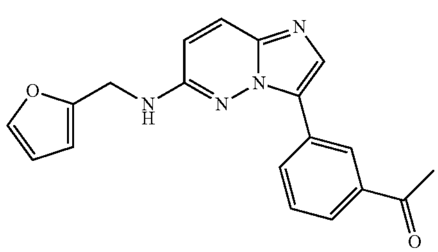 [SMILES: CC(=O)c1cccc(-c2cnc3ccc(NCc4ccco4)nn23)c1] | 18 | 1-[3-[6-(2-furyl-methylamino)imidazo[1,2-b]pyridazin-3-yl]phenyl]ethanone | 0.99711 | 2.63 | 229_0144_4145 |
| 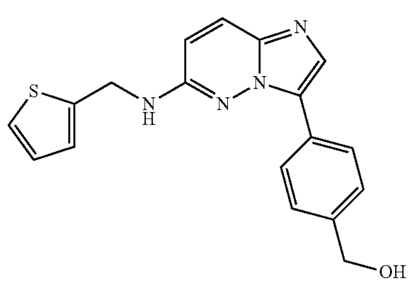 [SMILES: OCc1ccc(-c2cnc3ccc(NCc4cccs4)nn23)cc1] | 19 | [4-[6-(2-thienylmethyl-amino)imidazo[1,2-b]pyridazin-3-yl]phenyl]methanol | 1.09479 | 3.16 | 229_0146_0285 |

TABLE 3-continued

Primary screen- initial compounds.

| Structure | | IUPAC name | IC50 FYN (μM) | logP (consensus) | Compound ID. |
|---|---|---|---|---|---|
| 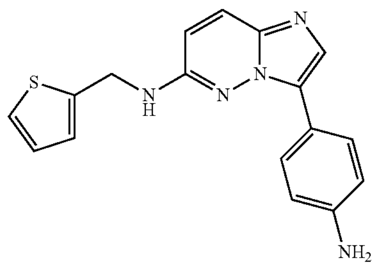 [SMILES: Nc1ccc(-c2cnc3ccc(NCc4cccs4)nn23)cc1] | 20 | 3-(4-aminophenyl)-N-(2-thienylmethyl)imidazo[1,2-b]pyridazin-6-amine | 5.42153 | 3.10 | 229_0146_0333 |
| 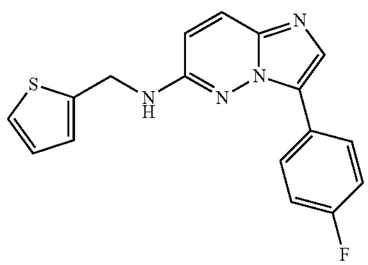 [SMILES: Fc1ccc(-c2cnc3ccc(NCc4cccs4)nn23)cc1] | 21 | 3-(4-fluorophenyl)-N-(2-thienylmethyl)imidazo[1,2-b]pyridazin-6-amine | 3.28447 | 4.07 | 229_0146_0339 |
| 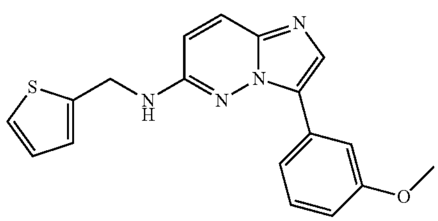 [SMILES: COc1cccc(-c2cnc3ccc(NCc4cccs4)nn23)c1] | 22 | 3-(3-methoxyphenyl)-N-(2-thienylmethyl)imidazo[1,2-b]pyridazin-6-amine | 2.94644 | 3.77 | 229_0146_4140 |
| 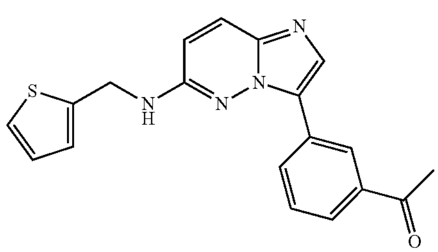 [SMILES: CC(=O)c1cccc(-c2cnc3ccc(NCc4cccs4)nn23)c1] | 23 | 1-[3-[6-(2-thienylmethylamino)imidazo[1,2-b]pyridazin-3-yl]phenyl]ethanone | 0.44073 | 3.48 | 229_0146_4145 |
| 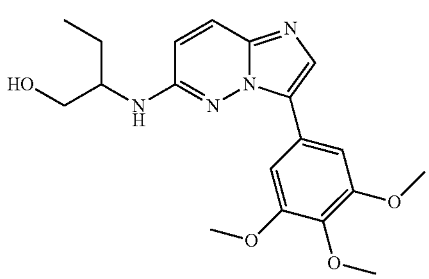 [SMILES: CCC(CO)Nc1ccc2ncc(-c3cc(OC)c(OC)c(OC)c3)n2n1] | 24 | 2-[[3-(3,4,5-trimethoxyphenyl)imidazo[1,2-b]pyridazin-6-yl]amino]butan-1-ol | 1.2806 | 2.06 | 229_0153_0087 |

TABLE 3-continued

Primary screen- initial compounds.

| Structure | | IUPAC name | IC50 FYN (μM) | logP (consensus) | Compound ID. |
|---|---|---|---|---|---|
| 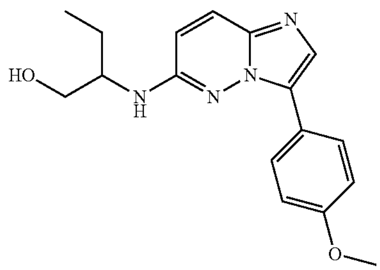 [SMILES: CCC(CO)Nc1ccc2ncc(-c3ccc(OC)cc3)n2n1] | 25 | 2-[[3-(4-methoxyphenyl)imidazo[1,2-b]pyridazin-6-yl]amino]butan-1-ol | 1.27502 | 2.38 | 229_0153_0280 |
| 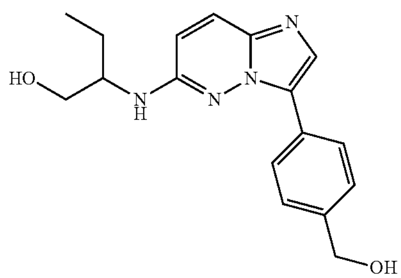 [SMILES: CCC(CO)Nc1ccc2ncc(-c3ccc(CO)cc3)n2n1] | 26 | 2-[[3-[4-(hydroxymethyl)phenyl]imidazo[1,2-b]pyridazin-6-yl]amino]butan-1-ol | 2.46631 | 1.77 | 229_0153_0285 |
| 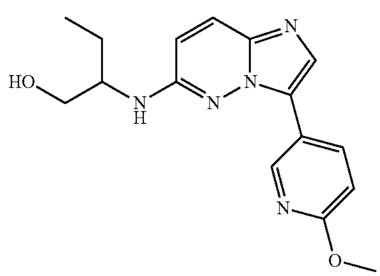 [SMILES: CCC(CO)Nc1ccc2ncc(-c3ccc(OC)nc3)n2n1] | 27 | 2-[[3-(6-methoxy-3-pyridyl)imidazo[1,2-b]pyridazin-6-yl]amino]butan-1-ol | 2.36648 | 1.76 | 229_0153_0311 |
| 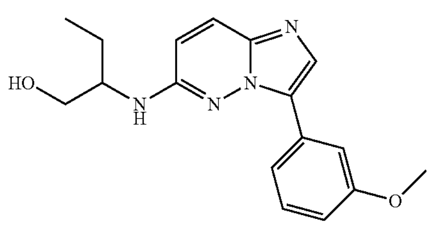 [SMILES: CCC(CO)Nc1ccc2ncc(-c3cccc(OC)c3)n2n1] | 28 | 2-[[3-(3-methoxyphenyl)imidazo[1,2-b]pyridazin-6-yl]amino]butan-1-ol | 1.55019 | 1.76 | 229_0153_4140 |
| 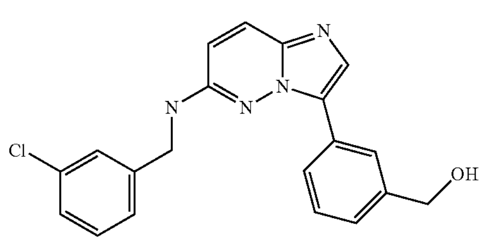 [SMILES: OCc1cccc(-c2cnc3ccc(NCc4cccc(Cl)c4)nn23)c1] | 29 | [3-[6-[(3-chlorophenyl)methylamino]imidazo[1,2-b]pyridazin-3-yl]phenyl]methanol | 5.10524 | 3.85 | 229_0223_0291 |

TABLE 3-continued

Primary screen- initial compounds.

| Structure | | IUPAC name | IC50 FYN (μM) | logP (consensus) | Compound ID. |
|---|---|---|---|---|---|
| 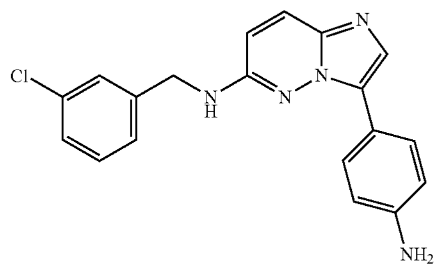 [SMILES: Nc1ccc(-c2cnc3ccc(NCc4cccc(Cl)c4)nn23)cc1] | 30 | 3-(4-aminophenyl)-N-[(3-chlorophenyl)methyl]imidazo[1,2-b]pyridazin-6-amine | 3.41043 | 3.79 | 229_0223_0333 |
| 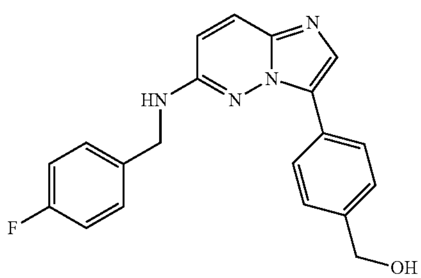 [SMILES: OCc1ccc(-c2cnc3ccc(NCc4ccc(F)cc4)nn23)cc1] | 31 | [4-[6-[(4-fluorophenyl)methylamino]imidazo[1,2-b]pyridazin-3-yl]phenyl]methanol | 2.4449 | 3.39 | 229_0224_0285 |
| 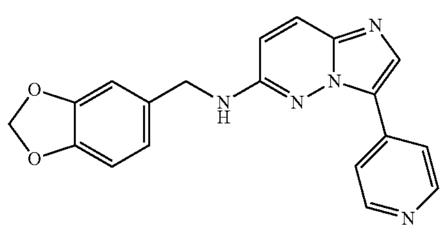 [SMILES: c1cc(-c2cnc3ccc(NCc4ccc5c(c4)OCO5)nn23)ccn1] | 32 | N-(1,3-benzodioxol-5-ylmethyl)-3-(4-pyridyl)imidazo[1,2-b]pyridazin-6-amine | 0.37966 | 2.42 | 229_0236_0069 |
| 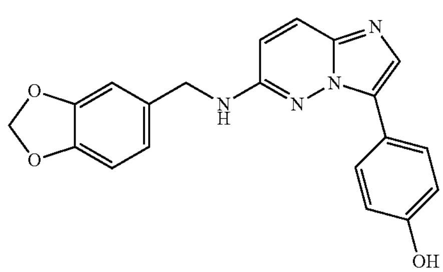 [SMILES: Oc1ccc(-c2cnc3ccc(NCc4ccc5c(c4)OCO5)nn23)cc1] | 33 | 4-[6-(1,3-benzodioxol-5-ylmethylamino)imidazo[1,2-b]pyridazin-3-yl]phenol | 5.67256 | 3.33 | 229_0236_0080 |
| 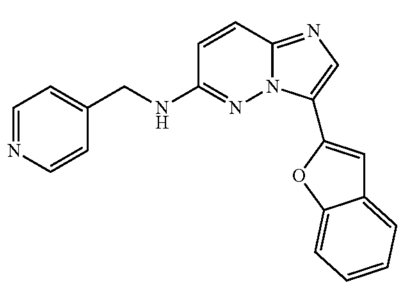 [SMILES: c1ccc2oc(-c3cnc4ccc(NCc5ccncc5)nn34)cc2c1] | 34 | 3-(benzofuran-2-yl)-N-(4-pyridylmethyl)imidazo[1,2-b]pyridazin-6-amine | 6.44995 | 2.87 | 229_0237_0073 |

TABLE 3-continued

Primary screen- initial compounds.

| Structure | | IUPAC name | IC50 FYN (μM) | logP (consensus) | Compound ID. |
|---|---|---|---|---|---|
| 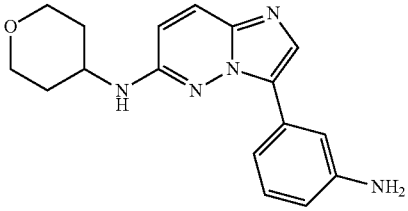 [SMILES: Nc1cccc(-c2cnc3ccc(NC4CCOCC4)nn23)c1] | 35 | 3-(3-aminophenyl)-N-tetrahydropyran-4-yl-imidazo[1,2-b]pyridazin-6-amine | 0.74599 | 1.42 | 229_0242_0005 |
| 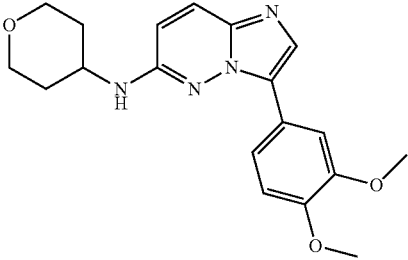 [SMILES: COc1ccc(-c2cnc3ccc(NC4CCOCC4)nn23)cc1OC] | 36 | 3-(3,4-dimethoxyphenyl)-N-tetrahydropyran-4-yl-imidazo[1,2-b]pyridazin-6-amine | 0.54713 | 1.93 | 229_0242_0079 |
| 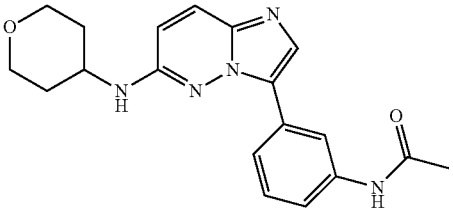 [SMILES: CC(=O)Nc1cccc(-c2cnc3ccc(NC4CCOCC4)nn23)c1] | 37 | N-[3-[6-(tetrahydropyran-4-ylamino)imidazo[1,2-b]pyridazin-3-yl]phenyl]acetamide | 0.58811 | 1.49 | 229_0242_0081 |
| 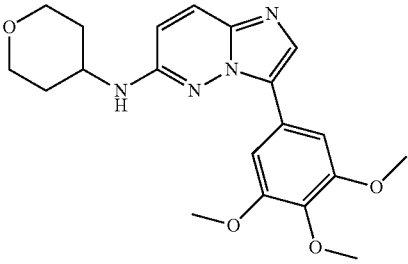 [SMILES: COc1cc(-c2cnc3ccc(NC4CCOCC4)nn23)cc(OC)c1OC] | 38 | N-tetrahydropyran-4-yl-3-(3,4,5-trimethoxyphenyl)imidazo[1,2-b]pyridazin-6-amine | 0.61737 | 1.78 | 229_0242_0087 |
| 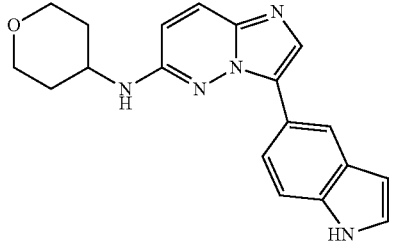 [SMILES: c1cc2cc(-c3cnc4ccc(NC5CCOCC5)nn34)ccc2[nH]1] | 39 | 3-(1H-indol-5-yl)-N-tetrahydropyran-4-yl-imidazo[1,2-b]pyridazin-6-amine | 1.16563 | 2.35 | 229_0242_0204 |
| 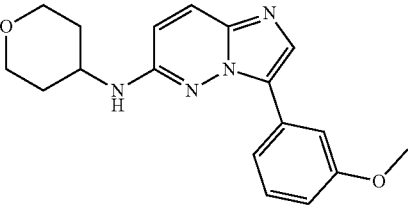 [SMILES: COc1cccc(-c2cnc3ccc(NC4CCOCC4)nn23)c1] | 40 | 3-(3-methoxyphenyl)-N-tetrahydropyran-4-yl-imidazo[1,2-b]pyridazin-6-amine | 0.87042 | 2.09 | 229_0242_4140 |

TABLE 3-continued

Primary screen- initial compounds.

| Structure | | IUPAC name | IC50 FYN (μM) | logP (consensus) | Compound ID. |
|---|---|---|---|---|---|
| 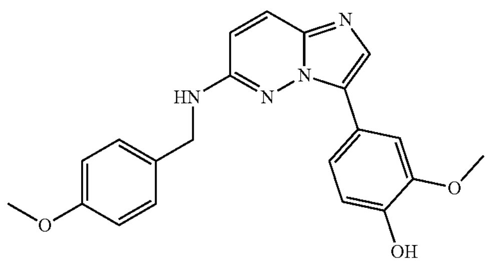 | 41 | 2-methoxy-4-[6-[(4-methoxyphenyl)methylamino]imidazo[1,2-b]pyridazin-3-yl]phenol | 4.01326 | 3.39 | 229_0244_0314 |
| 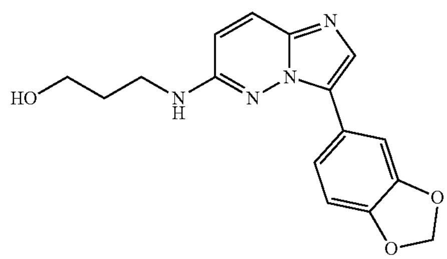 [SMILES: OCCCNc1ccc2ncc(-c3ccc4c(c3)OCO4)n2n1] | 42 | 3-[[3-(1,3-benzodioxol-5-yl)imidazo[1,2-b]pyridazin-6-yl]amino]propan-1-ol | 0.9286 | 1.28 | 229_0248_0068 |
| 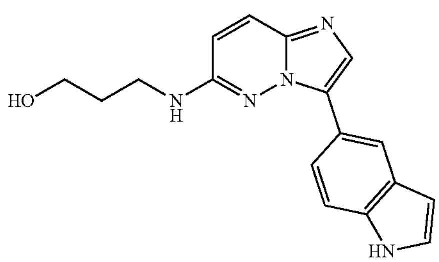 [SMILES: OCCCNc1ccc2ncc(-c3ccc4[nH]ccc4c3)n2n1] | 43 | 3-[[3-(1H-indol-5-yl)imidazo[1,2-b]pyridazin-6-yl]amino]propan-1-ol | 2.71742 | 1.76 | 229_0248_0204 |
| 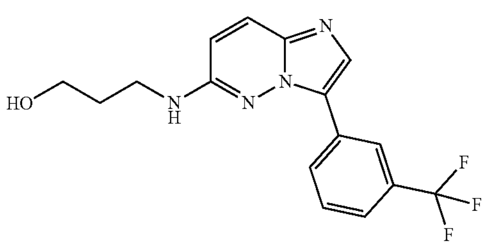 [SMILES: OCCCNc1ccc2ncc(-c3cccc(C(F)(F)F)c3)n2n1] | 44 | 3-[[3-[3-(trifluoromethyl)phenyl]imidazo[1,2-b]pyridazin-6-yl]amino]propan-1-ol | 3.41334 | 2.54 | 229_0248_0312 |
| 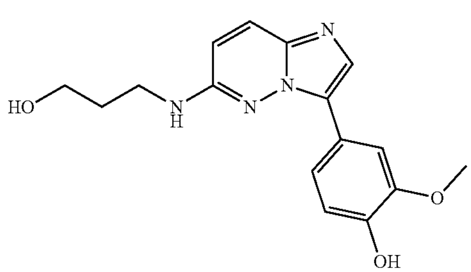 [SMILES: COc1cc(-c2cnc3ccc(NCCCO)nn23)ccc1O] | 45 | 4-[6-(3-hydroxypropylamino)imidazo[1,2-b]pyridazin-3-yl]-2-methoxyphenol | 0.32856 | 1.20 | 229_0248_0314 |

TABLE 3-continued

Primary screen- initial compounds.

| Structure | | IUPAC name | IC50 FYN (μM) | logP (consensus) | Compound ID. |
|---|---|---|---|---|---|
| 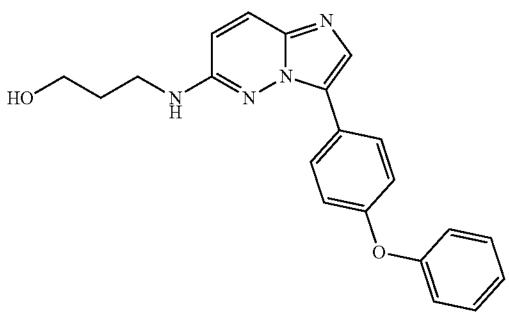 [SMILES: OCCCNc1ccc2ncc(-c3ccc(Oc4ccccc4)cc3)n2n1] | 46 | 3-[[3-(4-phenoxyphenyl)imidazo[1,2-b]pyridazin-6-yl]amino]propan-1-ol | 5.54336 | 3.16 | 229_0248_1029 |
| 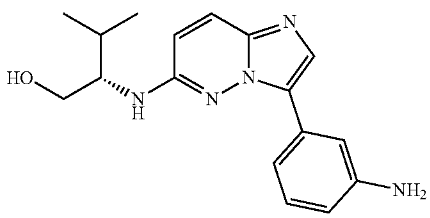 [SMILES: CC(C)[C@@H](CO)Nc1ccc2ncc(-c3cccc(N)c3)n2n1] | 47 | (2S)-2-[[3-(3-aminophenyl)imidazo[1,2-b]pyridazin-6-yl]amino]-3-methyl-butan-1-ol | 1.80698 | 2.07 | 229_0254_0005 |
| 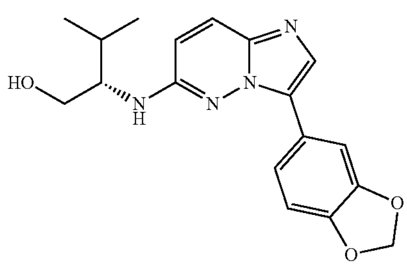 [SMILES: CC(C)[C@@H](CO)Nc1ccc2ncc(-c3ccc4c(c3)OCO4)n2n1] | 48 | (2S)-2-[[3-(1,3-benzodioxol-5-yl)imidazo[1,2-b]pyridazin-6-yl]amino]-3-methyl-butan-1-ol | 1.82017 | 2.52 | 229_0254_0068 |
| 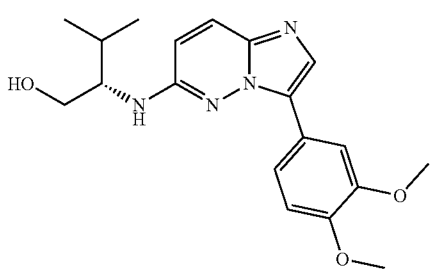 [SMILES: COc1ccc(-c2cnc3ccc(N[C@H](CO)C(C)C)nn23)cc1OC] | 49 | (2S)-2-[[3-(3,4-dimethoxyphenyl)imidazo[1,2-b]pyridazin-6-yl]amino]-3-methyl-butan-1-ol | 0.7782 | 2.59 | 229_0254_0079 |
| 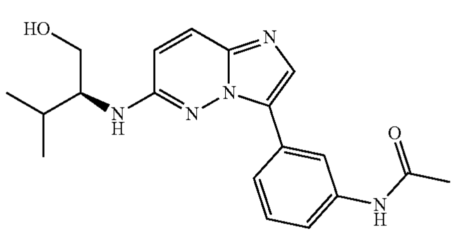 [SMILES: CC(=O)Nc1cccc(-c2cnc3ccc(N[C@H](CO)C(C)C)nn23)c1] | 50 | N-[3-[6-[[(1S)-1-(hydroxymethyl)-2-methyl-propyl]amino]imidazo[1,2-b]pyridazin-3-yl]phenyl]acetamide | 0.80076 | 2.14 | 229_0254_0081 |

TABLE 3-continued

Primary screen- initial compounds.

| Structure | | IUPAC name | IC50 FYN (μM) | logP (consensus) | Compound ID. |
|---|---|---|---|---|---|
| 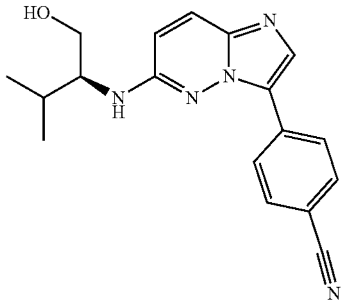 [SMILES: CC(C)[C@@H](CO)Nc1ccc2ncc(-c3ccc(C#N)cc3)n2n1] | 51 | 4-[6-[[(1S)-1-(hydroxymethyl)-2-methyl-propyl]amino]imidazo[1,2-b]pyridazin-3-yl]benzonitrile | 3.17911 | 2.76 | 229_0254_0086 |
| 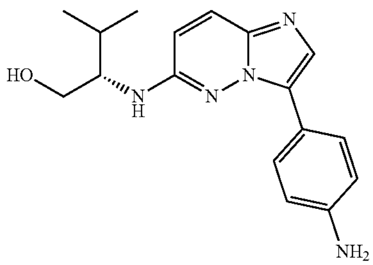 [SMILES: CC(C)[C@@H](CO)Nc1ccc2ncc(-c3ccc(N)cc3)n2n1] | 52 | (2S)-2-[[3-(4-aminophenyl)imidazo[1,2-b]pyridazin-6-yl]amino]-3-methyl-butan-1-ol | 3.05172 | 2.07 | 229_0254_0333 |
| 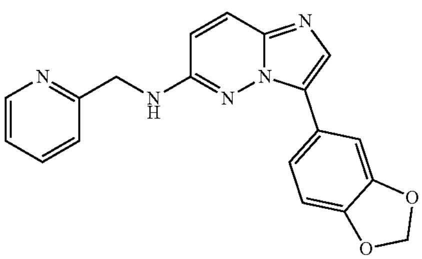 [SMILES: c1ccc(CNc2ccc3ncc(-c4ccc5c(c4)OCO5)n3n2)nc1] | 53 | 3-(1,3-benzodioxol-5-yl)-N-(2-pyridylmethyl)imidazo[1,2-b]pyridazin-6-amine | 0.79705 | 2.50 | 229_4007_0068 |
| 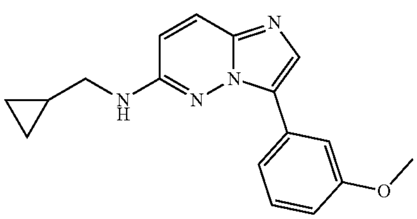 [SMILES: COc1cccc(-c2cnc3ccc(NCC4CC4)nn23)c1] | 54 | N-(cyclopropyl-methyl)-3-(3-methoxyphenyl)imidazo[1,2-b]pyridazin-6-amine | 3.29534 | 2.91 | 229_4051_4140 |
| 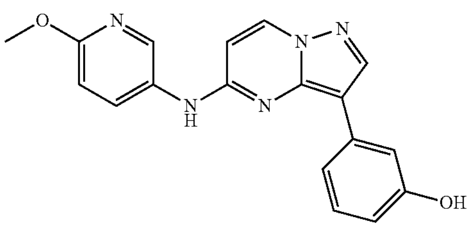 [SMILES: COc1ccc(Nc2ccn3ncc(-c4cccc(O)c4)c3n2)cn1] | 55 | 3-[5-[(6-methoxy-3-pyridyl)amino]pyrazolo[1,5-a]pyrimidin-3-yl]phenol | 3.39371 | 3.25 | 294_0042_0284 |
| 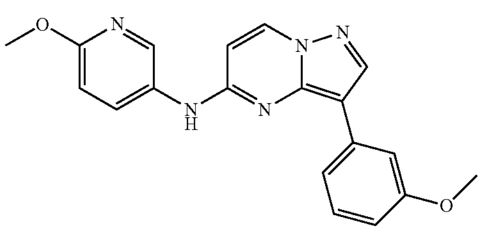 | 56 | 3-(3-methoxyphenyl)-N-(6-methoxy-3-pyridyl)pyrazolo[1,5-a]pyrimidin-5-amine | 5.3146 | 3.40 | 294_0042_4140 |

TABLE 3-continued

Primary screen- initial compounds.

| Structure | | IUPAC name | IC50 FYN (μM) | logP (consensus) | Compound ID. |
|---|---|---|---|---|---|
| 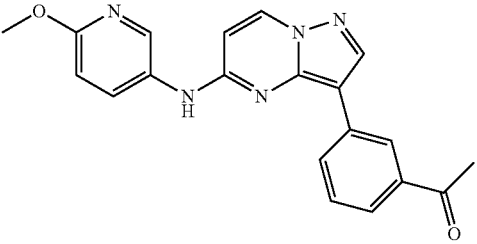 [SMILES: COc1ccc(Nc2ccn3ncc(-c4cccc(C(C)=O)c4)c3n2)cn1] | 57 | 1-[3-[5-[(6-methoxy-3-pyridyl)amino]pyrazolo[1,5-a]pyrimidin-3-yl]phenyl]ethanone | 1.63557 | 3.11 | 294_0042_4145 |
| 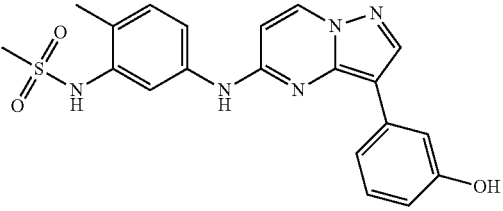 [SMILES: Cc1ccc(Nc2ccn3ncc(-c4cccc(O)c4)c3n2)cc1NS(C)(=O)=O] | 58 | N-[5-[[3-(3-hydroxyphenyl)pyrazolo[1,5-a]pyrimidin-5-yl]amino]-2-methyl-phenyl]methanesulfonamide | 3.17096 | 2.92 | 294_0123_0284 |
| 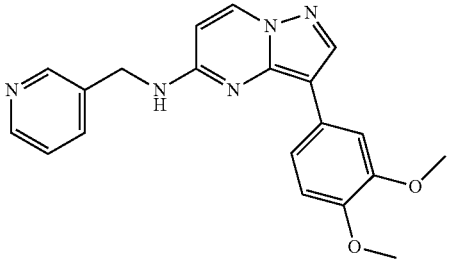 [SMILES: COc1ccc(-c2cnn3ccc(NCc4cccnc4)nc23)cc1OC] | 59 | 3-(3,4-dimethoxyphenyl)-N-(3-pyridylmethyl)pyrazolo[1,5-a]pyrimidin-5-amine | 1.63605 | 2.56 | 294_4003_0079 |
| 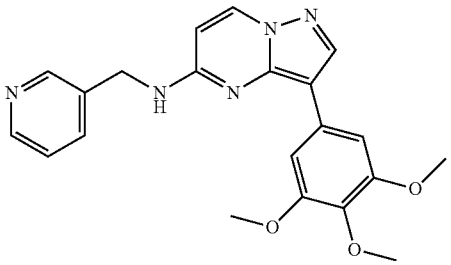 [SMILES: COc1cc(-c2cnn3ccc(NCc4cccnc4)nc23)cc(OC)c1OC] | 60 | N-(3-pyridylmethyl)-3-(3,4,5-trimethoxyphenyl)pyrazolo[1,5-a]pyrimidin-5-amine | 2.35332 | 2.40 | 294_4003_0087 |
| 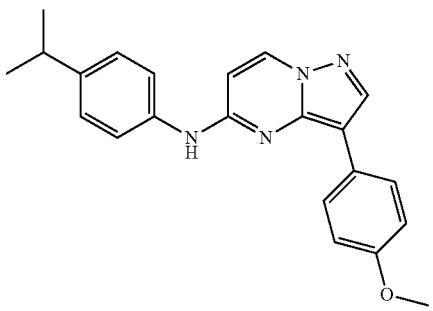 [SMILES: COc1ccc(-c2cnn3ccc(Nc4ccc(C(C)C)cc4)nc23)cc1] | 61 | N-(4-isopropylphenyl)-3-(4-methoxyphenyl)pyrazolo[1,5-a]pyrimidin-5-amine | 4.17999 | 5.42 | 294_6937_0280 |

TABLE 3-continued

Primary screen- initial compounds.

| Structure | | IUPAC name | IC50 FYN (μM) | logP (consensus) | Compound ID. |
|---|---|---|---|---|---|
| 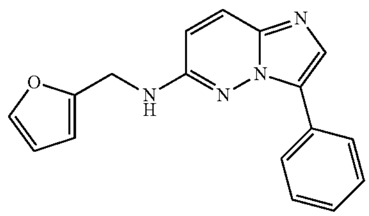 [SMILES: c1ccc(-c2cnc3ccc(NCc4ccco4)nn23)cc1] | 62 | N-(2-furylmethyl)-3-phenyl-imidazo[1,2-b]pyridazin-6-amine | 6.37501 | 3.07 | 229_0144_0061 |
| 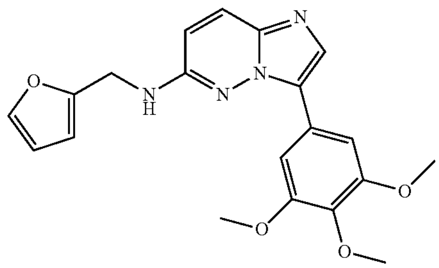 | 63 | N-(2-furylmethyl)-3-(3,4,5-trimethoxyphenyl)imidazo[1,2-b]pyridazin-6-amine | 4.89592 | 2.60 | 229_0144_0086 |
| 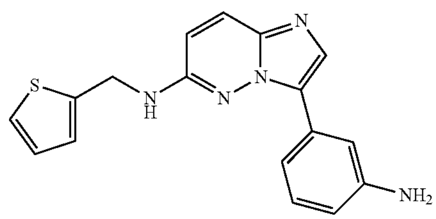 [SMILES: Nc1cccc(-c2cnc3ccc(NCc4cccs4)nn23)c1] | 64 | 3-(3-aminophenyl)-N-(2-thienylmethyl)imidazo[1,2-b]pyridazin-6-amine | 1.79421 | 3.10 | 229_0146_0005 |
| 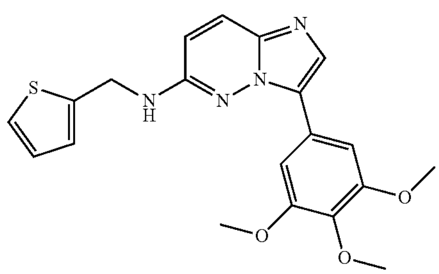 [SMILES: COc1cc(-c2cnc3ccc(NCc4cccs4)nn23)cc(OC)c1OC] | 65 | N-(2-thienylmethyl)-3-(3,4,5-trimethoxyphenyl)imidazo[1,2-b]pyridazin-6-amine | 3.10009 | 3.45 | 229_0146_0087 |
| 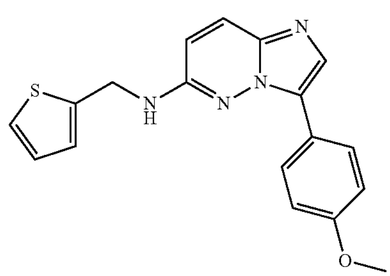 [SMILES: COc1ccc(-c2cnc3ccc(NCc4cccs4)nn23)cc1] | 66 | 3-(4-methoxyphenyl)-N-(2-thienylmethyl)imidazo[1,2-b]pyridazin-6-amine | 5.3884 | 3.77 | 229_0146_0280 |
| 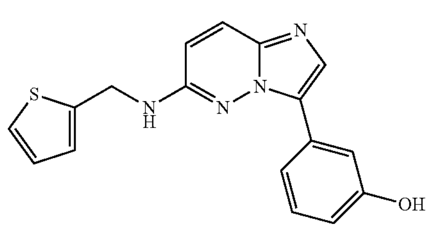 [SMILES: Oc1cccc(-c2cnc3ccc(NCc4cccs4)nn23)c1] | 67 | 3-[6-(2-thienylmethylamino)imidazo[1,2-b]pyridazin-3-yl]phenol | 1.70365 | 3.62 | 229_0146_0284 |

TABLE 3-continued

Primary screen- initial compounds.

| Structure | | IUPAC name | IC50 FYN (µM) | logP (consensus) | Compound ID. |
|---|---|---|---|---|---|
| 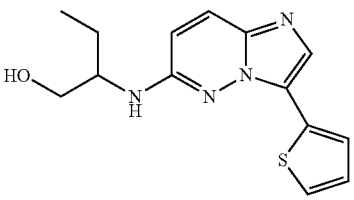 [SMILES: CCC(CO)Nc1ccc2ncc(-c3cccs3)n2n1] | 68 | 2-[[3-(2-thienyl)imidazo[1,2-b]pyridazin-6-yl]amino]butan-1-ol | 3.96823 | 2.31 | 229_0153_4147 |
| 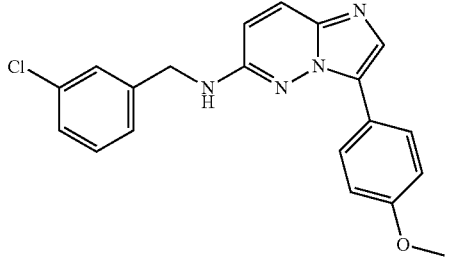 [SMILES: COc1ccc(-c2cnc3ccc(NCc4cccc(Cl)c4)nn23)cc1] | 69 | N-[(3-chlorophenyl)methyl]-3-(4-methoxyphenyl)imidazo[1,2-b]pyridazin-6-amine | 10.74649 | 4.46 | 229_0223_0280 |
| 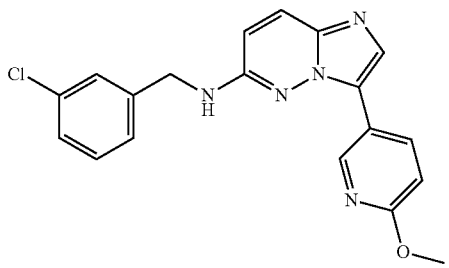 [SMILES: COc1ccc(-c2cnc3ccc(NCc4cccc(Cl)c4)nn23)cn1] | 70 | N-[(3-chlorophenyl)methyl]-3-(6-methoxy-3-pyridyl)imidazo[1,2-b]pyridazin-6-amine | 8.33916 | 3.84 | 229_0223_0311 |
| 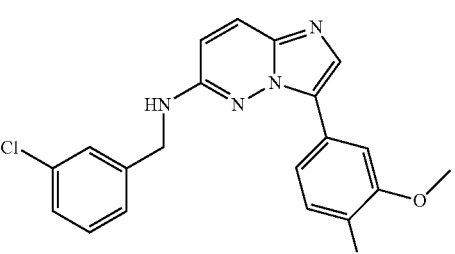 | 71 | 4-[6-[(3-chlorophenyl)methylamino]imidazo[1,2-b]pyridazin-3-yl]-2-methoxyphenol | 3.51753 | 4.15 | 229_0223_0314 |
| 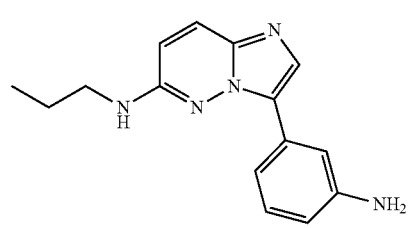 [SMILES: CCCNc1ccc2ncc(-c3cccc(N)c3)n2n1] | 72 | 3-(3-aminophenyl)-N-propyl-imidazo[1,2-b]pyridazin-6-amine | 0.93247 | 2.34 | 229_0226_0005 |
| 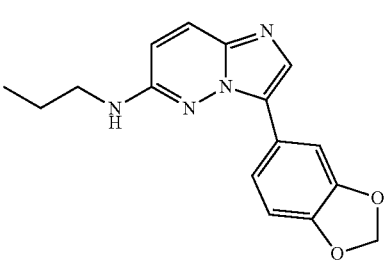 [SMILES: CCCNc1ccc2ncc(-c3ccc4c(c3)OCO4)n2n1] | 73 | 3-(1,3-benzodioxol-5-yl)-N-propyl-imidazo[1,2-b]pyridazin-6-amine | 2.05098 | 2.79 | 229_0226_0068 |

TABLE 3-continued

Primary screen- initial compounds.

| Structure | | IUPAC name | IC50 FYN (µM) | logP (consensus) | Compound ID. |
|---|---|---|---|---|---|
| 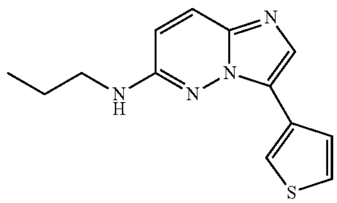 [SMILES: CCCNc1ccc2ncc(-c3ccsc3)n2n1] | 74 | N-propyl-3-(3-thienyl)imidazo[1,2-b]pyridazin-6-amine | 4.03981 | 2.95 | 229_0226_0074 |
| 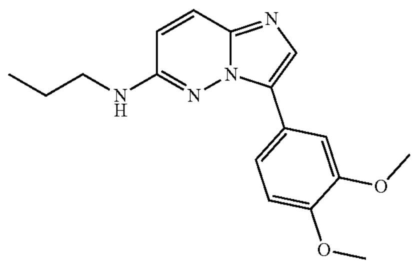 [SMILES: CCCNc1ccc2ncc(-c3ccc(OC)c(OC)c3)n2n1] | 75 | 3-(3,4-dimethoxyphenyl)-N-propyl-imidazo[1,2-b]pyridazin-6-amine | 0.51897 | 2.85 | 229_0226_0079 |
| 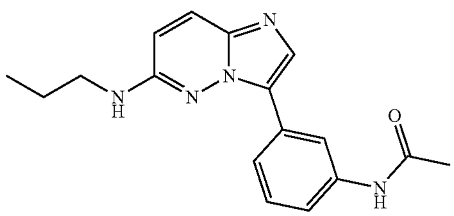 [SMILES: CCCNc1ccc2ncc(-c3cccc(NC(C)=O)c3)n2n1] | 76 | N-[3-[6-(propylamino)imidazo[1,2-b]pyridazin-3-yl]phenyl]acetamide | 0.62919 | 2.40 | 229_0226_0081 |
| 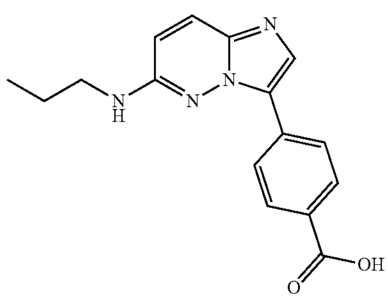 [SMILES: CCCNc1ccc2ncc(-c3ccc(C(=O)O)cc3)n2n1] | 77 | 4-[6-(propylamino)imidazo[1,2-b]pyridazin-3-yl]benzoic acid | 9.76838 | 2.82 | 229_0226_0140 |
| 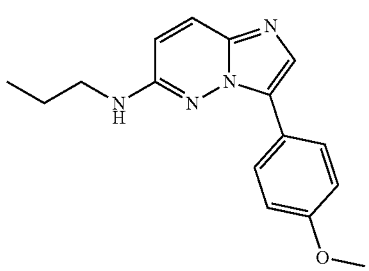 [SMILES: CCCNc1ccc2ncc(-c3ccc(OC)cc3)n2n1] | 78 | 3-(4-methoxyphenyl)-N-propyl-imidazo[1,2-b]pyridazin-6-amine | 5.42987 | 3.01 | 229_0226_0280 |
| 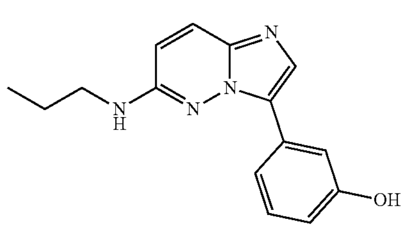 [SMILES: CCCNc1ccc2ncc(-c3cccc(O)c3)n2n1] | 79 | 3-[6-(propylamino)imidazo[1,2-b]pyridazin-3-yl]phenol | 0.93003 | 2.86 | 229_0226_0284 |

TABLE 3-continued

Primary screen- initial compounds.

| Structure | | IUPAC name | IC50 FYN (μM) | logP (consensus) | Compound ID. |
|---|---|---|---|---|---|
| 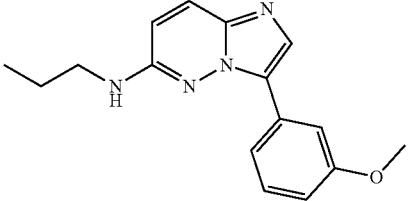 [SMILES: CCCNc1ccc2ncc(-c3cccc(OC)c3)n2n1] | 80 | 3-(3-methoxyphenyl)-N-propyl-imidazo[1,2-b]pyridazin-6-amine | 2.21992 | 3.01 | 229_0226_4140 |
| 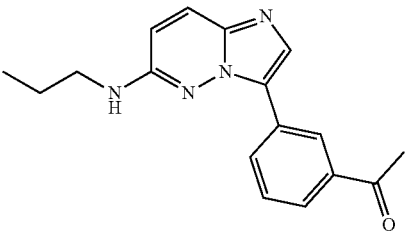 [SMILES: CCCNc1ccc2ncc(-c3cccc(C(C)=O)c3)n2n1] | 81 | 1-[3-[6-(propylamino)imidazo[1,2-b]pyridazin-3-yl]phenyl]ethanone | 0.36718 | 2.72 | 229_0226_4145 |
| 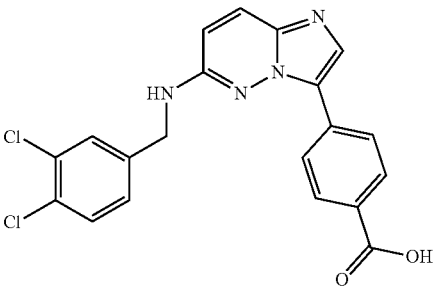 [SMILES: O=C(O)c1ccc(-c2cnc3ccc(NCc4ccc(Cl)c(Cl)c4)nn23)cc1] | 82 | 4-[6-[(3,4-dichlorophenyl)methylamino]imidazo[1,2-b]pyridazin-3-yl]benzoic acid | 1.00617 | 4.88 | 229_0227_0140 |
| 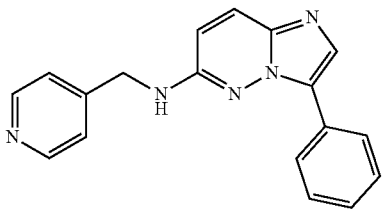 [SMILES: c1ccc(-c2cnc3ccc(NCc4ccncc4)nn23)cc1] | 83 | 3-phenyl-N-(4-pyridylmethyl)imidazo[1,2-b]pyridazin-6-amine | 4.05638 | 2.79 | 229_0237_0061 |
| 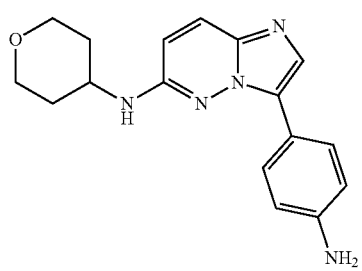 [SMILES: Nc1ccc(-c2cnc3ccc(NC4CCOCC4)nn23)cc1] | 84 | 3-(4-aminophenyl)-N-tetrahydropyran-4-yl-imidazo[1,2-b]pyridazin-6-amine | 3.12587 | 1.42 | 229_0242_0333 |
| 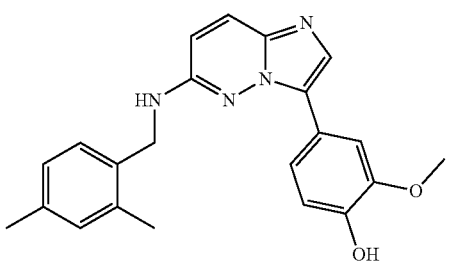 | 85 | 4-[6-[(2,4-dimethylphenyl)methylamino]imidazo[1,2-b]pyridazin-3-yl]-2-methoxy-phenol | 5.30595 | 4.58 | 229_4319_0314 |

TABLE 3-continued

Primary screen- initial compounds.

| Structure | | IUPAC name | IC50 FYN (μM) | logP (consensus) | Compound ID. |
|---|---|---|---|---|---|
| 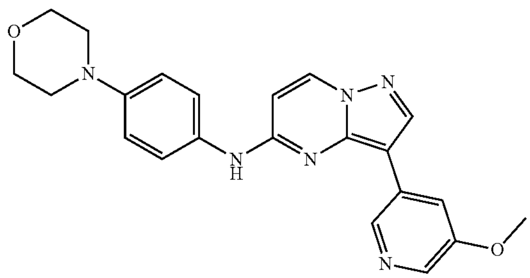 [SMILES: COc1cncc(-c2cnn3ccc(Nc4ccc(N5CCOCC5)cc4)nc23)c1] | 86 | 3-(5-methoxy-3-pyridyl)-N-(4-morpholinophenyl)pyrazolo[1,5-a]pyrimidin-5-amine | 2.24998 | 2.85 | 294_0088_0196 |
| 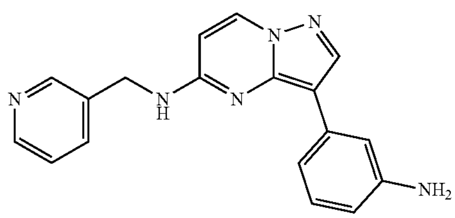 [SMILES: Nc1cccc(-c2cnn3ccc(NCc4cccnc4)nc23)c1] | 87 | 3-(3-aminophenyl)-N-(3-pyridylmethyl)pyrazolo[1,5-a]pyrimidin-5-amine | 2.5122 | 2.05 | 294_4003_0005 |
| 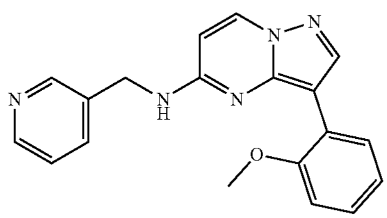 [SMILES: COc1ccccc1-c1cnn2ccc(NCc3cccnc3)nc12] | 88 | 3-(2-methoxyphenyl)-N-(3-pyridylmethyl)pyrazolo[1,5-a]pyrimidin-5-amine | 1.22114 | 2.72 | 294_4003_0083 |
| 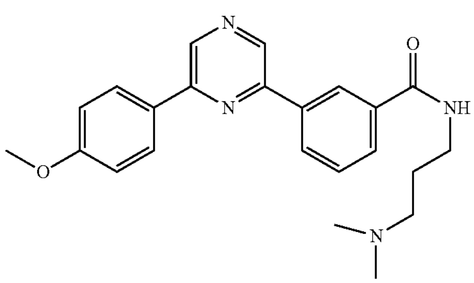 [SMILES: COc1ccc(-c2cncc(-c3cccc(C(=O)NCCCN(C)C)c3)n2)cc1] | 89 | N-[3-(dimethylamino)propyl]-3-[6-(4-methoxyphenyl)pyrazin-2-yl]benzamide | 9.05883 | 2.60 | 035_0280_0302 |
| 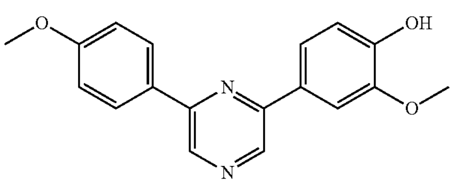 | 90 | 2-methoxy-4-[6-(4-methoxyphenyl)pyrazin-2-yl]phenol | 5.17907 | 2.99 | 035_0280_0314 |
| 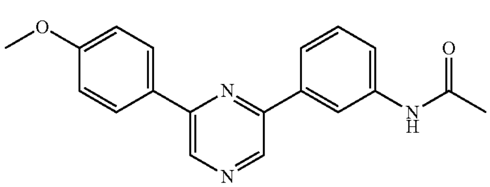 [SMILES: COc1ccc(-c2cncc(-c3cccc(NC(C)=O)c3)n2)cc1] | 91 | N-[3-[6-(4-methoxyphenyl)pyrazin-2-yl]phenyl]acetamide | 3.50136 | 2.68 | 035_0081_0280 |

TABLE 3-continued

Primary screen- initial compounds.

| Structure | | IUPAC name | IC50 FYN (μM) | logP (consensus) | Compound ID. |
|---|---|---|---|---|---|
| 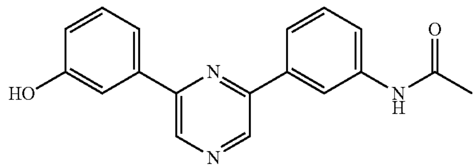 [SMILES: CC(=O)Nc1cccc(-c2cncc(-c3cccc(O)c3)n2)c1] | 92 | N-[3-[6-(3-hydroxyphenyl)pyrazin-2-yl]phenyl]acetamide | 3.87844 | 2.54 | 035_0081_0284 |
| 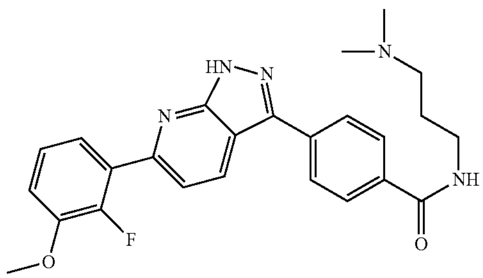 [SMILES: COc1cccc(-c2ccc3c(-c4ccc(C(=O)NCCCN(C)C)cc4)n[nH]c3n2)c1F] | 93 | N-[3-(dimethylamino)propyl]-4-[6-(2-fluoro-3-methoxyphenyl)-1H-pyrazolo[3,4-b]pyridin-3-yl]benzamide | 7.3354 | 3.65 | 267_0180_7936 |
| 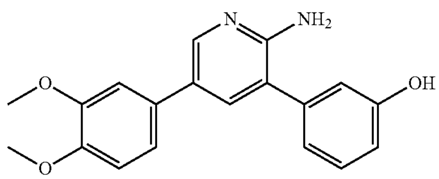 [SMILES: COc1ccc(-c2cnc(N)c(-c3cccc(O)c3)c2)cc1OC] | 94 | 3-[2-amino-5-(3,4-dimethoxyphenyl)-3-pyridyl]phenol | 2.00489 | 3.20 | 382_0284_0079 |
| 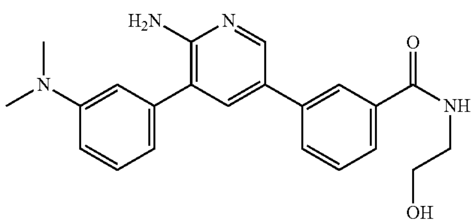 [SMILES: CN(C)c1cccc(-c2cc(-c3cccc(C(=O)NCCO)c3)cnc2N)c1] | 95 | 3-[6-amino-5-[3-(dimethylamino)phenyl]-3-pyridyl]-N-(2-hydroxyethyl)benzamide | 3.57159 | 2.31 | 382_0135_0192 |
| 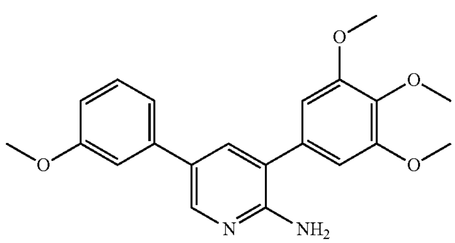 | 96 | 5-(3-methoxyphenyl)-3-(3,4,5-trimethoxyphenyl)pyridin-2-amine | 9.5028 | 3.18 | 382_0087_4140 |
| 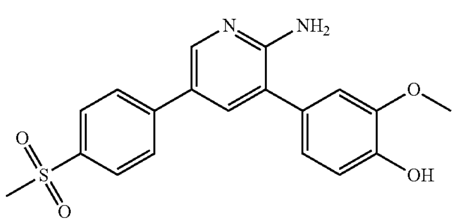 | 97 | 4-[2-amino-5-(4-methylsulfonylphenyl)-3-pyridyl]-2-methoxyphenol | 0.34919 | 2.19 | 382_0314_0174 |
| 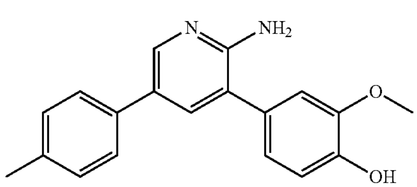 | 98 | 4-[2-amino-5-(p-tolyl)-3-pyridyl]-2-methoxyphenol | 4.3442 | 3.87 | 382_0314_4139 |

TABLE 3-continued

Primary screen- initial compounds.

| Structure | | IUPAC name | IC50 FYN (μM) | logP (consensus) | Compound ID. |
|---|---|---|---|---|---|
| 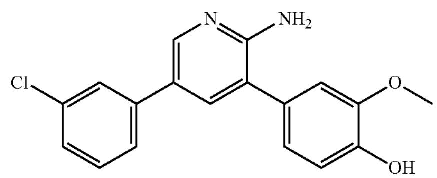 [SMILES: COc1cc(-c2cc(-c3cccc(Cl)c3)cnc2N)ccc1O] | 99 | 4-[2-amino-5-(3-chlorophenyl)-3-pyridyl]-2-methoxy-phenol | 3.5107 | 3.96 | 382_0314_0279 |
| 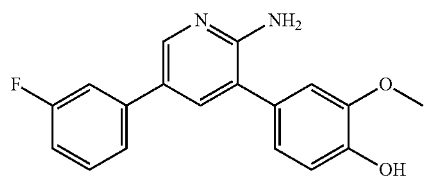 [SMILES: COc1cc(-c2cc(-c3cccc(F)c3)cnc2N)ccc1O] | 100 | 4-[2-amino-5-(3-fluorophenyl)-3-pyridyl]-2-methoxy-phenol | 2.02739 | 3.50 | 382_0314_0313 |
| 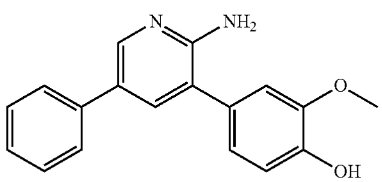 [SMILES: COc1cc(-c2cc(-c3ccccc3)cnc2N)ccc1O] | 101 | 4-(2-amino-5-phenyl-3-pyridyl)-2-methoxy-phenol | 1.47705 | 3.35 | 382_0314_0061 |
| 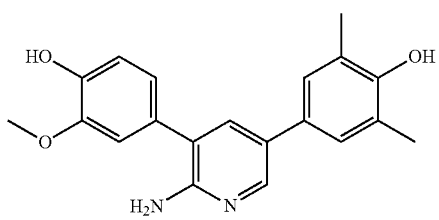 | 102 | 4-[6-amino-5-(4-hydroxy-3-methoxy-phenyl)-3-pyridyl]-2,6-dimethyl-phenol | 0.52648 | 4.08 | 382_0314_0315 |
| 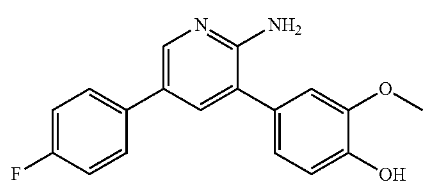 [SMILES: COc1cc(-c2cc(-c3ccc(F)cc3)cnc2N)ccc1O] | 103 | 4-[2-amino-5-(4-fluorophenyl)-3-pyridyl]-2-methoxy-phenol | 3.24026 | 3.50 | 382_0314_0339 |
| 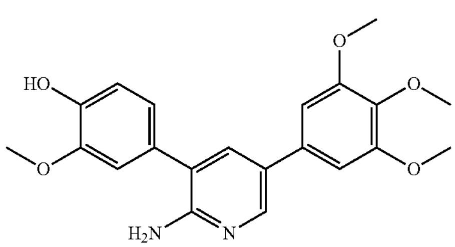 | 104 | 4-[2-amino-5-(3,4,5-trimethoxy-phenyl)-3-pyridyl]-2-methoxy-phenol | 0.08059 | 2.88 | 382_0314_0087 |
| 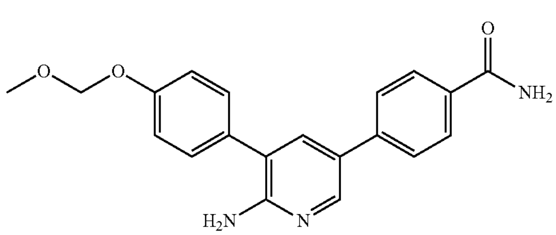 [SMILES: COCOc1ccc(-c2cc(-c3ccc(C(N)=O)cc3)cnc2N)cc1] | 105 | 4-[6-amino-5-[4-(methoxymethoxy)phenyl]-3-pyridyl]benzamide | 3.42268 | 2.57 | 382_0341_0346 |

TABLE 3-continued

Primary screen- initial compounds.

| Structure | | IUPAC name | IC50 FYN (µM) | logP (consensus) | Compound ID. |
|---|---|---|---|---|---|
| 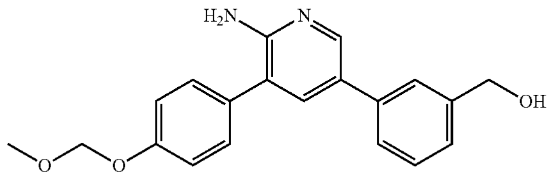 [SMILES: COCOc1ccc(-c2cc(-c3cccc(CO)c3)cnc2N)cc1] | 106 | [3-[6-amino-5-[4-(methoxymethoxy)phenyl]-3-pyridyl]phenyl]methanol | 4.62016 | 2.95 | 382_0341_0291 |
| 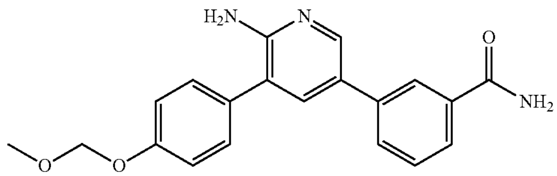 [SMILES: COCOc1ccc(-c2cc(-c3cccc(C(N)=O)c3)cnc2N)cc1] | 107 | 3-[6-amino-5-[4-(methoxymethoxy)phenyl]-3-pyridyl]benzamide | 3.02265 | 2.57 | 382_0341_0347 |
| 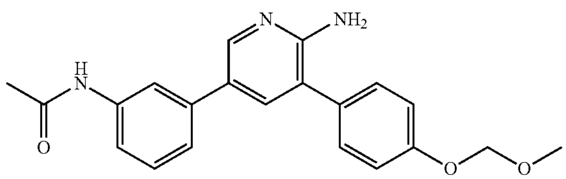 [SMILES: COCOc1ccc(-c2cc(-c3cccc(NC(C)=O)c3)cnc2N)cc1] | 108 | N-[3-[6-amino-5-4-(methoxymethoxy)phenyl]-3-pyridyl]phenyl]acetamide | 1.5493 | 2.96 | 382_0341_0081 |
| 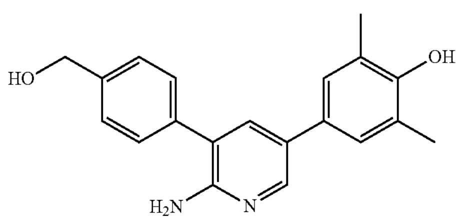 [SMILES: Cc1cc(-c2cnc(N)c(-c3ccc(CO)cc3)c2)cc(C)c1O] | 109 | 4-[6-amino-5-[4-(hydroxymethyl)phenyl]-3-pyridyl]-2,6-dimethyl-phenol | 4.64395 | 3.77 | 382_0285_0315 |
| 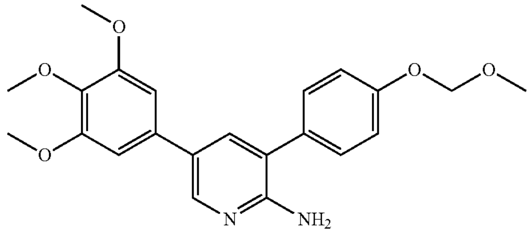 | 110 | 3-[4-(methoxymethoxy)phenyl]-5-(3,4,5-trimethoxy-phenyl)pyridin-2-amine | 1.90467 | 3.25 | 382_0341_0087 |
| 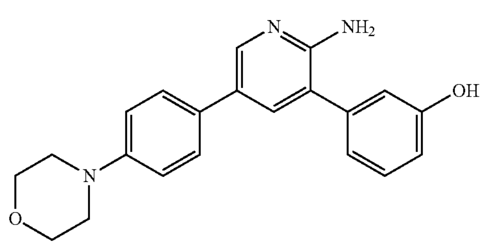 [SMILES: Nc1ncc(-c2ccc(N3CCOCC3)cc2)cc1-c1cccc(O)c1] | 111 | 3-[2-amino-5-(4-morpholino-phenyl)-3-pyridyl]phenol | 4.64154 | 3.40 | 382_0284_0001 |
| 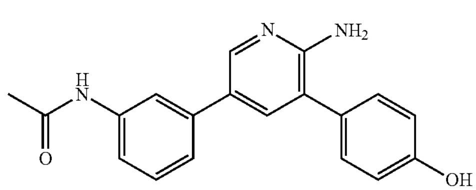 [SMILES: CC(=O)Nc1cccc(-c2cnc(N)c(-c3ccc(O)cc3)c2)c1] | 112 | N-[3-[6-amino-5-(4-hydroxyphenyl)-3-pyridyl]phenyl]acetamide | 0.83784 | 2.75 | 382_7249_0081 |

TABLE 3-continued

Primary screen- initial compounds.

| Structure | | IUPAC name | IC50 FYN (µM) | logP (consensus) | Compound ID. |
|---|---|---|---|---|---|
| 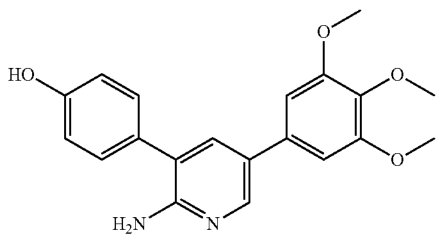 [SMILES: COc1cc(-c2cnc(N)c(-c3ccc(O)cc3)c2)cc(OC)c1OC] | 113 | 4-[2-amino-5-(3,4,5-trimethoxyphenyl)-3-pyridyl]phenol | 0.20886 | 3.04 | 382_7249_0087 |
| 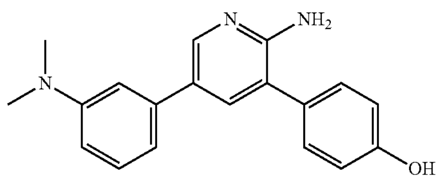 [SMILES: CN(C)c1cccc(-c2cnc(N)c(-c3ccc(O)cc3)c2)c1] | 114 | 4-[2-amino-5-[3-(dimethylamino)phenyl]-3-pyridyl]phenol | 2.19069 | 3.62 | 382_7249_0135 |
| 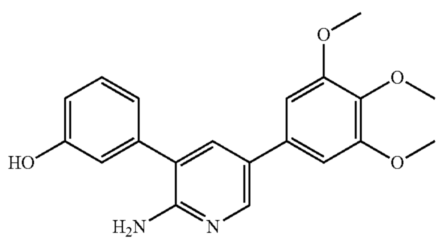 [SMILES: COc1cc(-c2cnc(N)c(-c3cccc(O)c3)c2)cc(OC)c1OC] | 115 | 3-[2-amino-5-(3,4,5-trimethoxyphenyl)-3-pyridyl]phenol | 1.01519 | 3.04 | 382_0284_0087 |
| 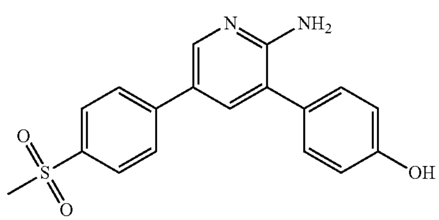 [SMILES: CS(=O)(=O)c1ccc(-c2cnc(N)c(-c3ccc(O)cc3)c2)cc1] | 116 | 4-[2-amino-5-(4-methylsulfonylphenyl)-3-pyridyl]phenol | 1.25339 | 2.35 | 382_7249_0174 |
| 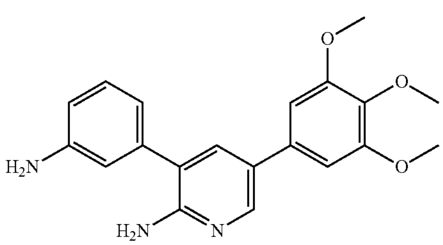 [SMILES: COc1cc(-c2cnc(N)c(-c3cccc(N)c3)c2)cc(OC)c1OC] | 117 | 3-(3-aminophenyl)-5-(3,4,5-trimethoxyphenyl)pyridin-2-amine | 2.96823 | 2.51 | 382_0005_0087 |
| 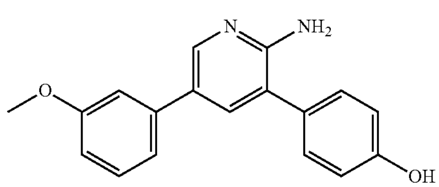 [SMILES: COc1cccc(-c2cnc(N)c(-c3ccc(O)cc3)c2)c1] | 118 | 4-[2-amino-5-(3-methoxyphenyl)-3-pyridyl]phenol | 3.49074 | 3.35 | 382_7249_4140 |

TABLE 3-continued

Primary screen- initial compounds.

| Structure | | IUPAC name | IC50 FYN (μM) | logP (consensus) | Compound ID. |
|---|---|---|---|---|---|
| 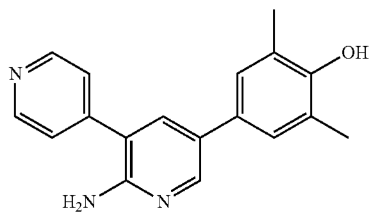 [SMILES: Cc1cc(-c2cnc(N)c(-c3ccncc3)c2)cc(C)c1O] | 119 | 4-[6-amino-5-(4-pyridyl)-3-pyridyl]-2,6-dimethyl-phenol | 1.70457 | 3.32 | 382_0069_0315 |
| 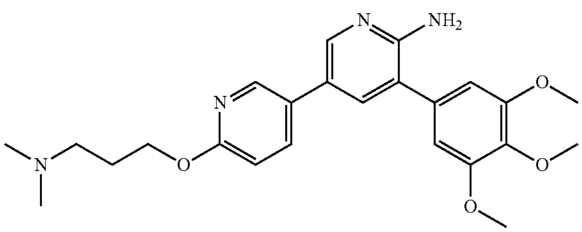 | 120 | 5-[6-[3-(dimethylamino)propoxy]-3-pyridyl]-3-(3,4,5-trimethoxyphenyl)pyridin-2-amine | 0.5304 | 2.64 | 382_0087_0002 |
| 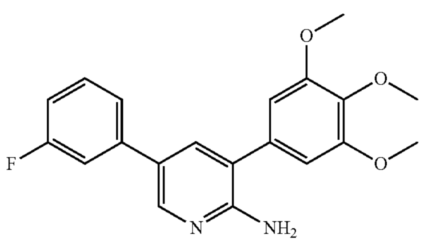 [SMILES: COc1cc(-c2cc(-c3cccc(F)c3)cnc2N)cc(OC)c1OC] | 121 | 5-(3-fluorophenyl)-3-(3,4,5-trimethoxyphenyl)pyridin-2-amine | 1.5198 | 3.49 | 382_0087_0313 |
| 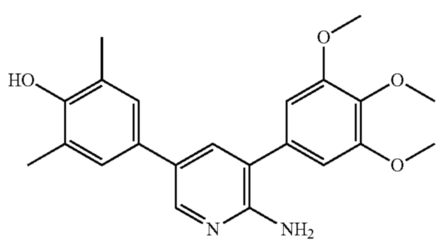 | 122 | 4-[6-amino-5-(3,4,5-trimethoxyphenyl)-3-pyridyl]-2,6-dimethyl-phenol | 0.71164 | 4.07 | 382_0087_0315 |
| 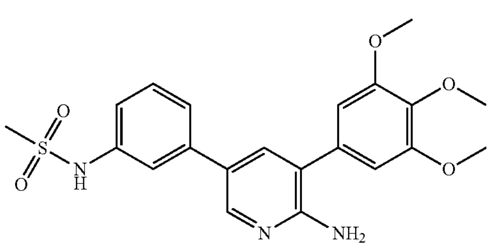 | 123 | N-[3-[6-amino-5-(3,4,5-trimethoxyphenyl)-3-pyridyl]phenyl]methanesulfonamide | 0.5248 | 1.72 | 382_0087_6488 |
| 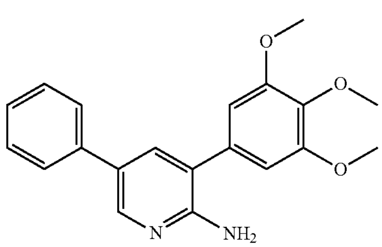 [SMILES: COc1cc(-c2cc(-c3ccccc3)cnc2N)cc(OC)c1OC] | 124 | 5-phenyl-3-(3,4,5-trimethoxyphenyl)pyridin-2-amine | 0.8934 | 3.34 | 382_0087_0061 |

TABLE 3-continued

Primary screen- initial compounds.

| Structure | | IUPAC name | IC50 FYN (μM) | logP (consensus) | Compound ID. |
|---|---|---|---|---|---|
| 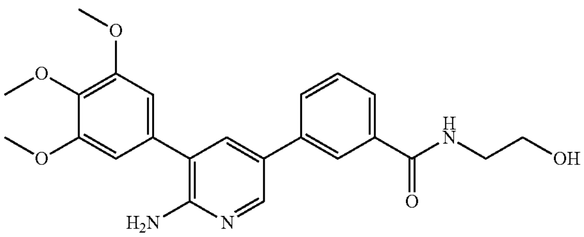 [SMILES: COc1cc(-c2cc(-c3cccc(C(=O)NCCO)c3)cnc2N)cc(OC)c1OC] | 125 | 3-[6-amino-5-(3,4,5-trimethoxyphenyl)-3-pyridyl]-N-(2-hydroxyethyl)benzamide | 0.48532 | 1.73 | 382_0087_0192 |
| 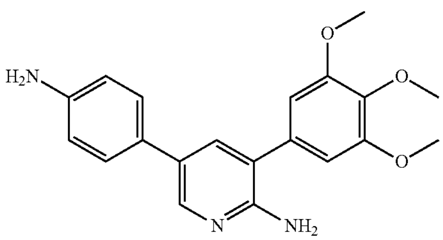 [SMILES: COc1cc(-c2cc(-c3ccc(N)cc3)cnc2N)cc(OC)c1OC] | 126 | 5-(4-aminophenyl)-3-(3,4,5-trimethoxyphenyl)pyridin-2-amine | 0.97087 | 2.51 | 382_0087_0333 |
| 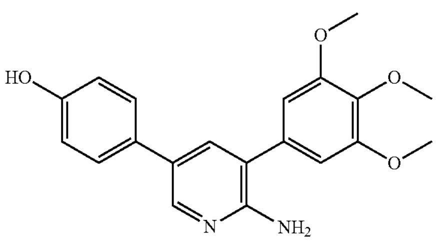 [SMILES: COc1cc(-c2cc(-c3ccc(O)cc3)cnc2N)cc(OC)c1OC] | 127 | 4-[6-amino-5-(3,4,5-trimethoxyphenyl)-3-pyridyl]phenol | 1.72584 | 3.04 | 382_0087_7249 |
| 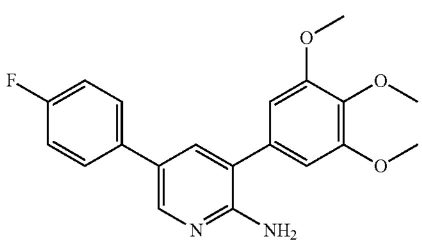 [SMILES: COc1cc(-c2cc(-c3ccc(F)cc3)cnc2N)cc(OC)c1OC] | 128 | 5-(4-fluorophenyl)-3-(3,4,5-trimethoxyphenyl)pyridin-2-amine | 2.85921 | 3.49 | 382_0087_0339 |
| 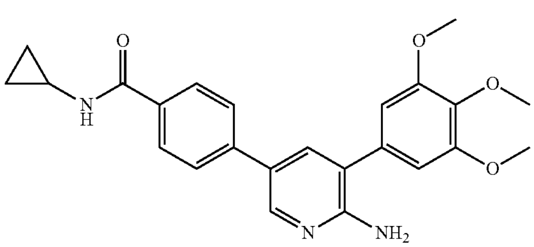 [SMILES: COc1cc(-c2cc(-c3ccc(C(=O)NC4CC4)cc3)cnc2N)cc(OC)c1OC] | 129 | 4-[6-amino-5-(3,4,5-trimethoxyphenyl)-3-pyridyl]-N-cyclopropylbenzamide | 0.5072 | 2.88 | 382_0087_7489 |
| 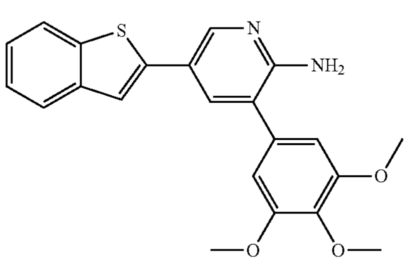 [SMILES: COc1cc(-c2cc(-c3cc4ccccc4s3)cnc2N)cc(OC)c1OC] | 130 | 5-(benzothiophen-2-yl)-3-(3,4,5-trimethoxyphenyl)pyridin-2-amine | 2.69043 | 4.22 | 382_0087_0076 |

TABLE 3-continued

Primary screen- initial compounds.

| Structure | | IUPAC name | IC50 FYN (μM) | logP (consensus) | Compound ID. |
|---|---|---|---|---|---|
| 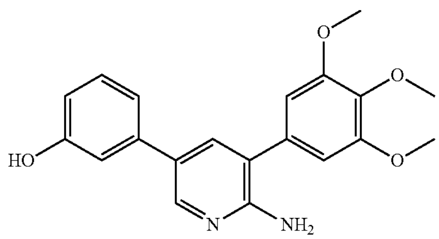 [SMILES: COc1cc(-c2cc(-c3cccc(O)c3)cnc2N)cc(OC)c1OC] | 131 | 3-[6-amino-5-(3,4,5-trimethoxy-phenyl)-3-pyridyl]phenol | 0.72322 | 3.04 | 382_0087_0284 |
| 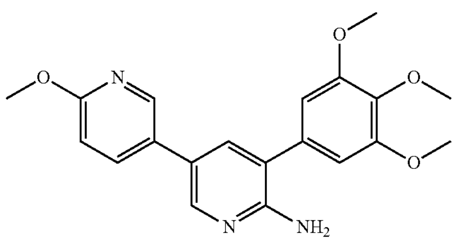 | 132 | 5-(6-methoxy-3-pyridyl)-3-(3,4,5-trimethoxyphenyl)pyridin-2-amine | 1.06095 | 2.56 | 382_0087_0311 |
| 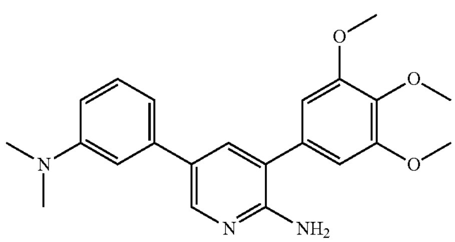 | 133 | 5-[3-(dimethylamino)phenyl]-3-(3,4,5-trimethoxyphenyl)pyridin-2-amine | 0.59506 | 3.45 | 382_0087_0135 |
| 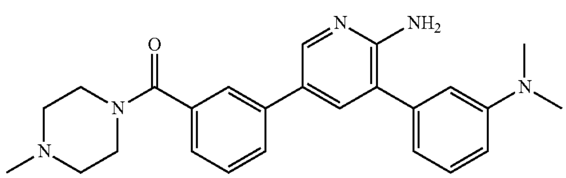 | 134 | [3-[6-amino-5-[3-(dimethylamino)phenyl]-3-pyridyl]phenyl]-(4-methyl-piperazin-1-yl)methanone | 4.43871 | 3.07 | 382_0135_0200 |
| 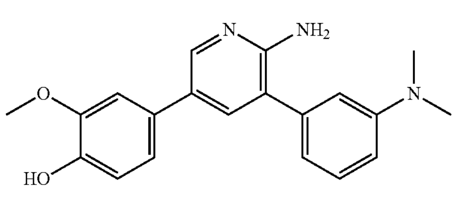 | 135 | 4-[6-amino-5-[3-(dimethylamino)phenyl]-3-pyridyl]-2-methoxy-phenol | 2.10895 | 3.46 | 382_0135_0314 |
| 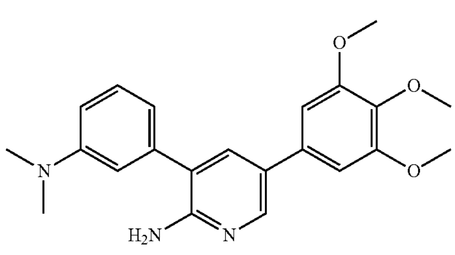 | 136 | 3-[3-(dimethylamino)phenyl]-5-(3,4,5-trimethoxy-phenyl)pyridin-2-amine | 3.13462 | 3.45 | 382_0135_0087 |

TABLE 3-continued

Primary screen- initial compounds.

| Structure | | IUPAC name | IC50 FYN (μM) | logP (consensus) | Compound ID. |
|---|---|---|---|---|---|
| 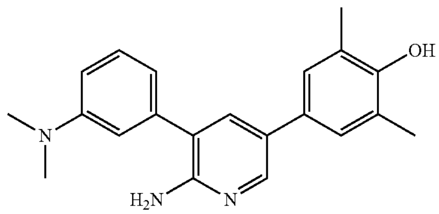 | 137 | 4-[6-amino-5-[3-(dimethylamino)phenyl]-3-pyridyl]-2,6-dimethyl-phenol | 4.20127 | 4.65 | 382_0135_0315 |
| 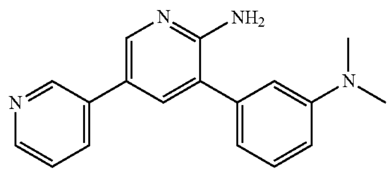 [SMILES: CN(C)c1cccc(-c2cc(-c3cccnc3)cnc2N)c1] | 138 | 3-[3-(dimethyl-amino)phenyl]-5-(3-pyridyl)pyridin-2-amine | 7.11159 | 2.71 | 382_0135_0071 |
| 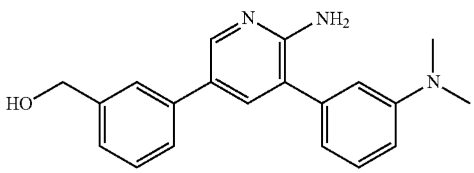 [SMILES: CN(C)c1cccc(-c2cc(-c3cccc(CO)c3)cnc2N)c1] | 139 | [3-[6-amino-5-[3-(dimethylamino)phenyl]-3-pyridyl]phenyl]methanol | 2.6979 | 3.16 | 382_0135_0291 |
| 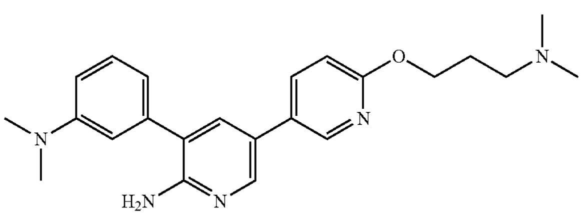 | 140 | 3-[3-(dimethylamino)phenyl]-5-[6-[3-(dimethylamino)propoxy]-3-pyridyl]pyridin-2-amine | 4.66462 | 3.22 | 382_0135_0002 |
| 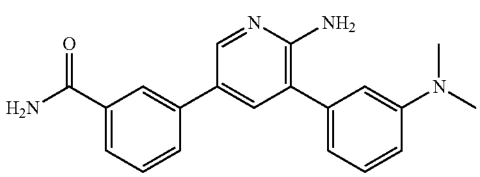 [SMILES: CN(C)c1cccc(-c2cc(-c3cccc(C(N)=O)c3)cnc2N)c1] | 141 | 3-[6-amino-5-[3-(dimethylamino)phenyl]-3-pyridyl]benzamide | 3.52109 | 2.77 | 382_0135_0347 |
| 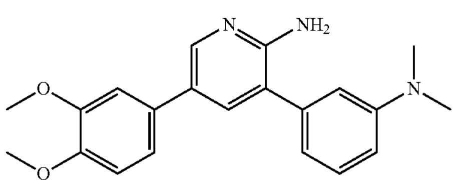 | 142 | 5-(3,4-dimethoxyphenyl)-3-[3-(dimethylamino)phenyl]pyridin-2-amine | 5.04712 | 3.61 | 382_0135_0079 |
| 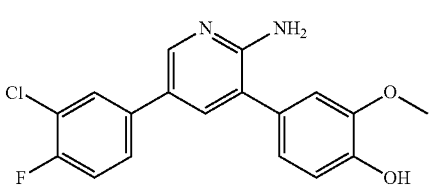 [SMILES: COc1cc(-c2cc(-c3ccc(F)c(Cl)c3)cnc2N)ccc1O] | 143 | 4-[2-amino-5-(3-chloro-4-fluorophenyl)-3-pyridyl]-2-methoxy-phenol | 11.34048 | 4.10 | 382_0314_0164 |

TABLE 3-continued

Primary screen- initial compounds.

| Structure | | IUPAC name | IC50 FYN (μM) | logP (consensus) | Compound ID. |
|---|---|---|---|---|---|
| 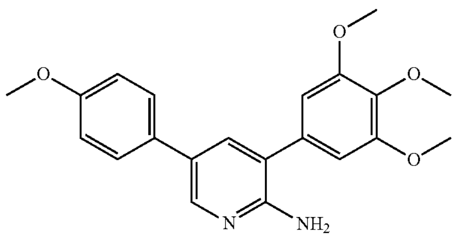 | 144 | 5-(4-methoxyphenyl)-3-(3,4,5-trimethoxyphenyl)pyridin-2-amine | 2.97729 | 3.18 | 382_0087_0280 |
| 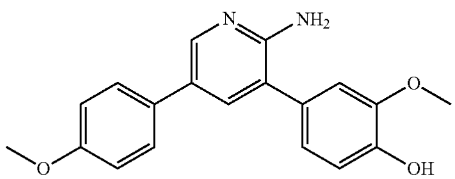 | 145 | 4-[2-amino-5-(4-methoxyphenyl)-3-pyridyl]-2-methoxy-phenol | 4.15847 | 3.20 | 382_0314_0280 |
| 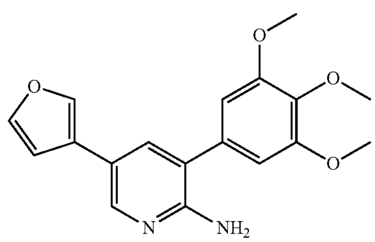 [SMILES: COc1cc(-c2cc(-c3ccoc3)cnc2N)cc(OC)c1OC] | 146 | 5-(3-furyl)-3-(3,4,5-trimethoxyphenyl)pyridin-2-amine | 12.0965 | 2.48 | 382_0087_0343 |
| 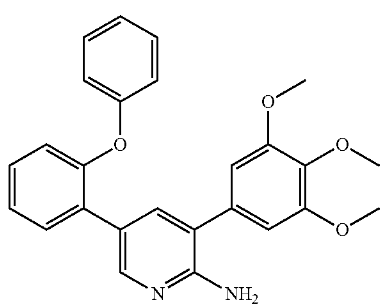 [SMILES: COc1cc(-c2cc(-c3ccccc3Oc3ccccc3)cnc2N)cc(OC)c1OC] | 147 | 5-(2-phenoxyphenyl)-3-(3,4,5-trimethoxyphenyl)pyridin-2-amine | 9.00592 | 4.84 | 382_0087_0063 |
| 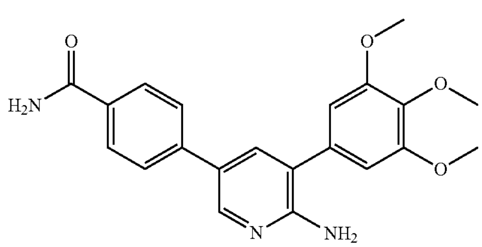 [SMILES: COc1cc(-c2cc(-c3ccc(C(N)=O)cc3)cnc2N)cc(OC)c1OC] | 148 | 4-[6-amino-5-(3,4,5-trimethoxyphenyl)-3-pyridyl]benzamide | 0.40043 | 2.19 | 382_0087_0346 |
| 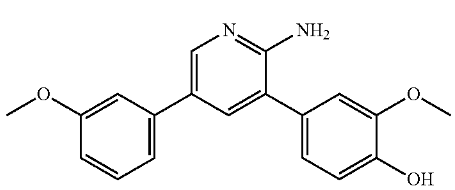 | 149 | 4-[2-amino-5-(3-methoxyphenyl)-3-pyridyl]-2-methoxy-phenol | 1.19944 | 3.20 | 382_0314_4140 |

TABLE 3-continued

Primary screen- initial compounds.

| Structure | | IUPAC name | IC50 FYN (µM) | logP (consensus) | Compound ID. |
|---|---|---|---|---|---|
| 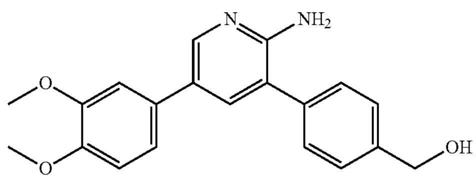 [SMILES: COc1ccc(-c2cnc(N)c(-c3ccc(CO)cc3)c2)cc1OC] | 150 | [4-[2-amino-5-(3,4-dimethoxyphenyl)-3-pyridyl]phenyl]methanol | 5.13242 | 2.73 | 382_0285_0079 |
| 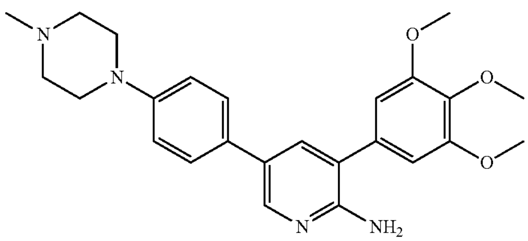 | 151 | 5-[4-(4-methylpiperazin-1-yl)phenyl]-3-(3,4,5-trimethoxyphenyl)pyridin-2-amine | 0.32234 | 3.30 | 382_0087_0218 |
| 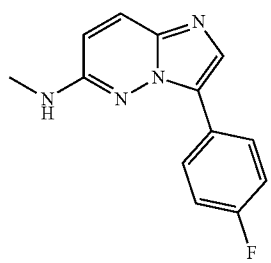 [SMILES: CNc1ccc2ncc(-c3ccc(F)cc3)n2n1] | 152 | 3-(4-fluorophenyl)-N-methyl-imidazo[1,2-b]pyridazin-6-amine | 3.25909 | 2.43 | 437_0339 |
| 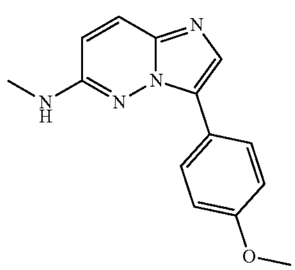 | 153 | 3-(4-methoxyphenyl)-N-methyl-imidazo[1,2-b]pyridazin-6-amine | 4.15763 | 2.13 | 437_0280 |
| 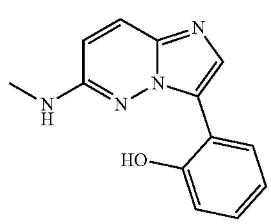 [SMILES: CNc1ccc2ncc(-c3ccccc3O)n2n1] | 154 | 2-[6-(methylamino)imidazo[1,2-b]pyridazin-3-yl]phenol | 1.13395 | 1.98 | 437_0340 |
| 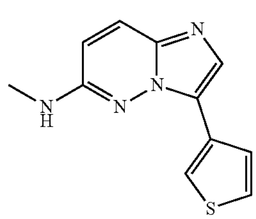 [SMILES: CNc1ccc2ncc(-c3ccsc3)n2n1] | 155 | N-methyl-3-(3-thienyl)imidazo[1,2-b]pyridazin-6-amine | 4.23169 | 2.07 | 437_0074 |

TABLE 3-continued

Primary screen- initial compounds.

| Structure | | IUPAC name | IC50 FYN (μM) | logP (consensus) | Compound ID. |
|---|---|---|---|---|---|
| 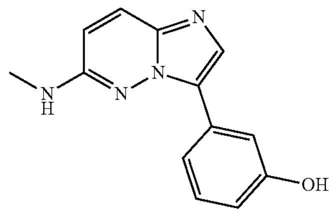 [SMILES: CNc1ccc2ncc(-c3cccc(O)c3)n2n1] | 156 | 3-[6-(methylamino) imidazo[1,2-b]pyridazin-3-yl]phenol | 2.17588 | 1.98 | 437_0284 |
| 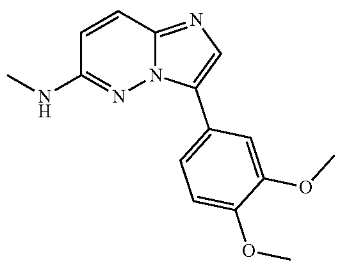 | 157 | 3-(3,4-dimethoxy phenyl)-N-methyl-imidazo[1,2-b]pyridazin-6-amine | 1.24313 | 1.97 | 437_0079 |
| 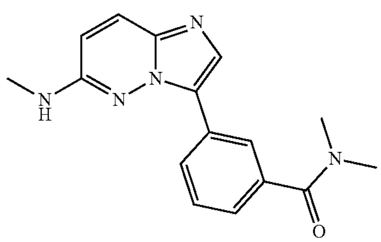 | 158 | N,N-dimethyl-3-[6-(methylamino) imidazo[1,2-b]pyridazin-3-yl]benzamide | 2.94156 | 1.59 | 437_0349 |
| 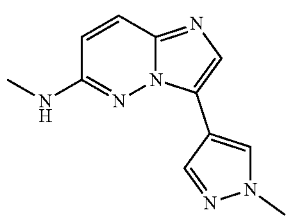 | 159 | N-methyl-3-(1-methylpyrazol-4-yl)imidazo[1,2-b]pyridazin-6-amine | 5.63446 | 0.72 | 437_7468 |
| 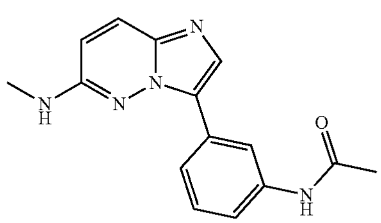 [SMILES: CNc1ccc2ncc(-c3cccc(NC(C)=O)c3)n2n1] | 160 | N-[3-[6-(methylamino) imidazo[1,2-b]pyridazin-3-yl]phenyl] acetamide | 1.75426 | 1.53 | 437_0081 |
| 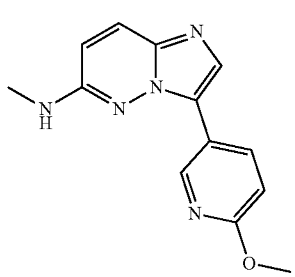 | 161 | 3-(6-methoxy-3-pyridyl)-N-methyl-imidazo[1,2-b]pyridazin-6-amine | 4.46164 | 1.51 | 437_0311 |

TABLE 3-continued

Primary screen- initial compounds.

| Structure | | IUPAC name | IC50 FYN (μM) | logP (consensus) | Compound ID. |
|---|---|---|---|---|---|
| 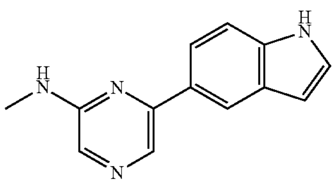 [SMILES: CNc1cncc(-c2ccc3[nH]ccc3c2)n1] | 162 | 6-(1H-indol-5-yl)-N-methyl-pyrazin-2-amine | 14.94246 | 1.74 | 445_0204 |
| 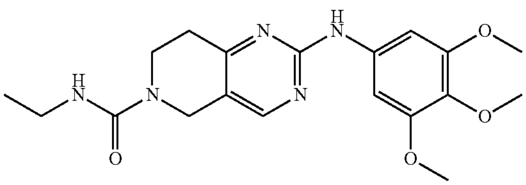 [SMILES: CCNC(=O)N1CCc2nc(Nc3cc(OC)c(OC)c(OC)c3)ncc2C1] | 163 | N-ethyl-2-(3,4,5-trimethoxy-anilino)-7,8-dihydro-5H-pyrido[4,3-d]pyrimidine-6-carboxamide | 4.24682 | 1.18 | 582_9377_5725 |
| 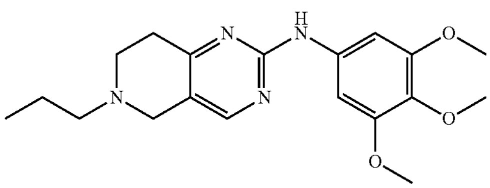 [SMILES: CCCN1CCc2nc(Nc3cc(OC)c(OC)c(OC)c3)ncc2C1] | 164 | 6-propyl-N-(3,4,5-trimethoxy-phenyl)-7,8-dihydro-5H-pyrido[4,3-d]pyrimidin-2-amine | 14.67829 | 2.59 | 582_9377_5632 |
| 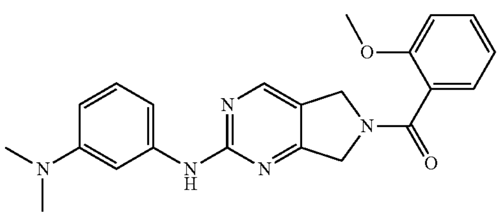 [SMILES: COc1ccccc1C(=O)N1Cc2cnc(Nc3cccc(N(C)C)c3)nc2C1] | 165 | [2-[3-(dimethylamino)anilino]-5,7-dihydropyrrolo[3,4-d]pyrimidin-6-yl]-(2-methoxyphenyl)methanone | 10.08397 | 2.97 | 585_9372_5053 |
| 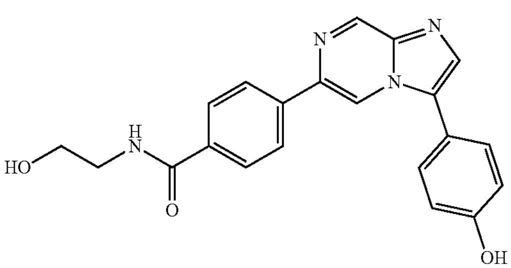 [SMILES: O=C(NCCO)c1ccc(-c2cn3c(-c4ccc(O)cc4)cnc3cn2)cc1] | 166 | N-(2-hydroxyethyl)-4-[3-(4-hydroxyphenyl)imidazo[1,2-a]pyrazin-6-yl]benzamide | 0.64093 | 1.22 | 388_0080_0328 |
| 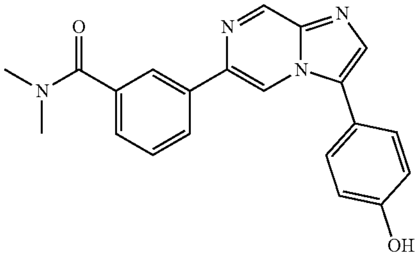 [SMILES: CN(C)C(=O)c1cccc(-c2cn3c(-c4ccc(O)cc4)cnc3cn2)c1] | 167 | 3-[3-(4-hydroxyphenyl)imidazo[1,2-a]pyrazin-6-yl]-N,N-dimethyl-benzamide | 0.97398 | 2.14 | 388_0080_0349 |

TABLE 3-continued

Primary screen- initial compounds.

| Structure | | IUPAC name | IC50 FYN (μM) | logP (consensus) | Compound ID. |
|---|---|---|---|---|---|
| 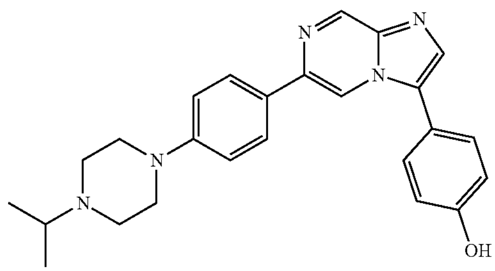 [SMILES: CC(C)N1CCN(c2ccc(-c3cn4c(-c5ccc(O)cc5)cnc4cn3)cc2)CC1] | 168 | 4-[6-[4-(4-isopropyl-piperazin-1-yl)phenyl]imidazo[1,2-a]pyrazin-3-yl]phenol | 0.63733 | 3.57 | 388_0080_0182 |
| 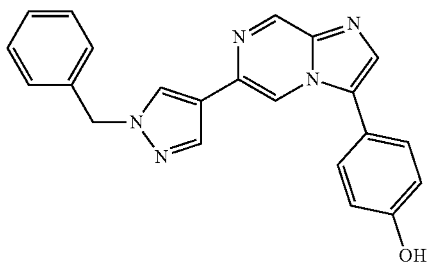 [SMILES: Oc1ccc(-c2cnc3cnc(-c4cnn(Cc5ccccc5)c4)cn23)cc1] | 169 | 4-[6-(1-benzylpyrazol-4-yl)imidazo[1,2-a]pyrazin-3-yl]phenol | 6.6194 | 2.99 | 388_0080_7469 |
| 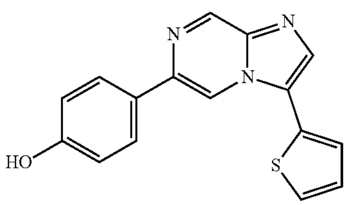 [SMILES: Oc1ccc(-c2cn3c(-c4cccs4)cnc3cn2)cc1] | 170 | 4-[3-(2-thienyl)imidazo[1,2-a]pyrazin-6-yl]phenol | 6.25235 | 2.62 | 388_4147_0080 |
| 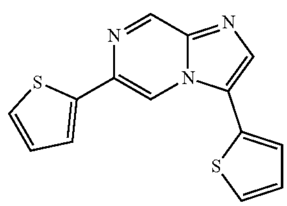 [SMILES: c1csc(-c2cn3c(-c4cccs4)cnc3cn2)c1] | 171 | 3,6-bis(2-thienyl)imidazo[1,2-a]pyrazine | 5.02752 | 2.70 | 388_4147_4147 |
| 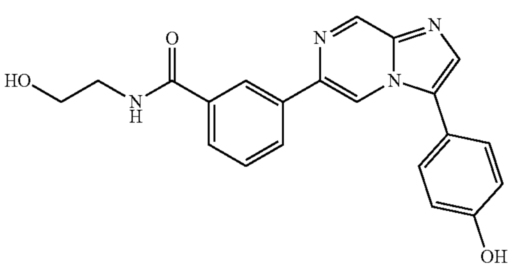 [SMILES: O=C(NCCO)c1cccc(-c2cn3c(-c4ccc(O)cc4)cnc3cn2)c1] | 172 | N-(2-hydroxy-ethyl)-3-[3-(4-hydroxyphenyl)imidazo[1,2-a]pyrazin-6-yl]benzamide | 1.03081 | 1.22 | 388_0080_0192 |
| 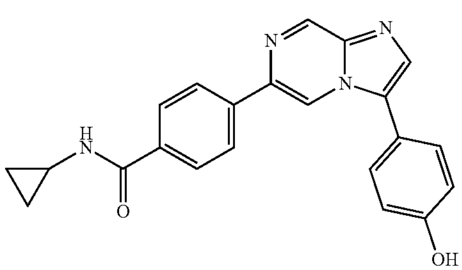 [SMILES: O=C(NC1CC1)c1ccc(-c2cn3c(-c4ccc(O)cc4)cnc3cn2)cc1] | 173 | N-cyclopropyl-4-[3-(4-hydroxyphenyl)imidazo[1,2-a]pyrazin-6-yl]benzamide | 1.95812 | 2.38 | 388_0080_7489 |

TABLE 3-continued

Primary screen- initial compounds.

| Structure | | IUPAC name | IC50 FYN (μM) | logP (consensus) | Compound ID. |
|---|---|---|---|---|---|
| 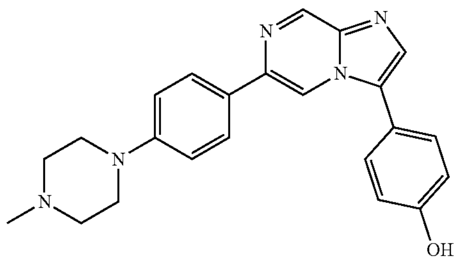 [SMILES: CN1CCN(c2ccc(-c3cn4c(-c5ccc(O)cc5)cnc4cn3)cc2)CC1] | 174 | 4-[6-[4-(4-methyl-piperazin-1-yl)phenyl]imidazo[1,2-a]pyrazin-3-yl]phenol | 0.67809 | 2.79 | 388_0080_0218 |
| 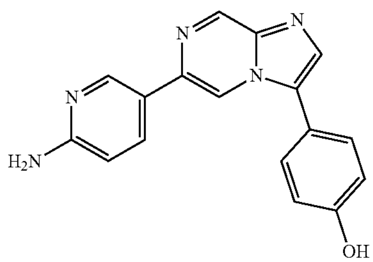 [SMILES: Nc1ccc(-c2cn3c(-c4ccc(O)cc4)cnc3cn2)cn1] | 175 | 4-[6-(6-amino-3-pyridyl)imidazo[1,2-a]pyrazin-3-yl]phenol | 1.9327 | 1.39 | 388_0080_7905 |
| 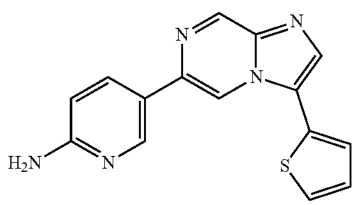 [SMILES: Nc1ccc(-c2cn3c(-c4cccs4)cnc3cn2)cn1] | 176 | 5-[3-(2-thienyl)imidazo[1,2-a]pyrazin-6-yl]pyridin-2-amine | 8.16191 | 1.47 | 388_4147_7905 |
| 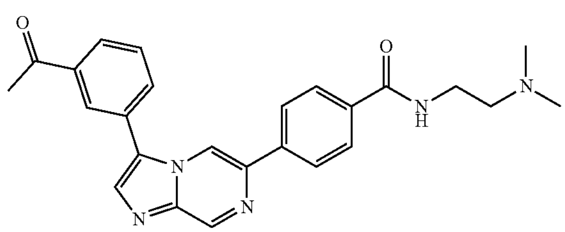 [SMILES: CC(=O)c1cccc(-c2cnc3cnc(-c4ccc(C(=O)NCCN(C)C)cc4)cn23)c1] | 177 | 4-[3-(3-acetylphenyl)imidazo[1,2-a]pyrazin-6-yl]-N-(2-dimethylaminoethyl)benzamide | 4.07021 | 1.79 | 388_4145_0327 |
| 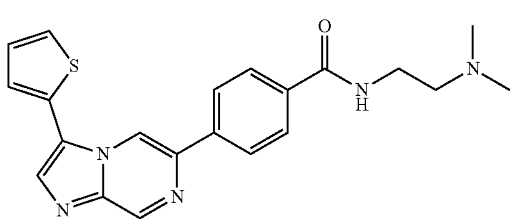 [SMILES: CN(C)CCNC(=O)c1ccc(-c2cn3c(-c4cccs4)cnc3cn2)cc1] | 178 | N-(2-dimethylamino-ethyl)-4-[3-(2-thienyl)imidazo[1,2-a]pyrazin-6-yl]benzamide | 8.52139 | 2.01 | 388_4147_0327 |
| 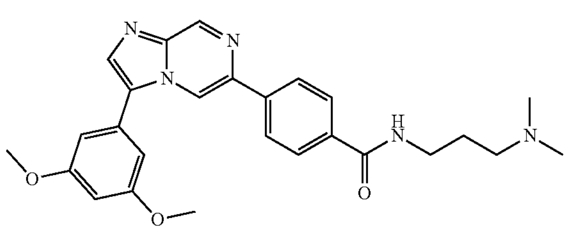 | 179 | 4-[3-(3,5-dimethoxyphenyl)imidazo[1,2-a]pyrazin-6-yl]-N-[3-(dimethylamino)propyl]benzamide | 6.69112 | 1.98 | 388_7492_0180 |

TABLE 3-continued

Primary screen- initial compounds.

| Structure | | IUPAC name | IC50 FYN (μM) | logP (consensus) | Compound ID. |
|---|---|---|---|---|---|
| 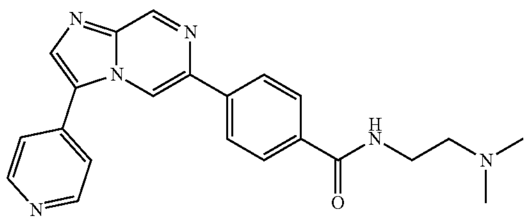 [SMILES: CN(C)CCNC(=O)c1ccc(-c2cn3c(-c4ccncc4)cnc3cn2)cc1] | 180 | N-(2-dimethylamino-ethyl)-4-[3-(4-pyridyl)imidazo[1,2-a]pyrazin-6-yl]benzamide | 6.90909 | 1.02 | 388_0069_0327 |
| 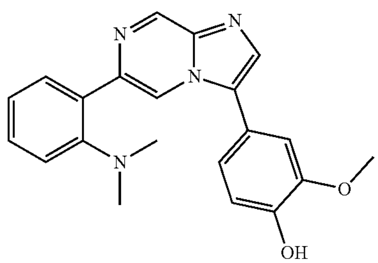 [SMILES: COc1cc(-c2cnc3cnc(-c4ccccc4N(C)C)cn23)ccc1O] | 181 | 4-[6-[2-(dimethylamino)phenyl]imidazo[1,2-a]pyrazin-3-yl]-2-methoxy-phenol | 1.75434 | 2.79 | 388_0314_0006 |
| 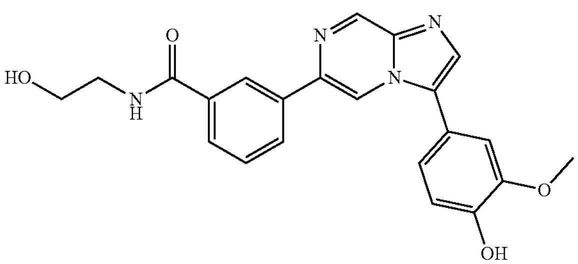 [SMILES: COc1cc(-c2cnc3cnc(-c4cccc(C(=O)NCCO)c4)cn23)ccc1O] | 182 | N-(2-hydroxyethyl)-3-[3-(4-hydroxy-3-methoxy-phenyl)imidazo[1,2-a]pyrazin-6-yl]benzamide | 0.8957 | 1.07 | 388_0314_0192 |
| 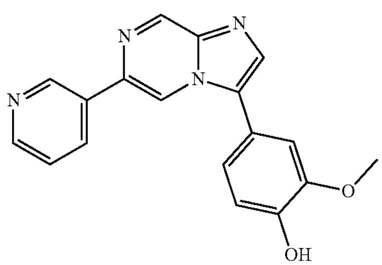 [SMILES: COc1cc(-c2cnc3cnc(-c4cccnc4)cn23)ccc1O] | 183 | 2-methoxy-4-[6-(3-pyridyl)imidazo[1,2-a]pyrazin-3-yl]phenol | 3.06577 | 1.46 | 388_0314_0071 |
| 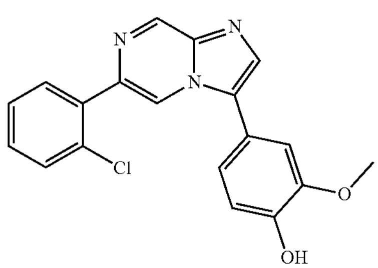 [SMILES: COc1cc(-c2cnc3cnc(-c4ccccc4Cl)cn23)ccc1O] | 184 | 4-[6-(2-chlorophenyl)imidazo[1,2-a]pyrazin-3-yl]-2-methoxy-phenol | 2.53905 | 3.28 | 388_0314_4027 |

TABLE 3-continued

Primary screen- initial compounds.

| Structure | | IUPAC name | IC50 FYN (μM) | logP (consensus) | Compound ID. |
|---|---|---|---|---|---|
| 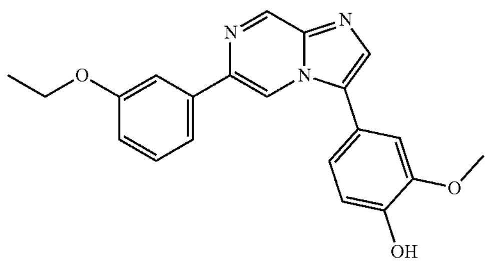 [SMILES: CCOc1cccc(-c2cn3c(-c4ccc(O)c(OC)c4)cnc3cn2)c1] | 185 | 4-[6-(3-ethoxyphenyl)imidazo[1,2-a]pyrazin-3-yl]-2-methoxyphenol | 1.36347 | 2.88 | 388_0314_0205 |
| 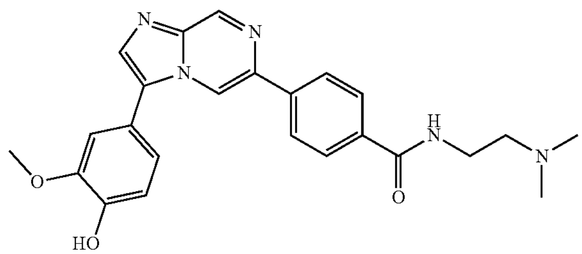 | 186 | N-(2-dimethylaminoethyl)-4-[3-(4-hydroxy-3-methoxyphenyl)imidazo[1,2-a]pyrazin-6-yl]benzamide | 0.44033 | 1.77 | 388_0314_0327 |
| 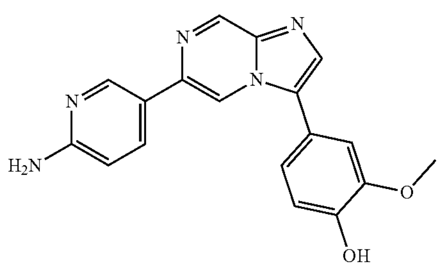 [SMILES: COc1cc(-c2cnc3cnc(-c4ccc(N)nc4)cn23)ccc1O] | 187 | 4-[6-(6-amino-3-pyridyl)imidazo[1,2-a]pyrazin-3-yl]-2-methoxyphenol | 1.41172 | 1.23 | 388_0314_7905 |
| 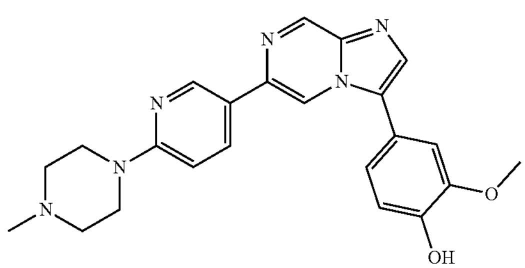 | 188 | 2-methoxy-4-[6-[6-(4-methylpiperazin-1-yl)-3-pyridyl]imidazo[1,2-a]pyrazin-3-yl]phenol | 1.13372 | 2.01 | 388_0314_0016 |
| 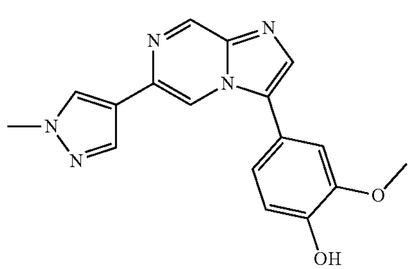 | 189 | 2-methoxy-4-[6-(1-methylpyrazol-4-yl)imidazo[1,2-a]pyrazin-3-yl]phenol | 0.74595 | 1.11 | 388_0314_8400 |

TABLE 3-continued

Primary screen- initial compounds.

| Structure | | IUPAC name | IC50 FYN (μM) | logP (consensus) | Compound ID. |
|---|---|---|---|---|---|
| 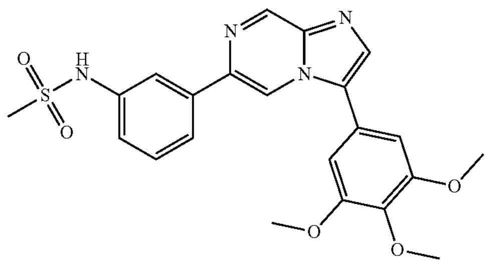 | 190 | N-[3-[3-(3,4,5-trimethoxyphenyl)imidazo[1,2-a]pyrazin-6-yl]phenyl]methanesulfonamide | 2.79564 | 1.04 | 388_0087_6488 |
| 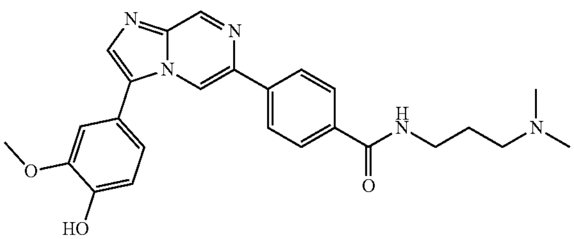 | 191 | N-[3-(dimethylamino)propyl]-4-[3-(4-hydroxy-3-methoxyphenyl)imidazo[1,2-a]pyrazin-6-yl]benzamide | 0.60574 | 1.83 | 388_0314_0180 |
| 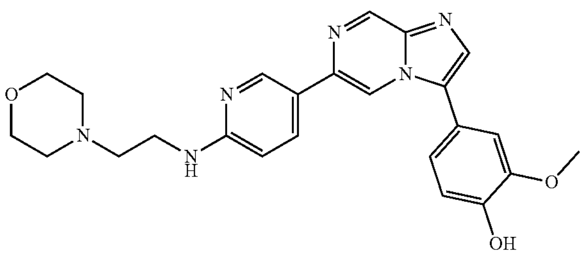 [SMILES: COc1cc(-c2cnc3cnc(-c4ccc(NCCN5CCOCC5)nc4)cn23)ccc1O] | 192 | 2-methoxy-4-[6-[6-(2-morpholinoethylamino)-3-pyridyl]imidazo[1,2-a]pyrazin-3-yl]phenol | 1.35363 | 1.33 | 388_0314_0003 |
| 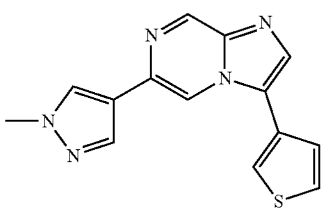 [SMILES: Cn1cc(-c2cn3c(-c4ccsc4)cnc3cn2)cn1] | 193 | 6-(1-methylpyrazol-4-yl)-3-(3-thienyl)imidazo[1,2-a]pyrazine | 6.37648 | 1.35 | 388_0074_8400 |
| 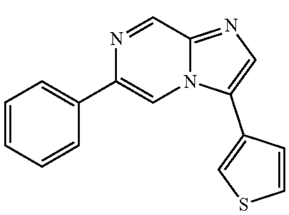 [SMILES: c1ccc(-c2cn3c(-c4ccsc4)cnc3cn2)cc1] | 194 | 6-phenyl-3-(3-thienyl)imidazo[1,2-a]pyrazine | 3.94995 | 2.92 | 388_0074_0061 |
| 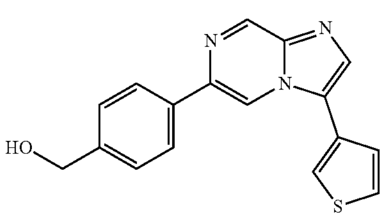 [SMILES: OCc1ccc(-c2cn3c(-c4ccsc4)cnc3cn2)cc1] | 195 | [4-[3-(3-thienyl)imidazo[1,2-a]pyrazin-6-yl]phenyl]methanol | 2.3518 | 2.16 | 388_0074_0285 |

TABLE 3-continued

Primary screen- initial compounds.

| Structure | | IUPAC name | IC50 FYN (μM) | logP (consensus) | Compound ID. |
|---|---|---|---|---|---|
| 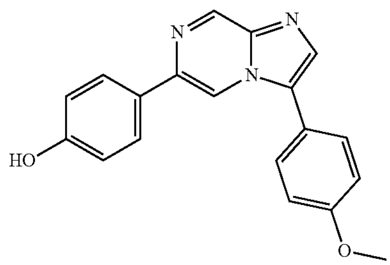 [SMILES: COc1ccc(-c2cnc3cnc(-c4ccc(O)cc4)cn23)cc1] | 196 | 4-[3-(4-methoxyphenyl)imidazo[1,2-a]pyrazin-6-yl]phenol | 10.45826 | 2.68 | 388_0280_0080 |
| 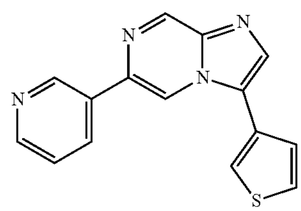 [SMILES: c1cncc(-c2cn3c(-c4ccsc4)cnc3cn2)c1] | 197 | 6-(3-pyridyl)-3-(3-thienyl)imidazo[1,2-a]pyrazine | 4.33598 | 1.70 | 388_0074_0071 |
| 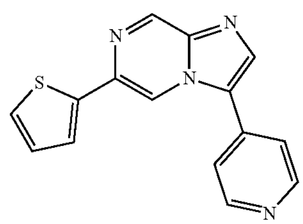 [SMILES: c1csc(-c2cn3c(-c4ccncc4)cnc3cn2)c1] | 198 | 3-(4-pyridyl)-6-(2-thienyl)imidazo[1,2-a]pyrazine | 5.68757 | 1.70 | 388_0069_4147 |
| 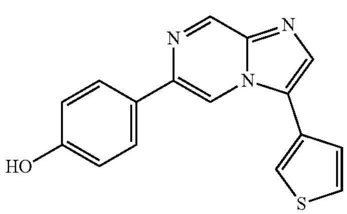 [SMILES: Oc1ccc(-c2cn3c(-c4ccsc4)cnc3cn2)cc1] | 199 | 4-[3-(3-thienyl)imidazo[1,2-a]pyrazin-6-yl]phenol | 2.70168 | 2.62 | 388_0074_0080 |
| 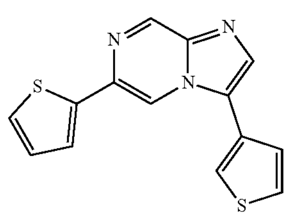 [SMILES: c1csc(-c2cn3c(-c4ccsc4)cnc3cn2)c1] | 200 | 6-(2-thienyl)-3-(3-thienyl)imidazo[1,2-a]pyrazine | 2.24904 | 2.70 | 388_0074_4147 |
| 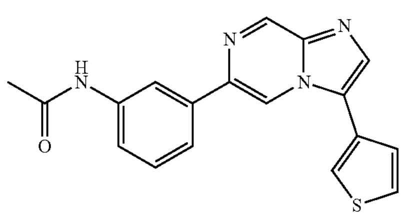 [SMILES: CC(=O)Nc1cccc(-c2cn3c(-c4ccsc4)cnc3cn2)c1] | 201 | N-[3-[3-(3-thienyl)imidazo[1,2-a]pyrazin-6-yl]phenyl]acetamide | 2.32941 | 2.16 | 388_0074_0081 |

TABLE 3-continued

Primary screen- initial compounds.

| Structure | | IUPAC name | IC50 FYN (μM) | logP (consensus) | Compound ID. |
|---|---|---|---|---|---|
| 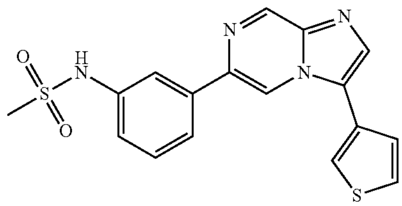 [SMILES: CS(=O)(=O)Nc1cccc(-c2cn3c(-c4ccsc4)cnc3cn2)c1] | 202 | N-[3-[3-(3-thienyl)imidazo[1,2-a]pyrazin-6-yl]phenyl]methanesulfonamide | 3.32047 | 1.30 | 388_0074_6488 |
| 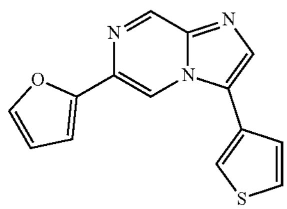 [SMILES: c1coc(-c2cn3c(-c4ccsc4)cnc3cn2)c1] | 203 | 6-(2-furyl)-3-(3-thienyl)imidazo[1,2-a]pyrazine | 6.25008 | 1.98 | 388_0074_0142 |
| 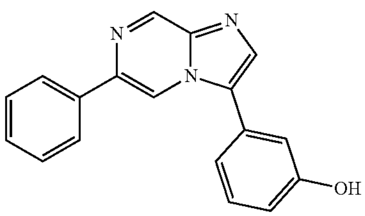 [SMILES: Oc1cccc(-c2cnc3cnc(-c4ccccc4)cn23)c1] | 204 | 3-(6-phenylimidazo[1,2-a]pyrazin-3-yl)phenol | 6.54588 | 2.84 | 388_0284_0061 |
| 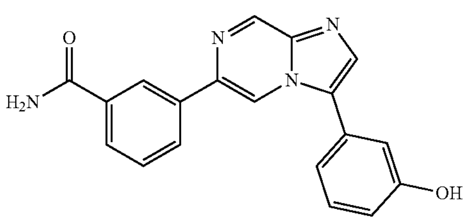 [SMILES: NC(=O)c1cccc(-c2cn3c(-c4cccc(O)c4)cnc3cn2)c1] | 205 | 3-[3-(3-hydroxyphenyl)imidazo[1,2-a]pyrazin-6-yl]benzamide | 1.58014 | 1.69 | 388_0284_0347 |
| 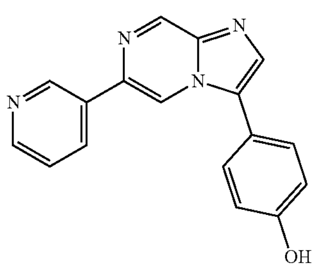 [SMILES: Oc1ccc(-c2cnc3cnc(-c4cccnc4)cn23)cc1] | 206 | 4-[6-(3-pyridyl)imidazo[1,2-a]pyrazin-3-yl]phenol | 2.72591 | 1.62 | 388_0080_0071 |
| 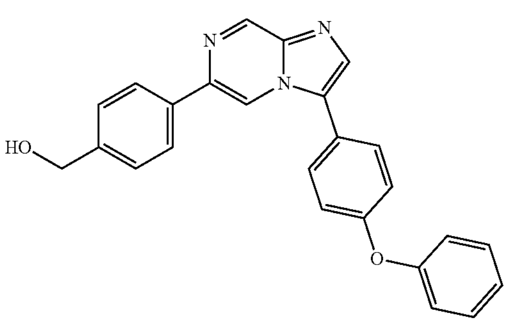 [SMILES: OCc1ccc(-c2cn3c(-c4ccc(Oc5ccccc5)cc4)cnc3cn2)cc1] | 207 | 4-[3-(4-phenoxyphenyl)imidazo[1,2-a]pyrazin-6-yl]phenyl]methanol | 4.72246 | 3.88 | 388_1029_0285 |

TABLE 3-continued

Primary screen- initial compounds.

| Structure | | IUPAC name | IC50 FYN (μM) | logP (consensus) | Compound ID. |
|---|---|---|---|---|---|
| 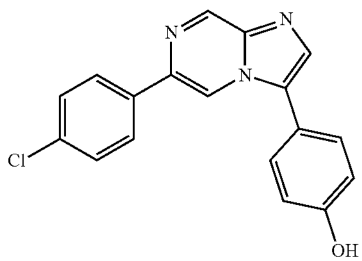 [SMILES: Oc1ccc(-c2cnc3cnc(-c4ccc(Cl)cc4)cn23)cc1] | 208 | 4-[6-(4-chlorophenyl)imidazo[1,2-a]pyrazin-3-yl]phenol | 6.37838 | 3.44 | 388_0080_0160 |
| 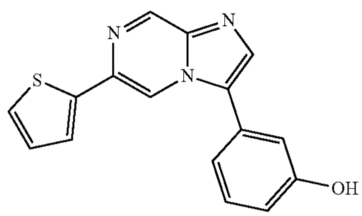 [SMILES: Oc1cccc(-c2cnc3cnc(-c4cccs4)cn23)c1] | 209 | 3-[6-(2-thienyl)imidazo[1,2-a]pyrazin-3-yl]phenol | 2.78435 | 2.62 | 388_0284_4147 |
| 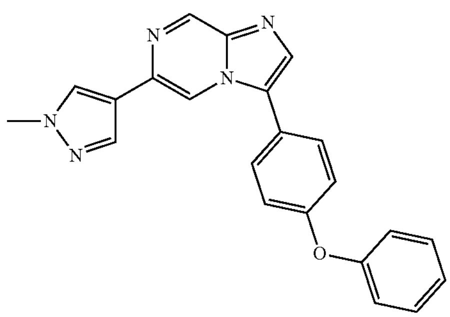 [SMILES: Cn1cc(-c2cn3c(-c4ccc(Oc5ccccc5)cc4)cnc3cn2)cn1] | 210 | 6-(1-methylpyrazol-4-yl)-3-(4-phenoxyphenyl)imidazo[1,2-a]pyrazine | 1.92958 | 3.07 | 388_1029_8400 |
| 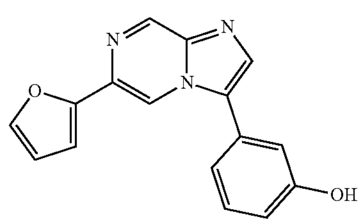 [SMILES: Oc1cccc(-c2cnc3cnc(-c4ccco4)cn23)c1] | 211 | 3-[6-(2-furyl)imidazo[1,2-a]pyrazin-3-yl]phenol | 6.11196 | 1.90 | 388_0284_0142 |
| 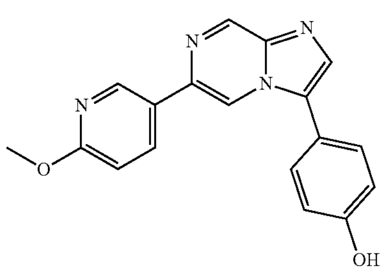 [SMILES: COc1ccc(-c2cn3c(-c4ccc(O)cc4)cnc3cn2)cn1] | 212 | 4-[6-(6-methoxy-3-pyridyl)imidazo[1,2-a]pyrazin-3-yl]phenol | 1.97871 | 2.06 | 388_0080_0311 |
| 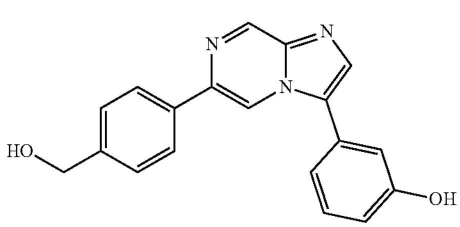 [SMILES: OCc1ccc(-c2cn3c(-c4cccc(O)c4)cnc3cn2)cc1] | 213 | 3-[6-[4-(hydroxymethyl)phenyl]imidazo[1,2-a]pyrazin-3-yl]phenol | 3.35687 | 2.07 | 388_0284_0285 |

TABLE 3-continued

Primary screen- initial compounds.

| Structure | | IUPAC name | IC50 FYN (µM) | logP (consensus) | Compound ID. |
|---|---|---|---|---|---|
| 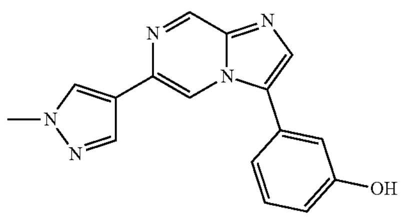 [SMILES: Cn1cc(-c2cn3c(-c4cccc(O)c4)cnc3cn2)cn1] | 214 | 3-[6-(1-methylpyrazol-4-yl)imidazo[1,2-a]pyrazin-3-yl]phenol | 2.78229 | 1.27 | 388_0284_8400 |
| 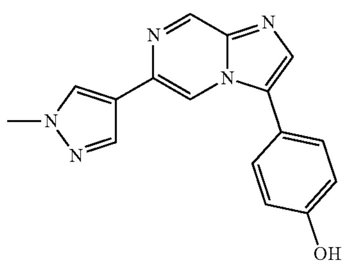 [SMILES: Cn1cc(-c2cn3c(-c4ccc(O)cc4)cnc3cn2)cn1] | 215 | 4-[6-(1-methylpyrazol-4-yl)imidazo[1,2-a]pyrazin-3-yl]phenol | 1.58926 | 1.27 | 388_0080_8400 |
| 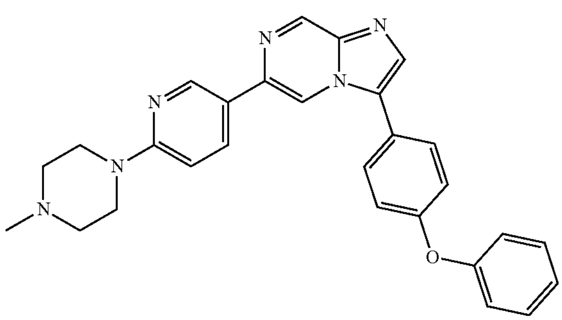 [SMILES: CN1CCN(c2ccc(-c3cn4c(-c5ccc(Oc6ccccc6)cc5)cnc4cn3)cn2)CC1] | 216 | 6-[6-(4-methylpiperazin-1-yl)-3-pyridyl]-3-(4-phenoxyphenyl)imidazo[1,2-a]pyrazine | 2.13162 | 3.97 | 388_1029_0016 |
| 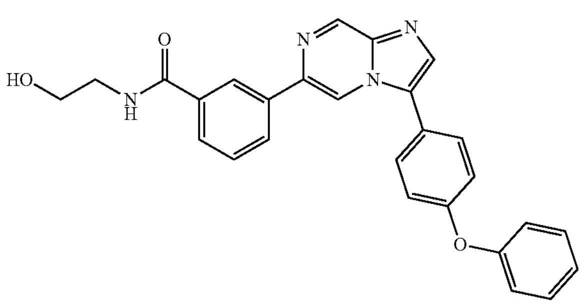 [SMILES: O=C(NCCO)c1cccc(-c2cn3c(-c4ccc(Oc5ccccc5)cc4)cnc3cn2)c1] | 217 | N-(2-hydroxyethyl)-3-[3-(4-phenoxyphenyl)imidazo[1,2-a]pyrazin-6-yl]benzamide | 1.48118 | 3.03 | 388_1029_0192 |
| 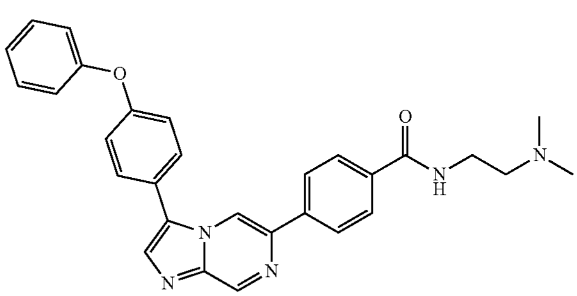 [SMILES: CN(C)CCNC(=O)c1ccc(-c2cn3c(-c4ccc(Oc5ccccc5)cc4)cnc3cn2)cc1] | 218 | N-(2-dimethylaminoethyl)-4-[3-(4-phenoxyphenyl)imidazo[1,2-a]pyrazin-6-yl]benzamide | 0.1649 | 3.74 | 388_1029_0327 |

TABLE 3-continued

Primary screen- initial compounds.

| Structure | | IUPAC name | IC50 FYN (μM) | logP (consensus) | Compound ID. |
|---|---|---|---|---|---|
| 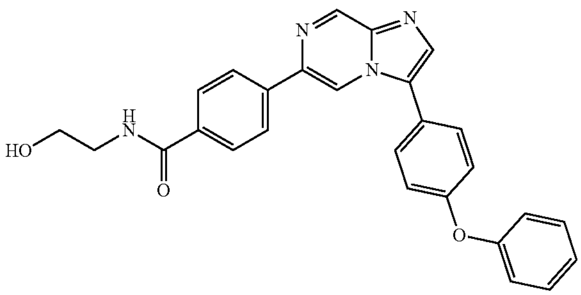 [SMILES: O=C(NCCO)c1ccc(-c2cn3c(-c4ccc(Oc5ccccc5)cc4)cnc3cn2)cc1] | 219 | N-(2-hydroxyethyl)-4-[3-(4-phenoxyphenyl)imidazo[1,2-a]pyrazin-6-yl]benzamide | 0.62307 | 3.03 | 388_1029_0328 |
| 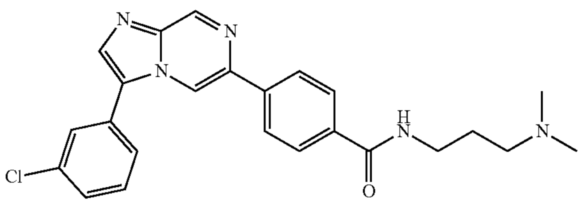 [SMILES: CN(C)CCCNC(=O)c1ccc(-c2cn3c(-c4cccc(Cl)c4)cnc3cn2)cc1] | 220 | 4-[3-(3-chlorophenyl)imidazo[1,2-a]pyrazin-6-yl]-N-[3-(dimethylamino)propyl]benzamide | 8.43215 | 2.90 | 388_0279_0180 |
| 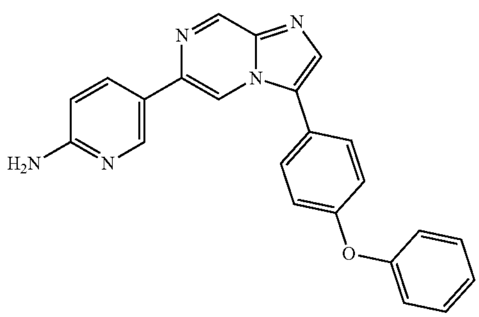 [SMILES: Nc1ccc(-c2cn3c(-c4ccc(Oc5ccccc5)cc4)cnc3cn2)cn1] | 221 | 5-[3-(4-phenoxyphenyl)imidazo[1,2-a]pyrazin-6-yl]pyridin-2-amine | 1.71808 | 3.19 | 388_1029_7905 |
| 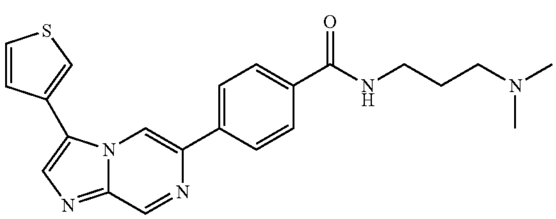 [SMILES: CN(C)CCCNC(=O)c1ccc(-c2cn3c(-c4ccsc4)cnc3cn2)cc1] | 222 | N-[3-(dimethylamino)propyl]-4-[3-(3-thienyl)imidazo[1,2-a]pyrazin-6-yl]benzamide | 3.87213 | 2.08 | 388_0074_0180 |
| 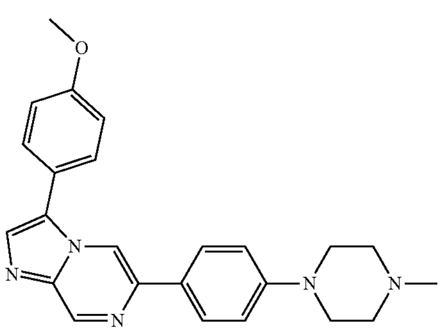 [SMILES: COc1ccc(-c2cnc3cnc(-c4ccc(N5CCN(C)CC5)cc4)cn23)cc1] | 223 | 3-(4-methoxyphenyl)-6-[4-(4-methyl-piperazin-1-yl)phenyl]imidazo[1,2-a]pyrazine | 5.25112 | 2.94 | 388_0280_0218 |

TABLE 3-continued

Primary screen- initial compounds.

| Structure | | IUPAC name | IC50 FYN (μM) | logP (consensus) | Compound ID. |
|---|---|---|---|---|---|
| 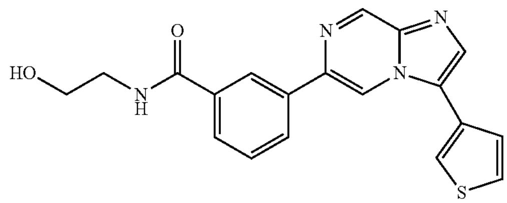 [SMILES: O=C(NCCO)c1cccc(-c2cn3c(-c4ccsc4)cnc3cn2)c1] | 224 | N-(2-hydroxyethyl)-3-[3-(3-thienyl)imidazo[1,2-a]pyrazin-6-yl]benzamide | 3.67126 | 1.31 | 388_0074_0192 |
| 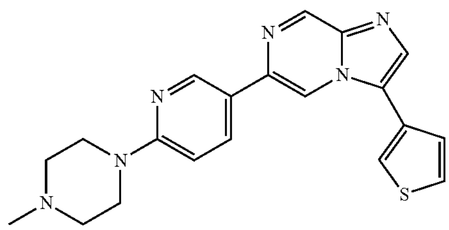 [SMILES: CN1CCN(c2ccc(-c3cn4c(-c5ccsc5)cnc4cn3)cn2)CC1] | 225 | 6-[6-(4-methylpiperazin-1-yl)-3-pyridyl]-3-(3-thienyl)imidazo[1,2-a]pyrazine | 7.04574 | 2.25 | 388_0074_0016 |
| 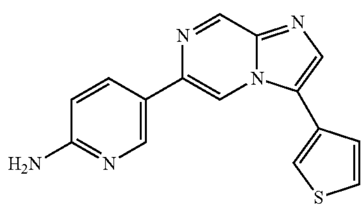 [SMILES: Nc1ccc(-c2cn3c(-c4ccsc4)cnc3cn2)cn1] | 226 | 5-[3-(3-thienyl)imidazo[1,2-a]pyrazin-6-yl]pyridin-2-amine | 2.45583 | 1.47 | 388_0074_7905 |
| 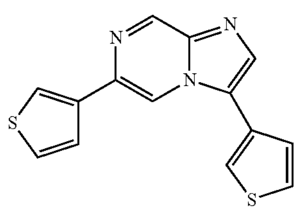 [SMILES: c1cc(-c2cn3c(-c4ccsc4)cnc3cn2)cs1] | 227 | 3,6-bis(3-thienyl)imidazo[1,2-a]pyrazine | 8.47406 | 2.70 | 388_0074_0074 |
| 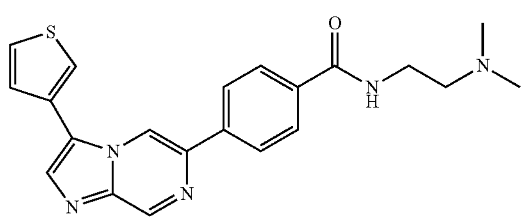 [SMILES: CN(C)CCNC(=O)c1ccc(-c2cn3c(-c4ccsc4)cnc3cn2)cc1] | 228 | N-(2-dimethylaminoethyl)-4-[3-(3-thienyl)imidazo[1,2-a]pyrazin-6-yl]benzamide | 1.89752 | 2.02 | 388_0074_0327 |
| 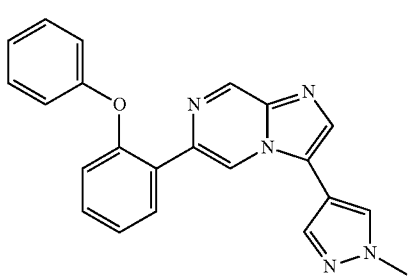 [SMILES: Cn1cc(-c2cnc3cnc(-c4ccccc4Oc4ccccc4)cn23)cn1] | 229 | 3-(1-methylpyrazol-4-yl)-6-(2-phenoxyphenyl)imidazo[1,2-a]pyrazine | 1.81873 | 3.07 | 388_8400_0063 |

TABLE 3-continued

Primary screen- initial compounds.

| Structure | | IUPAC name | IC50 FYN (μM) | logP (consensus) | Compound ID. |
|---|---|---|---|---|---|
| 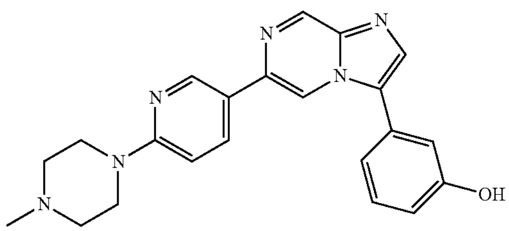 [SMILES: CN1CCN(c2ccc(-c3cn4c(-c5cccc(O)c5)cnc4cn3)cn2)CC1] | 230 | 3-[6-[6-(4-methylpiperazin-1-yl)-3-pyridyl]imidazo[1,2-a]pyrazin-3-yl]phenol | 3.14141 | 2.17 | 388_0284_0016 |
| 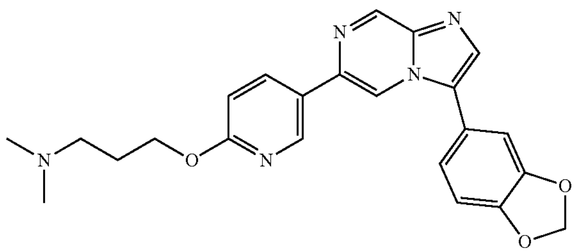 [SMILES: CN(C)CCCOc1ccc(-c2cn3c(-c4ccc5c(c4)OCO5)cnc3cn2)cn1] | 231 | 3-[[5-[3-(1,3-benzodioxol-5-yl)imidazo[1,2-a]pyrazin-6-yl]-2-pyridyl]oxy]-N,N-dimethyl-propan-1-amine | 9.85132 | 2.06 | 388_0068_0002 |
| 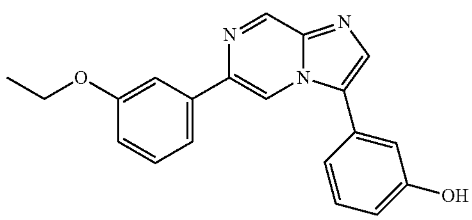 [SMILES: CCOc1cccc(-c2cn3c(-c4cccc(O)c4)cnc3cn2)c1] | 232 | 3-[6-(3-ethoxyphenyl)imidazo[1,2-a]pyrazin-3-yl]phenol | 6.6859 | 3.04 | 388_0284_0205 |
| 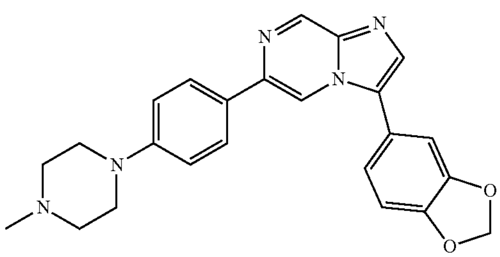 [SMILES: CN1CCN(c2ccc(-c3cn4c(-c5ccc6c(c5)OCO6)cnc4cn3)cc2)CC1] | 233 | 3-(1,3-benzodioxol-5-yl)-6-[4-(4-methylpiperazin-1-yl)phenyl]imidazo[1,2-a]pyrazine | 7.93105 | 2.72 | 388_0068_0218 |
| 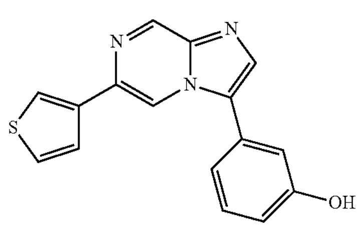 [SMILES: Oc1cccc(-c2cnc3cnc(-c4ccsc4)cn23)c1] | 234 | 3-[6-(3-thienyl)imidazo[1,2-a]pyrazin-3-yl]phenol | 2.51787 | 2.62 | 388_0284_0074 |
| 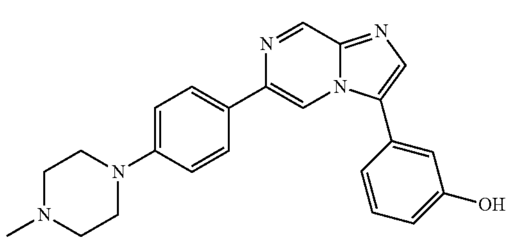 [SMILES: CN1CCN(c2ccc(-c3cn4c(-c5cccc(O)c5)cnc4cn3)cc2)CC1] | 235 | 3-[6-[4-(4-methyl-piperazin-1-yl)phenyl]imidazo[1,2-a]pyrazin-3-yl]phenol | 1.58793 | 2.79 | 388_0284_0218 |

TABLE 3-continued

Primary screen- initial compounds.

| Structure | | IUPAC name | IC50 FYN (μM) | logP (consensus) | Compound ID. |
|---|---|---|---|---|---|
| 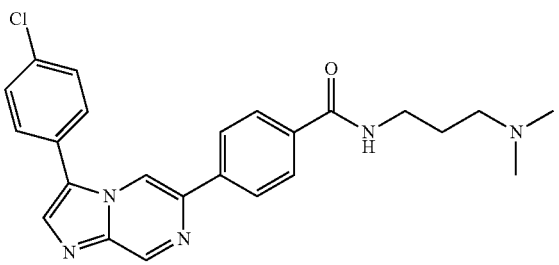 [SMILES: CN(C)CCCNC(=O)c1ccc(-c2cn3c(-c4ccc(Cl)cc4)cnc3cn2)cc1] | 236 | 4-[3-(4-chlorophenyl)imidazo[1,2-a]pyrazin-6-yl]-N-[3-(dimethylamino)propyl]benzamide | 4.90272 | 2.90 | 388_0160_0180 |
| 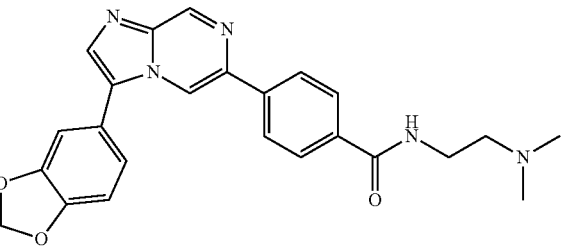 | 237 | 4-[3-(1,3-benzodioxol-5-yl)imidazo[1,2-a]pyrazin-6-yl]-N-(2-dimethylaminoethyl)benzamide | 3.79881 | 1.86 | 388_0068_0327 |
| 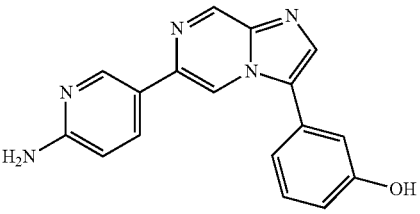 [SMILES: Nc1ccc(-c2cn3c(-c4cccc(O)c4)cnc3cn2)cn1] | 238 | 3-[6-(6-amino-3-pyridyl)imidazo[1,2-a]pyrazin-3-yl]phenol | 2.88877 | 1.39 | 388_0284_7905 |
| 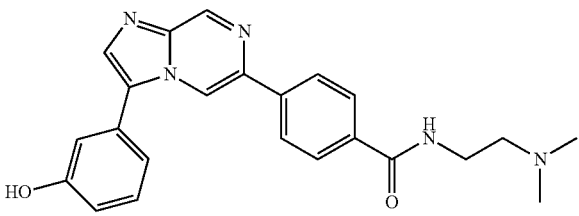 [SMILES: CN(C)CCNC(=O)c1ccc(-c2cn3c(-c4cccc(O)c4)cnc3cn2)cc1] | 239 | N-(2-dimethylaminoethyl)-4-[3-(3-hydroxyphenyl)imidazo[1,2-a]pyrazin-6-yl]benzamide | 0.81226 | 1.93 | 388_0284_0327 |
| 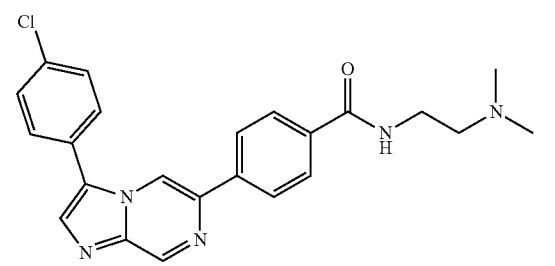 [SMILES: CN(C)CCNC(=O)c1ccc(-c2cn3c(-c4ccc(Cl)cc4)cnc3cn2)cc1] | 240 | 4-[3-(4-chlorophenyl)imidazo[1,2-a]pyrazin-6-yl]-N-(2-dimethylaminoethyl)benzamide | 4.15862 | 2.84 | 388_0160_0327 |
| 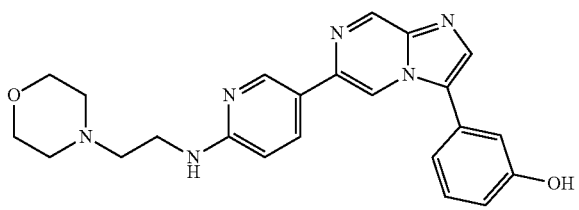 [SMILES: Oc1cccc(-c2cnc3cnc(-c4ccc(NCCN5CCOCC5)nc4)cn23)c1] | 241 | 3-[6-[6-(2-morpholinoethylamino)-3-pyridyl]imidazo[1,2-a]pyrazin-3-yl]phenol | 2.93938 | 1.49 | 388_0284_0003 |

TABLE 3-continued

Primary screen- initial compounds.

| Structure | | IUPAC name | IC50 FYN (μM) | logP (consensus) | Compound ID. |
|---|---|---|---|---|---|
| 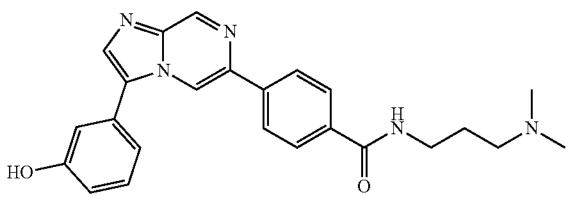 [SMILES: CN(C)CCCNC(=O)c1ccc(-c2cn3c(-c4cccc(O)c4)cnc3cn2)cc1] | 242 | N-[3-(dimethylamino)propyl]-4-[3-(3-hydroxyphenyl)imidazo[1,2-a]pyrazin-6-yl]benzamide | 1.61113 | 1.99 | 388_0284_0180 |
| 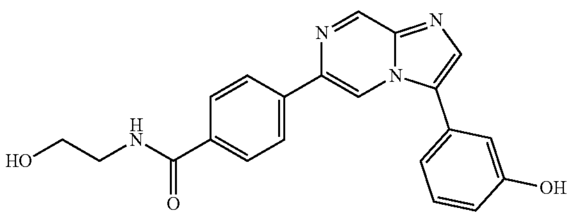 [SMILES: O=C(NCCO)c1ccc(-c2cn3c(-c4cccc(O)c4)cnc3cn2)cc1] | 243 | N-(2-hydroxyethyl)-4-[3-(3-hydroxyphenyl)imidazo[1,2-a]pyrazin-6-yl]benzamide | 1.72336 | 1.22 | 388_0284_0328 |
| 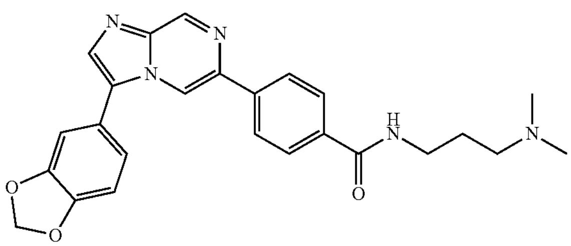 [SMILES: CN(C)CCCNC(=O)c1ccc(-c2cn3c(-c4ccc5c(c4)OCO5)cnc3cn2)cc1] | 244 | 4-[3-(1,3-benzodioxol-5-yl)imidazo[1,2-a]pyrazin-6-yl]-N-[3-(dimethylamino)propyl]benzamide | 6.03233 | 1.92 | 388_0068_0180 |
| 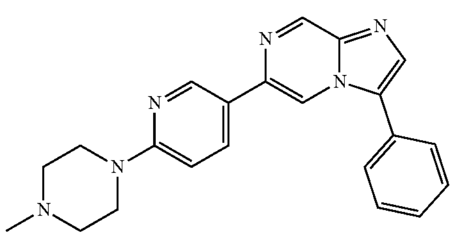 [SMILES: CN1CCN(c2ccc(-c3cn4c(-c5ccccc5)cnc4cn3)cn2)CC1] | 245 | 6-[6-(4-methylpiperazin-1-yl)-3-pyridyl]-3-phenyl-imidazo[1,2-a]pyrazine | 10.85328 | 2.47 | 388_0061_0016 |
| 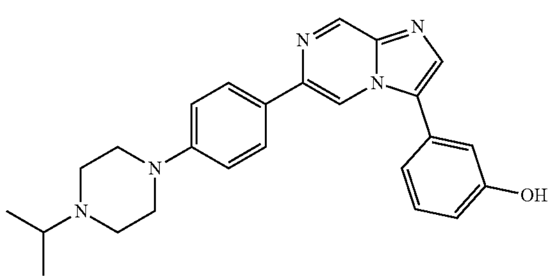 [SMILES: CC(C)N1CCN(c2ccc(-c3cn4c(-c5cccc(O)c5)cnc4cn3)cc2)CC1] | 246 | 3-[6-[4-(4-isopropyl-piperazin-1-yl)phenyl]imidazo[1,2-a]pyrazin-3-yl]phenol | 2.61352 | 3.57 | 388_0284_0182 |
| 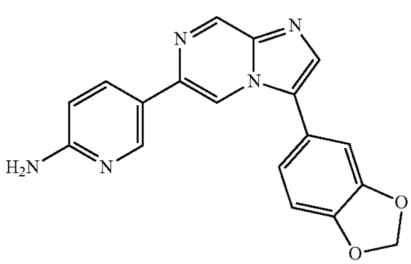 [SMILES: Nc1ccc(-c2cn3c(-c4ccc5c(c4)OCO5)cnc3cn2)cn1] | 247 | 5-[3-(1,3-benzodioxol-5-yl)imidazo[1,2-a]pyrazin-6-yl]pyridin-2-amine | 10.23913 | 1.31 | 388_0068_7905 |

TABLE 3-continued

Primary screen- initial compounds.

| Structure | | IUPAC name | IC50 FYN (μM) | logP (consensus) | Compound ID. |
|---|---|---|---|---|---|
| 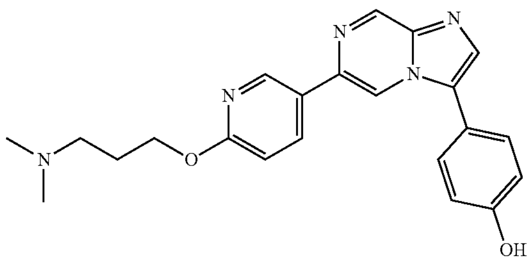 [SMILES: CN(C)CCCOc1ccc(-c2cn3c(-c4ccc(O)cc4)cnc3cn2)cn1] | 248 | 4-[6-[6-[3-(dimethylamino)propoxy]-3-pyridyl]imidazo[1,2-a]pyrazin-3-yl]phenol | 1.32178 | 2.14 | 388_0080_0002 |
| 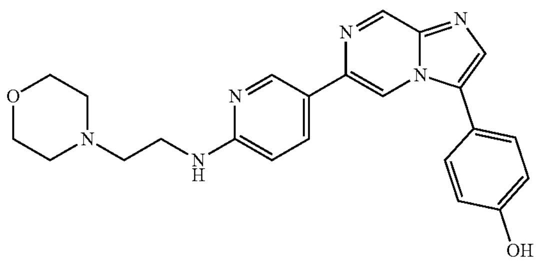 [SMILES: Oc1ccc(-c2cnc3cnc(-c4ccc(NCCN5CCOCC5)nc4)cn23)cc1] | 249 | 4-[6-[6-(2-morpholinoethylamino)-3-pyridyl]imidazo[1,2-a]pyrazin-3-yl]phenol | 1.31444 | 1.49 | 388_0080_0003 |
| 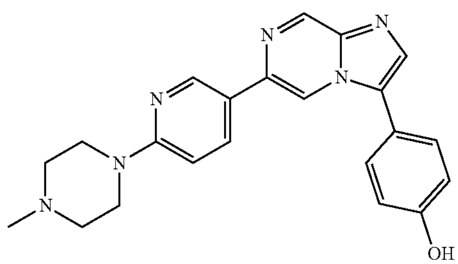 [SMILES: CN1CCN(c2ccc(-c3cn4c(-c5ccc(O)cc5)cnc4cn3)cn2)CC1] | 250 | 4-[6-[6-(4-methylpiperazin-1-yl)-3-pyridyl]imidazo[1,2-a]pyrazin-3-yl]phenol | 2.21078 | 2.17 | 388_0080_0016 |
| 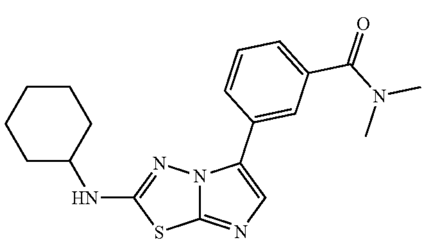 [SMILES: CN(C)C(=O)c1cccc(-c2cnc3sc(NC4CCCCC4)nn23)c1] | 251 | 3-[2-(cyclohexylamino)imidazo[2,1-a][1,3,4]thiadiazol-5-yl]-N,N-dimethylbenzamide | 0.71795 | 3.60 | 699_0052_0349 |
| 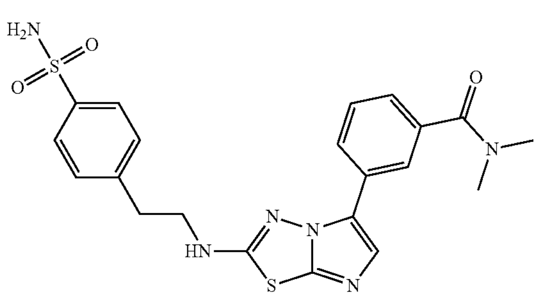 [SMILES: CN(C)C(=O)c1cccc(-c2cnc3sc(NCCc4ccc(S(N)(=O)=O)cc4)nn23)c1] | 252 | N,N-dimethyl-3-[2-[2-(4-sulfamoylphenyl)ethylamino]imidazo[2,1-a][1,3,4]thiadiazol-5-yl]benzamide | 0.9091 | 2.42 | 699_6182_0349 |

TABLE 3-continued

Primary screen- initial compounds.

| Structure | | IUPAC name | IC50 FYN (μM) | logP (consensus) | Compound ID. |
|---|---|---|---|---|---|
| 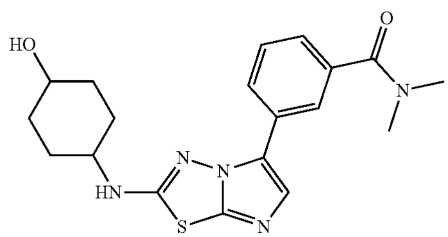 [SMILES: CN(C)C(=O)c1cccc(-c2cnc3sc(NC4CCC(O)CC4)nn23)c1] | 253 | 3-[2-[(4-hydroxycyclohexyl)amino]imidazo[2,1-b][1,3,4]thiadiazol-5-yl]-N,N-dimethylbenzamide | 0.53282 | 2.22 | 699_0240_0349 |
| 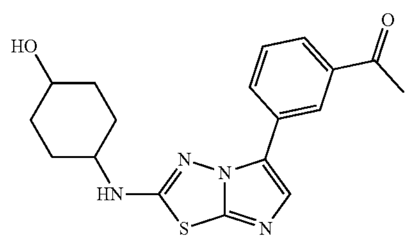 [SMILES: CC(=O)c1cccc(-c2cnc3sc(NC4CCC(O)CC4)nn23)c1] | 254 | 1-[3-[2-[(4-hydroxycyclohexyl)amino]imidazo[2,1-a][1,3,4]thiadiazol-5-yl]phenyl]ethanone | 0.48712 | 2.48 | 699_0240_4145 |
| 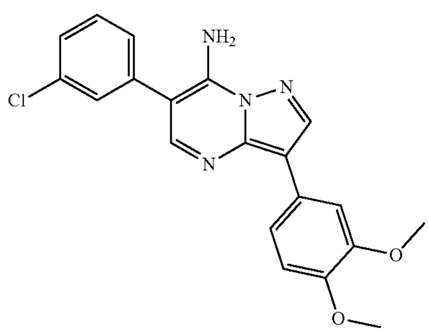 [SMILES: COc1ccc(-c2cnn3c(N)c(-c4cccc(Cl)c4)cnc23)cc1OC] | 255 | 6-(3-chlorophenyl)-3-(3,4-dimethoxyphenyl)pyrazolo[1,5-a]pyrimidin-7-amine | 0.80424 | 3.50 | DT2008-0028664 |
| 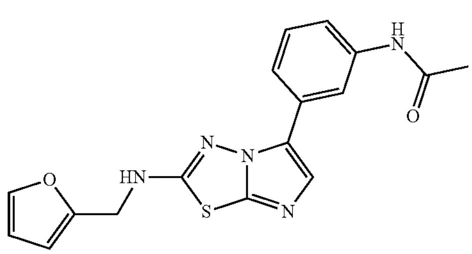 | 256 | N-[3-[2-(2-furylmethylamino)imidazo[2,1-a][1,3,4]thiadiazol-5-yl]phenyl]acetamide | 4.56802 | 2.53 | 699_0144_0081 |
| 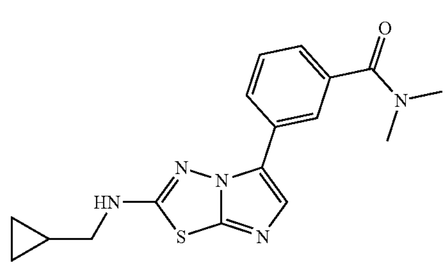 [SMILES: CN(C)C(=O)c1cccc(-c2cnc3sc(NCC4CC4)nn23)c1] | 257 | 3-[2-(cyclopropylmethylamino)imidazo[2,1-d][1,3,4]thiadiazol-5-yl]-N,N-dimethylbenzamide | 0.97667 | 2.59 | 699_4051_0349 |

TABLE 3-continued

Primary screen- initial compounds.

| Structure | | IUPAC name | IC50 FYN (μM) | logP (consensus) | Compound ID. |
|---|---|---|---|---|---|
| 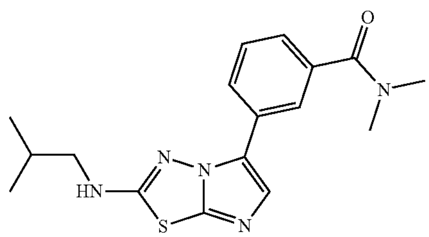 [SMILES: CC(C)CNc1nn2c(-c3cccc(C(=O)N(C)C)c3)cnc2s1] | 258 | 3-[2-(isobutylamino)imidazo[2,1-d][1,3,4]thiadiazol-5-yl]-N,N-dimethyl-benzamide | 0.28265 | 3.05 | 699_0149_0349 |
| 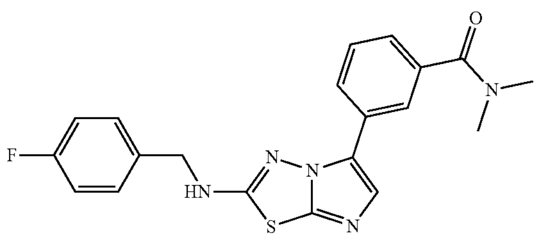 [SMILES: CN(C)C(=O)c1cccc(-c2cnc3sc(NCc4ccc(F)cc4)nn23)c1] | 259 | 3-[2-[(4-fluorophenyl)methylamino]imidazo[2,1-b][1,3,4]thiadiazol-5-yl]-N,N-dimethyl-benzamide | 2.76099 | 3.67 | 699_0224_0349 |
| 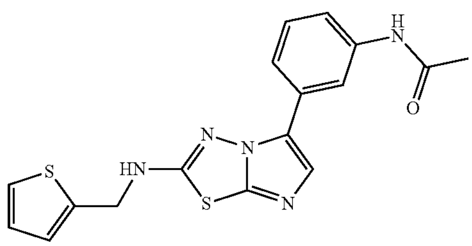 [SMILES: CC(=O)Nc1cccc(-c2cnc3sc(NCc4cccs4)nn23)c1] | 260 | N-[3-[2-(2-thienylmethylamino)imidazo[2,1-b][1,3,4]thiadiazol-5-yl]phenyl]acetamide | 3.92554 | 3.38 | 699_0146_0081 |
| 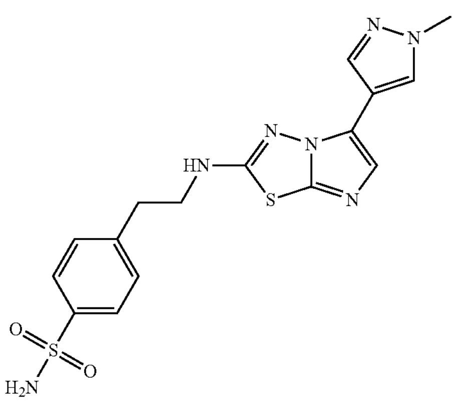 [SMILES: Cn1cc(-c2cnc3sc(NCCc4ccc(S(N)(=O)=O)cc4)nn23)cn1] | 261 | 4-[2-[[5-(1-methylpyrazol-4-yl)imidazo[2,1-d][1,3,4]thiadiazol-2-yl]amino]ethyl]benzenesulfonamide | 2.26191 | 1.55 | 699_6182_7468 |
| 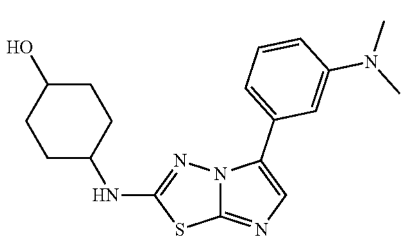 [SMILES: CN(C)c1cccc(-c2cnc3sc(NC4CCC(O)CC4)nn23)c1] | 262 | 4-[[5-[3-(dimethylamino)phenyl]imidazo[2,1-a][1,3,4]thiadiazol-2-yl]amino]cyclohexanol | 5.79421 | 3.03 | 699_0240_0135 |

TABLE 3-continued

Primary screen- initial compounds.

| Structure | | IUPAC name | IC50 FYN (μM) | logP (consensus) | Compound ID. |
|---|---|---|---|---|---|
| 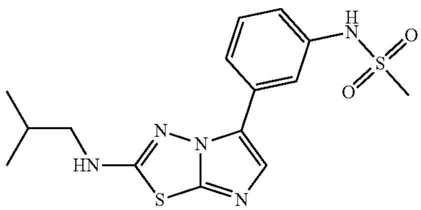 [SMILES: CC(C)CNc1nn2c(-c3cccc(NS(C)(=O)=O)c3)cnc2s1] | 263 | N-[3-[2-(isobutylamino)imidazo[2,1-b][1,3,4]thiadiazol-5-yl]phenyl]methane-sulfonamide | 7.06833 | 2.12 | 699_0149_6488 |
| 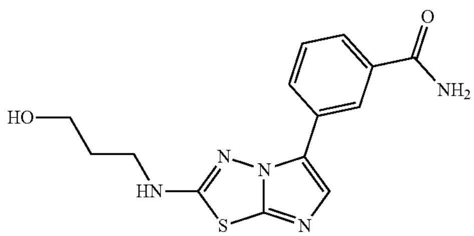 [SMILES: NC(=O)c1cccc(-c2cnc3sc(NCCCO)nn23)c1] | 264 | 3-[2-(3-hydroxypropyl-amino)imidazo[2,1-b][1,3,4]thiadiazol-5-yl]benzamide | 2.87875 | 0.73 | 699_0248_0347 |
| 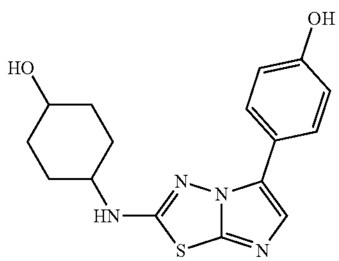 [SMILES: Oc1ccc(-c2cnc3sc(NC4CCC(O)CC4)nn23)cc1] | 265 | 4-[2-[(4-hydroxycyclohexyl)amino]imidazo[2,1-b][1,3,4]thiadiazol-5-yl]phenol | 3.804 | 2.62 | 699_0240_0080 |
| 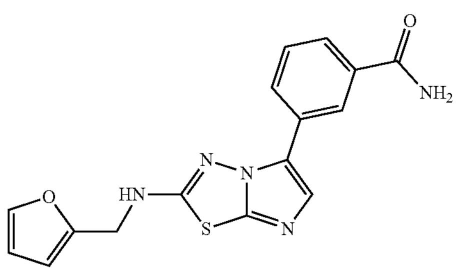 [SMILES: NC(=O)c1cccc(-c2cnc3sc(NCc4ccco4)nn23)c1] | 266 | 3-[2-(2-furylmethyl-amino)imidazo[2,1-b][1,3,4]thiadiazol-5-yl]benzamide | 1.22619 | 2.14 | 699_0144_0347 |
| 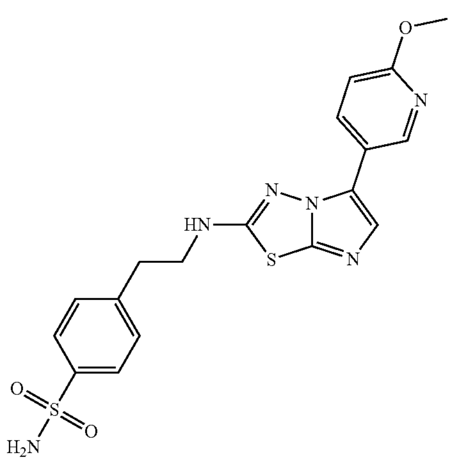 [SMILES: COc1ccc(-c2cnc3sc(NCCc4ccc(S(N)(=O)=O)cc4)nn23)cn1] | 267 | 4-[2-[[5-(6-methoxy-3-pyridyl)imidazo[2,1-b][1,3,4]thiadiazol-2-yl]amino]ethyl]benzene-sulfonamide | 2.61127 | 2.35 | 699_6182_0311 |

TABLE 3-continued

Primary screen- initial compounds.

| Structure | | IUPAC name | IC50 FYN (µM) | logP (consensus) | Compound ID. |
|---|---|---|---|---|---|
| 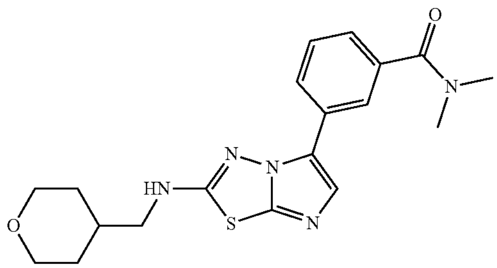 [SMILES: CN(C)C(=O)c1cccc(-c2cnc3sc(NCC4CCOCC4)nn23)c1] | 268 | N,N-dimethyl-3-[2-(tetrahydropyran-4-ylmethylamino)imidazo[2,1-b][1,3,4]thiadiazol-5-yl]benzamide | 2.72692 | 2.23 | 699_0243_0349 |
| 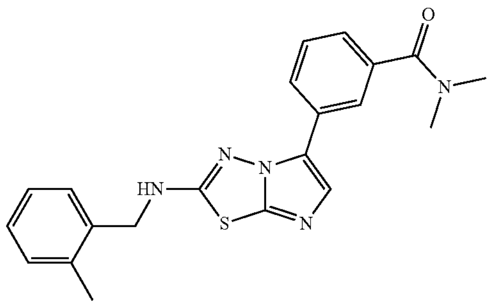 [SMILES: Cc1ccccc1CNc1nn2c(-c3cccc(C(=O)N(C)C)c3)cnc2s1] | 269 | N,N-dimethyl-3-[2-(o-tolylmethylamino)imidazo[2,1-b][1,3,4]thiadiazol-5-yl]benzamide | 3.73043 | 4.04 | 699_8074_0349 |
| 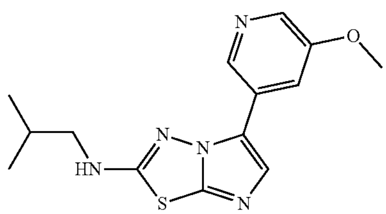 [SMILES: COc1cncc(-c2cnc3sc(NCC(C)C)nn23)c1] | 270 | N-isobutyl-5-(5-methoxy-3-pyridyl)imidazo[2,1-b][1,3,4]thiadiazol-2-amine | 5.16693 | 2.38 | 699_0149_0196 |
| 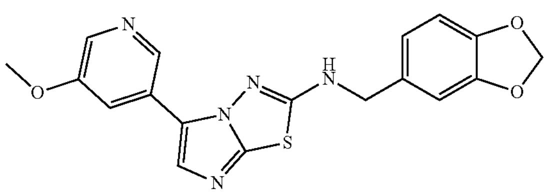 [SMILES: COc1cncc(-c2cnc3sc(NCc4ccc5c(c4)OCO5)nn23)c1] | 271 | N-(1,3-benzodioxol-5-ylmethyl)-5-(5-methoxy-3-pyridyl)imidazo[2,1-b][1,3,4]thiadiazol-2-amine | 0.44781 | 2.48 | 699_0236_0196 |
| 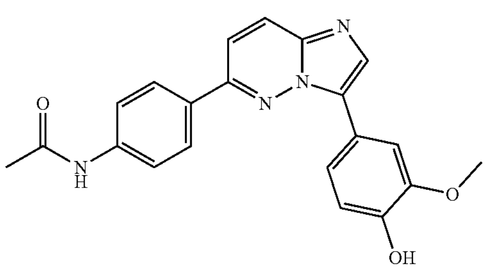 [SMILES: COc1cc(-c2cnc3ccc(-c4ccc(NC(C)=O)cc4)nn23)ccc1O] | 272 | N-[4-[3-(4-hydroxy-3-methoxyphenyl)imidazo[1,2-b]pyridazin-6-yl]phenyl]acetamide | 0.16907 | 3.03 | 828_0314_0722 |
| 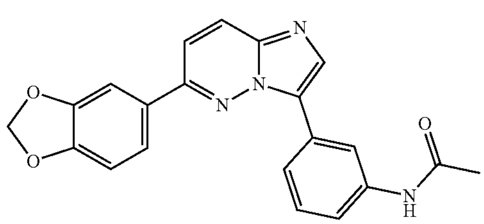 [SMILES: CC(=O)Nc1cccc(-c2cnc3ccc(-c4ccc5c(c4)OCO5)nn23)c1] | 273 | N-[3-[6-(1,3-benzodioxol-5-yl)imidazo[1,2-b]pyridazin-3-yl]phenyl]acetamide | 1.16817 | 3.11 | 828_0081_0068 |

TABLE 3-continued

Primary screen- initial compounds.

| Structure | | IUPAC name | IC50 FYN (μM) | logP (consensus) | Compound ID. |
|---|---|---|---|---|---|
| 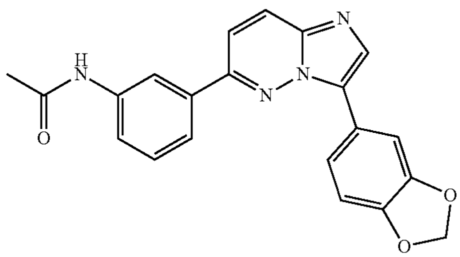 [SMILES: CC(=O)Nc1cccc(-c2ccc3ncc(-c4ccc5c(c4)OCO5)n3n2)c1] | 274 | N-[3-[3-(1,3-benzodioxol-5-yl)imidazo[1,2-b]pyridazin-6-yl]phenyl]acetamide | 1.10979 | 3.11 | 828_0068_0081 |
| 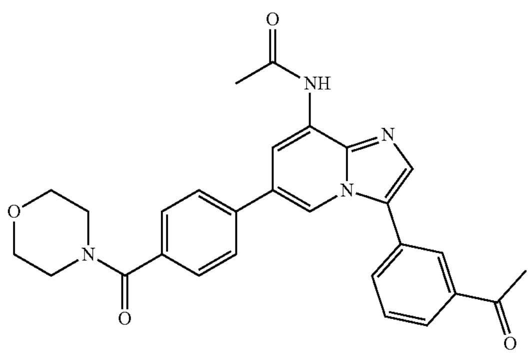 [SMILES: CC(=O)Nc1cc(-c2ccc(C(=O)N3CCOCC3)cc2)cn2c(-c3cccc(C(C)=O)c3)cnc12] | 275 | N-[3-[3-(3-acetylphenyl)-6-4-(morpholine-4-carbonyl)phenyl]imidazo[1,2-a]pyridin-8-yl]acetamide | 2.02757 | 1.85 | 802_4145_0337 |
| 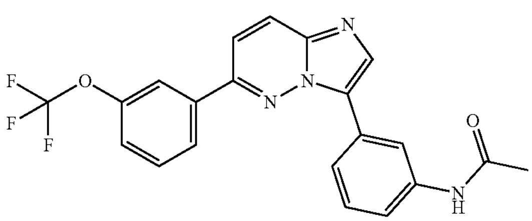 [SMILES: CC(=O)Nc1cccc(-c2cnc3ccc(-c4cccc(OC(F)(F)F)c4)nn23)c1] | 276 | N-[3-[6-[3-(trifluoromethoxy)phenyl]imidazo[1,2-b]pyridazin-3-yl]phenyl]acetamide | 1.5009 | 4.92 | 828_0081_0168 |
| 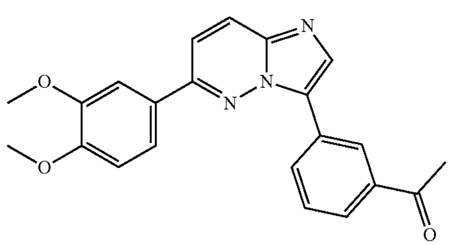 [SMILES: COc1ccc(-c2ccc3ncc(-c4cccc(C(C)=O)c4)n3n2)cc1OC] | 277 | 1-[3-[6-(3,4-dimethoxyphenyl)imidazo[1,2-b]pyridazin-3-yl]phenyl]ethanone | 0.65302 | 3.50 | 828_4145_0079 |
| 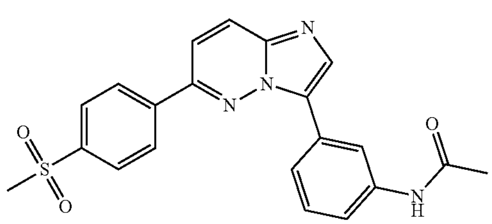 [SMILES: CC(=O)Nc1cccc(-c2cnc3ccc(-c4ccc(S(C)(=O)=O)cc4)nn23)c1] | 278 | N-[3-[6-(4-methylsulfonylphenyl)imidazo[1,2-b]pyridazin-3-yl]phenyl]acetamide | 1.08226 | 2.33 | 828_0081_0174 |
| 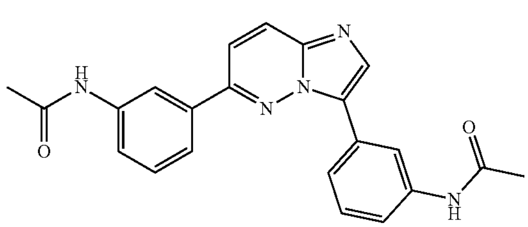 [SMILES: CC(=O)Nc1cccc(-c2ccc3ncc(-c4cccc(NC(C)=O)c4)n3n2)c1] | 279 | N-[3-[3-(3-acetamidophenyl)imidazo[1,2-b]pyridazin-6-yl]phenyl]acetamide | 0.55312 | 2.73 | 828_0081_0081 |

TABLE 3-continued

Primary screen- initial compounds.

| Structure | | IUPAC name | IC50 FYN (μM) | logP (consensus) | Compound ID. |
|---|---|---|---|---|---|
| 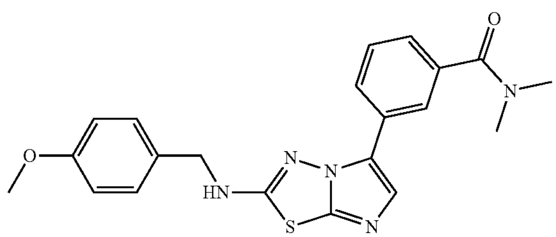 | 280 | 3-[2-[(4-methoxyphenyl)methylamino]imidazo[2,1-b][1,3,4]thiadiazol-5-yl]-N,N-dimethyl-benzamide | 2.33054 | 3.37 | 699_0244_0349 |
| 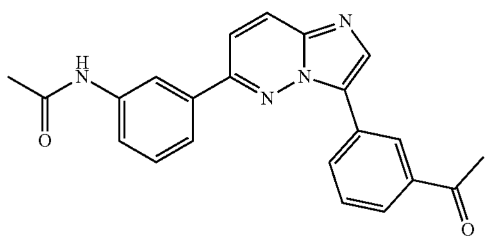 [SMILES: CC(=O)Nc1cccc(-c2ccc3ncc(-c4cccc(C(C)=O)c4)n3n2)c1] | 281 | N-[3-[3-(3-acetylphenyl)imidazo[1,2-b]pyridazin-6-yl]phenyl]acetamide | 0.6205 | 3.05 | 828_4145_0081 |
| 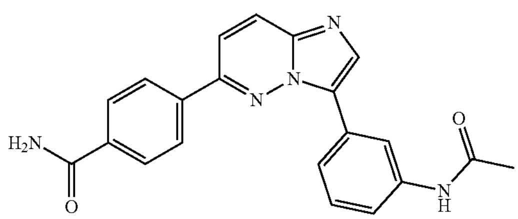 [SMILES: CC(=O)Nc1cccc(-c2cnc3ccc(-c4ccc(C(N)=O)cc4)nn23)c1] | 282 | 4-[3-(3-acetamidophenyl)imidazo[1,2-b]pyridazin-6-yl]benzamide | 0.22155 | 2.34 | 828_0081_0346 |
| 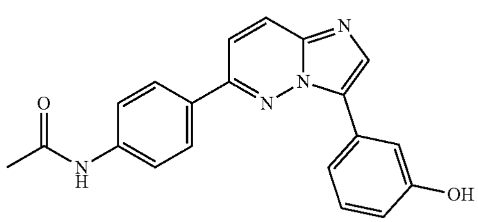 [SMILES: CC(=O)Nc1ccc(-c2ccc3ncc(-c4cccc(O)c4)n3n2)cc1] | 283 | N-[4-[3-(3-hydroxyphenyl)imidazo[1,2-b]pyridazin-6-yl]phenyl]acetamide | 0.51873 | 3.19 | 828_0284_0722 |
| 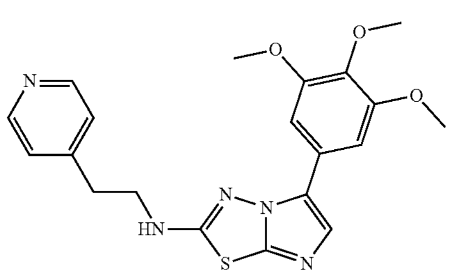 [SMILES: COc1cc(-c2cnc3sc(NCCc4ccncc4)nn23)cc(OC)c1OC] | 284 | N-[2-(4-pyridyl)ethyl]-5-(3,4,5-trimethoxyphenyl)imidazo[2,1-b][1,3,4]thiadiazol-2-amine | 1.77014 | 2.83 | 699_0039_0087 |

TABLE 3-continued

Primary screen- initial compounds.

| Structure | | IUPAC name | IC50 FYN (μM) | logP (consensus) | Compound ID. |
|---|---|---|---|---|---|
| 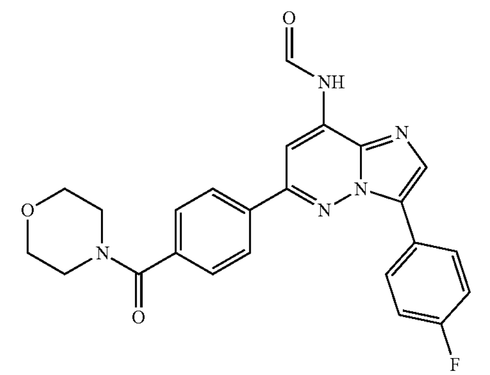 [SMILES: O=CNc1cc(-c2ccc(C(=O)N3CCOCC3)cc2)nn2c(-c3ccc(F)cc3)cnc12] | 285 | N-[3-(4-fluorophenyl)-6-[4-(morpholine-4-carbonyl)phenyl]imidazo[1,2-a]pyridin-8-yl]formamide | 3.59432 | 2.39 | 788_0339_0337 |
| 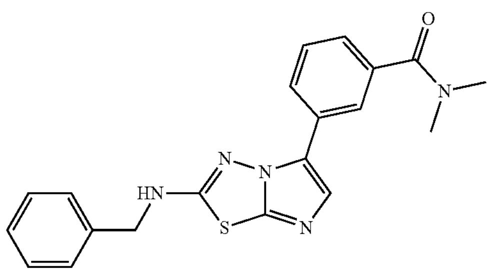 [SMILES: CN(C)C(=O)c1cccc(-c2cnc3sc(NCc4ccccc4)nn23)c1] | 286 | 3-[2-(benzylamino)imidazo[2,1-d][1,3,4]thiadiazol-5-yl]-N,N-dimethyl-benzamide | 1.50507 | 3.53 | 699_0232_0349 |
| 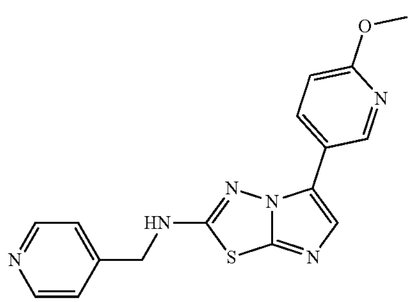 [SMILES: COc1ccc(-c2cnc3sc(NCc4ccncc4)nn23)cn1] | 287 | 5-(6-methoxy-3-pyridyl)-N-(4-pyridylmethyl)imidazo[2,1-b][1,3,4]thiadiazol-2-amine | 2.58601 | 2.23 | 699_0237_0311 |
| 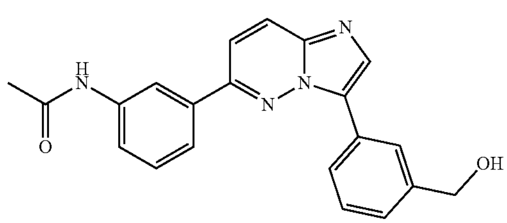 [SMILES: CC(=O)Nc1cccc(-c2ccc3ncc(-c4cccc(CO)c4)n3n2)c1] | 288 | N-[3-[3-[3-(hydroxymethyl)phenyl]imidazo[1,2-b]pyridazin-6-yl]phenyl]acetamide | 1.63929 | 2.72 | 828_0291_0081 |
| 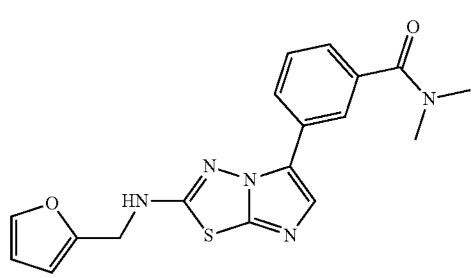 [SMILES: CN(C)C(=O)c1cccc(-c2cnc3sc(NCc4ccco4)nn23)c1] | 289 | 3-[2-(2-furylmethylamino)imidazo[2,1-p][1,3,4]thiadiazol-5-yl]-N,N-dimethyl-benzamide | 2.46273 | 2.59 | 699_0144_0349 |

TABLE 3-continued

Primary screen- initial compounds.

| Structure | | IUPAC name | IC50 FYN (μM) | logP (consensus) | Compound ID. |
|---|---|---|---|---|---|
| 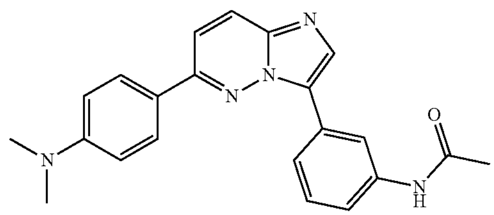 [SMILES: CC(=O)Nc1cccc(-c2cnc3ccc(-c4ccc(N(C)C)cc4)nn23)c1] | 290 | N-[3-[6-(4-dimethylamino-phenyl)imidazo[1,2-a]pyridazin-3-yl]phenyl]acetamide | 1.09863 | 3.60 | 828_0081_0004 |
| 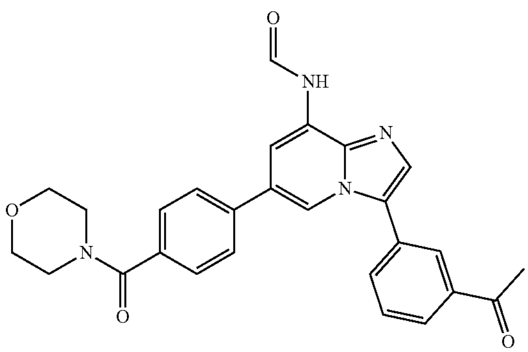 [SMILES: CC(=O)c1cccc(-c2cnc3c(NC=O)cc(-c4ccc(C(=O)N5CCOCC5)cc4)cn23)c1] | 291 | N-[3-(3-acetylphenyl)-6-[4-(morpholine-4-carbonyl)phenyl]imidazo[1,2-a]pyridin-8-yl]formamide | 2.99487 | 1.80 | 788_4145_0337 |
| 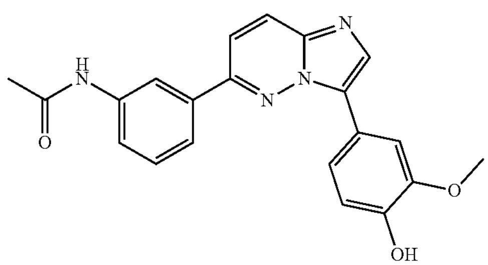 [SMILES: COc1cc(-c2cnc3ccc(-c4cccc(NC(C)=O)c4)nn23)ccc1O] | 292 | N-[3-[3-(4-hydroxy-3-methoxy-phenyl)imidazo[1,2-b]pyridazin-6-yl]phenyl]acetamide | 0.10208 | 3.03 | 828_0314_0081 |
| 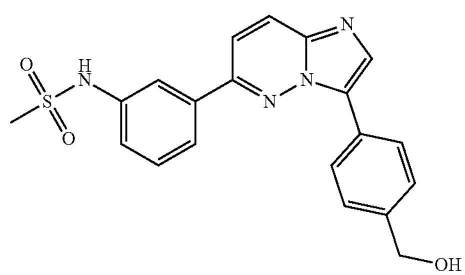 [SMILES: CS(=O)(=O)Nc1cccc(-c2ccc3ncc(-c4ccc(CO)cc4)n3n2)c1] | 293 | N-[3-[3-[4-(hydroxymethyl)phenyl]imidazo[1,2-b]pyridazin-6-yl]phenyl]methanesulfonamide | 0.83024 | 1.86 | 828_0285_6488 |
| 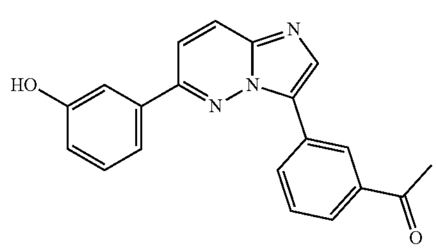 [SMILES: CC(=O)c1cccc(-c2cnc3ccc(-c4cccc(O)c4)nn23)c1] | 294 | 1-[3-[6-(3-hydroxyphenyl)imidazo[1,2-a]pyridazin-3-yl]phenyl]ethanone | 0.99396 | 3.51 | 828_4145_0284 |

TABLE 3-continued

Primary screen- initial compounds.

| Structure | | IUPAC name | IC50 FYN (μM) | logP (consensus) | Compound ID. |
|---|---|---|---|---|---|
| 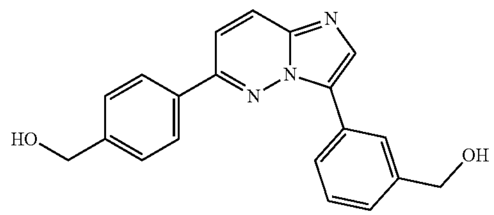 [SMILES: OCc1ccc(-c2ccc3ncc(-c4cccc(CO)c4)n3n2)cc1] | 295 | [4-[3-[3-(hydroxymethyl) phenyl]imidazo [1,2-b]pyridazin-6-yl]phenyl] methanol | 2.22994 | 2.72 | 828_0291_0285 |
| 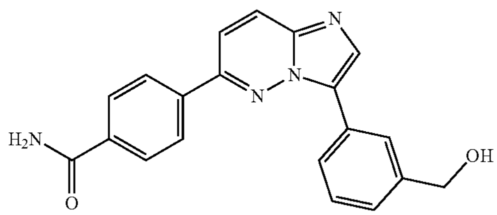 [SMILES: NC(=O)c1ccc(-c2ccc3ncc(-c4cccc(CO)c4)n3n2)cc1] | 296 | 4-[3-[3-(hydroxymethyl) phenyl]imidazo [1,2-b]pyridazin-6-yl]benzamide | 1.89185 | 2.34 | 828_0291_0346 |
| 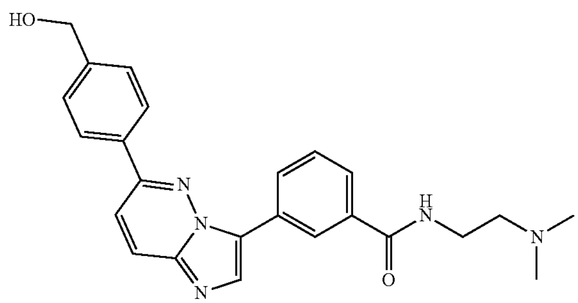 [SMILES: CN(C)CCNC(=O)c1cccc(-c2cnc3ccc(-c4ccc(CO)cc4)nn23)c1] | 297 | N-(2-dimethylamino-ethyl)-3-[6-[4-(hydroxymethyl) phenyl]imidazo [1,2-b]pyridazin-3-yl]benzamide | 1.47637 | 2.58 | 828_0176_0285 |
| 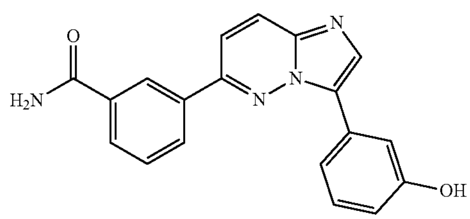 [SMILES: NC(=O)c1cccc(-c2ccc3ncc(-c4cccc(O)c4)n3n2)c1] | 298 | 3-[3-(3-hydroxyphenyl) imidazo[1,2-b]pyridazin-6-yl]benzamide | 0.31104 | 2.80 | 828_0284_0347 |
| 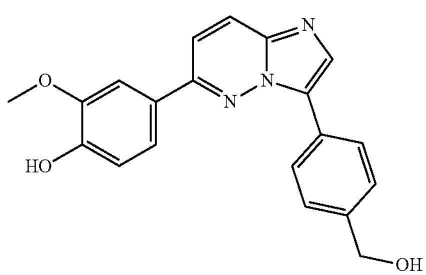 [SMILES: COc1cc(-c2ccc3ncc(-c4ccc(CO)cc4)n3n2)ccc1O] | 299 | 4-[3-[4-(hydroxymethyl) phenyl]imidazo [1,2-b]pyridazin-6-yl]-2-methoxy-phenol | 0.22297 | 3.02 | 828_0285_0314 |
| 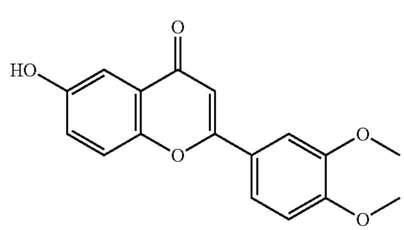 [SMILES: COc1ccc(-c2cc(=O)c3cc(O)ccc3o2)cc1OC] | 300 | 2-(3,4-dimethoxy-phenyl)-6-hydroxy-chromen-4-one | 8.95228 | 2.35 | DT2012-0347380 |

TABLE 3-continued

Primary screen- initial compounds.

| Structure | | IUPAC name | IC50 FYN (μM) | logP (consensus) | Compound ID. |
|---|---|---|---|---|---|
| 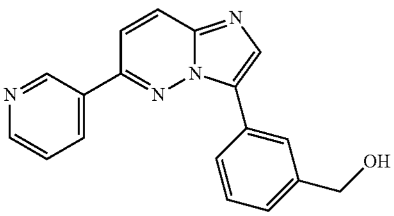 [SMILES: OCc1cccc(-c2cnc3ccc(-c4cccnc4)nn23)c1] | 301 | [3-[6-(3-pyridyl)imidazo[1,2-b]pyridazin-3-yl]phenyl]methanol | 2.03689 | 2.27 | 828_0291_0071 |
| 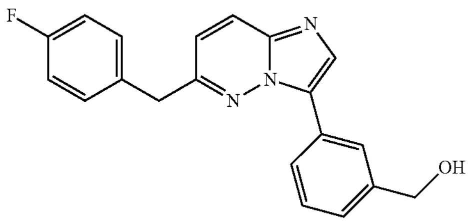 [SMILES: OCc1cccc(-c2cnc3ccc(Cc4ccc(F)cc4)nn23)c1] | 302 | [3-[6-[(4-fluorophenyl)methyl]imidazo[1,2-b]pyridazin-3-yl]phenyl]methanol | 3.9747 | 3.56 | 828_0291_6370 |
| 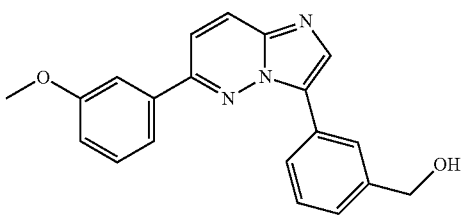 [SMILES: COc1cccc(-c2ccc3ncc(-c4cccc(CO)c4)n3n2)c1] | 303 | [3-[6-(3-methoxyphenyl)imidazo[1,2-b]pyridazin-3-yl]phenyl]methanol | 2.74495 | 3.33 | 828_0291_4140 |
| 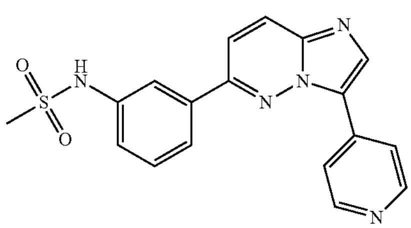 [SMILES: CS(=O)(=O)Nc1cccc(-c2ccc3ncc(-c4ccncc4)n3n2)c1] | 304 | N-[3-[3-(4-pyridyl)imidazo[1,2-b]pyridazin-6-yl]phenyl]methanesulfonamide | 0.29796 | 1.41 | 828_0069_6488 |
| 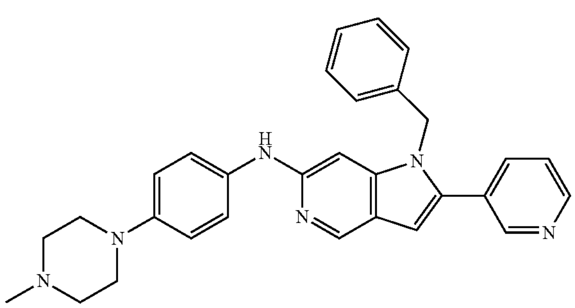 [SMILES: CN1CCN(c2ccc(Nc3cc4c(cn3)cc(-c3cccnc3)n4Cc3ccccc3)cc2)CC1] | 305 | 1-benzyl-N-[4-(4-methyl-piperazin-1-yl)phenyl]-2-(3-pyridyl)pyrrolo[3,2-c]pyridin-6-amine | 13.73604 | 5.14 | 809_2675_6001_0091 |
| 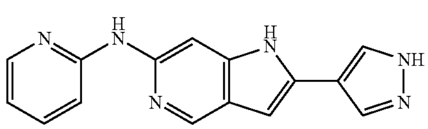 [SMILES: c1ccc(Nc2cc3[nH]c(-c4cn[nH]c4)cc3cn2)nc1] | 306 | 2-(1H-pyrazol-4-yl)-N-(2-pyridyl)-1H-pyrrolo[3,2-c]pyridin-6-amine | 7.566 | 2.14 | 809_2678_0263_0259 |
| 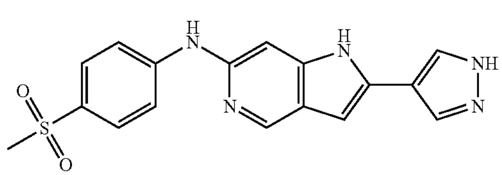 [SMILES: CS(=O)(=O)c1ccc(Nc2cc3[nH]c(-c4cn[nH]c4)cc3cn2)cc1] | 307 | N-(4-methylsulfonylphenyl)-2-(1H-pyrazol-4-yl)-1H-pyrrolo[3,2-c]pyridin-6-amine | 4.77594 | 1.60 | 809_2678_0263_9248 |

TABLE 3-continued

Primary screen- initial compounds.

| Structure | | IUPAC name | IC50 FYN (μM) | logP (consensus) | Compound ID. |
|---|---|---|---|---|---|
| 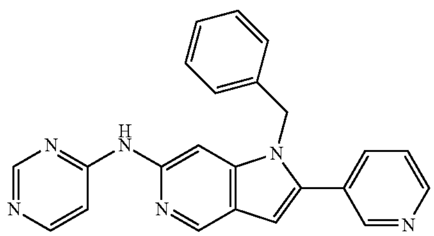 [SMILES: c1ccc(Cn2c(-c3cccnc3)cc3cnc(Nc4ccncn4)cc32)cc1] | 308 | 1-benzyl-2-(3-pyridyl)-N-pyrimidin-4-yl-pyrrolo[3,2-c]pyridin-6-amine | 6.84653 | 3.86 | 809_2675_6001_6410 |
| 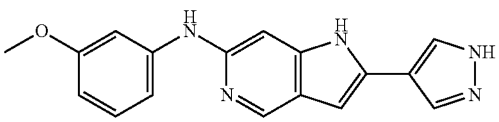 [SMILES: COc1cccc(Nc2cc3[nH]c(-c4cn[nH]c4)cc3cn2)c1] | 309 | N-(3-methoxyphenyl)-2-(1H-pyrazol-4-yl)-1H-pyrrolo[3,2-c]pyridin-6-amine | 16.58236 | 2.60 | 809_2678_0263_0026 |
| 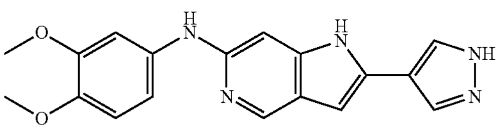 [SMILES: COc1ccc(Nc2cc3[nH]c(-c4cn[nH]c4)cc3cn2)cc1OC] | 310 | N-(3,4-dimethoxy-phenyl)-2-(1H-pyrazol-4-yl)-1H-pyrrolo[3,2-2]pyridin-6-amine | 12.71137 | 2.44 | 809_2678_0263_0036 |
| 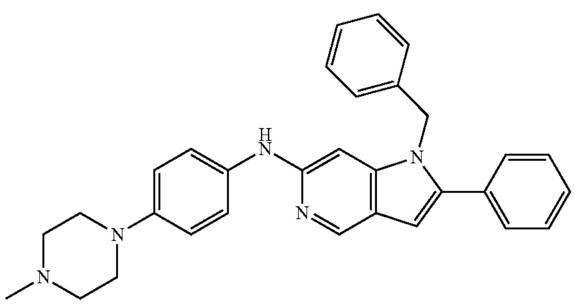 [SMILES: CN1CCN(c2ccc(Nc3cc4c(cn3)cc(-c3ccccc3)n4Cc3ccccc3)cc2)CC1] | 311 | 1-benzyl-N-[4-(4-methylpiperazin-1-yl)phenyl]-2-phenyl-pyrrolo[3,2-c]pyridin-6-amine | 15.018 | 6.36 | 809_9960_6001_0091 |
| 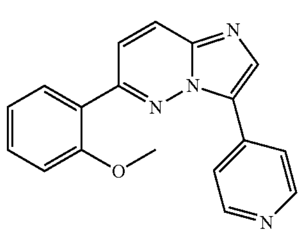 [SMILES: COc1ccccc1-c1ccc2ncc(-c3ccncc3)n2n1] | 312 | 6-(2-methoxyphenyl)-3-(4-pyridyl)imidazo[1,2-b]pyridazine | 0.58491 | 2.88 | 828_0069_0083 |
| 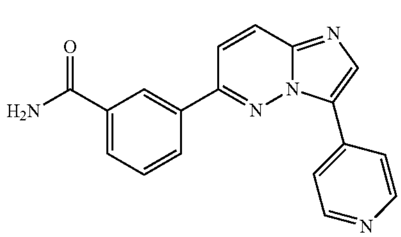 [SMILES: NC(=O)c1cccc(-c2ccc3ncc(-c4ccncc4)n3n2)c1] | 313 | 3-[3-(4-pyridyl)imidazo[1,2-b]pyridazin-6-yl]benzamide | 1.2024 | 1.89 | 828_0069_0347 |

TABLE 3-continued

Primary screen- initial compounds.

| Structure | | IUPAC name | IC50 FYN (μM) | logP (consensus) | Compound ID. |
|---|---|---|---|---|---|
| 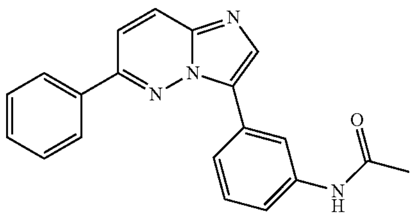 [SMILES: CC(=O)Nc1cccc(-c2cnc3ccc(-c4ccccc4)nn23)c1] | 314 | N-[3-(6-phenylimidazo[1,2-b]pyridazin-3-yl)phenyl]acetamide | 0.77278 | 3.49 | 828_0081_0061 |
| 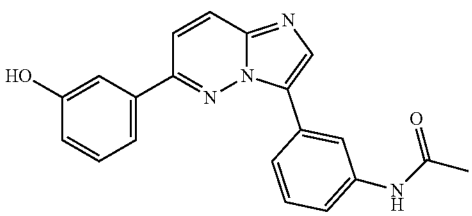 [SMILES: CC(=O)Nc1cccc(-c2cnc3ccc(-c4cccc(O)c4)nn23)c1] | 315 | N-[3-[6-(3-hydroxyphenyl)imidazo[1,2-b]pyridazin-3-yl]phenyl]acetamide | 1.0711 | 3.19 | 828_0081_0284 |
| 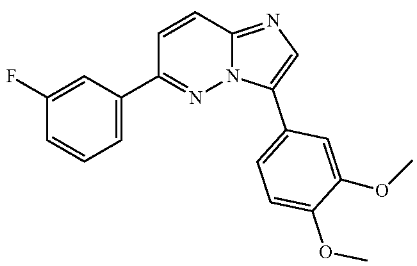 [SMILES: COc1ccc(-c2cnc3ccc(-c4cccc(F)c4)nn23)cc1OC] | 316 | 3-(3,4-dimethoxyphenyl)-6-(3-fluorophenyl)imidazo[1,2-b]pyridazine | 1.0392 | 4.08 | 828_0079_0313 |
| 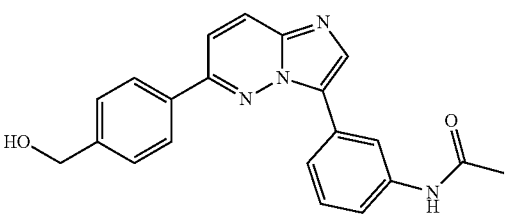 [SMILES: CC(=O)Nc1cccc(-c2cnc3ccc(-c4ccc(CO)cc4)nn23)c1] | 317 | N-[3-[6-[4-(hydroxymethyl)phenyl]imidazo[1,2-b]pyridazin-3-yl]phenyl]acetamide | 0.49363 | 2.72 | 828_0081_0285 |
| 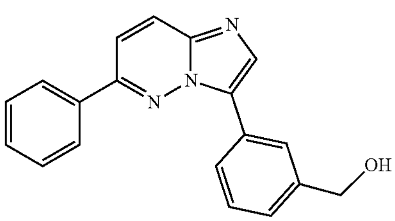 [SMILES: OCc1cccc(-c2cnc3ccc(-c4ccccc4)nn23)c1] | 318 | [3-(6-phenylimidazo[1,2-b]pyridazin-3-yl)phenyl]methanol | 1.74526 | 3.49 | 828_0291_0061 |
| 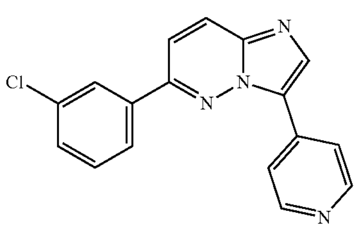 [SMILES: Clc1cccc(-c2ccc3ncc(-c4ccncc4)n3n2)c1] | 319 | 6-(3-chlorophenyl)-3-(4-pyridyl)imidazo[1,2-b]pyridazine | 0.25819 | 3.64 | 828_0069_0279 |

TABLE 3-continued

Primary screen- initial compounds.

| Structure | | IUPAC name | IC50 FYN (μM) | logP (consensus) | Compound ID. |
|---|---|---|---|---|---|
| 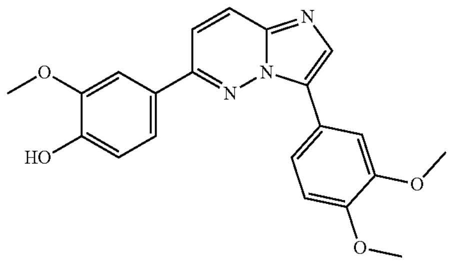 | 320 | 4-[3-(3,4-dimethoxyphenyl)imidazo[1,2-b]pyridazin-6-yl]-2-methoxyphenol | 0.22231 | 3.48 | 828_0079_0314 |
| 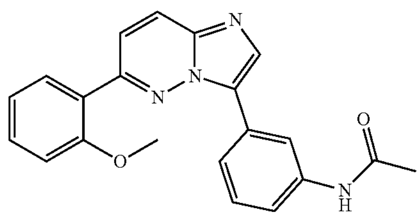 [SMILES: COc1ccccc1-c1ccc2ncc(-c3cccc(NC(C)=O)c3)n2n1] | 321 | N-[3-[6-(2-methoxyphenyl)imidazo[1,2-b]pyridazin-3-yl]phenyl]acetamide | 2.85447 | 3.33 | 828_0081_0083 |
| 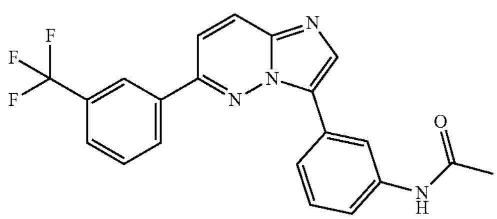 [SMILES: CC(=O)Nc1cccc(-c2cnc3ccc(-c4cccc(C(F)(F)F)c4)nn23)c1] | 322 | N-[3-[6-[3-(trifluoromethyl)phenyl]imidazo[1,2-b]pyridazin-3-yl]phenyl]acetamide | 1.6027 | 4.37 | 828_0081_0312 |
| 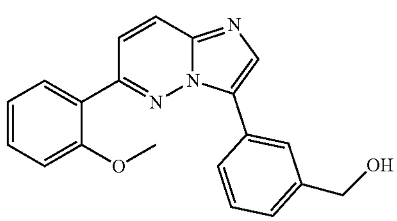 [SMILES: COc1ccccc1-c1ccc2ncc(-c3cccc(CO)c3)n2n1] | 323 | [3-[6-(2-methoxyphenyl)imidazo[1,2-b]pyridazin-3-yl]phenyl]methanol | 1.06972 | 3.33 | 828_0291_0083 |
| 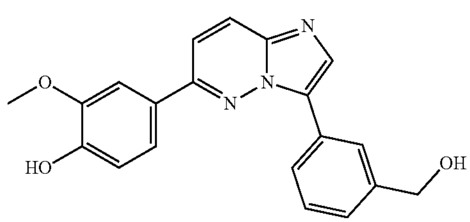 [SMILES: COc1cc(-c2ccc3ncc(-c4cccc(CO)c4)n3n2)ccc1O] | 324 | 4-[3-[3-(hydroxymethyl)phenyl]imidazo[1,2-b]pyridazin-6-yl]-2-methoxyphenol | 0.15309 | 3.02 | 828_0291_0314 |
| 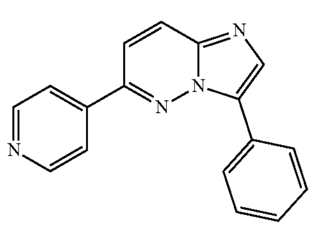 [SMILES: c1ccc(-c2cnc3ccc(-c4ccncc4)nn23)cc1] | 325 | 3-phenyl-6-(4-pyridyl)imidazo[1,2-b]pyridazine | 6.92543 | 3.04 | 828_0061_0069 |

TABLE 3-continued

Primary screen- initial compounds.

| Structure | | IUPAC name | IC50 FYN (μM) | logP (consensus) | Compound ID. |
|---|---|---|---|---|---|
| 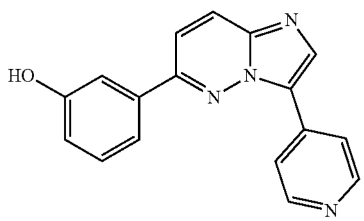 [SMILES: Oc1cccc(-c2ccc3ncc(-c4ccncc4)n3n2)c1] | 326 | 3-[3-(4-pyridyl)imidazo[1,2-b]pyridazin-6-yl]phenol | 0.22268 | 2.73 | 828_0069_0284 |
| 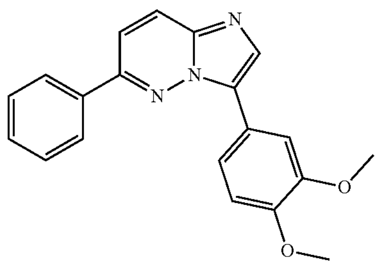 [SMILES: COc1ccc(-c2cnc3ccc(-c4ccccc4)nn23)cc1OC] | 327 | 3-(3,4-dimethoxyphenyl)-6-phenyl-imidazo[1,2-b]pyridazine | 0.42017 | 3.94 | 828_0079_0061 |
| 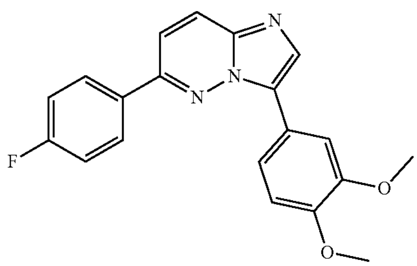 [SMILES: COc1ccc(-c2cnc3ccc(-c4ccc(F)cc4)nn23)cc1OC] | 328 | 3-(3,4-dimethoxyphenyl)-6-(4-fluorophenyl)imidazo[1,2-b]pyridazine | 1.33171 | 4.08 | 828_0079_0339 |
| 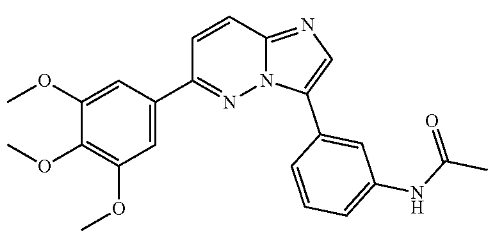 [SMILES: COc1cc(-c2ccc3ncc(-c4cccc(NC(C)=O)c4)n3n2)cc(OC)c1OC] | 329 | N-[3-[6-(3,4,5-trimethoxyphenyl)imidazo[1,2-b]pyridazin-3-yl]phenyl]acetamide | 3.13438 | 3.02 | 828_0081_0087 |
| 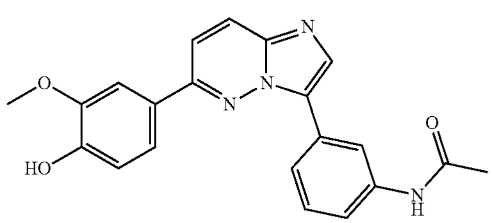 [SMILES: COc1cc(-c2ccc3ncc(-c4cccc(NC(C)=O)c4)n3n2)ccc1O] | 330 | N-[3-[6-(4-hydroxy-3-methoxyphenyl)imidazo[1,2-b]pyridazin-3-yl]phenyl]acetamide | 0.09296 | 3.03 | 828_0081_0314 |
| 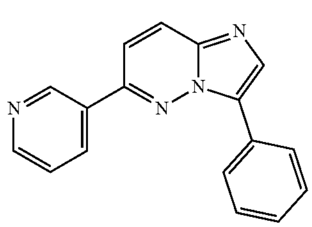 [SMILES: c1ccc(-c2cnc3ccc(-c4cccnc4)nn23)cc1] | 331 | 3-phenyl-6-(3-pyridyl)imidazo[1,2-b]pyridazine | 3.84274 | 3.04 | 828_0061_0071 |

TABLE 3-continued

Primary screen- initial compounds.

| Structure | | IUPAC name | IC50 FYN (μM) | logP (consensus) | Compound ID. |
|---|---|---|---|---|---|
| 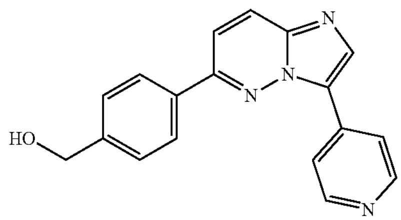 [SMILES: OCc1ccc(-c2ccc3ncc(-c4ccncc4)n3n2)cc1] | 332 | 4-[3-(4-pyridyl)imidazo[1,2-b]pyridazin-6-yl]phenyl]methanol | 0.2553 | 2.27 | 828_0069_0285 |
| 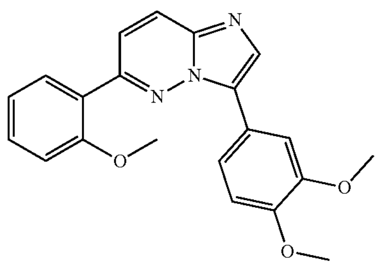 [SMILES: COc1ccc(-c2cnc3ccc(-c4ccccc4OC)nn23)cc1OC] | 333 | 3-(3,4-dimethoxyphenyl)-6-(2-methoxyphenyl)imidazo[1,2-b]pyridazine | 3.12222 | 3.78 | 828_0079_0083 |
| 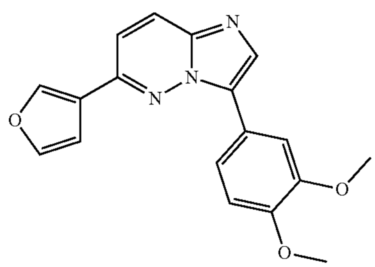 [SMILES: COc1ccc(-c2cnc3ccc(-c4ccoc4)nn23)cc1OC] | 334 | 3-(3,4-dimethoxyphenyl)-6-(3-furyl)imidazo[1,2-b]pyridazine | 0.98263 | 3.08 | 828_0079_0343 |
| 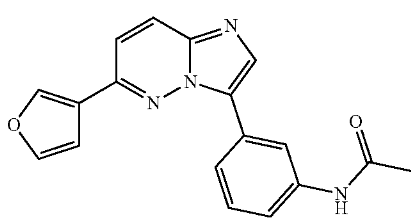 [SMILES: CC(=O)Nc1cccc(-c2cnc3ccc(-c4ccoc4)nn23)c1] | 335 | N-[3-[6-(3-furyl)imidazo[1,2-b]pyridazin-3-yl]phenyl]acetamide | 1.2569 | 2.63 | 828_0081_0343 |
| 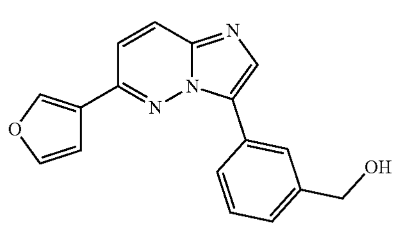 [SMILES: OCc1cccc(-c2cnc3ccc(-c4ccoc4)nn23)c1] | 336 | [3-[6-(3-furyl)imidazo[1,2-b]pyridazin-3-yl]phenyl]methanol | 3.99398 | 2.63 | 828_0291_0343 |
| 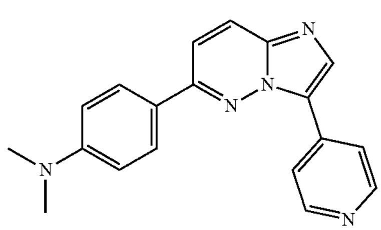 [SMILES: CN(C)c1ccc(-c2ccc3ncc(-c4ccncc4)n3n2)cc1] | 337 | N,N-dimethyl-4-[3-(4-pyridyl)imidazo[1,2-b]pyridazin-6-yl]aniline | 0.39834 | 3.14 | 828_0069_0004 |

TABLE 3-continued

Primary screen- initial compounds.

| Structure | | IUPAC name | IC50 FYN (μM) | logP (consensus) | Compound ID. |
|---|---|---|---|---|---|
| 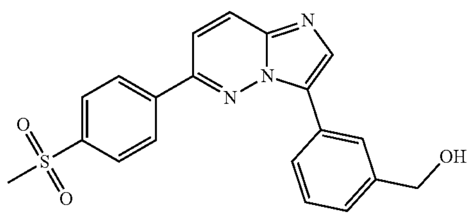 [SMILES: CS(=O)(=O)c1ccc(-c2ccc3ncc(-c4cccc(CO)c4)n3n2)cc1] | 338 | [3-[6-(4-methylsulfonyl-phenyl)imidazo[1,2-b]pyridazin-3-yl]phenyl] methanol | 3.03776 | 2.33 | 828_0291_0174 |
| 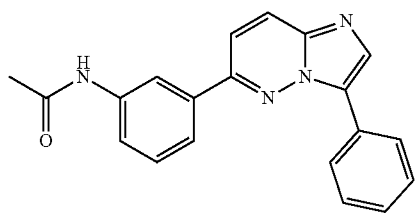 [SMILES: CC(=O)Nc1cccc(-c2ccc3ncc(-c4ccccc4)n3n2)c1] | 339 | N-[3-(3-phenylimidazo[1,2-b]pyridazin-6-yl)phenyl] acetamide | 3.66176 | 3.49 | 828_0061_0081 |
| 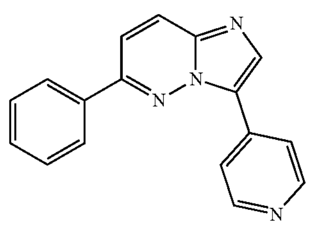 [SMILES: c1ccc(-c2ccc3ncc(-c4ccncc4)n3n2)cc1] | 340 | 6-phenyl-3-(4-pyridyl)imidazo[1,2-b]pyridazine | 0.22894 | 3.04 | 828_0069_0061 |
| 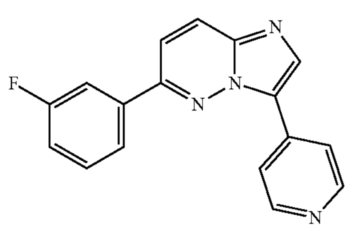 [SMILES: Fc1cccc(-c2ccc3ncc(-c4ccncc4)n3n2)c1] | 341 | 6-(3-fluorophenyl)-3-(4-pyridyl)imidazo[1,2-b]pyridazine | 0.35611 | 3.18 | 828_0069_0313 |
| 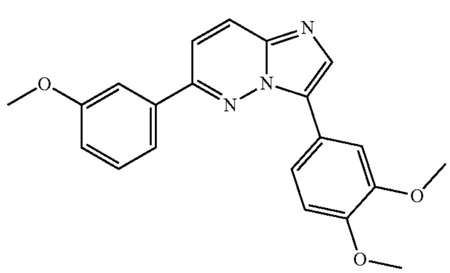 | 342 | 3-(3,4-dimethoxy-phenyl)-6-(3-methoxyphenyl)imidazo[1,2-b]pyridazine | 0.95169 | 3.78 | 828_0079_4140 |
| 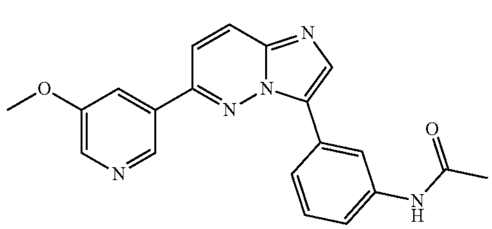 [SMILES: COc1cncc(-c2ccc3ncc(-c4cccc(NC(C)=O)c4)n3n2)c1] | 343 | N-[3-[6-(5-methoxy-3-pyridyl)imidazo[1,2-b]pyridazin-3-yl]phenyl] acetamide | 0.614 | 2.12 | 828_0081_0196 |

TABLE 3-continued

Primary screen- initial compounds.

| Structure | | IUPAC name | IC50 FYN (µM) | logP (consensus) | Compound ID. |
|---|---|---|---|---|---|
| 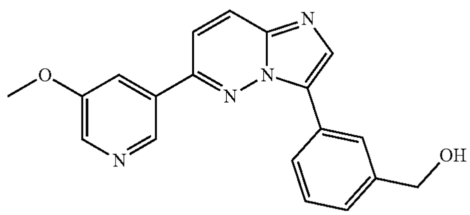 [SMILES: COc1cncc(-c2ccc3ncc(-c4cccc(CO)c4)n3n2)c1] | 344 | 3-[6-(5-methoxy-3-pyridyl)imidazo[1,2-b]pyridazin-3-yl]phenyl]methanol | 2.14052 | 2.11 | 828_0291_0196 |
| 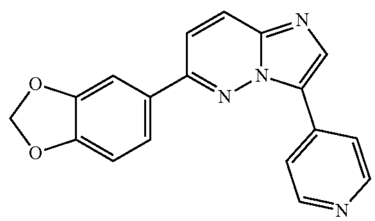 [SMILES: c1cc(-c2cnc3ccc(-c4ccc5c(c4)OCO5)nn23)ccn1] | 345 | 6-(1,3-benzodioxol-5-yl)-3-(4-pyridyl)imidazo[1,2-b]pyridazine | 0.21745 | 2.66 | 828_0069_0068 |
| 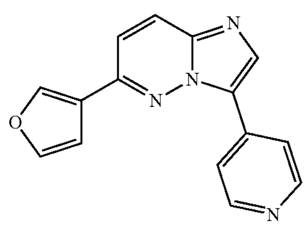 [SMILES: c1cc(-c2cnc3ccc(-c4ccoc4)nn23)ccn1] | 346 | 6-(3-furyl)-3-(4-pyridyl)imidazo[1,2-b]pyridazine | 1.02049 | 2.18 | 828_0069_0343 |
| 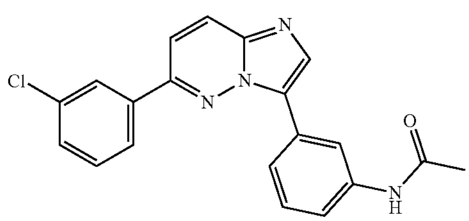 [SMILES: CC(=O)Nc1cccc(-c2cnc3ccc(-c4cccc(Cl)c4)nn23)c1] | 347 | N-[3-[6-(3-chlorophenyl)imidazo[1,2-b]pyridazin-3-yl]phenyl]acetamide | 0.3705 | 4.10 | 828_0081_0279 |
| 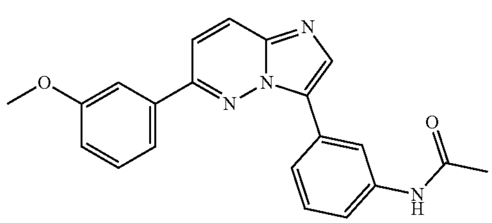 [SMILES: COc1cccc(-c2ccc3ncc(-c4cccc(NC(C)=O)c4)n3n2)c1] | 348 | N-[3-[6-(3-methoxyphenyl)imidazo[1,2-b]pyridazin-3-yl]phenyl]acetamide | 0.40863 | 3.33 | 828_0081_4140 |
| 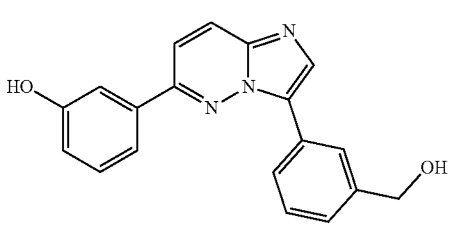 [SMILES: OCc1cccc(-c2cnc3ccc(-c4cccc(O)c4)nn23)c1] | 349 | 3-[3-[3-(hydroxymethyl)phenyl]imidazo[1,2-b]pyridazin-6-yl]phenol | 0.95381 | 3.18 | 828_0291_0284 |

TABLE 3-continued

Primary screen- initial compounds.

| Structure | | IUPAC name | IC50 FYN (μM) | logP (consensus) | Compound ID. |
|---|---|---|---|---|---|
| 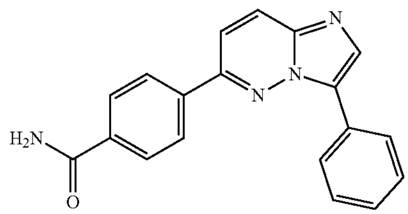 [SMILES: NC(=O)c1ccc(-c2ccc3ncc(-c4ccccc4)n3n2)cc1] | 350 | 4-(3-phenylimidazo[1,2-b]pyridazin-6-yl)benzamide | 2.14265 | 3.10 | 828_0061_0346 |
| 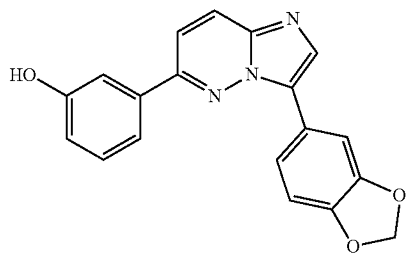 [SMILES: Oc1cccc(-c2ccc3ncc(-c4ccc5c(c4)OCO5)n3n2)c1] | 351 | 3-[3-(1,3-benzodioxol-5-yl)imidazo[1,2-b]pyridazin-6-yl]phenol | 0.91497 | 3.57 | 828_0068_0284 |
| 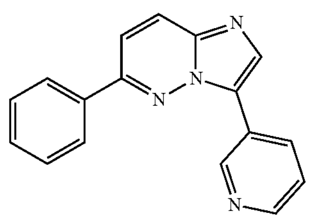 [SMILES: c1ccc(-c2ccc3ncc(-c4cccnc4)n3n2)cc1] | 352 | 6-phenyl-3-(3-pyridyl)imidazo[1,2-b]pyridazine | 1.94131 | 3.04 | 828_0071_0061 |
| 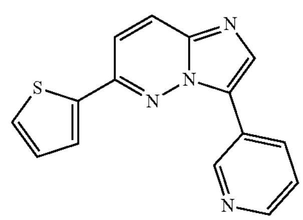 [SMILES: c1cncc(-c2cnc3ccc(-c4cccs4)nn23)c1] | 353 | 3-(3-pyridyl)-6-(2-thienyl)imidazo[1,2-b]pyridazine | 0.34617 | 2.81 | 828_0071_4147 |
| 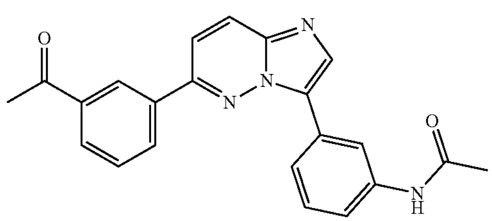 [SMILES: CC(=O)Nc1cccc(-c2cnc3ccc(-c4cccc(C(C)=O)c4)nn23)c1] | 354 | N-[3-[6-(3-acetylphenyl)imidazo[1,2-b]pyridazin-3-yl]phenyl]acetamide | 0.46574 | 3.05 | 828_0081_4145 |
| 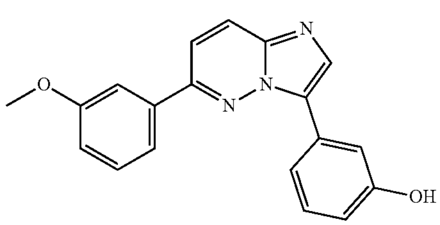 [SMILES: COc1cccc(-c2ccc3ncc(-c4cccc(O)c4)n3n2)c1] | 355 | 3-[6-(3-methoxyphenyl)imidazo[1,2-b]pyridazin-3-yl]phenol | 1.2357 | 3.79 | 828_0284_4140 |

TABLE 3-continued

Primary screen- initial compounds.

| Structure | | IUPAC name | IC50 FYN (µM) | logP (consensus) | Compound ID. |
|---|---|---|---|---|---|
| 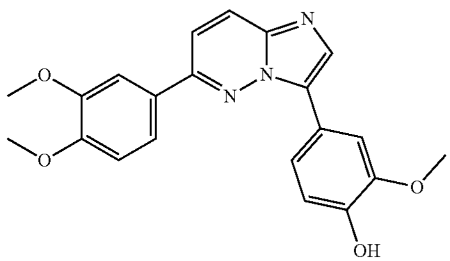 | 356 | 4-[6-(3,4-dimethoxyphenyl)imidazo[1,2-b]pyridazin-3-yl]-2-methoxyphenol | 0.04451 | 3.48 | 828_0314_0079 |
| 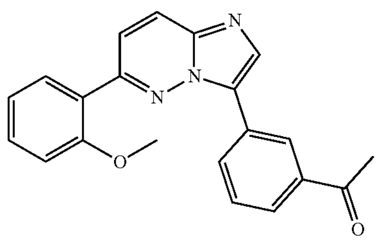 [SMILES: COc1ccccc1-c1ccc2ncc(-c3cccc(C(C)=O)c3)n2n1] | 357 | 1-[3-[6-(2-methoxyphenyl)imidazo[1,2-b]pyridazin-3-yl]phenyl]ethanone | 2.3343 | 3.65 | 828_4145_0083 |
| 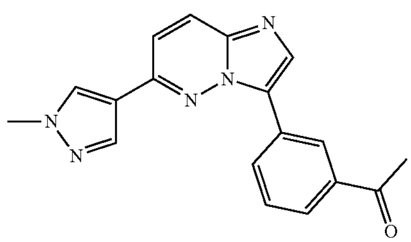 [SMILES: CC(=O)c1cccc(-c2cnc3ccc(-c4cnn(C)c4)nn23)c1] | 358 | 1-[3-[6-(1-methylpyrazol-4-yl)imidazo[1,2-3]pyridazin-3-yl]phenyl]ethanone | 0.37322 | 2.24 | 828_4145_7468 |
| 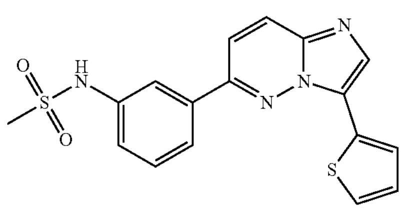 [SMILES: CS(=O)(=O)Nc1cccc(-c2ccc3ncc(-c4cccs4)n3n2)c1] | 359 | N-[3-[3-(2-thienyl)imidazo[1,2-b]pyridazin-6-yl]phenyl]methanesulfonamide | 1.20815 | 2.40 | 828_4147_6488 |
| 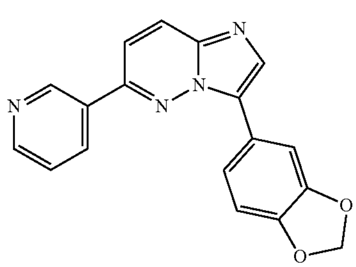 [SMILES: c1cncc(-c2ccc3ncc(-c4ccc5c(c4)OCO5)n3n2)c1] | 360 | 3-(1,3-benzodioxol-5-yl)-6-(3-pyridyl)imidazo[1,2-b]pyridazine | 0.68757 | 2.66 | 828_0068_0071 |
| 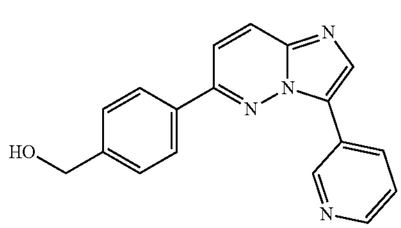 [SMILES: OCc1ccc(-c2ccc3ncc(-c4cccnc4)n3n2)cc1] | 361 | [4-[3-(3-pyridyl)imidazo[1,2-b]pyridazin-6-yl]phenyl]methanol | 2.9094 | 2.27 | 828_0071_0285 |

TABLE 3-continued

Primary screen- initial compounds.

| Structure | | IUPAC name | IC50 FYN (μM) | logP (consensus) | Compound ID. |
|---|---|---|---|---|---|
| 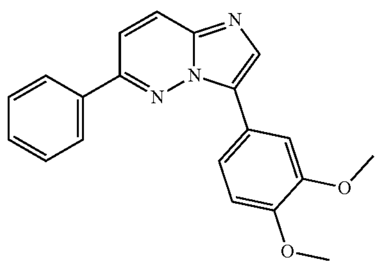 [SMILES: COc1ccc(-c2cnc3ccc(-c4ccccc4)nn23)cc1OC] | 362 | 6-benzyl-3-(3,4-dimethoxyphenyl)imidazo[1,2-b]pyridazine | 0.97448 | 3.87 | 828_0079_6001 |
| 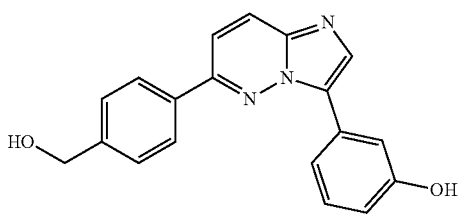 [SMILES: OCc1ccc(-c2ccc3ncc(-c4cccc(O)c4)n3n2)cc1] | 363 | 3-[6-[4-(hydroxymethyl)phenyl]imidazo[1,2-b]pyridazin-3-yl]phenol | 0.28545 | 3.18 | 828_0284_0285 |
| 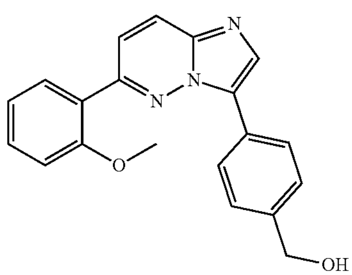 [SMILES: COc1ccccc1-c1ccc2ncc(-c3ccc(CO)cc3)n2n1] | 364 | 4-[6-(2-methoxyphenyl)imidazo[1,2-3]pyridazin-3-yl]phenyl]methanol | 3.90029 | 3.33 | 828_0285_0083 |
| 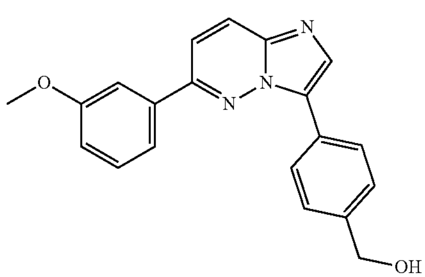 [SMILES: COc1cccc(-c2ccc3ncc(-c4ccc(CO)cc4)n3n2)c1] | 365 | [4-[6-(3-methoxyphenyl)imidazo[1,2-b]pyridazin-3-yl]phenyl]methanol | 1.55838 | 3.33 | 828_0285_4140 |
| 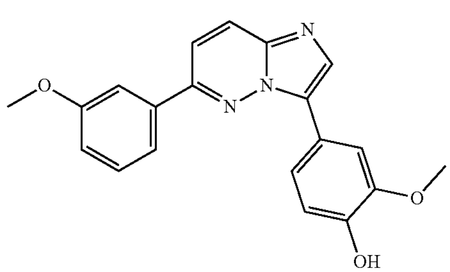 | 366 | 2-methoxy-4-[6-(3-methoxyphenyl)imidazo[1,2-b]pyridazin-3-yl]phenol | 0.22071 | 3.63 | 828_0314_4140 |

TABLE 3-continued

Primary screen- initial compounds.

| Structure | | IUPAC name | IC50 FYN (μM) | logP (consensus) | Compound ID. |
|---|---|---|---|---|---|
| 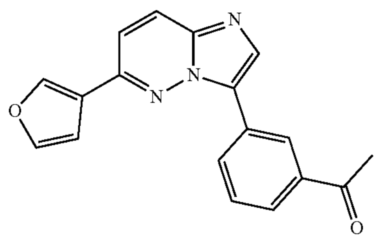 [SMILES: CC(=O)c1cccc(-c2cnc3ccc(-c4ccoc4)nn23)c1] | 367 | 1-[3-[6-(3-furyl)imidazo[1,2-b]pyridazin-3-yl]phenyl]ethanone | 3.4398 | 2.95 | 828_4145_0343 |
| 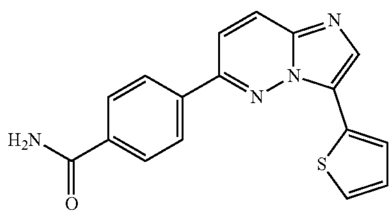 [SMILES: NC(=O)c1ccc(-c2ccc3ncc(-c4cccs4)n3n2)cc1] | 368 | 4-[3-(2-thienyl)imidazo[1,2-b]pyridazin-6-yl]benzamide | 0.95101 | 2.88 | 828_4147_0346 |
| 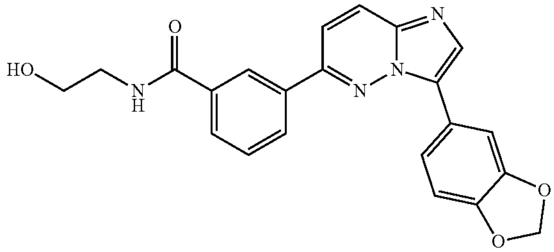 [SMILES: O=C(NCCO)c1cccc(-c2ccc3ncc(-c4ccc5c(c4)OCO5)n3n2)c1] | 369 | 3-[3-(1,3-benzodioxol-5-yl)imidazo[1,2-b]pyridazin-6-yl]-N-(2-hydroxyethyl)benzamide | 0.36748 | 2.26 | 828_0068_0192 |
| 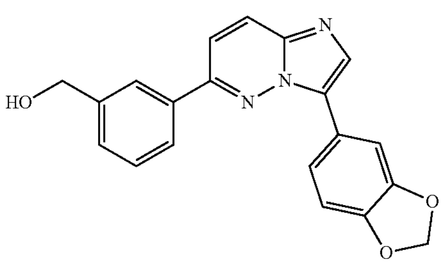 [SMILES: OCc1cccc(-c2ccc3ncc(-c4ccc5c(c4)OCO5)n3n2)c1] | 370 | [3-[3-(1,3-benzodioxol-5-yl)imidazo[1,2-b]pyridazin-6-yl]phenyl]methanol | 0.33166 | 3.11 | 828_0068_0291 |
| 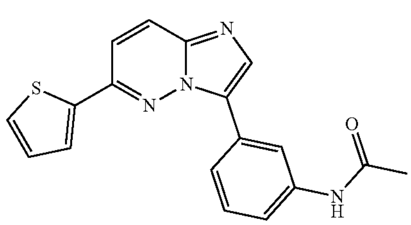 [SMILES: CC(=O)Nc1cccc(-c2cnc3ccc(-c4cccs4)nn23)c1] | 371 | N-[3-[6-(2-thienyl)imidazo[1,2-b]pyridazin-3-yl]phenyl]acetamide | 0.20995 | 3.27 | 828_0081_4147 |
| 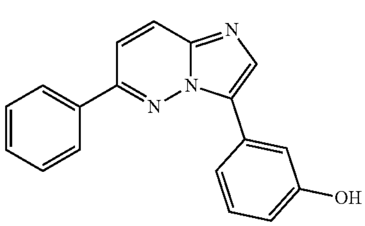 [SMILES: Oc1cccc(-c2cnc3ccc(-c4ccccc4)nn23)c1] | 372 | 3-(6-phenylimidazo[1,2-b]pyridazin-3-yl)phenol | 0.89352 | 3.95 | 828_0284_0061 |

TABLE 3-continued

Primary screen- initial compounds.

| Structure | | IUPAC name | IC50 FYN (μM) | logP (consensus) | Compound ID. |
|---|---|---|---|---|---|
| 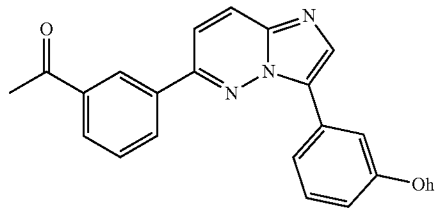 | 373 | 1-[3-[3-(3-hydroxyphenyl)imidazo[1,2-b]pyridazin-6-yl]phenyl]ethanone | 1.60026 | 3.51 | 828_0284_4145 |
| 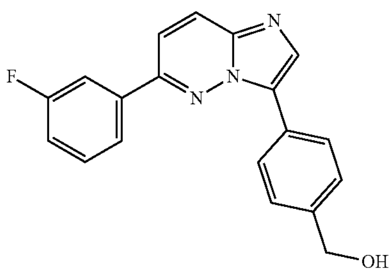 [SMILES: OCc1ccc(-c2cnc3ccc(-c4cccc(F)c4)nn23)cc1] | 374 | [4-[6-(3-fluorophenyl)imidazo[1,2-b]pyridazin-3-yl]phenyl]methanol | 2.95859 | 3.63 | 828_0285_0313 |
| 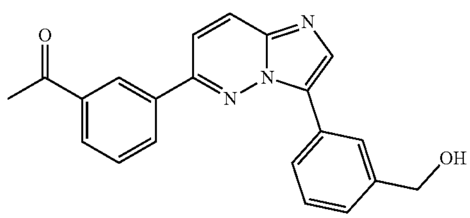 [SMILES: CC(=O)c1cccc(-c2ccc3ncc(-c4cccc(CO)c4)n3n2)c1] | 375 | 1-[3-[3-[3-(hydroxymethyl)phenyl]imidazo[1,2-b]pyridazin-6-yl]phenyl]ethanone | 2.16824 | 3.04 | 828_0291_4145 |
| 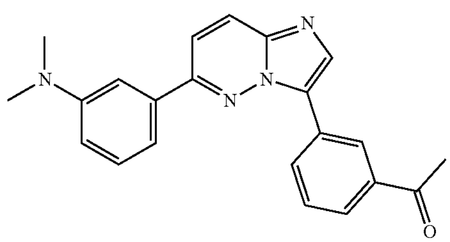 [SMILES: CC(=O)c1cccc(-c2cnc3ccc(-c4cccc(N(C)C)c4)nn23)c1] | 376 | 1-[3-[6-[3-(dimethylamino)phenyl]imidazo[1,2-b]pyridazin-3-yl]phenyl]ethanone | 0.88623 | 3.92 | 828_4145_0135 |
| 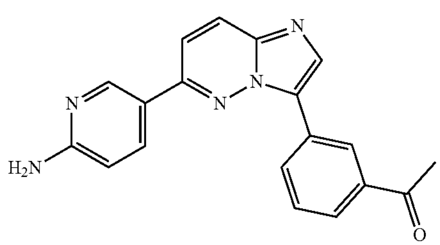 [SMILES: CC(=O)c1cccc(-c2cnc3ccc(-c4ccc(N)nc4)nn23)c1] | 377 | 1-[3-[6-(6-amino-3-pyridyl)imidazo[1,2-b]pyridazin-3-yl]phenyl]ethanone | 0.28267 | 2.36 | 828_4145_7905 |
| 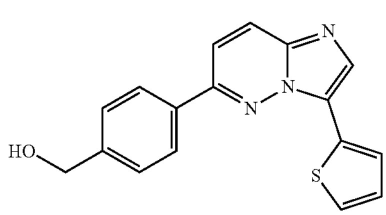 [SMILES: OCc1ccc(-c2ccc3ncc(-c4cccs4)n3n2)cc1] | 378 | [4-[3-(2-thienyl)imidazo[1,2-b]pyridazin-6-yl]phenyl]methanol | 2.35649 | 3.26 | 828_4147_0285 |

TABLE 3-continued

Primary screen- initial compounds.

| Structure | | IUPAC name | IC50 FYN (μM) | logP (consensus) | Compound ID. |
|---|---|---|---|---|---|
| 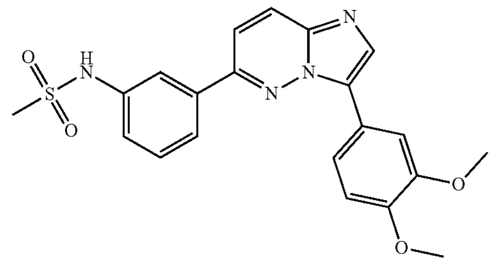 | 379 | N-[3-[3-(3,4-dimethoxyphenyl)imidazo[1,2-b]pyridazin-6-yl]phenyl]methanesulfonamide | 0.70252 | 2.31 | 828_0079_6488 |
| 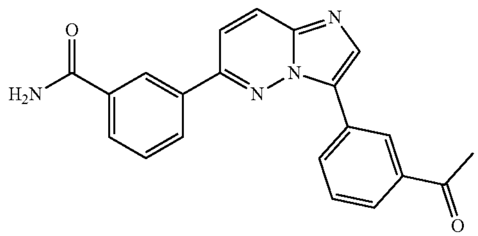 [SMILES: CC(=O)c1cccc(-c2cnc3ccc(-c4cccc(C(N)=O)c4)nn23)c1] | 380 | 3-[3-(3-acetylphenyl)imidazo[1,2-b]pyridazin-6-yl]benzamide | 0.51895 | 2.66 | 828_4145_0347 |
| 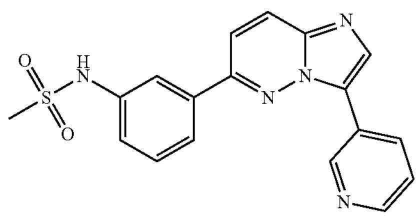 [SMILES: CS(=O)(=O)Nc1cccc(-c2ccc3ncc(-c4cccnc4)n3n2)c1] | 381 | N-[3-[3-(3-pyridyl)imidazo[1,2-b]pyridazin-6-yl]phenyl]methanesulfonamide | 1.41022 | 1.41 | 828_0071_6488 |
| 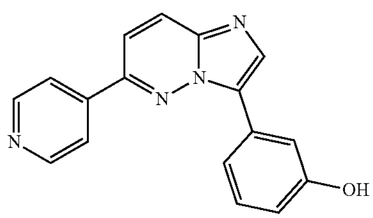 [SMILES: Oc1cccc(-c2cnc3ccc(-c4ccncc4)nn23)c1] | 382 | 3-[6-(4-pyridyl)imidazo[1,2-b]pyridazin-3-yl]phenol | 0.20283 | 2.73 | 828_0284_0069 |
| 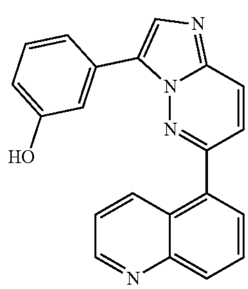 [SMILES: Oc1cccc(-c2cnc3ccc(-c4cccc5ncccc45)nn23)c1] | 383 | 3-[6-(5-quinolyl)imidazo[1,2-b]pyridazin-3-yl]phenol | 14.63638 | 4.11 | 828_0284_6831 |
| 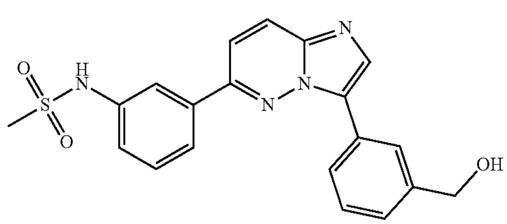 [SMILES: CS(=O)(=O)Nc1cccc(-c2ccc3ncc(-c4cccc(CO)c4)n3n2)c1] | 384 | N-[3-[3-[3-(hydroxymethyl)phenyl]imidazo[1,2-b]pyridazin-6-yl]phenyl]methanesulfonamide | 1.15032 | 1.86 | 828_0291_6488 |

TABLE 3-continued

Primary screen- initial compounds.

| Structure | | IUPAC name | IC50 FYN (μM) | logP (consensus) | Compound ID. |
|---|---|---|---|---|---|
| 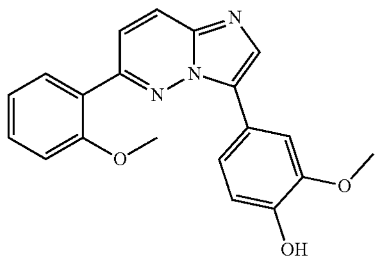 [SMILES: COc1cc(-c2cnc3ccc(-c4ccccc4OC)nn23)ccc1O] | 385 | 2-methoxy-4-[6-(2-methoxyphenyl)imidazo[1,2-b]pyridazin-3-yl]phenol | 0.95886 | 3.63 | 828_0314_0083 |
| 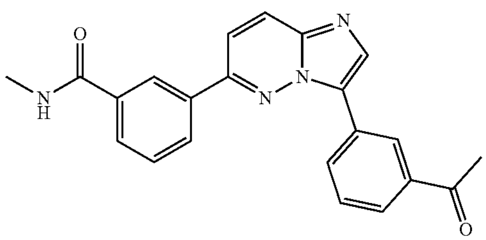 [SMILES: CNC(=O)c1cccc(-c2ccc3ncc(-c4cccc(C(C)=O)c4)n3n2)c1] | 386 | 3-[3-(3-acetylphenyl)imidazo[1,2-b]pyridazin-6-yl]-N-methylbenzamide | 1.71793 | 2.89 | 828_4145_7965 |
| 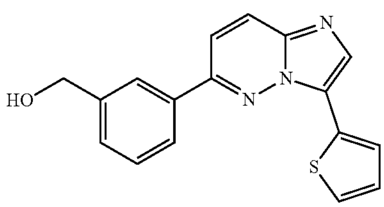 [SMILES: OCc1cccc(-c2ccc3ncc(-c4cccs4)n3n2)c1] | 387 | [3-[3-(2-thienyl)imidazo[1,2-b]pyridazin-6-yl]phenyl]methanol | 1.68324 | 3.26 | 828_4147_0291 |
| 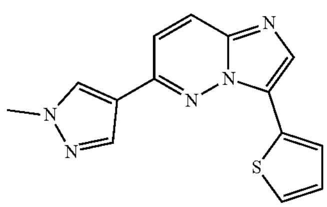 [SMILES: Cn1cc(-c2ccc3ncc(-c4cccs4)n3n2)cn1] | 388 | 6-(1-methylpyrazol-4-yl)-3-(2-thienyl)imidazo[1,2-b]pyridazine | 1.3135 | 2.46 | 828_4147_7468 |
| 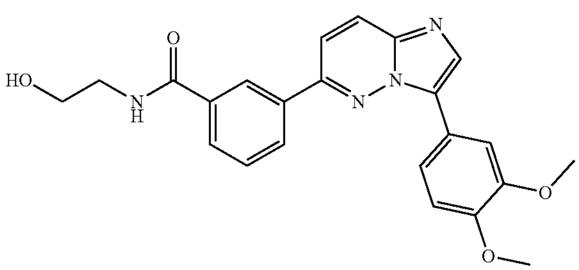 [SMILES: COc1ccc(-c2cnc3ccc(-c4cccc(C(=O)NCCO)c4)nn23)cc1OC] | 389 | 3-[3-(3,4-dimethoxyphenyl)imidazo[1,2-a]pyridazin-6-yl]-N-(2-hydroxyethyl)benzamide | 0.3666 | 2.32 | 828_0079_0192 |
| 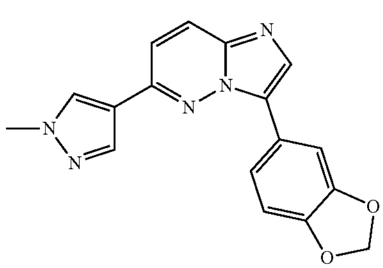 [SMILES: Cn1cc(-c2ccc3ncc(-c4ccc5c(c4)OCO5)n3n2)cn1] | 390 | 3-(1,3-benzodioxol-5-yl)-6-(1-methylpyrazol-4-yl)imidazo[1,2-b]pyridazine | 0.95557 | 2.30 | 828_0068_7468 |

TABLE 3-continued

Primary screen- initial compounds.

| Structure | | IUPAC name | IC50 FYN (μM) | logP (consensus) | Compound ID. |
|---|---|---|---|---|---|
| 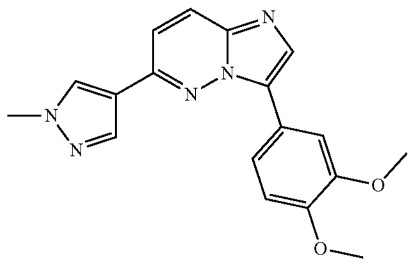 | 391 | 3-(3,4-dimethoxyphenyl)-6-(1-methylpyrazol-4-yl)imidazo[1,2-b]pyridazine | 0.36693 | 2.37 | 828_0079_7468 |
| 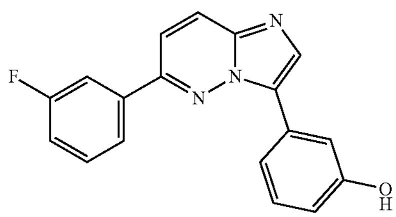 [SMILES: Oc1cccc(-c2cnc3ccc(-c4cccc(F)c4)nn23)c1] | 392 | 3-[6-(3-fluorophenyl)imidazo[1,2-b]pyridazin-3-yl]phenol | 2.26441 | 4.09 | 828_0284_0313 |
| 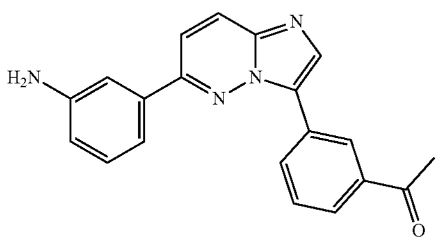 [SMILES: CC(=O)c1cccc(-c2cnc3ccc(-c4cccc(N)c4)nn23)c1] | 393 | 1-[3-[6-(3-aminophenyl)imidazo[1,2-b]pyridazin-3-yl]phenyl]ethanone | 1.12246 | 2.98 | 828_4145_0005 |
| 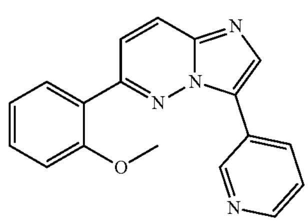 [SMILES: COc1ccccc1-c1ccc2ncc(-c3cccnc3)n2n1] | 394 | 6-(2-methoxyphenyl)-3-(3-pyridyl)imidazo[1,2-b]pyridazine | 2.3503 | 2.88 | 828_0071_0083 |
| 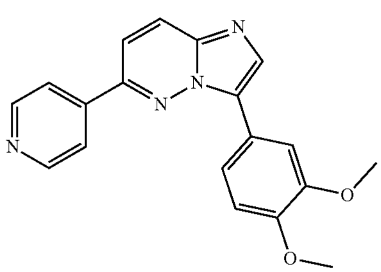 [SMILES: COc1ccc(-c2cnc3ccc(-c4ccncc4)nn23)cc1OC] | 395 | 3-(3,4-dimethoxyphenyl)-6-(4-pyridyl)imidazo[1,2-b]pyridazine | 0.40386 | 2.72 | 828_0079_0069 |
| 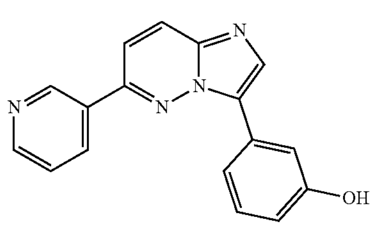 [SMILES: Oc1cccc(-c2cnc3ccc(-c4cccnc4)nn23)c1] | 396 | 3-[6-(3-pyridyl)imidazo[1,2-b]pyridazin-3-yl]phenol | 0.58643 | 2.73 | 828_0284_0071 |

TABLE 3-continued

Primary screen- initial compounds.

| Structure | | IUPAC name | IC50 FYN (μM) | logP (consensus) | Compound ID. |
|---|---|---|---|---|---|
| 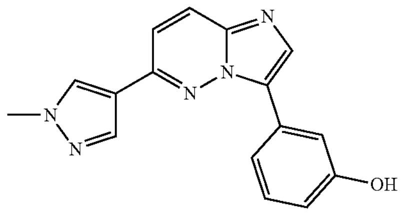 [SMILES: Cn1cc(-c2ccc3ncc(-c4cccc(O)c4)n3n2)cn1] | 397 | 3-[6-(1-methylpyrazol-4-yl)imidazo[1,2-b]pyridazin-3-yl]phenol | 0.38762 | 2.38 | 828_0284_7468 |
| 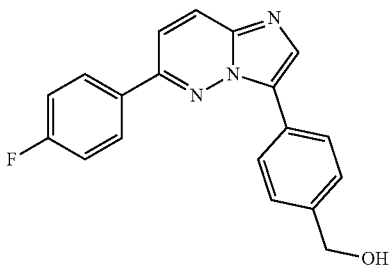 [SMILES: OCc1ccc(-c2cnc3ccc(-c4ccc(F)cc4)nn23)cc1] | 398 | [4-[6-(4-fluorophenyl)imidazo[1,2-3]pyridazin-3-yl]phenyl]methanol | 2.94383 | 3.63 | 828_0285_0339 |
| 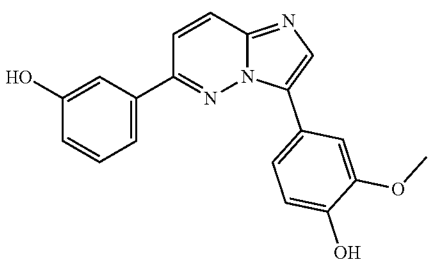 [SMILES: COc1cc(-c2cnc3ccc(-c4cccc(O)c4)nn23)ccc1O] | 399 | 4-[6-(3-hydroxyphenyl)imidazo[1,2-b]pyridazin-3-yl]-2-methoxy-phenol | 0.29478 | 3.49 | 828_0314_0284 |
| 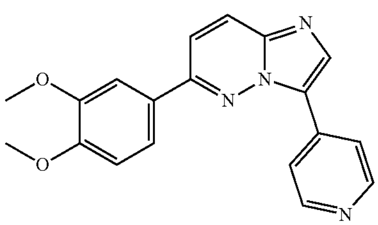 [SMILES: COc1ccc(-c2ccc3ncc(-c4ccncc4)n3n2)cc1OC] | 400 | 6-(3,4-dimethoxy-phenyl)-3-(4-pyridyl)imidazo[1,2-b]pyridazine | 0.28231 | 2.72 | 828_0069_0079 |
| 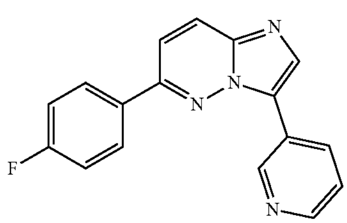 [SMILES: Fc1ccc(-c2ccc3ncc(-c4cccnc4)n3n2)cc1] | 401 | 6-(4-fluorophenyl)-3-(3-pyridyl)imidazo[1,2-b]pyridazine | 2.77876 | 3.18 | 828_0071_0339 |
| 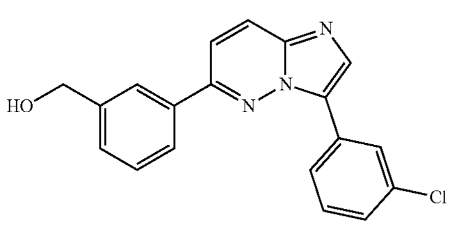 [SMILES: OCc1cccc(-c2ccc3ncc(-c4cccc(Cl)c4)n3n2)c1] | 402 | [3-[3-(3-chlorophenyl)imidazo[1,2-b]pyridazin-6-yl]phenyl]methanol | 9.81893 | 4.09 | 828_0279_0291 |

TABLE 3-continued

Primary screen- initial compounds.

| Structure | | IUPAC name | IC50 FYN (μM) | logP (consensus) | Compound ID. |
|---|---|---|---|---|---|
| 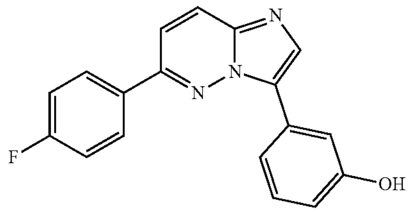 [SMILES: Oc1cccc(-c2cnc3ccc(-c4ccc(F)cc4)nn23)c1] | 403 | 3-[6-(4-fluorophenyl)imidazo[1,2-b]pyridazin-3-yl]phenol | 11.87843 | 4.09 | 828_0284_0339 |
| 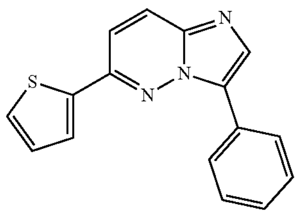 [SMILES: c1ccc(-c2cnc3ccc(-c4cccs4)nn23)cc1] | 404 | 3-phenyl-6-(2-thienyl)imidazo[1,2-b]pyridazine | 1.9697 | 4.03 | 828_0061_4147 |
| 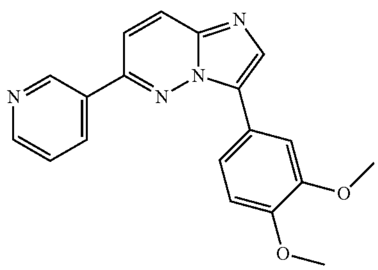 [SMILES: COc1ccc(-c2cnc3ccc(-c4cccnc4)nn23)cc1OC] | 405 | 3-(3,4-dimethoxyphenyl)-6-(3-pyridyl)imidazo[1,2-b]pyridazine | 0.54944 | 2.72 | 828_0079_0071 |
| 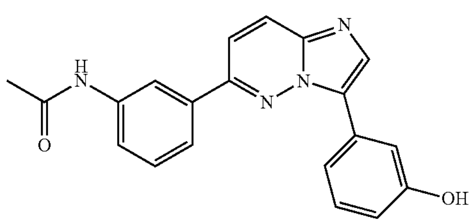 [SMILES: CC(=O)Nc1cccc(-c2ccc3ncc(-c4cccc(O)c4)n3n2)c1] | 406 | N-[3-[3-(3-hydroxyphenyl)imidazo[1,2-b]pyridazin-6-yl]phenyl]acetamide | 1.64512 | 3.19 | 828_0284_0081 |
| 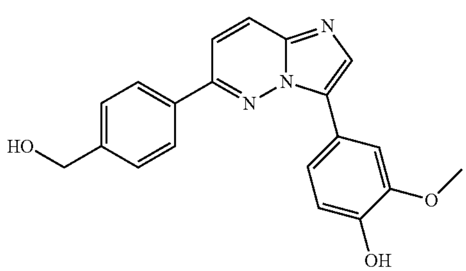 [SMILES: COc1cc(-c2cnc3ccc(-c4ccc(CO)cc4)nn23)ccc1O] | 407 | 4-[6-[4-(hydroxymethyl)phenyl]imidazo[1,2-b]pyridazin-3-yl]-2-methoxyphenol | 0.12455 | 3.02 | 828_0314_0285 |
| 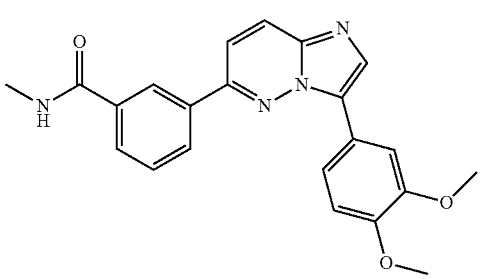 | 408 | 3-[3-(3,4-dimethoxyphenyl)imidazo[1,2-b]pyridazin-6-yl]-N-methylbenzamide | 3.49397 | 3.01 | 828_0079_7965 |

TABLE 3-continued

Primary screen- initial compounds.

| Structure | | IUPAC name | IC50 FYN (μM) | logP (consensus) | Compound ID. |
|---|---|---|---|---|---|
| 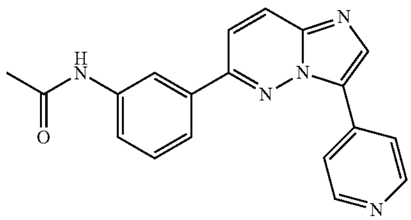 [SMILES: CC(=O)Nc1cccc(-c2ccc3ncc(-c4ccncc4)n3n2)c1] | 409 | N-[3-[3-(4-pyridyl)imidazo[1,2-b]pyridazin-6-yl]phenyl]acetamide | 0.59778 | 2.27 | 828_0069_0081 |
| 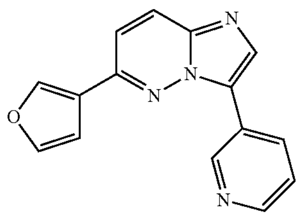 [SMILES: c1cncc(-c2cnc3ccc(-c4ccoc4)nn23)c1] | 410 | 6-(3-furyl)-3-(3-pyridyl)imidazo[1,2-b]pyridazine | 2.34906 | 2.18 | 828_0071_0343 |
| 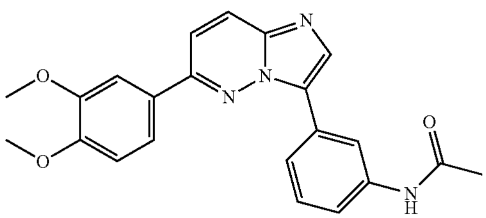 [SMILES: COc1ccc(-c2ccc3ncc(-c4cccc(NC(C)=O)c4)n3n2)cc1OC] | 411 | N-[3-[6-(3,4-dimethoxyphenyl)imidazo[1,2-p]pyridazin-3-yl]phenyl]acetamide | 0.25932 | 3.18 | 828_0081_0079 |
| 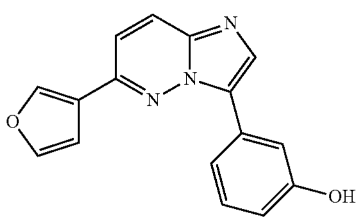 [SMILES: Oc1cccc(-c2cnc3ccc(-c4ccoc4)nn23)c1] | 412 | 3-[6-(3-furyl)imidazo[1,2-b]pyridazin-3-yl]phenol | 1.05684 | 3.09 | 828_0284_0343 |
| 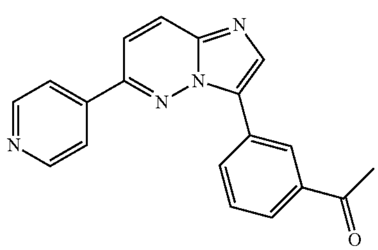 [SMILES: CC(=O)c1cccc(-c2cnc3ccc(-c4ccncc4)nn23)c1] | 413 | 1-[3-[6-(4-pyridyl)imidazo[1,2-b]pyridazin-3-yl]phenyl]ethanone | 0.37149 | 2.59 | 828_4145_0069 |
| 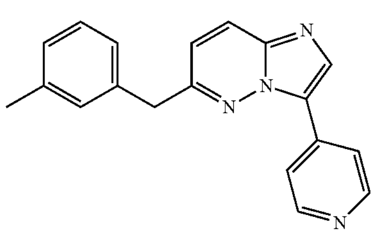 [SMILES: Cc1cccc(Cc2ccc3ncc(-c4ccncc4)n3n2)c1] | 414 | 6-(m-tolylmethyl)-3-(4-pyridyl)imidazo[1,2-b]pyridazine | 0.97706 | 3.48 | 828_0069_6291 |

TABLE 3-continued

Primary screen- initial compounds.

| Structure | | IUPAC name | IC50 FYN (μM) | logP (consensus) | Compound ID. |
|---|---|---|---|---|---|
| 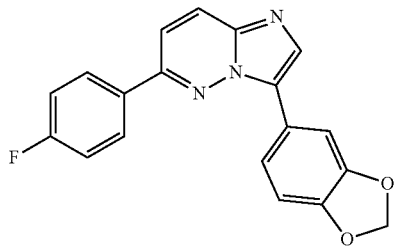 [SMILES: Fc1ccc(-c2ccc3ncc(-c4ccc5c(c4)OCO5)n3n2)cc1] | 415 | 3-(1,3-benzodioxol-5-yl)-6-(4-fluorophenyl)imidazo[1,2-b]pyridazine | 7.60066 | 4.02 | 828_0068_0339 |
| 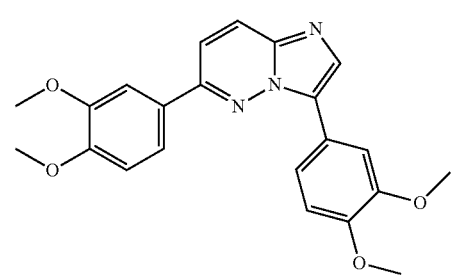 | 416 | 3,6-bis(3,4-dimethoxyphenyl)imidazo[1,2-b]pyridazine | 0.53841 | 3.62 | 828_0079_0079 |
| 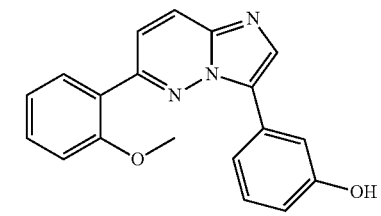 [SMILES: COc1ccccc1-c1ccc2ncc(-c3cccc(O)c3)n2n1] | 417 | 3-[6-(2-methoxyphenyl)imidazo[1,2-b]pyridazin-3-yl]phenol | 2.73595 | 3.79 | 828_0284_0083 |
| 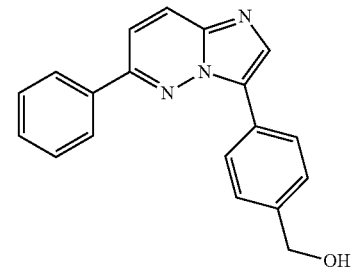 [SMILES: OCc1ccc(-c2cnc3ccc(-c4ccccc4)nn23)cc1] | 418 | [4-(6-phenylimidazo[1,2-b]pyridazin-3-yl)phenyl]methanol | 1.45898 | 3.49 | 828_0285_0061 |
| 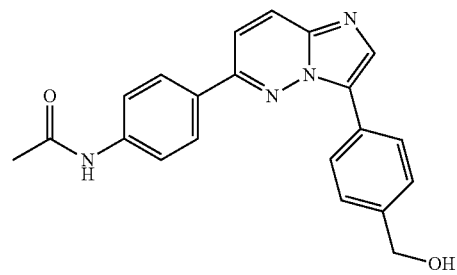 [SMILES: CC(=O)Nc1ccc(-c2ccc3ncc(-c4ccc(CO)cc4)n3n2)cc1] | 419 | N-[4-[3-[4-(hydroxymethyl)phenyl]imidazo[1,2-b]pyridazin-6-yl]phenyl]acetamide | 21.45348 | 2.72 | 828_0285_0722 |

TABLE 3-continued

Primary screen- initial compounds.

| Structure | | IUPAC name | IC50 FYN (μM) | logP (consensus) | Compound ID. |
|---|---|---|---|---|---|
| 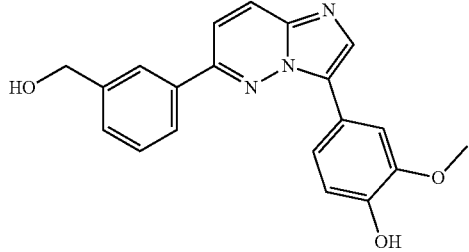 [SMILES: COc1cc(-c2cnc3ccc(-c4cccc(CO)c4)nn23)ccc1O] | 420 | 4-[6-[3-(hydroxymethyl)phenyl]imidazo[1,2-b]pyridazin-3-yl]-2-methoxyphenol | 0.10235 | 3.02 | 828_0314_0291 |
| 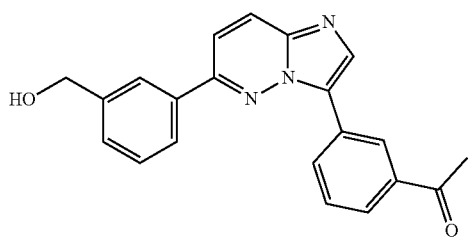 [SMILES: CC(=O)c1cccc(-c2cnc3ccc(-c4cccc(CO)c4)nn23)c1] | 421 | 1-[3-[6-[3-(hydroxymethyl)phenyl]imidazo[1,2-b]pyridazin-3-yl]phenyl]ethanone | 0.17883 | 3.04 | 828_4145_0291 |
| 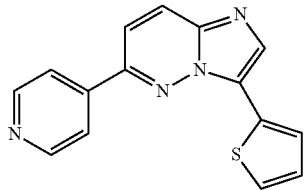 [SMILES: c1csc(-c2cnc3ccc(-c4ccncc4)nn23)c1] | 422 | 3-(4-pyridyl)-3-(2-thienyl)imidazo[1,2-b]pyridazine | 0.49696 | 2.81 | 828_4147_0069 |
| 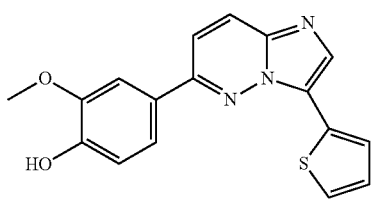 [SMILES: COc1cc(-c2ccc3ncc(-c4cccs4)n3n2)ccc1O] | 423 | 2-methoxy-4-[3-(2-thienyl)imidazo[1,2-b]pyridazin-6-yl]phenol | 0.69396 | 3.57 | 828_4147_0314 |
| 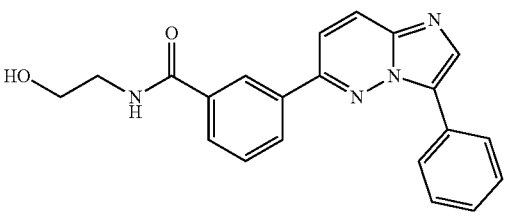 [SMILES: O=C(NCCO)c1cccc(-c2ccc3ncc(-c4ccccc4)n3n2)c1] | 424 | N-(2-hydroxyethyl)-3-(3-phenyl-imidazo[1,2-b]pyridazin-6-yl)benzamide | 13.86362 | 2.64 | 828_0061_0192 |
| 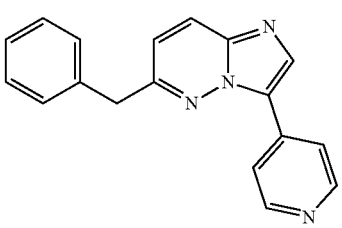 [SMILES: c1ccc(Cc2ccc3ncc(-c4ccncc4)n3n2)cc1] | 425 | 6-benzyl-3-(4-pyridyl)imidazo[1,2-b]pyridazine | 0.6243 | 2.97 | 828_0069_6001 |

TABLE 3-continued

Primary screen- initial compounds.

| Structure | | IUPAC name | IC50 FYN (μM) | logP (consensus) | Compound ID. |
|---|---|---|---|---|---|
| 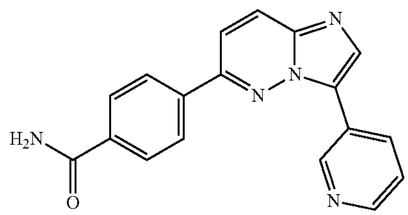 [SMILES: NC(=O)c1ccc(-c2ccc3ncc(-c4cccnc4)n3n2)cc1] | 426 | 4-[3-(3-pyridyl)imidazo[1,2-b]pyridazin-6-yl]benzamide | 11.24348 | 1.89 | 828_0071_0346 |
| 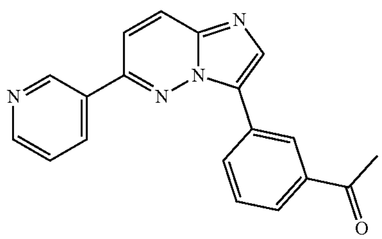 [SMILES: CC(=O)c1cccc(-c2cnc3ccc(-c4cccnc4)nn23)c1] | 427 | 1-[3-[6-(3-pyridyl)imidazo[1,2-b]pyridazin-3-yl]phenyl]ethanone | 1.23395 | 2.59 | 828_4145_0071 |
| 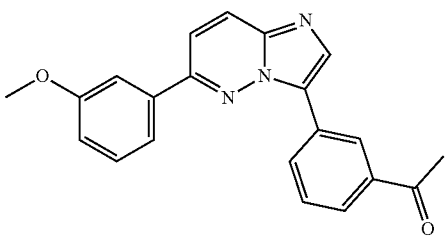 [SMILES: COc1cccc(-c2ccc3ncc(-c4cccc(C(C)=O)c4)n3n2)c1] | 428 | 1-[3-[6-(3-methoxyphenyl)imidazo[1,2-b]pyridazin-3-yl]phenyl]ethanone | 1.78495 | 3.65 | 828_4145_4140 |
| 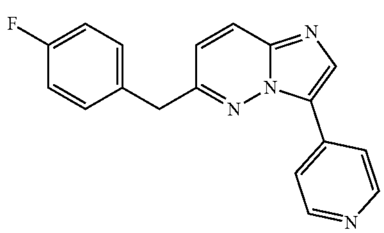 [SMILES: Fc1ccc(Cc2ccc3ncc(-c4ccncc4)n3n2)cc1] | 429 | 6-[(4-fluorophenyl)methyl]-3-(4-pyridyl)imidazo[1,2-b]pyridazine | 1.44642 | 3.11 | 828_0069_6370 |
| 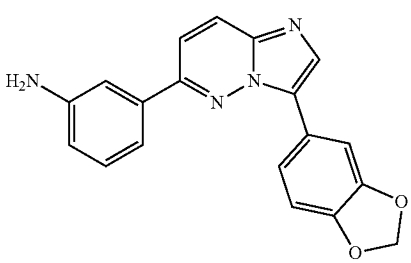 [SMILES: Nc1cccc(-c2ccc3ncc(-c4ccc5c(c4)OCO5)n3n2)c1] | 430 | 3-[3-(1,3-benzodioxol-5-yl)imidazo[1,2-b]pyridazin-6-yl]aniline | 0.84313 | 3.05 | 828_0068_0005 |
| 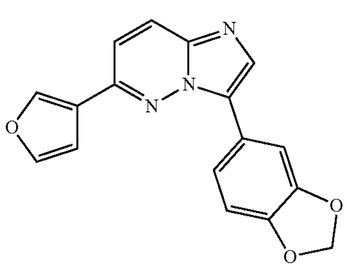 [SMILES: c1cc(-c2ccc3ncc(-c4ccc5c(c4)OCO5)n3n2)co1] | 431 | 3-(1,3-benzodioxol-5-yl)-6-(3-furyl)imidazo[1,2-b]pyridazine | 1.60154 | 3.02 | 828_0068_0343 |

TABLE 3-continued

Primary screen- initial compounds.

| Structure | | IUPAC name | IC50 FYN (μM) | logP (consensus) | Compound ID. |
|---|---|---|---|---|---|
| 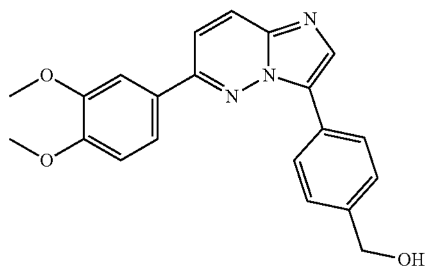 [SMILES: COc1ccc(-c2ccc3ncc(-c4ccc(CO)cc4)n3n2)cc1OC] | 432 | [4-[6-(3,4-dimethoxyphenyl)imidazo[1,2-b]pyridazin-3-yl]phenyl]methanol | 3.9402 | 3.17 | 828_0285_0079 |
| 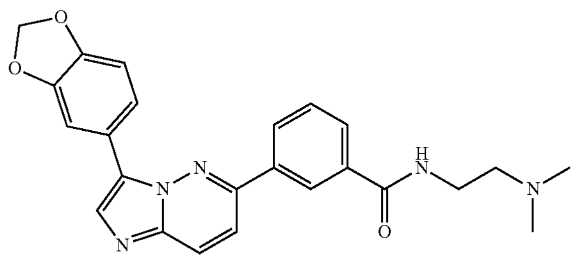 [SMILES: CN(C)CCNC(=O)c1cccc(-c2ccc3ncc(-c4ccc5c(c4)OCO5)n3n2)c1] | 433 | 3-[3-(1,3-benzodioxol-5-yl)imidazo[1,2-b]pyridazin-6-yl]-N-(2-dimethylaminoethyl)benzamide | 0.39289 | 2.97 | 828_0068_0176 |
| 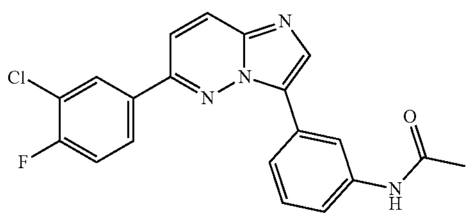 [SMILES: CC(=O)Nc1cccc(-c2cnc3ccc(-c4ccc(F)c(Cl)c4)nn23)c1] | 434 | N-[3-[6-(3-chloro-4-fluorophenyl)imidazo[1,2-b]pyridazin-3-yl]phenyl]acetamide | 0.52521 | 4.24 | 828_0081_0164 |
| 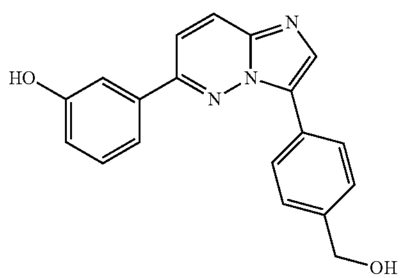 [SMILES: OCc1ccc(-c2cnc3ccc(-c4cccc(O)c4)nn23)cc1] | 435 | 3-[3-[4-(hydroxymethyl)phenyl]imidazo[1,2-b]pyridazin-6-yl]phenol | 1.13696 | 3.18 | 828_0285_0284 |
| 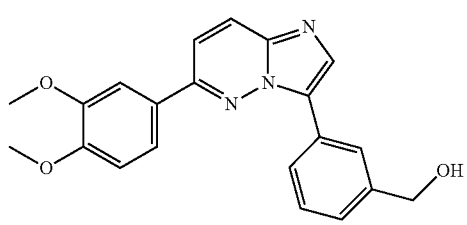 [SMILES: COc1ccc(-c2ccc3ncc(-c4cccc(CO)c4)n3n2)cc1OC] | 436 | [3-[6-(3,4-dimethoxyphenyl)imidazo[1,2-b]pyridazin-3-yl]phenyl]methanol | 0.74933 | 6.29 | 828_0291_0079 |
| 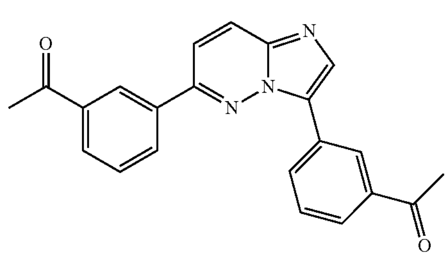 [SMILES: CC(=O)c1cccc(-c2ccc3ncc(-c4cccc(C(C)=O)c4)n3n2)c1] | 437 | 1-[3-[3-(3-acetylphenyl)imidazo[1,2-b]pyridazin-6-yl]phenyl]ethanone | 0.58173 | 3.37 | 828_4145_4145 |

TABLE 3-continued

Primary screen- initial compounds.

| Structure | | IUPAC name | IC50 FYN (μM) | logP (consensus) | Compound ID. |
|---|---|---|---|---|---|
| 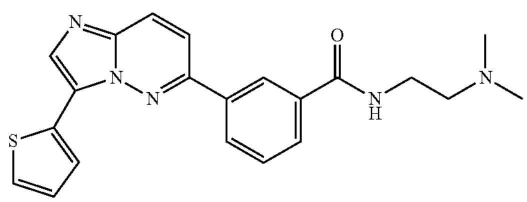 [SMILES: CN(C)CCNC(=O)c1cccc(-c2ccc3ncc(-c4cccs4)n3n2)c1] | 438 | N-(2-dimethyl-aminoethyl)-3-[3-(2-thienyl)imidazo[1,2-b]pyridazin-6-yl]benzamide | 1.1611 | 3.12 | 828_4147_0176 |
| 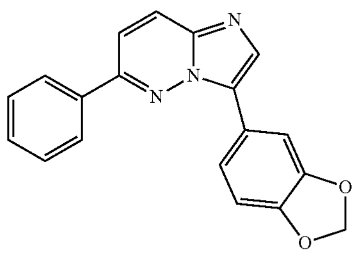 [SMILES: c1ccc(-c2ccc3ncc(-c4ccc5c(c4)OCO5)n3n2)cc1] | 439 | 3-(1,3-benzodioxol-5-yl)-6-phenyl-imidazo[1,2-b]pyridazine | 3.08798 | 3.88 | 828_0068_0061 |
| 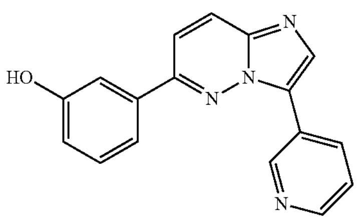 [SMILES: Oc1cccc(-c2ccc3ncc(-c4cccnc4)n3n2)c1] | 440 | 3-[3-(3-pyridyl)imidazo[1,2-b]pyridazin-6-yl]phenol | 1.81461 | 2.73 | 828_0071_0284 |
| 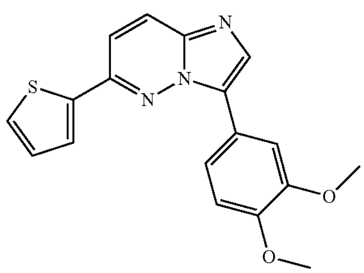 [SMILES: COc1ccc(-c2cnc3ccc(-c4cccs4)nn23)cc1OC] | 441 | 3-(3,4-dimethoxy-phenyl)-6-(2-thienyl)imidazo[1,2-b]pyridazine | 0.21139 | 3.72 | 828_0079_4147 |
| 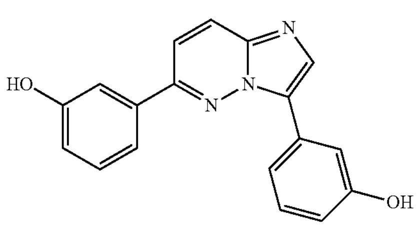 [SMILES: Oc1cccc(-c2ccc3ncc(-c4cccc(O)c4)n3n2)c1] | 442 | 3-[3-(3-hydroxyphenyl)imidazo[1,2-b]pyridazin-6-yl]phenol | 0.98714 | 3.65 | 828_0284_0284 |
| 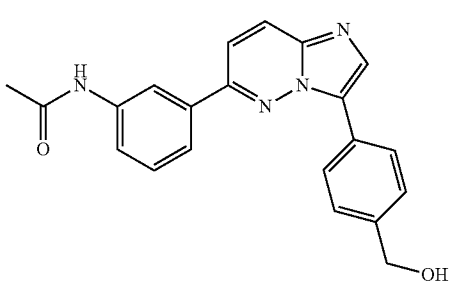 [SMILES: CC(=O)Nc1cccc(-c2ccc3ncc(-c4ccc(CO)cc4)n3n2)c1] | 443 | N-[3-[3-[4-(hydroxymethyl)phenyl]imidazo[1,2-b]pyridazin-6-yl]phenyl]acetamide | 2.2389 | 2.72 | 828_0285_0081 |

TABLE 3-continued

Primary screen- initial compounds.

| Structure | | IUPAC name | IC50 FYN (μM) | logP (consensus) | Compound ID. |
|---|---|---|---|---|---|
| 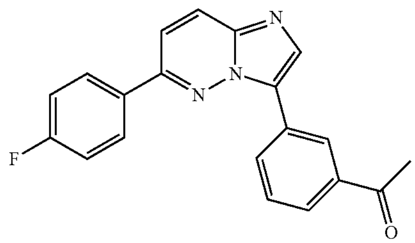 [SMILES: CC(=O)c1cccc(-c2cnc3ccc(-c4ccc(F)cc4)nn23)c1] | 444 | 1-[3-[6-(4-fluorophenyl)imidazo[1,2-b]pyridazin-3-yl]phenyl]ethanone | 4.81048 | 3.95 | 828_4145_0339 |
| 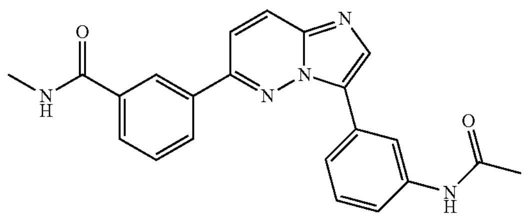 [SMILES: CNC(=O)c1cccc(-c2ccc3ncc(-c4cccc(NC(C)=O)c4)n3n2)c1] | 445 | 3-[3-(3-acetamido-phenyl)imidazo[1,2-b]pyridazin-6-yl]-N-methyl-benzamide | 1.3298 | 2.57 | 828_0081_7965 |
| 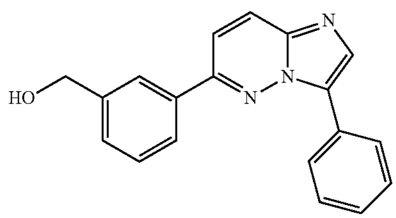 [SMILES: OCc1cccc(-c2ccc3ncc(-c4ccccc4)n3n2)c1] | 446 | [3-(3-phenylimidazo[1,2-b]pyridazin-6-yl)phenyl]methanol | 1.92857 | 3.49 | 828_0061_0291 |
| 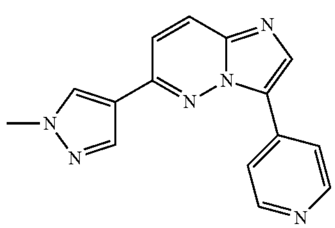 [SMILES: Cn1cc(-c2ccc3ncc(-c4ccncc4)n3n2)cn1] | 447 | 6-(1-methylpyrazol-4-yl)-3-(4-pyridyl)imidazo[1,2-b]pyridazine | 30 | 1.46 | 828_0069_7468 |
| 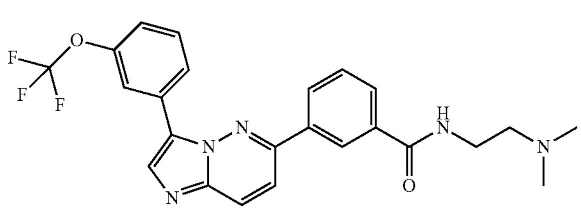 [SMILES: CN(C)CCNC(=O)c1cccc(-c2ccc3ncc(-c4cccc(OC(F)(F)F)c4)n3n2)c1] | 448 | N-(2-dimethylamino-ethyl)-3-[3-[3-(trifluoromethoxy)phenyl]imidazo[1,2-b]pyridazin-6-yl]benzamide | 3.93108 | 4.78 | 828_0168_0176 |
| 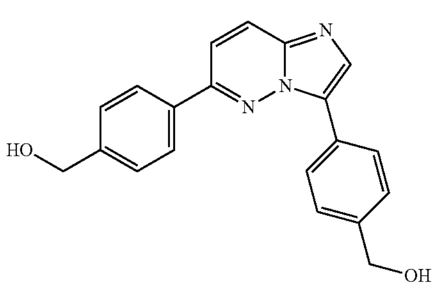 [SMILES: OCc1ccc(-c2ccc3ncc(-c4ccc(CO)cc4)n3n2)cc1] | 449 | [4-[3-[4-(hydroxymethyl)phenyl]imidazo[1,2-b]pyridazin-6-yl]phenyl]methanol | 1.03522 | 2.72 | 828_0285_0285 |

TABLE 3-continued

Primary screen- initial compounds.

| Structure | | IUPAC name | IC50 FYN (μM) | logP (consensus) | Compound ID. |
|---|---|---|---|---|---|
| 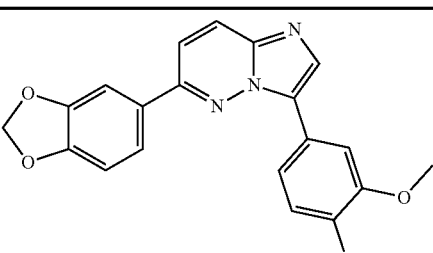 | 450 | 4-[6-(1,3-benzodioxol-5-yl)imidazo[1,2-b]pyridazin-3-yl]-2-methoxyphenol | 0.1999 | 3.42 | 828_0314_0068 |
| 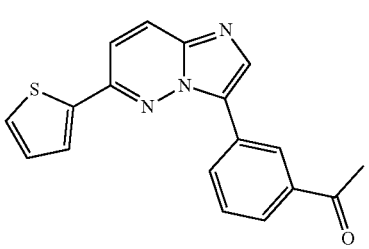 [SMILES: CC(=O)c1cccc(-c2cnc3ccc(-c4cccs4)nn23)c1] | 451 | 1-[3-[6-(2-thienyl)imidazo[1,2-b]pyridazin-3-yl]phenyl]ethanone | 0.41575 | 3.59 | 828_4145_4147 |
| 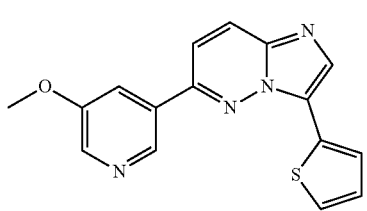 [SMILES: COc1cncc(-c2ccc3ncc(-c4cccs4)n3n2)c1] | 452 | 6-(5-methoxy-3-pyridyl)-3-(2-thienyl)imidazo[1,2-b]pyridazine | 2.86231 | 2.66 | 828_4147_0196 |
| 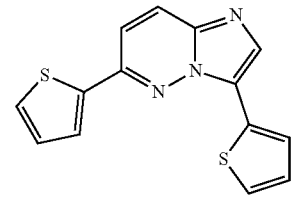 [SMILES: c1csc(-c2ccc3ncc(-c4cccs4)n3n2)c1] | 453 | 3,6-bis(2-thienyl)imidazo[1,2-b]pyridazine | 4.89416 | 3.81 | 828_4147_4147 |
| 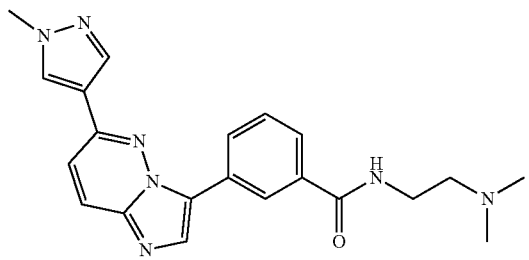 | 454 | N-(2-dimethylaminoethyl)-3-[6-(1-methylpyrazol-4-yl)imidazo[1,2-b]pyridazin-3-yl]benzamide | 1.76458 | 1.77 | 828_0176_7468 |
| 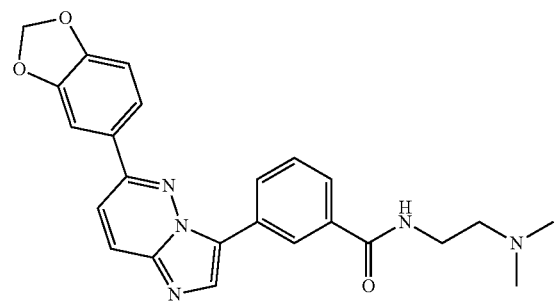 [SMILES: CN(C)CCNC(=O)c1cccc(-c2cnc3ccc(-c4ccc5c(c4)OCO5)nn23)c1] | 455 | 3-[6-(1,3-benzodioxol-5-yl)imidazo[1,2-b]pyridazin-3-yl]-N-(2-dimethylaminoethyl)benzamide | 2.01862 | 2.97 | 828_0176_0068 |

TABLE 3-continued

Primary screen- initial compounds.

| Structure | | IUPAC name | IC50 FYN (μM) | logP (consensus) | Compound ID. |
|---|---|---|---|---|---|
| 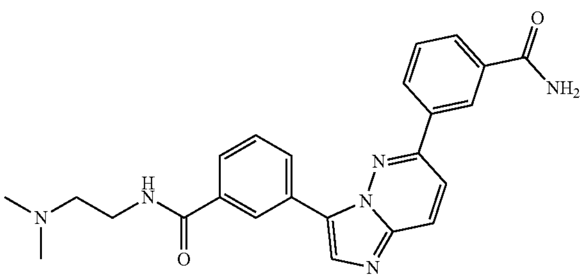 [SMILES: CN(C)CCNC(=O)c1cccc(-c2cnc3ccc(-c4cccc(C(N)=O)c4)nn23)c1] | 456 | 3-[3-[3-(2-dimethylamino-ethylcarbamoyl)phenyl]imidazo[1,2-b]pyridazin-6-yl]benzamide | 4.14881 | 2.20 | 828_0176_0347 |
| 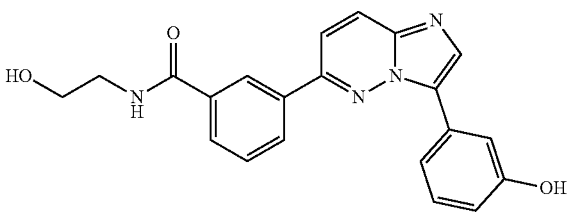 [SMILES: O=C(NCCO)c1cccc(-c2ccc3ncc(-c4cccc(O)c4)n3n2)c1] | 457 | N-(2-hydroxyethyl)-3-[3-(3-hydroxyphenyl)imidazo[1,2-b]pyridazin-6-yl]benzamide | 0.35163 | 2.33 | 828_0284_0192 |
| 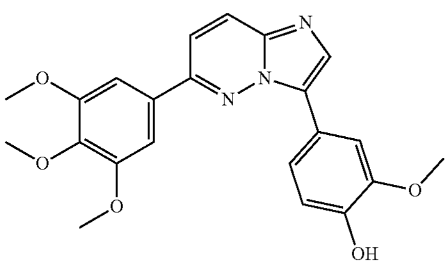 | 458 | 2-methoxy-4-[6-(3,4,5-trimethoxyphenyl)imidazo[1,2-b]pyridazin-3-yl]phenol | 1.81139 | 3.32 | 828_0314_0087 |
| 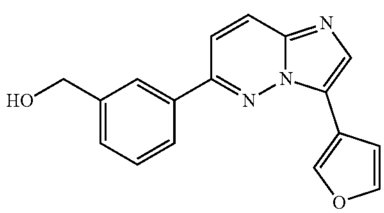 [SMILES: OCc1cccc(-c2ccc3ncc(-c4ccoc4)n3n2)c1] | 459 | [3-[3-(3-furyl)imidazo[1,2-b]pyridazin-6-yl]phenyl]methanol | 7.32807 | 2.63 | 828_0343_0291 |
| 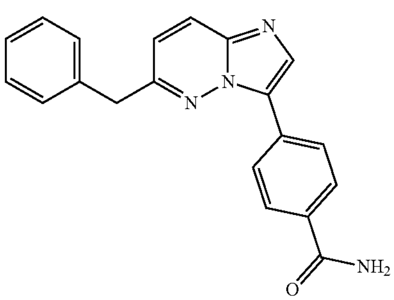 [SMILES: NC(=O)c1ccc(-c2cnc3ccc(Cc4ccccc4)nn23)cc1] | 460 | 4-(6-benzylimidazo[1,2-b]pyridazin-3-yl)benzamide | 0.71127 | 3.04 | 828_0346_6001 |

TABLE 3-continued

Primary screen- initial compounds.

| Structure | | IUPAC name | IC50 FYN (μM) | logP (consensus) | Compound ID. |
|---|---|---|---|---|---|
| 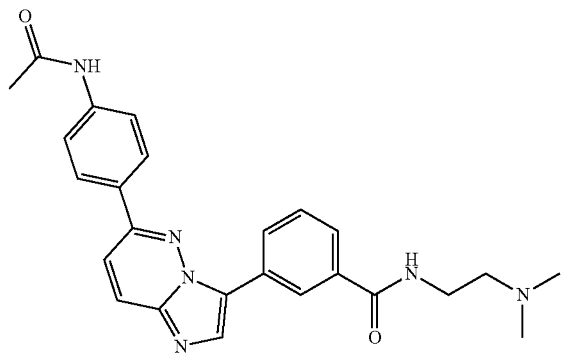 [SMILES: CC(=O)Nc1ccc(-c2ccc3ncc(-c4cccc(C(=O)NCCN(C)C)c4)n3n2)cc1] | 461 | 3-[6-(4-acetamidophenyl)imidazo[1,2-b]pyridazin-3-yl]-N-(2-dimethylamino-ethyl)benzamide | 0.98309 | 2.58 | 828_0176_0722 |
| 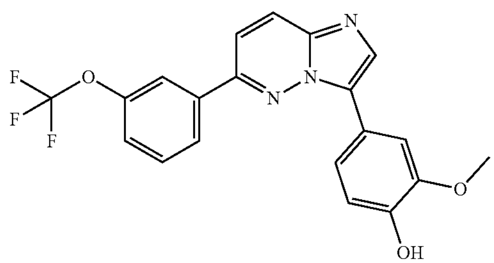 [SMILES: COc1cc(-c2cnc3ccc(-c4cccc(OC(F)(F)F)c4)nn23)ccc1O] | 462 | 2-methoxy-4-[6-[3-(trifluoro-methoxy)phenyl]imidazo[1,2-b]pyridazin-3-yl]phenol | 0.83451 | 5.22 | 828_0314_0168 |
| 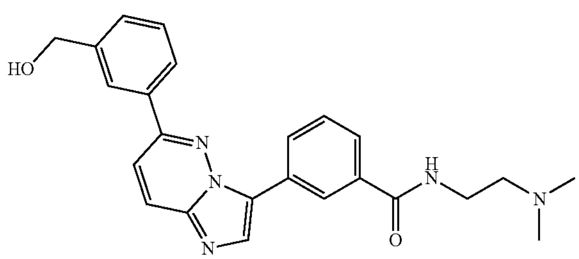 [SMILES: CN(C)CCNC(=O)c1cccc(-c2cnc3ccc(-c4cccc(CO)c4)nn23)c1] | 463 | N-(2-dimethylamino-ethyl)-3-[6-[3-(hydroxymethyl)phenyl]imidazo[1,2-b]pyridazin-3-yl]benzamide | 0.81608 | 2.58 | 828_0176_0291 |
| 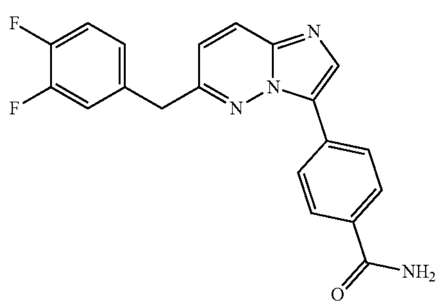 [SMILES: NC(=O)c1ccc(-c2cnc3ccc(Cc4ccc(F)c(F)c4)nn23)cc1] | 464 | 4-[6-[(3,4-difluorophenyl)methyl]imidazo[1,2-b]pyridazin-3-yl]benzamide | 3.07271 | 3.52 | 828_0346_6007 |
| 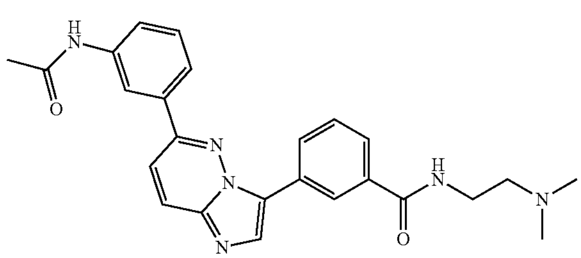 [SMILES: CC(=O)Nc1cccc(-c2ccc3ncc(-c4cccc(C(=O)NCCN(C)C)c4)n3n2)c1] | 465 | 3-[6-(3-acetamidophenyl)imidazo[1,2-b]pyridazin-3-yl]-N-(2-dimethylamino-ethyl)benzamide | 3.16865 | 2.58 | 828_0176_0081 |

TABLE 3-continued

Primary screen- initial compounds.

| Structure | | IUPAC name | IC50 FYN (µM) | logP (consensus) | Compound ID. |
|---|---|---|---|---|---|
| 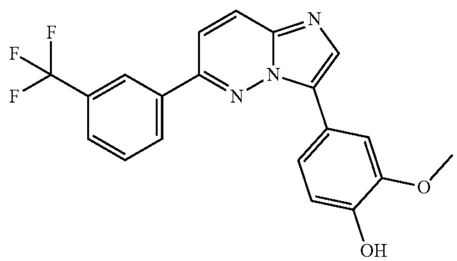 [SMILES: COc1cc(-c2cnc3ccc(-c4cccc(C(F)(F)F)c4)nn23)ccc1O] | 466 | 2-methoxy-4-[6-[3-(trifluoromethyl)phenyl]imidazo[1,2-b]pyridazin-3-yl]phenol | 1.08271 | 4.67 | 828_0314_0312 |
| 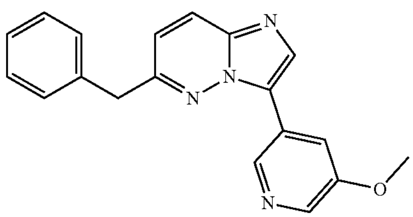 [SMILES: COc1cncc(-c2cnc3ccc(Cc4ccccc4)nn23)c1] | 467 | 6-benzyl-3-(5-methoxy-3-pyridyl)imidazo[1,2-b]pyridazine | 2.67306 | 2.81 | 828_0196_6001 |
| 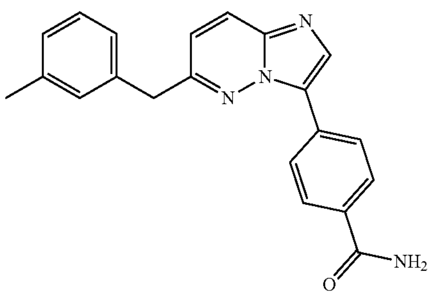 [SMILES: Cc1cccc(Cc2ccc3ncc(-c4ccc(C(N)=O)cc4)n3n2)c1] | 468 | 4-[6-(m-tolylmethyl)imidazo[1,2-b]pyridazin-3-yl]benzamide | 3.10262 | 3.55 | 828_0346_6291 |
| 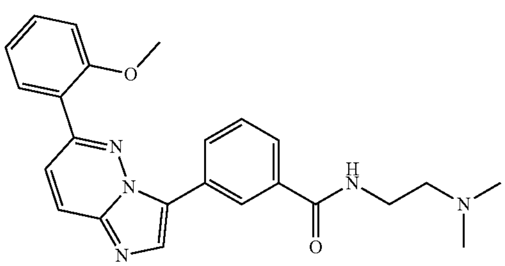 [SMILES: COc1ccccc1-c1ccc2ncc(-c3cccc(C(=O)NCCN(C)C)c3)n2n1] | 469 | N-(2-dimethylaminoethyl)-3-[6-(2-methoxyphenyl)imidazo[1,2-b]pyridazin-3-yl]benzamide | 2.13745 | 3.19 | 828_0176_0083 |
| 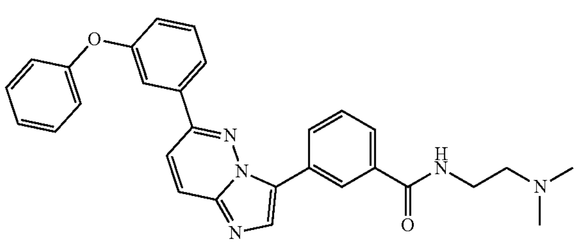 [SMILES: CN(C)CCNC(=O)c1cccc(-c2cnc3ccc(-c4cccc(Oc5ccccc5)c4)nn23)c1] | 470 | N-(2-dimethylaminoethyl)-3-[6-(3-phenoxyphenyl)imidazo[1,2-b]pyridazin-3-yl]benzamide | 19.18297 | 4.85 | 828_0176_4032 |
| 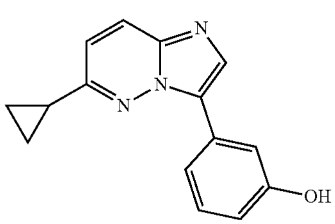 [SMILES: Oc1cccc(-c2cnc3ccc(C4CC4)nn23)c1] | 471 | 3-(6-cyclopropylimidazo[1,2-b]pyridazin-3-yl)phenol | 1.88565 | 2.83 | 828_0284_7494 |

TABLE 3-continued

Primary screen- initial compounds.

| Structure | | IUPAC name | IC50 FYN (µM) | logP (consensus) | Compound ID. |
|---|---|---|---|---|---|
| 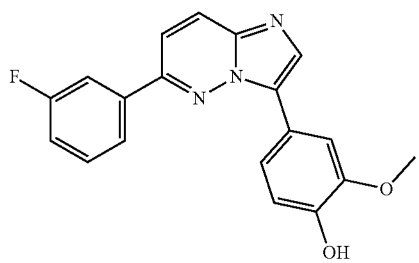 [SMILES: COc1cc(-c2cnc3ccc(-c4cccc(F)c4)nn23)ccc1O] | 472 | 4-[6-(3-fluorophenyl)imidazo[1,2-b]pyridazin-3-yl]-2-methoxyphenol | 0.28065 | 3.93 | 828_0314_0313 |
| 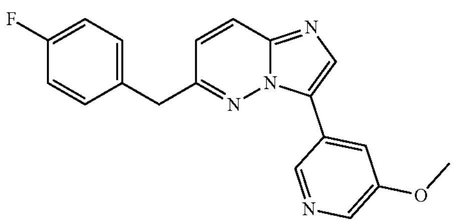 [SMILES: COc1cncc(-c2cnc3ccc(Cc4ccc(F)cc4)nn23)c1] | 473 | 6-[(4-fluorophenyl)methyl]-3-(5-methoxy-3-pyridyl)imidazo[1,2-b]pyridazine | 4.41614 | 2.95 | 828_0196_6370 |
| 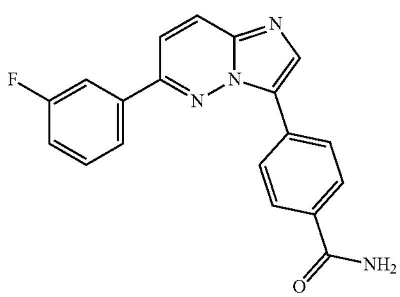 [SMILES: NC(=O)c1ccc(-c2cnc3ccc(-c4cccc(F)c4)nn23)cc1] | 474 | 4-[6-[(4-fluorophenyl)methyl]imidazo[1,2-b]pyridazin-3-yl]benzamide | 1.30064 | 3.18 | 828_0346_6340 |
| 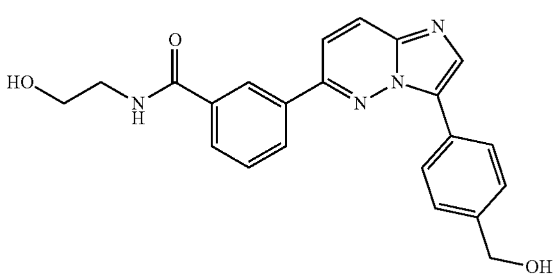 [SMILES: O=C(NCCO)c1cccc(-c2ccc3ncc(-c4ccc(CO)cc4)n3n2)c1] | 475 | N-(2-hydroxyethyl)-3-[3-[4-(hydroxymethyl)phenyl]imidazo[1,2-b]pyridazin-6-yl]benzamide | 2.14389 | 1.87 | 828_0285_0192 |
| 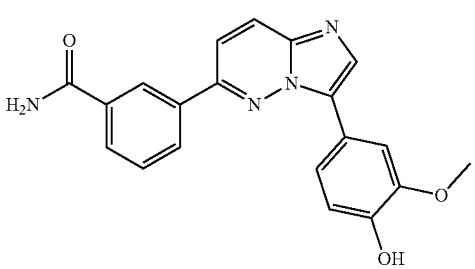 [SMILES: COc1cc(-c2cnc3ccc(-c4cccc(C(N)=O)c4)nn23)ccc1O] | 476 | 3-[3-(4-hydroxy-3-methoxyphenyl)imidazo[1,2-b]pyridazin-6-yl]benzamide | 0.22316 | 2.64 | 828_0314_0347 |

TABLE 3-continued

Primary screen- initial compounds.

| Structure | | IUPAC name | IC50 FYN (μM) | logP (consensus) | Compound ID. |
|---|---|---|---|---|---|
| 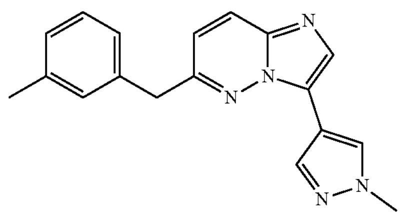 | 477 | 3-(1-methylpyrazol-4-yl)-6-(m-tolylmethyl)imidazo[1,2-b]pyridazine | 1.79534 | 3.13 | 828_7468_6291 |
| 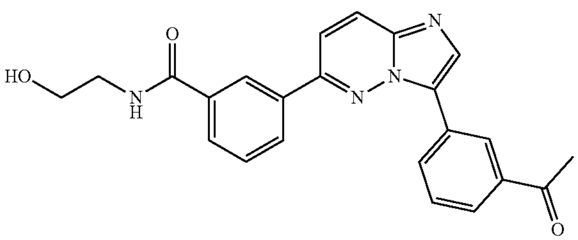 [SMILES: CC(=O)c1cccc(-c2cnc3ccc(-c4cccc(C(=O)NCCO)c4)nn23)c1] | 478 | 3-[3-(3-acetylphenyl)imidazo[1,2-b]pyridazin-6-yl]-N-(2-hydroxyethyl)benzamide | 0.6293 | 2.20 | 828_4145_0192 |
| 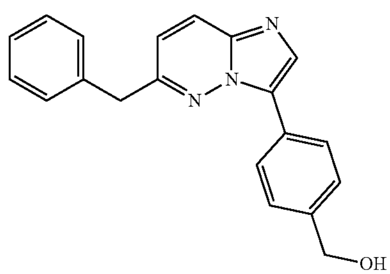 [SMILES: OCc1ccc(-c2cnc3ccc(Cc4ccccc4)nn23)cc1] | 479 | [4-(6-benzylimidazo[1,2-b]pyridazin-3-yl)phenyl]methanol | 3.22675 | 3.42 | 828_0285_6001 |
| 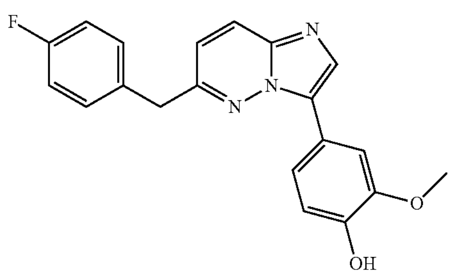 [SMILES: COc1cc(-c2cnc3ccc(Cc4ccc(F)cc4)nn23)ccc1O] | 480 | 4-[6-[(4-fluorophenyl)methyl]imidazo[1,2-b]pyridazin-3-yl]-2-methoxyphenol | 2.08974 | 3.87 | 828_0314_6370 |
| 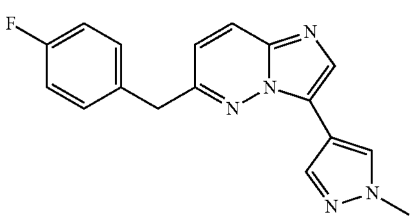 [SMILES: Cn1cc(-c2cnc3ccc(Cc4ccc(F)cc4)nn23)cn1] | 481 | 6-[(4-fluorophenyl)methyl]-3-(1-methylpyrazol-4-yl)imidazo[1,2-b]pyridazine | 1.29697 | 2.76 | 828_7468_6370 |
| 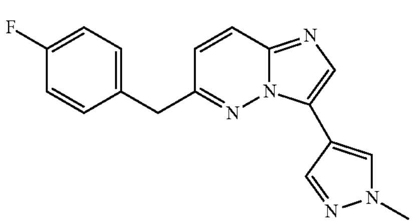 [SMILES: Cn1cc(-c2cnc3ccc(Cc4ccc(F)cc4)nn23)cn1] | 482 | N-(2-dimethylaminoethyl)-3-[6-(4-fluorophenyl)imidazo[1,2-b]pyridazin-3-yl]benzamide | 2.23882 | 3.49 | 828_0176_0339 |

TABLE 3-continued

Primary screen- initial compounds.

| Structure | | IUPAC name | IC50 FYN (μM) | logP (consensus) | Compound ID. |
|---|---|---|---|---|---|
| 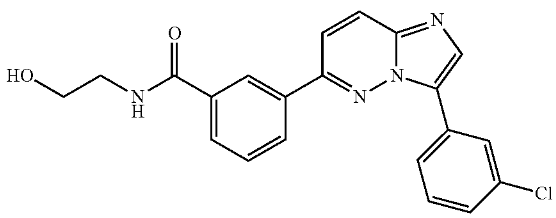 [SMILES: O=C(NCCO)c1cccc(-c2ccc3ncc(-c4cccc(Cl)c4)n3n2)c1] | 483 | 3-[3-(3-chlorophenyl)imidazo[1,2-b]pyridazin-6-yl]-N-(2-hydroxyethyl)benzamide | 30 | 3.24 | 828_0279_0192 |
| 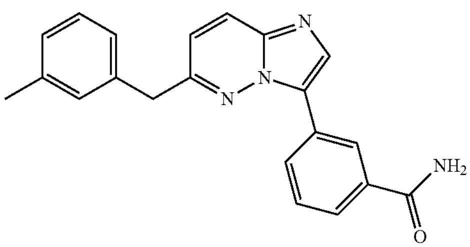 [SMILES: Cc1cccc(Cc2ccc3ncc(-c4cccc(C(N)=O)c4)n3n2)c1] | 484 | 3-[6-(m-tolylmethyl)imidazo[1,2-b]pyridazin-3-yl]benzamide | 2.16636 | 3.55 | 828_0347_6291 |
| 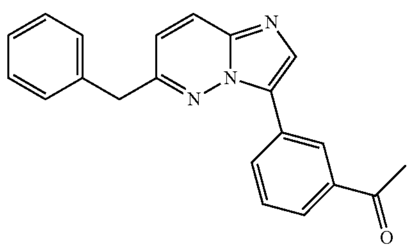 [SMILES: CC(=O)c1cccc(-c2cnc3ccc(Cc4ccccc4)nn23)c1] | 485 | 1-[3-(6-benzylimidazo[1,2-b]pyridazin-3-yl)phenyl]ethanone | 3.9717 | 3.74 | 828_4145_6001 |
| 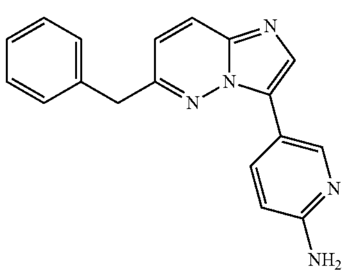 [SMILES: Nc1ccc(-c2cnc3ccc(Cc4ccccc4)nn23)cn1] | 486 | 5-(6-benzylimidazo[1,2-b]pyridazin-3-yl)pyridin-2-amine | 3.63637 | 2.73 | 828_7905_6001 |
| 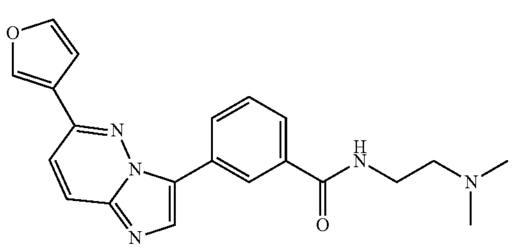 [SMILES: CN(C)CCNC(=O)c1cccc(-c2cnc3ccc(-c4ccoc4)nn23)c1] | 487 | N-(2-dimethylaminoethyl)-3-[6-(3-furyl)imidazo[1,2-b]pyridazin-3-yl]benzamide | 3.88391 | 2.49 | 828_0176_0343 |
| 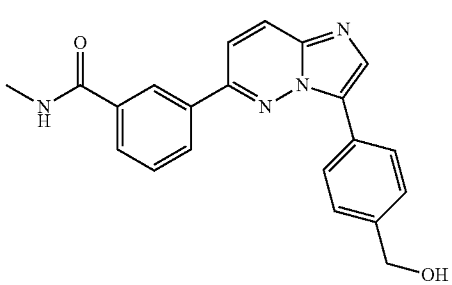 [SMILES: CNC(=O)c1cccc(-c2ccc3ncc(-c4ccc(CO)cc4)n3n2)c1] | 488 | 3-[3-[4-(hydroxymethyl)phenyl]imidazo[1,2-b]pyridazin-6-yl]-N-methyl-benzamide | 14.94149 | 2.56 | 828_0285_7965 |

TABLE 3-continued
Primary screen- initial compounds.
| Structure | | IUPAC name | IC50 FYN (μM) | logP (consensus) | Compound ID. |
|---|---|---|---|---|---|
| 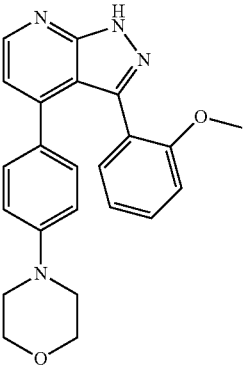 [SMILES: COc1ccccc1-c1n[nH]c2nccc(-c3ccc(N4CCOCC4)cc3)c12] | 489 | 4-[4-[3-(2-methoxyphenyl)-1H-pyrazolo[3,4-b]pyridin-4-yl]phenyl]morpholine | 1.38698 | 3.86 | 932_2105_0001 |
| 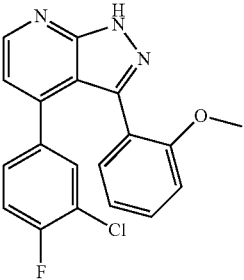 [SMILES: COc1ccccc1-c1n[nH]c2nccc(-c3ccc(F)c(Cl)c3)c12] | 490 | 4-(3-chloro-4-fluoro-phenyl)-3-(2-methoxy-phenyl)-1H-pyrazolo[3,4-b]pyridine | 1.28108 | 4.72 | 932_2105_0164 |
| 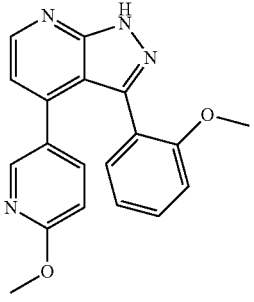 [SMILES: COc1ccc(-c2ccnc3[nH]nc(-c4ccccc4OC)c23)cn1] | 491 | 3-(2-methoxyphenyl)-4-(6-methoxy-3-pyridyl)-1H-pyrazolo[3,4-b]pyridine | 2.93037 | 3.19 | 932_2105_0311 |
| 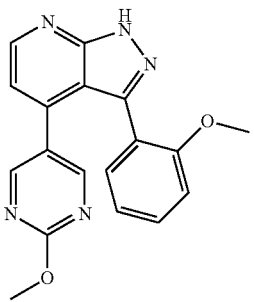 [SMILES: COc1ncc(-c2ccnc3[nH]nc(-c4ccccc4OC)c23)cn1] | 492 | 3-(2-methoxyphenyl)-4-(2-methoxy-pyrimidin-5-yl)-1H-pyrazolo[3,4-b]pyridine | 6.43118 | 2.57 | 932_2105_7628 |

TABLE 3-continued

Primary screen- initial compounds.

| Structure | | IUPAC name | IC50 FYN (μM) | logP (consensus) | Compound ID. |
|---|---|---|---|---|---|
| 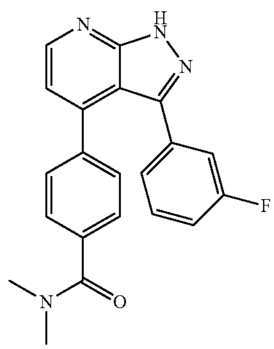 [SMILES: CN(C)C(=O)c1ccc(-c2ccnc3[nH]nc(-c4cccc(F)c4)c23)cc1] | 493 | 4-[3-(3-fluorophenyl)-1H-pyrazolo[3,4-b]pyridin-4-yl]-N,N-dimethyl-benzamide | 3.86464 | 3.57 | 932_5640_7464 |
| 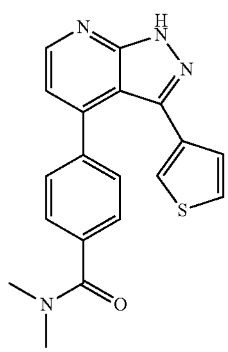 [SMILES: CN(C)C(=O)c1ccc(-c2ccnc3[nH]nc(-c4ccsc4)c23)cc1] | 494 | N,N-dimethyl-4-[3-(3-thienyl)-1H-pyrazolo[3,4-b]pyridin-4-yl]benzamide | 11.19371 | 3.20 | 932_2055_7464 |
| 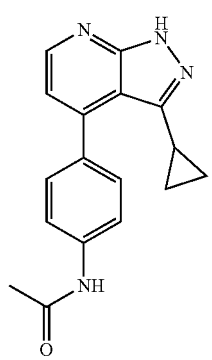 [SMILES: CC(=O)Nc1ccc(-c2ccnc3[nH]nc(C4CC4)c23)cc1] | 495 | N-[4-(3-cyclopropyl-1H-pyrazolo[3,4-b]pyridin-4-yl)phenyl]acetamide | 8.88989 | 2.24 | 932_2070_0722 |
| 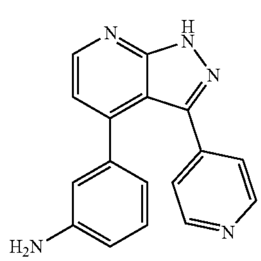 [SMILES: Nc1cccc(-c2ccnc3[nH]nc(-c4ccncc4)c23)c1] | 496 | 3-[3-(4-pyridyl)-1H-pyrazolo[3,4-b]pyridin-4-yl]aniline | 18.00668 | 2.08 | 932_5650_0005 |

TABLE 3-continued

Primary screen- initial compounds.

| Structure | | IUPAC name | IC50 FYN (μM) | logP (consensus) | Compound ID. |
|---|---|---|---|---|---|
| 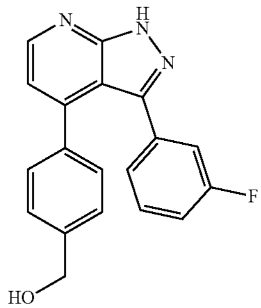 [SMILES: OCc1ccc(-c2ccnc3[nH]nc(-c4cccc(F)c4)c23)cc1] | 497 | 4-[3-(3-fluorophenyl)-1H-pyrazolo[3,4-b]pyridin-4-yl]phenyl] methanol | 3.87681 | 3.50 | 932_5640_0285 |
| 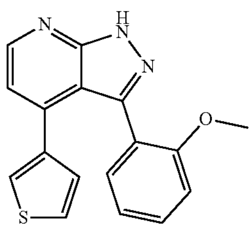 [SMILES: COc1ccccc1-c1n[nH]c2nccc(-c3ccsc3)c12] | 498 | 3-(2-methoxyphenyl)-4-(3-thienyl)-1H-pyrazolo[3,4-b]pyridine | 2.66842 | 3.75 | 932_2105_0074 |
| 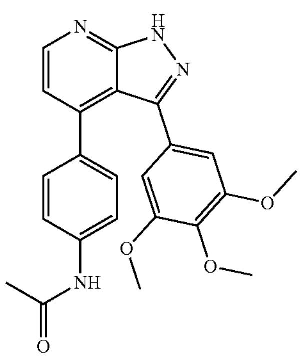 [SMILES: COc1cc(-c2n[nH]c3nccc(-c4ccc(NC(C)=O)cc4)c23)cc(OC)c1OC] | 499 | N-[4-[3-(3,4,5-trimethoxyphenyl)-1H-pyrazolo[3,4-b]pyridin-4-yl]phenyl] acetamide | 2.02053 | 2.89 | 932_4516_0722 |
| 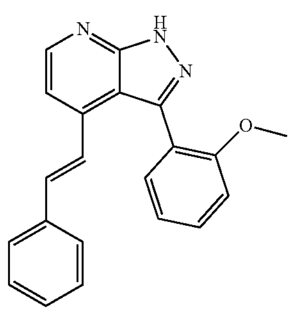 [SMILES: COc1ccccc1-c1n[nH]c2nccc(/C=C/c3ccccc3)c12] | 500 | 3-(2-methoxyphenyl)-4-[(E)-styryl]-1H-pyrazolo[3,4-b]pyridine | 1.12832 | 4.66 | 932_2105_0170 |
| 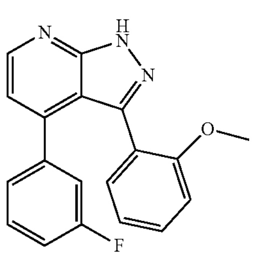 [SMILES: COc1ccccc1-c1n[nH]c2nccc(-c3cccc(F)c3)c12] | 501 | 4-(3-fluorophenyl)-3-[2-methoxyphenyl)-1H-pyrazolo[3,4-b]pyridine | 1.35112 | 4.11 | 932_2105_0313 |

TABLE 3-continued

Primary screen- initial compounds.

| Structure | | IUPAC name | IC50 FYN (μM) | logP (consensus) | Compound ID. |
|---|---|---|---|---|---|
| 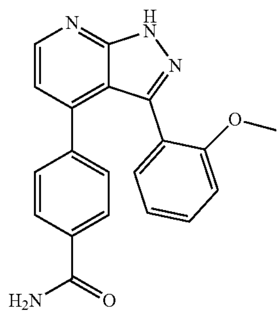 [SMILES: COc1ccccc1-c1n[nH]c2nccc(-c3ccc(C(N)=O)cc3)c12] | 502 | 4-[3-(2-methoxyphenyl)-1H-pyrazolo[3,4-b]pyridin-4-yl]benzamide | 1.47616 | 2.82 | 932_2105_0346 |
| 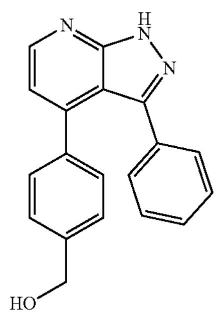 [SMILES: OCc1ccc(-c2ccnc3[nH]nc(-c4ccccc4)c23)cc1] | 503 | [4-(3-phenyl-1H-pyrazolo[3,4-b]pyridin-4-yl)phenyl]methanol | 7.10693 | 3.36 | 932_2047_0285 |
| 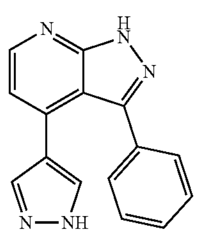 [SMILES: c1ccc(-c2n[nH]c3nccc(-c4cn[nH]c4)c23)cc1] | 504 | 3-phenyl-4-(1H-pyrazol-4-yl)-1H-pyrazolo[3,4-b]pyridine | 0.8524 | 2.43 | 932_2047_7467 |
| 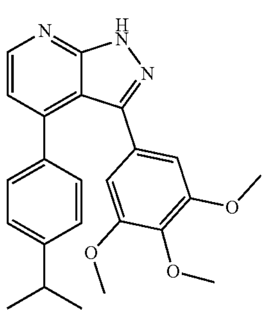 [SMILES: COc1cc(-c2n[nH]c3nccc(-c4ccc(C(C)C)cc4)c23)cc(OC)c1OC] | 505 | 4-(4-isopropylphenyl)-3-(3,4,5-trimethoxyphenyl)-1H-pyrazolo[3,4-b]pyridine | 20.88874 | 4.90 | 932_4516_0283 |
| 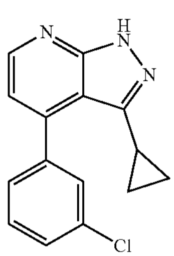 [SMILES: Clc1cccc(-c2ccnc3[nH]nc(C4CC4)c23)c1] | 506 | 4-(3-chlorophenyl)-3-cyclopropyl-1H-pyrazolo[3,4-b]pyridine | 30 | 3.61 | 932_2070_0279 |

TABLE 3-continued

Primary screen- initial compounds.

| Structure | | IUPAC name | IC50 FYN (μM) | logP (consensus) | Compound ID. |
|---|---|---|---|---|---|
| 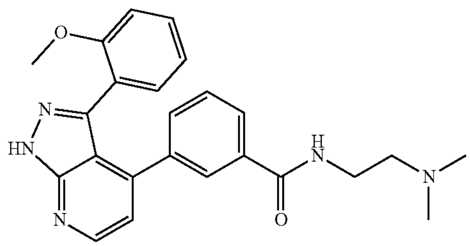 [SMILES: COc1ccccc1-c1n[nH]c2nccc(-c3cccc(C(=O)NCCN(C)C)c3)c12] | 507 | N-(2-dimethylamino-ethyl)-3-[3-(2-methoxyphenyl)-1H-pyrazolo[3,4-b]pyridin-4-yl]benzamide | 4.85182 | 3.06 | 932_2105_0176 |
| 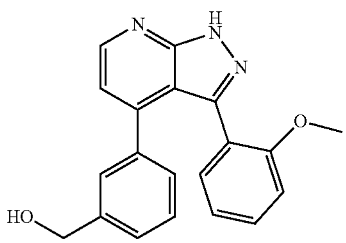 [SMILES: COc1ccccc1-c1n[nH]c2nccc(-c3cccc(CO)c3)c12] | 508 | [3-[3-(2-methoxyphenyl)-1H-pyrazolo[3,4-b]pyridin-4-yl]phenyl]methanol | 1.66776 | 3.20 | 932_2105_0291 |
| 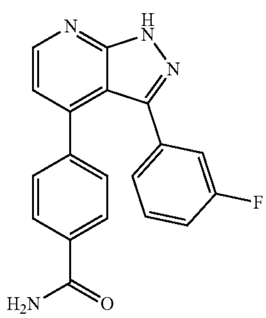 [SMILES: NC(=O)c1ccc(-c2ccnc3[nH]nc(-c4cccc(F)c4)c23)cc1] | 509 | 4-[3-(3-fluorophenyl)-1H-pyrazolo[3,4-b]pyridin-4-yl]benzamide | 2.04666 | 3.12 | 932_5640_0346 |
| 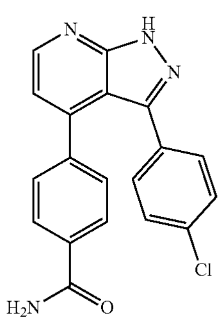 [SMILES: NC(=O)c1ccc(-c2ccnc3[nH]nc(-c4ccc(Cl)cc4)c23)cc1] | 510 | 4-[3-(4-chlorophenyl)-1H-pyrazolo[3,4-b]pyridin-4-yl]benzamide | 5.71214 | 3.58 | 932_5666_0346 |
| 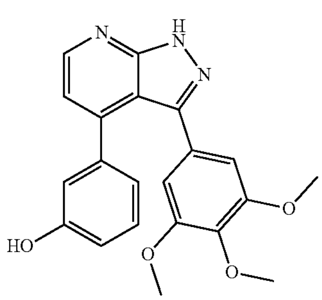 [SMILES: COc1cc(-c2n[nH]c3nccc(-c4cccc(O)c4)c23)cc(OC)c1OC] | 511 | 3-[3-(3,4,5-trimethoxy-phenyl)-1H-pyrazolo[3,4-b]pyridin-4-yl]phenol | 5.02812 | 3.35 | 932_4516_0284 |

TABLE 3-continued

Primary screen- initial compounds.

| Structure | | IUPAC name | IC50 FYN (μM) | logP (consensus) | Compound ID. |
|---|---|---|---|---|---|
| 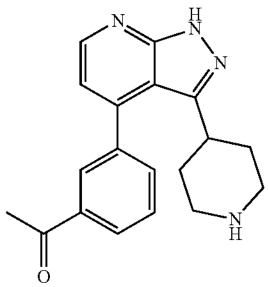 [SMILES: CC(=O)c1cccc(-c2ccnc3[nH]nc(C4CCNCC4)c23)c1] | 512 | 1-[3-[3-(4-piperidyl)-1H-pyrazolo[3,4-b]pyridin-4-yl]phenyl] ethanone | 19.65771 | 1.89 | 932_2802_4145 |
| 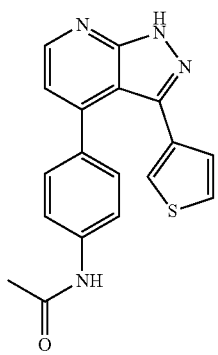 [SMILES: CC(=O)Nc1ccc(-c2ccnc3[nH]nc(-c4ccsc4)c23)cc1] | 513 | N-[4-[3-(3-thienyl)-1H-pyrazolo[3,4-b]pyridin-4-yl]phenyl] acetamide | 4.86579 | 3.14 | 932_2055_0722 |
| 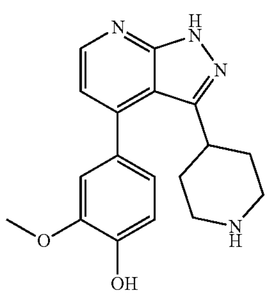 [SMILES: COc1cc(-c2ccnc3[nH]nc(C4CCNCC4)c23)ccc1O] | 514 | 2-methoxy-4-[3-(4-piperidyl)-1H-pyrazolo[3,4-b]pyridin-4-yl]phenol | 11.88451 | 1.87 | 932_2802_0314 |
| 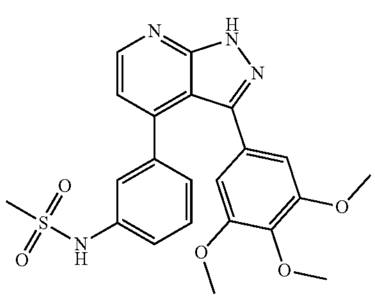 | 515 | N-[3-[3-(3,4,5-trimethoxy-phenyl)-1H-pyrazolo[3,4-b]pyridin-4-yl]phenyl] methane-sulfonamide | 12.76436 | 2.03 | 932_4516_6488 |
| 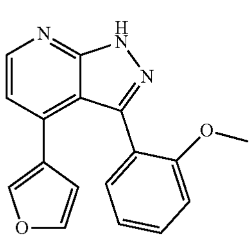 [SMILES: COc1ccccc1-c1n[nH]c2nccc(-c3ccoc3)c12] | 516 | 4-(3-furyl)-3-(2-methoxyphenyl)-1H-pyrazolo[3,4-b]pyridine | 4.89672 | 3.11 | 932_2105_0343 |

TABLE 3-continued

Primary screen- initial compounds.

| Structure | | IUPAC name | IC50 FYN (μM) | logP (consensus) | Compound ID. |
|---|---|---|---|---|---|
| 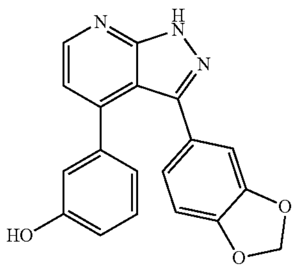 [SMILES: Oc1cccc(-c2ccnc3[nH]nc(-c4ccc5c(c4)OCO5)c23)c1] | 517 | 3-[3-(1,3-benzodioxol-5-yl)-1H-pyrazolo[3,4-b]pyridin-4-yl]phenol | 6.24902 | 3.45 | 932_5654_0284 |
| 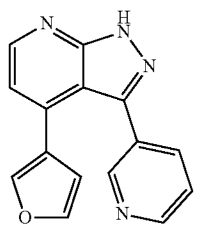 [SMILES: c1cncc(-c2n[nH]c3nccc(-c4ccoc4)c23)c1] | 518 | 4-(3-furyl)-3-(3-pyridyl)-1H-pyrazolo[3,4-b]pyridine | 14.29835 | 2.05 | 932_2094_0343 |
| 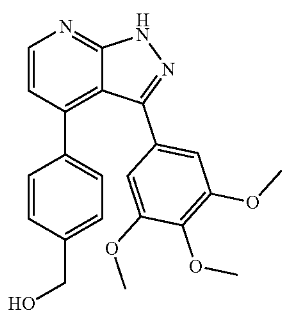 [SMILES: COc1cc(-c2n[nH]c3nccc(-c4ccc(CO)cc4)c23)cc(OC)c1OC] | 519 | [4-[3-(3,4,5-trimethoxyphenyl)-1H-pyrazolo[3,4-b]pyridin-4-yl]phenyl]methanol | 5.38048 | 2.89 | 932_4516_0285 |
| 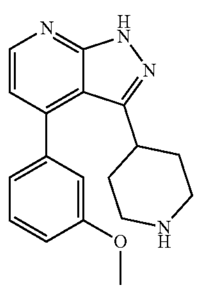 [SMILES: COc1cccc(-c2ccnc3[nH]nc(C4CCNCC4)c23)c1] | 520 | 4-(3-methoxyphenyl)-3-(4-piperidyl)-1H-pyrazolo[3,4-b]pyridine | 17.59629 | 2.17 | 932_2802_4140 |
| 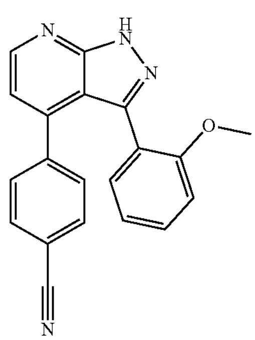 [SMILES: COc1ccccc1-c1n[nH]c2nccc(-c3ccc(C#N)cc3)c12] | 521 | 4-[3-(2-methoxyphenyl)-1H-pyrazolo[3,4-b]pyridin-4-yl]benzonitrile | 1.58329 | 3.82 | 932_2105_0086 |

TABLE 3-continued

Primary screen- initial compounds.

| Structure | | IUPAC name | IC50 FYN (μM) | logP (con- sen- sus) | Compound ID. |
|---|---|---|---|---|---|
| 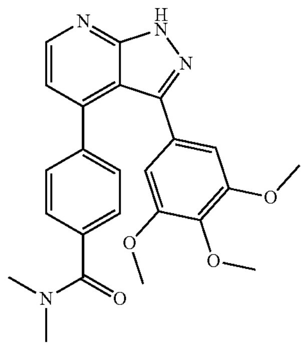 | 522 | N,N-dimethyl-4-[3-(3,4,5-trimethoxy-phenyl)-1H-pyrazolo[3,4-b]pyridin-4-yl]benzamide | 11.14532 | 2.95 | 932_4516_7464 |
| 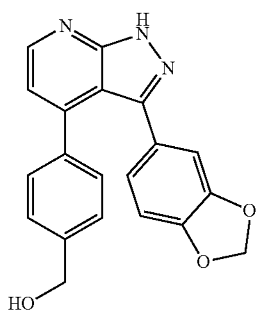 [SMILES: OCc1ccc(-c2ccnc3[nH]nc(-c4ccc5c(c4)OCO5)c23)cc1] | 523 | [4-[3-(1,3-benzodioxol-5-yl)-1H-pyrazolo[3,4-b]pyridin-4-yl]phenyl]methanol | 4.64328 | 2.98 | 932_5654_0285 |
| 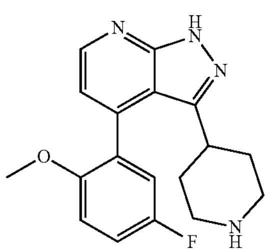 [SMILES: COc1ccc(F)cc1-c1ccnc2[nH]nc(C3CCNCC3)c12] | 524 | 4-(5-fluoro-2-methoxy-phenyl)-3-(4-piperidyl)-1H-pyrazolo[3,4-b]pyridine | 11.69312 | 2.31 | 932_2802_8363 |
| 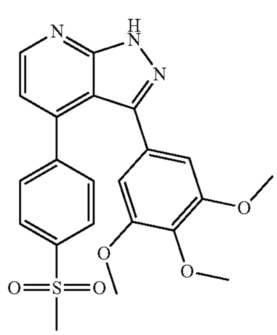 [SMILES: COc1cc(-c2n[nH]c3nccc(-c4ccc(S(C)(=O)=O)cc4)c23)cc(OC)c1OC] | 525 | 4-(4-methylsulfonyl-phenyl)-3-(3,4,5-trimethoxy-phenyl)-1H-pyrazolo[3,4-b]pyridlne | 11.16027 | 2.49 | 932_4516_0174 |

TABLE 3-continued

Primary screen- initial compounds.

| Structure | | IUPAC name | IC50 FYN (μM) | logP (consensus) | Compound ID. |
|---|---|---|---|---|---|
| 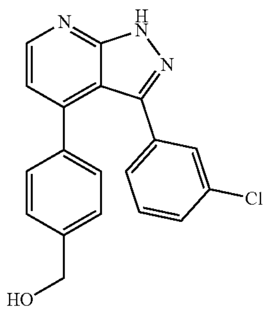 [SMILES: OCc1ccc(-c2ccnc3[nH]nc(-c4cccc(Cl)c4)c23)cc1] | 526 | [4-[3-(3-chlorophenyl)-1H-pyrazolo[3,4-b]pyridin-4-yl]phenyl] methanol | 6.49611 | 3.96 | 932_2049_0285 |
| 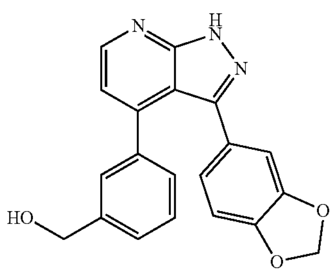 [SMILES: OCc1cccc(-c2ccnc3[nH]nc(-c4ccc5c(c4)OCO5)c23)c1] | 527 | [3-[3-(1,3-benzodioxol-5-yl)-1H-pyrazolo[3,4-b]pyridin-4-yl]phenyl] methanol | 3.09057 | 2.98 | 932_5654_0291 |
| 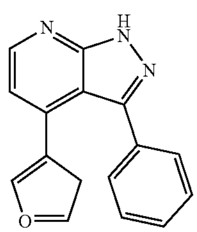 | 528 | 4-(3-furyl)-3-phenyl-1H-pyrazolo[3,4-b]pyridine | 8.62504 | 3.27 | 932_2047_0343 |
| 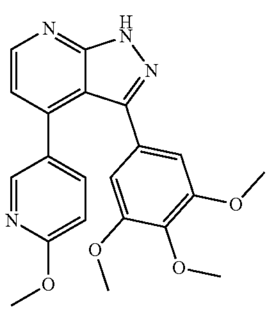 [SMILES: COc1ccc(-c2ccnc3[nH]nc(-c4cc(OC)c(OC)c(OC)c4)c23)cn1] | 529 | 4-(6-methoxy-3-pyridyl)-3-(3,4,5-trimethoxy-phenyl)-1H-pyrazolo[3,4-b]pyridine | 16.92312 | 2.87 | 932_4516_0311 |
| 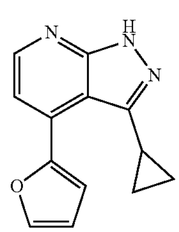 [SMILES: c1coc(-c2ccnc3[nH]nc(C4CC4)c23)c1] | 530 | 3-cyclopropyl-4-(2-furyl)-1H-pyrazolo[3,4-b]pyridine | 12.61441 | 2.06 | 932_2070_0142 |

TABLE 3-continued

Primary screen- initial compounds.

| Structure | | IUPAC name | IC50 FYN (μM) | logP (consensus) | Compound ID. |
|---|---|---|---|---|---|
| 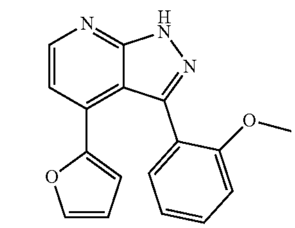 [SMILES: COc1ccccc1-c1n[nH]c2nccc(-c3ccco3)c12] | 531 | 4-(2-furyl)-3-(2-methoxyphenyl)-1H-pyrazolo[3,4-b]pyridine | 2.27665 | 3.03 | 932_2105_0142 |
| 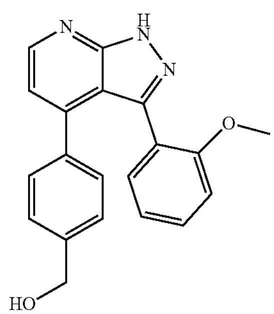 [SMILES: COc1ccccc1-c1n[nH]c2nccc(-c3ccc(CO)cc3)c12] | 532 | [4-[3-(2-methoxyphenyl)-1H-pyrazolo[3,4-b]pyridin-4-yl]phenyl]methanol | 1.10049 | 3.20 | 932_2105_0285 |
| 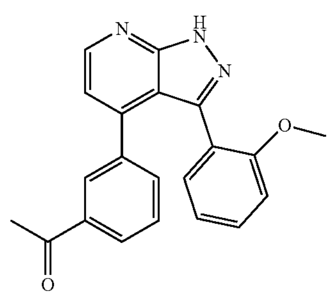 [SMILES: COc1ccccc1-c1n[nH]c2nccc(-c3cccc(C(C)=O)c3)c12] | 533 | 1-[3-[3-(2-methoxyphenyl)-1H-pyrazolo[3,4-b]pyridin-4-yl]phenyl]ethanone | 6.60309 | 3.53 | 932_2105_4145 |
| 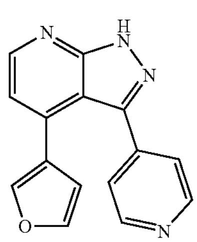 [SMILES: c1cc(-c2n[nH]c3nccc(-c4ccoc4)c23)ccn1] | 534 | 4-(3-furyl)-3-(4-pyridyl)-1H-pyrazolo[3,4-b]pyridine | 20.24336 | 2.05 | 932_5650_0343 |
| 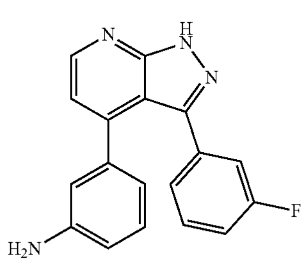 [SMILES: Nc1cccc(-c2ccnc3[nH]nc(-c4cccc(F)c4)c23)c1] | 535 | 3-[3-(3-fluorophenyl)-1H-pyrazolo[3,4-b]pyridin-4-yl]aniline | 15.07442 | 3.44 | 932_5640_0005 |

TABLE 3-continued

Primary screen- initial compounds.

| Structure | | IUPAC name | IC50 FYN (μM) | logP (consensus) | Compound ID. |
|---|---|---|---|---|---|
| 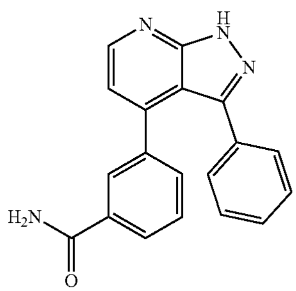 [SMILES: NC(=O)c1cccc(-c2ccnc3[nH]nc(-c4ccccc4)c23)c1] | 536 | 3-(3-phenyl-1H-pyrazolo[3,4-b]pyridin-4-yl)benzamide | 11.71738 | 2.98 | 932_2047_0347 |
| 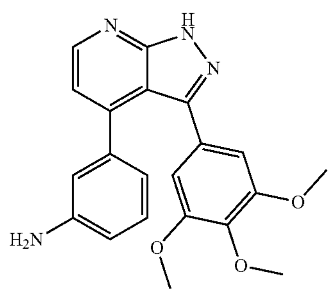 [SMILES: COc1cc(-c2n[nH]c3nccc(-c4cccc(N)c4)c23)cc(OC)c1OC] | 537 | 3-[3-(3,4,5-trimethoxyphenyl)-1H-pyrazolo[3,4-b]pyridin-4-yl]aniline | 14.80741 | 2.82 | 932_4516_0005 |
| 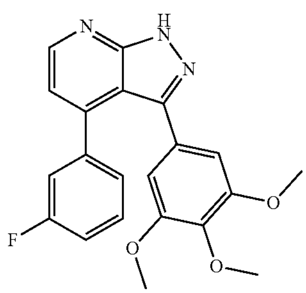 [SMILES: COc1cc(-c2n[nH]c3nccc(-c4cccc(F)c4)c23)cc(OC)c1OC] | 538 | 4-(3-fluorophenyl)-3-(3,4,5-trimethoxyphenyl)-1H-pyrazolo[3,4-b]pyridine | 5.22838 | 3.80 | 932_4516_0313 |
| 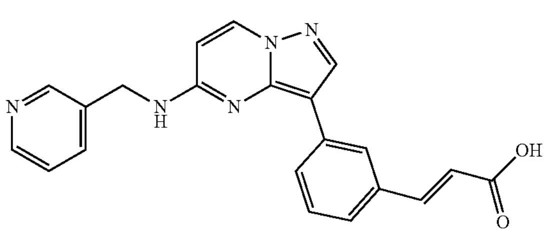 [SMILES: O=C(O)/C=C/c1cccc(-c2cnn3ccc(NCc4cccnc4)nc23)c1] | 539 | (E)-3-[3-[5-(3-pyridylmethylamino)pyrazolo[1,5-a]pyrimidin-3-yl]phenyl]prop-2-enoic acid | 2.27421 | 3.04 | 294_4003_0289 |
| 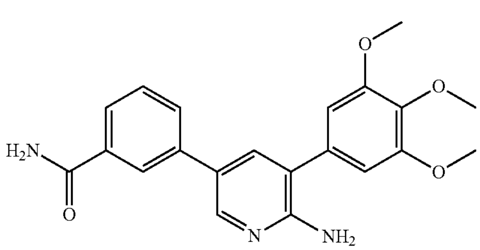 [SMILES: COc1cc(-c2cc(-c3cccc(C(N)=O)c3)cnc2N)cc(OC)c1OC] | 540 | 3-[6-amino-5-(3,4,5-trimethoxyphenyl)-3-pyridyl]benzamide | 0.44196 | 2.19 | 382_0087_0347 |

TABLE 3-continued

Primary screen- initial compounds.

| Structure | | IUPAC name | IC50 FYN (µM) | logP (consensus) | Compound ID. |
|---|---|---|---|---|---|
| 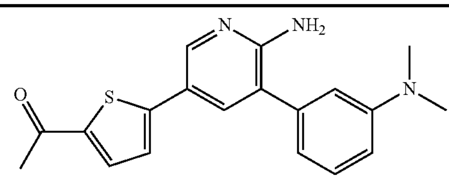 | 541 | 1-[5-[6-amino-5-[3-(dimethyl-amino)phenyl]-3-pyridyl]-2-thienyl]ethanone | 3.41528 | 3.39 | 382_0135_0066 |
| 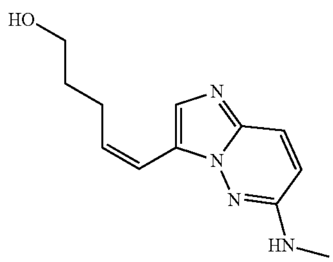 [SMILES: CNc1ccc2ncc(/C=C\CCCO)n2n1] | 542 | (Z)-5-[6-(methylamino)imidazo[1,2-b]pyridazin-3-yl]pent-4-en-1-ol | 31.48029 | 1.22 | 437_0299 |
| 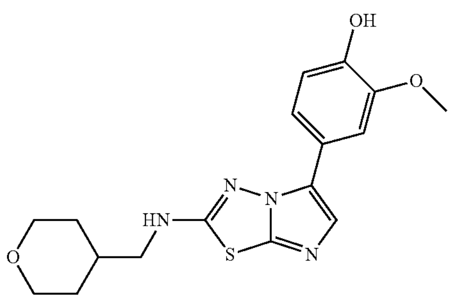 [SMILES: COc1cc(-c2cnc3sc(NCC4CCOCC4)nn23)ccc1O] | 543 | 2-methoxy-4-[2-(tetrahydropyran-4-ylmethyl-amino)imidazo[2,1-b][1,3,4]thiadiazo-5-yl]phenol | 2.16407 | 2.47 | 699_0243_0314 |
| 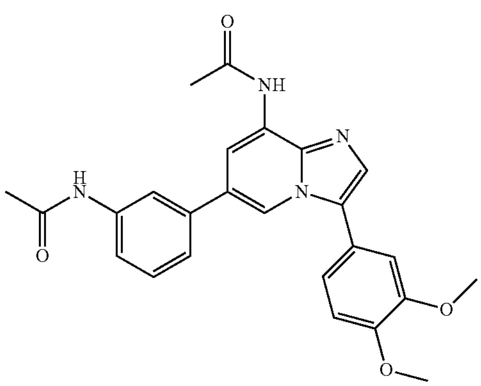 [SMILES: COc1ccc(-c2cnc3c(NC(C)=O)cc(-c4cccc(NC(C)=O)c4)cn23)cc1OC] | 544 | N-[3-[8-acetamido-3-(3,4-dimethoxy-phenyl)imidazo[1,2-a]pyridin-6-yl]phenyl]acetamide | 1.59766 | 2.13 | 802_0079_0081 |
| 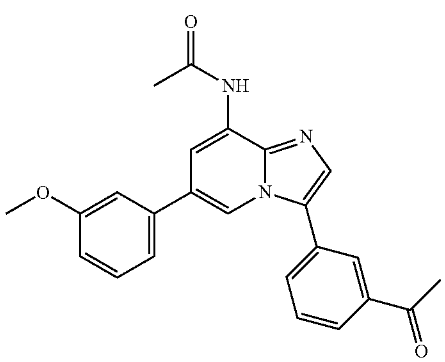 [SMILES: COc1cccc(-c2cc(NC(C)=O)c3ncc(-c4cccc(C(C)=O)c4)n3c2)c1] | 545 | N-[3-(3-acetylphenyl)-6-[3-methoxy-phenyl)imidazo[1,2-a]pyridin-8-yl]acetamide | 3.05101 | 2.61 | 802_4145_4140 |

TABLE 3-continued

Primary screen- initial compounds.

| Structure | | IUPAC name | IC50 FYN (μM) | logP (consensus) | Compound ID. |
|---|---|---|---|---|---|
| 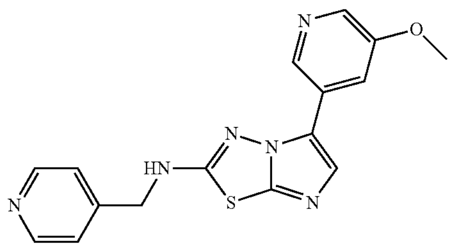 [SMILES: COc1cncc(-c2cnc3sc(NCc4ccncc4)nn23)c1] | 546 | 5-(5-methoxy-3-pyridyl)-N-(4-pyridylmethyl)imidazo[2,1-b][1,3,4]thiadiazol-2-amine | 0.93173 | 1.64 | 699_0237_0196 |
| 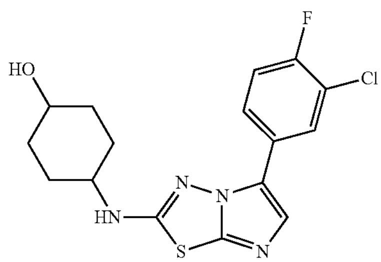 [SMILES: OC1CCC(Nc2nn3c(-c4ccc(F)c(Cl)c4)cnc3s2)CC1] | 547 | 4-[[5-(3-chloro-4-fluoro-phenyl)imidazo[2,1-b][1,3,4]thiadiazol-2-yl]amino]cyclohexanol | 4.05722 | 3.67 | 699_0240_0164 |
| 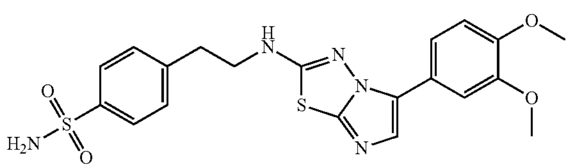 [SMILES: COc1ccc(-c2cnc3sc(NCCc4ccc(S(N)(=O)=O)cc4)nn23)cc1OC] | 548 | 4-[2-[[5-(3,4-dimethoxyphenyl)imidazo[2,1-b][1,3,4]thiadiazol-2-yl]amino]ethyl]benzenesulfonamide | 5.11606 | 2.81 | 699_6182_0079 |
| 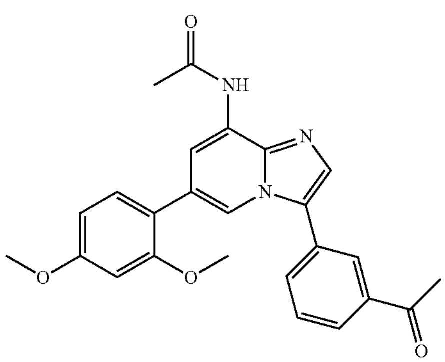 [SMILES: COc1ccc(-c2cc(NC(C)=O)c3ncc(-c4cccc(C(C)=O)c4)n3c2)c(OC)c1] | 549 | N-[3-(3-acetylphenyl)-6-(2,4-dimethoxy-phenyl)imidazo[1,2-a]pyridin-8-yl]acetamide | 2.50187 | 2.45 | 802_4145_4141 |
| 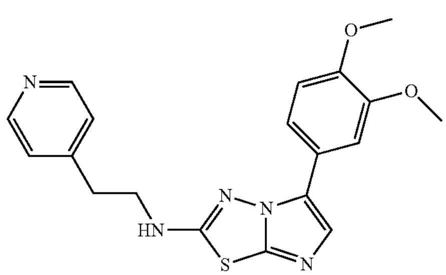 [SMILES: COc1ccc(-c2cnc3sc(NCCc4ccncc4)nn23)cc1OC] | 550 | 5-(3,4-dimethoxy-phenyl)-N-[2-(4-pyridyl)ethyl]imidazo[2,1-b][1,3,4]thiadiazol-2-amine | 3.1387 | 2.99 | 699_0039_0079 |

TABLE 3-continued

Primary screen- initial compounds.

| Structure | | IUPAC name | IC50 FYN (μM) | logP (consensus) | Compound ID. |
|---|---|---|---|---|---|
| 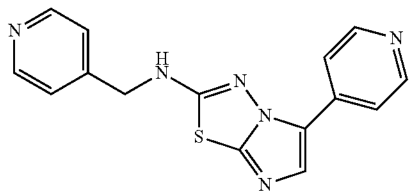 [SMILES: c1cc(CNc2nn3c(-c4ccncc4)cnc3s2)ccn1] | 551 | 5-(4-pyridyl)-N-(4-pyridylmethyl)imidazo[2,1-b][1,3,4]thiadiazol-2-amine | 2.64747 | 1.80 | 699_0237_0069 |
| 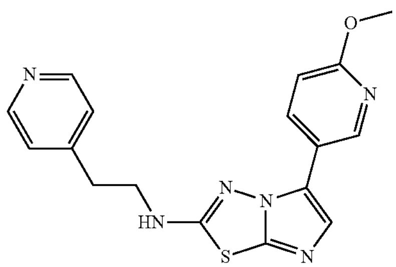 [SMILES: COc1ccc(-c2cnc3sc(NCCc4ccncc4)nn23)cn1] | 552 | 5-(6-methoxy-3-pyridyl)-N-[2-(4-pyridyl)ethyl]imidazo[2,1-b][1,3,4]thiadiazol-2-amine | 2.03015 | 2.52 | 699_0039_0311 |
| 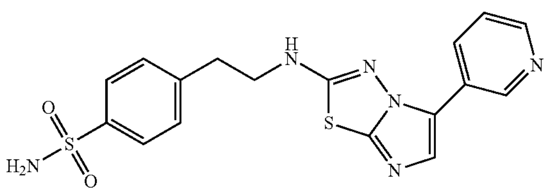 [SMILES: NS(=O)(=O)c1ccc(CCNc2nn3c(-c4cccnc4)cnc3s2)cc1] | 553 | 4-[2-[[5-(3-pyridyl)imidazo[2,1-d][1,3,4]thiadiazol-2-yl]amino]ethyl]benzenesulfonamide | 1.87926 | 1.91 | 699_6182_0071 |
| 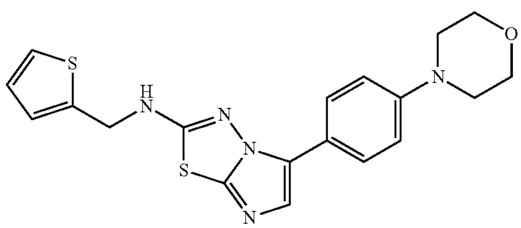 [SMILES: c1csc(CNc2nn3c(-c4ccc(N5CCOCC5)cc4)cnc3s2)c1] | 554 | 5-(4-morpholinophenyl)-N-(2-thienylmethyl)imidazo[2,1-b][1,3,4]thiadiazol-2-amine | 3.82253 | 4.03 | 699_0146_0001 |
| 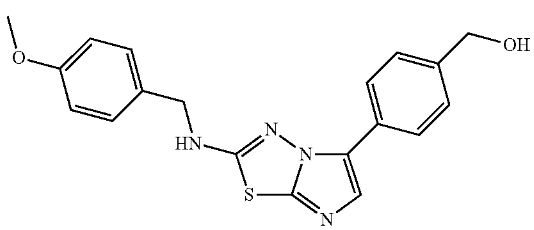 [SMILES: COc1ccc(CNc2nn3c(-c4ccc(CO)cc4)cnc3s2)cc1] | 555 | [4-[2-[(4-methoxyphenyl)methylamino]imidazo[2,1-b][1,3,4]thiadiazol-5-yl]phenyl]methanol | 2.8094 | 3.31 | 699_0244_0285 |
| 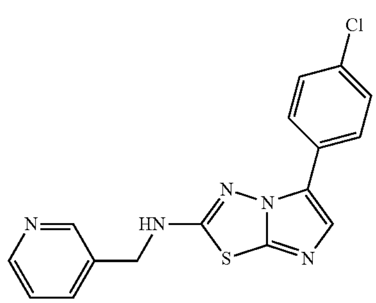 [SMILES: Clc1ccc(-c2cnc3sc(NCc4cccnc4)nn23)cc1] | 556 | 5-(4-chlorophenyl)-N-(3-pyridylmethyl)imidazo[2,1-b][1,3,4]thiadiazol-2-amine | 3.65935 | 3.62 | 699_4003_0160 |

TABLE 3-continued

Primary screen- initial compounds.

| Structure | | IUPAC name | IC50 FYN (μM) | logP (consensus) | Compound ID. |
|---|---|---|---|---|---|
| 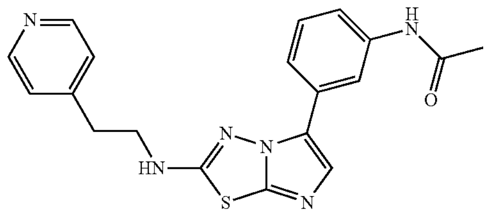 [SMILES: CC(=O)Nc1cccc(-c2cnc3sc(NCCc4ccncc4)nn23)c1] | 557 | N-[3-[2-[2-(4-pyridyl)ethylamino]imidazo[2,1-b][1,3,4]thiadiazol-5-yl]phenyl]acetamide | 1.31627 | 2.54 | 699_0039_0081 |
| 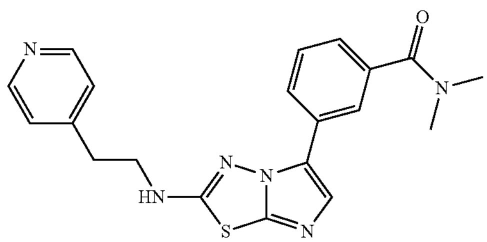 [SMILES: CN(C)C(=O)c1cccc(-c2cnc3sc(NCCc4ccncc4)nn23)c1] | 558 | N,N-dimethyl-3-[2-[2-(4-pyridyl)ethylamino]imidazo[2,1-b][1,3,4]thiadiazol-5-yl]benzamide | 0.72142 | 2.60 | 699_0039_0349 |
| 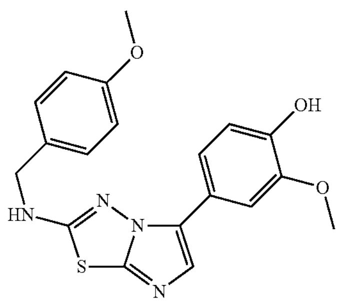 [SMILES: COc1ccc(CNc2nn3c(-c4ccc(O)c(OC)c4)cnc3s2)cc1] | 559 | 2-methoxy-4-[2-[(4-methoxyphenyl)methylamino]imidazo[2,1-b][1,3,4]thiadiazol-5-yl]phenol | 1.77761 | 3.61 | 699_0244_0314 |
| 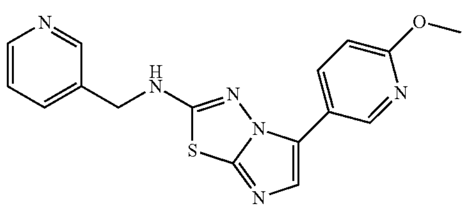 [SMILES: COc1ccc(-c2cnc3sc(NCc4cccnc4)nn23)cn1] | 560 | 5-(6-methoxy-3-pyridyl)-N-(3-pyridylmethyl)imidazo[2,1-b][1,3,4]thiadiazol-2-amine | 2.93804 | 2.23 | 699_4003_0311 |
| 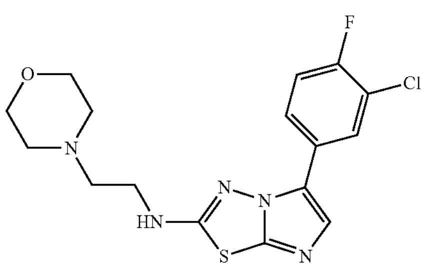 [SMILES: Fc1ccc(-c2cnc3sc(NCCN4CCOCC4)nn23)cc1Cl] | 561 | 5-(3-chloro-4-fluoro-phenyl)-N-(2-morpholinoethyl)imidazo[2,1-b][1,3,4]thiadiazol-2-amine | 4.81646 | 3.05 | 699_0252_0164 |
| 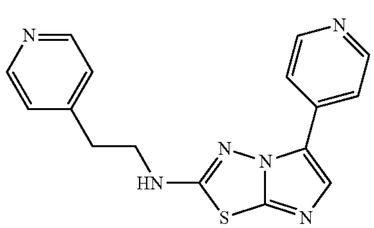 [SMILES: c1cc(CCNc2nn3c(-c4ccncc4)cnc3s2)ccn1] | 562 | 5-(4-pyridyl)-N-2-(4-pyridyl)ethyl]imidazo[2,1-b][1,3,4]thiadiazol-2-amine | 2.42663 | 2.08 | 699_0039_0069 |

TABLE 3-continued

Primary screen- initial compounds.

| Structure | | IUPAC name | IC50 FYN (μM) | logP (consensus) | Compound ID. |
|---|---|---|---|---|---|
| 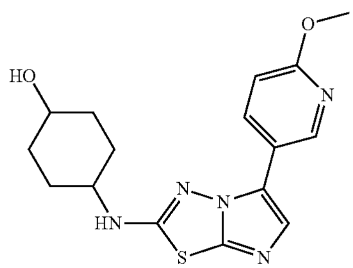 [SMILES: COc1ccc(-c2cnc3sc(NC4CCC(O)CC4)nn23)cn1] | 563 | 4-[[5-(6-methoxy-3-pyridyl)imidazo[2,1-b][1,3,4]thiadiazol-2-yl]amino]cyclohexanol | 1.61261 | 2.14 | 699_0240_0311 |
| 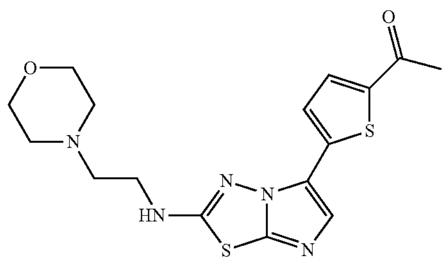 [SMILES: CC(=O)c1ccc(-c2cnc3sc(NCCN4CCOCC4)nn23)s1] | 564 | 1-[5-[2-(2-morpholinoethyl-amino)imidazo[2,1-b][1,3,4]thiadiazol-5-yl]-2-thienyl]ethanone | 3 | 1.77 | 699_0252_0066 |
| 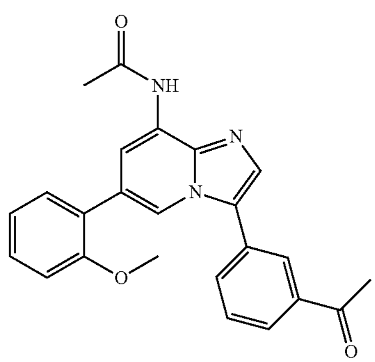 [SMILES: COc1ccccc1-c1cc(NC(C)=O)c2ncc(-c3cccc(C(C)=O)c3)n2c1] | 565 | N-[3-(3-acetylphenyl)-6-[2-methoxy-phenyl)imidazo[1,2-a]pyridin-8-yl]acetamide | 1.58352 | 2.61 | 802_4145_0083 |
| 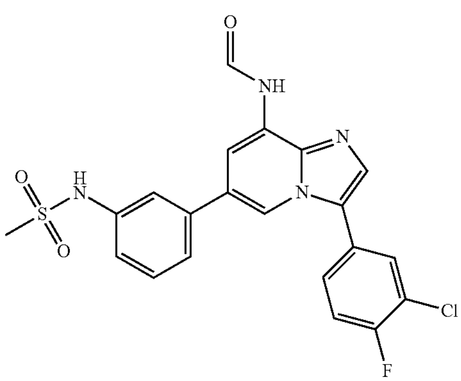 [SMILES: CS(=O)(=O)Nc1cccc(-c2cc(NC=O)c3ncc(-c4ccc(F)c(Cl)c4)n3c2)c1] | 566 | N-[3-(3-chloro-4-fluoro-phenyl)-6-[3-(methane-sulfonamido)phenyl]imidazo[1,2-a]pyridin-8-yl]formamide | 2.85911 | 2.28 | 788_0164_6488 |
| 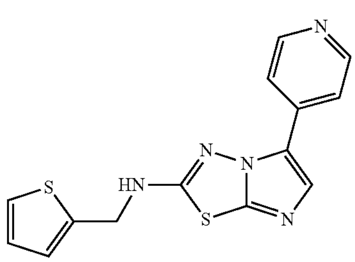 [SMILES: c1csc(CNc2nn3c(-c4ccncc4)cnc3s2)c1] | 567 | 5-(4-pyridyl)-N-(2-thienylmethyl)imidazo[2,1-b][1,3,4]thiadiazol-2-amine | 3.61591 | 2.93 | 699_0146_0069 |

TABLE 3-continued

Primary screen- initial compounds.

| Structure | | IUPAC name | IC50 FYN (μM) | logP (consensus) | Compound ID. |
|---|---|---|---|---|---|
| 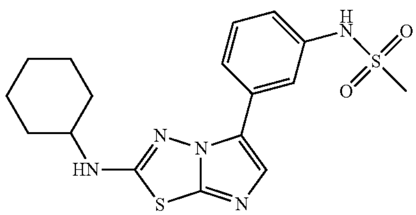 [SMILES: CS(=O)(=O)Nc1cccc(-c2cnc3sc(NC4CCCCC4)nn23)c1] | 568 | N-[3-[2-(cyclohexylamino)imidazo[2,1-b][1,3,4]thiadiazol-5-yl]phenyl]methanesulfonamide | 4.33348 | 2.68 | 699_0052_6488 |
| 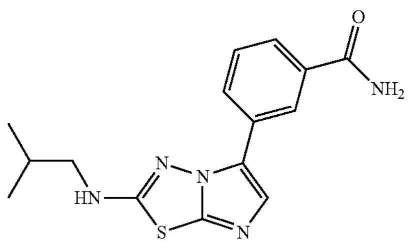 [SMILES: CC(C)CNc1nn2c(-c3cccc(C(N)=O)c3)cnc2s1] | 569 | 3-[2-(isobutylamino)imidazo[2,1-b][1,3,4]thiadiazol-5-yl]benzamide | 1.13221 | 2.60 | 699_0149_0347 |
| 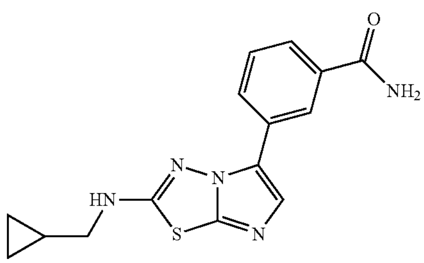 [SMILES: NC(=O)c1cccc(-c2cnc3sc(NCC4CC4)nn23)c1] | 570 | 3-[2-(cyclopropylmethylamino)imidazo[2,1-b][1,3,4]thiadiazol-5-yl]benzamide | 1.94081 | 2.14 | 699_4051_0347 |
| 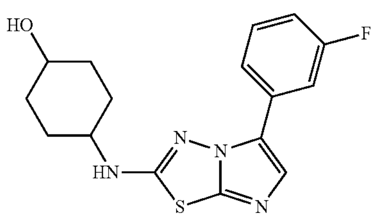 [SMILES: OC1CCC(Nc2nn3c(-c4cccc(F)c4)cnc3s2)CC1] | 571 | 4-[[5-(3-fluorophenyl)imidazo[2,1-b][1,3,4]thiadiazol-2-yl]amino]cyclohexanol | 2.92063 | 3.06 | 699_0240_0313 |
| 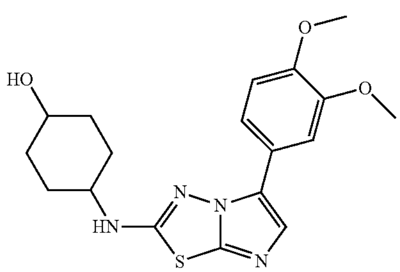 [SMILES: COc1ccc(-c2cnc3sc(NC4CCC(O)CC4)nn23)cc1OC] | 572 | 4-[[5-(3,4-dimethoxyphenyl)imidazo[2,1-b][1,3,4]thiadiazol-2-yl]amino]cyclohexanol | 0.48307 | 2.60 | 699_0240_0079 |
| 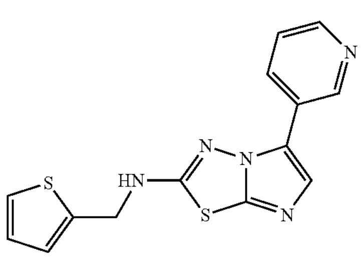 [SMILES: c1cncc(-c2cnc3sc(NCc4cccs4)nn23)c1] | 573 | 5-(3-pyridyl)-N-(2-thienylmethyl)imidazo[2,1-b][1,3,4]thiadiazol-2-amine | 1.94173 | 2.93 | 699_0146_0071 |

TABLE 3-continued

Primary screen- initial compounds.

| Structure | | IUPAC name | IC50 FYN (μM) | logP (consensus) | Compound ID. |
|---|---|---|---|---|---|
| 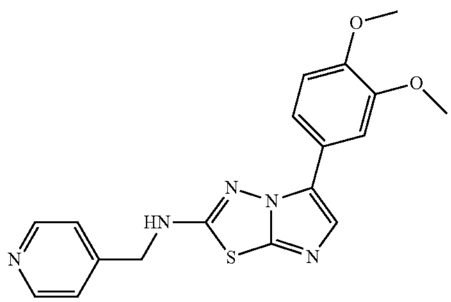 [SMILES: COc1ccc(-c2cnc3sc(NCc4ccncc4)nn23)cc1OC] | 574 | 5-(3,4-dimethoxyphenyl)-N-(4-pyridylmethyl)imidazo[2,1-b][1,3,4]thiadiazol-2-amine | 2.1285 | 2.70 | 699_0237_0079 |
| 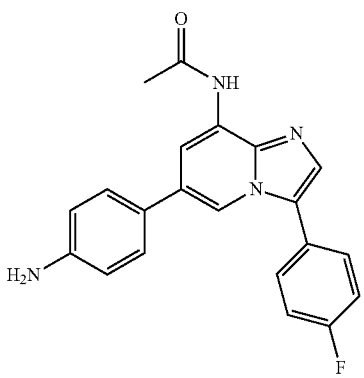 [SMILES: CC(=O)Nc1cc(-c2ccc(N)cc2)cn2c(-c3ccc(F)cc3)cnc12] | 575 | N-[6-(4-aminophenyl)-3-(4-fluorophenyl)imidazo[1,2-a]pyridin-8-yl]acetamide | 5.25032 | 2.53 | 802_0339_7917 |
| 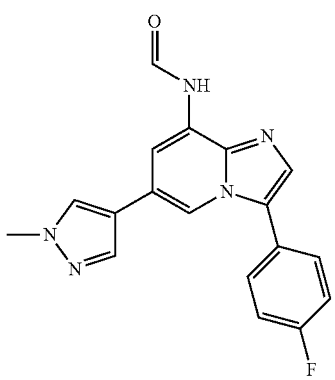 [SMILES: Cn1cc(-c2cc(NC=O)c3ncc(-c4ccc(F)cc4)n3c2)cn1] | 576 | N-[3-(4-fluorophenyl)-6-(1-methylpyrazol-4-yl)imidazo[1,2-a]pyridin-8-yl]formamide | 8.08703 | 1.73 | 788_0339_8400 |
| 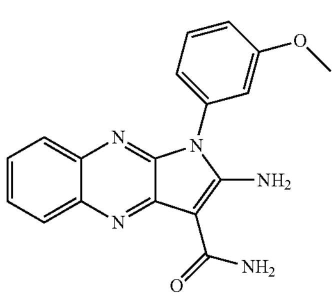 [SMILES: COc1cccc(-n2c(N)c(C(N)=O)c3nc4ccccc4nc32)c1] | 577 | 2-amino-1-(3-methoxyphenyl)pyrrolo[3,2-b]quinoxaline-3-carboxamide | 1.18486 | 2.64 | DT2012-0375412 |

TABLE 3-continued

Primary screen- initial compounds.

| Structure | | IUPAC name | IC50 FYN (μM) | logP (consensus) | Compound ID. |
|---|---|---|---|---|---|
| 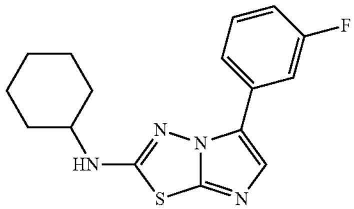 [SMILES: Fc1cccc(-c2cnc3sc(NC4CCCCC4)nn23)c1] | 578 | N-cyclohexyl-5-(3-fluorophenyl)imidazo[2,1-d][1,3,4]thiadiazol-2-amine | 4.07753 | 4.45 | 699_0052_0313 |
| 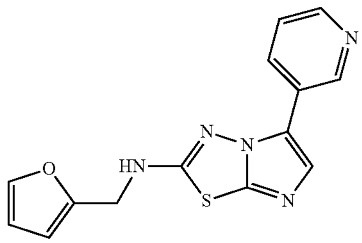 [SMILES: c1cncc(-c2cnc3sc(NCc4ccco4)nn23)c1] | 579 | N-(2-furylmethyl)-5-(3-pyridyl)imidazo[2,1-a][1,3,4]thiadiazol-2-amine | 3.16405 | 2.07 | 699_0144_0071 |
| 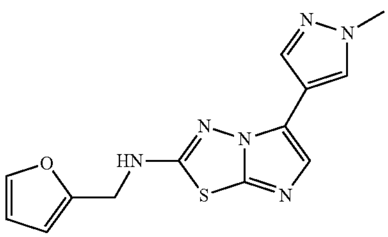 [SMILES: Cn1cc(-c2cnc3sc(NCc4ccco4)nn23)cn1] | 580 | N-(2-furylmethyl)-5-(1-methylpyrazol-4-yl)imidazo[2,1-b][1,3,4]thiadiazol-2-amine | 5.63578 | 1.72 | 699_0144_7468 |
| 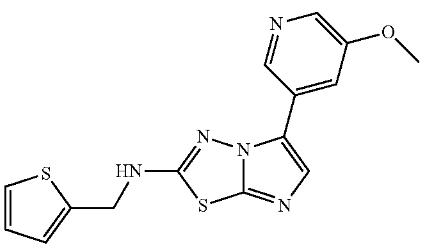 [SMILES: COc1cncc(-c2cnc3sc(NCc4cccs4)nn23)c1] | 581 | 5-(5-methoxy-3-pyridyl)-N-(2-thienylmethyl)imidazo[2,1-b][1,3,4]thiadiazol-2-amine | 0.72859 | 2.77 | 699_0146_0196 |
| 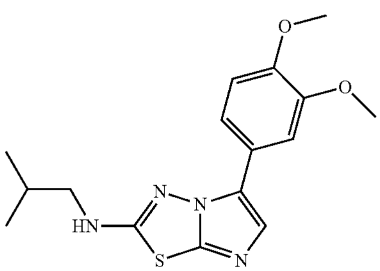 [SMILES: COc1ccc(-c2cnc3sc(NCC(C)C)nn23)cc1OC] | 582 | 5-(3,4-dimethoxyphenyl)-N-isobutyl-imidazo[2,1-b][1,3,4]thiadiazol-2-amine | 2.74508 | 3.44 | 699_0149_0079 |
| 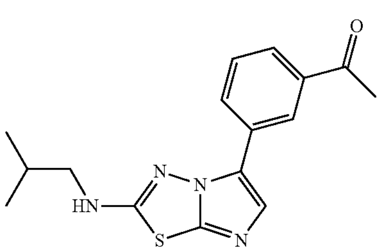 [SMILES: CC(=O)c1cccc(-c2cnc3sc(NCC(C)C)nn23)c1] | 583 | 1-[3-[2-(isobutylamino)imidazo[2,1-a][1,3,4]thiadiazol-5-yl]phenyl]ethanone | 15.11833 | 3.31 | 699_0149_4145 |

TABLE 3-continued

Primary screen- initial compounds.

| Structure | | IUPAC name | IC50 FYN (μM) | logP (consensus) | Compound ID. |
|---|---|---|---|---|---|
| 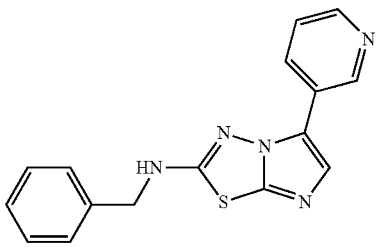 [SMILES: c1ccc(CNc2nn3c(-c4cccnc4)cnc3s2)cc1] | 584 | N-benzyl-5-(3-pyridyl)imidazo[2,1-b][1,3,4]thiadiazol-2-amine | 0.8393 | 3.01 | 699_0232_0071 |
| 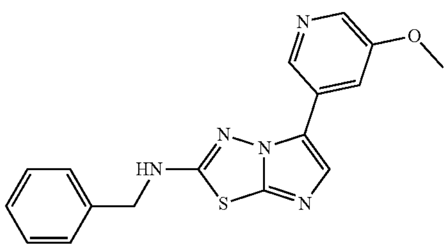 [SMILES: COc1cncc(-c2cnc3sc(NCc4ccccc4)nn23)c1] | 585 | N-benzyl-5-(5-methoxy-3-pyridyl)imidazo[2,1-b][1,3,4]thiadiazol-2-amine | 0.34323 | 2.86 | 699_0232_0196 |
| 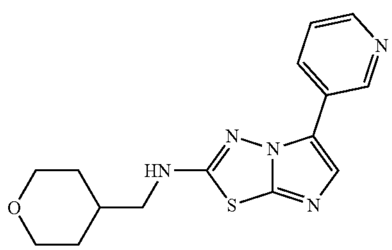 [SMILES: c1cncc(-c2cnc3sc(NCC4CCOCC4)nn23)c1] | 586 | 5-(3-pyridyl)-N-(tetrahydropyran-4-ylmethyl)imidazo[2,1-b][1,3,4]thiadiazol-2-amine | 4.84876 | 1.71 | 699_0243_0071 |
| 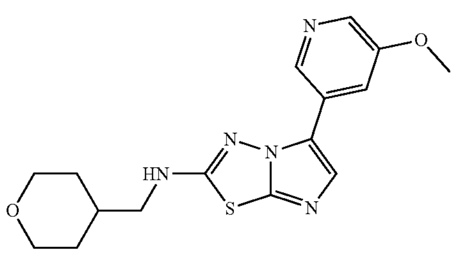 [SMILES: COc1cncc(-c2cnc3sc(NCC4CCOCC4)nn23)c1] | 587 | 5-(5-methoxy-3-pyridyl)-N-(tetrahydropyran-4-ylmethyl)imidazo[2,1-d][1,3,4]thiadiazol-2-amine | 0.38423 | 1.55 | 699_0243_0196 |
| 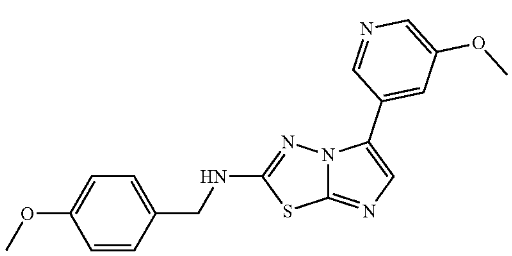 | 588 | N-[(4-methoxyphenyl)methyl]-5-(5-methoxy-3-pyridyl)imidazo[2,1-3][1,3,4]thiadiazol-2-amine | 9.65333 | 2.70 | 699_0244_0196 |

TABLE 3-continued

Primary screen- initial compounds.

| Structure | | IUPAC name | IC50 FYN (μM) | logP (consensus) | Compound ID. |
|---|---|---|---|---|---|
| 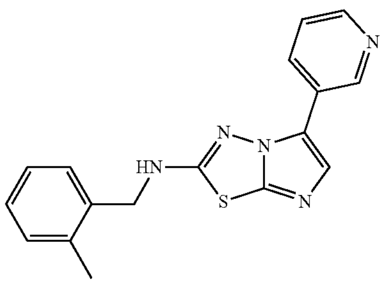 [SMILES: Cc1ccccc1CNc1nn2c(-c3cccnc3)cnc2s1] | 589 | N-(o-tolylmethyl)-5-(3-pyridyl)imidazo[2,1-b][1,3,4]thiadiazol-2-amine | 1.07729 | 3.53 | 699_8074_0071 |
| 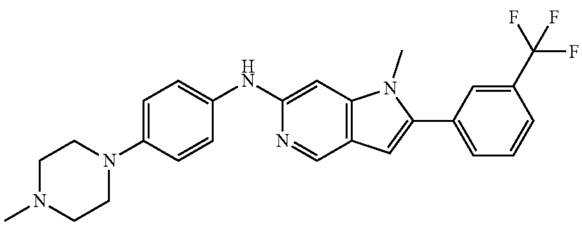 [SMILES: CN1CCN(c2ccc(Nc3cc4c(cn3)cc(-c3cccc(C(F)(F)F)c3)n4C)cc2)CC1] | 590 | 1-methyl-N-[4-(4-methylpiperazin-1-yl)phenyl]-2-[3-(trifluoromethyl)phenyl]pyrrolo[3,2-c]pyridin-6-amine | 30 | 5.51 | 809_2669_5837_0091 |
| 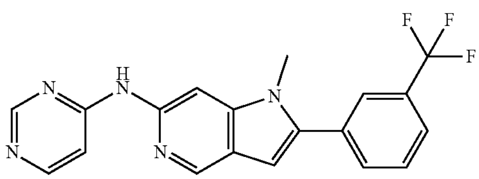 [SMILES: Cn1c(-c2cccc(C(F)(F)F)c2)cc2cnc(Nc3ccncn3)cc21] | 591 | 1-methyl-N-pyrimidin-4-yl-2-[3-(trifluoromethyl)phenyl]pyrrolo[3,2-c]pyridin-6-amine | 16.77669 | 4.23 | 809_2669_5837_6410 |
| 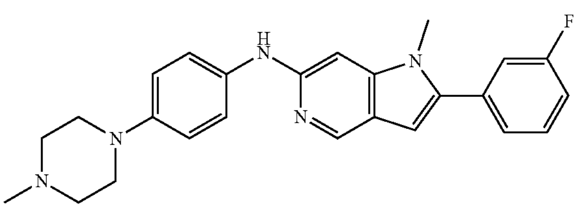 [SMILES: CN1CCN(c2ccc(Nc3cc4c(cn3)cc(-c3cccc(F)c3)n4C)cc2)CC1] | 592 | 2-(3-fluorophenyl)-1-methyl-N-[4-(4-methylpiperazin-1-yl)phenyl]pyrrolo[3,2-c]pyridin-6-amine | 12.86554 | 4.78 | 809_2670_5837_0091 |
| 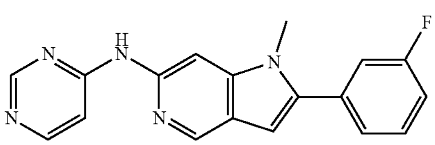 [SMILES: Cn1c(-c2cccc(F)c2)cc2cnc(Nc3ccncn3)cc21] | 593 | 2-(3-fluorophenyl)-1-methyl-N-pyrimidin-4-ylpyrrolo[3,2-c]pyridin-6-amine | 9.08728 | 3.49 | 809_2670_5837_6410 |
| 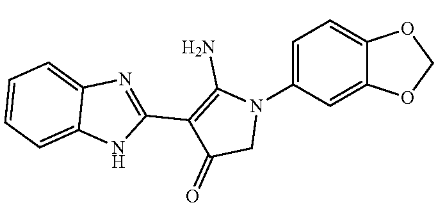 [SMILES: NC1=C(c2nc3ccccc3[nH]2)C(=O)CN1c1ccc2c(c1)OCO2] | 594 | 5-amino-4-(1H-benzimidazol-2-yl)-1-(1,3-benzodioxol-5-yl)-2H-pyrrol-3-one | 4.06818 | 2.64 | DT2009-0160159 |

TABLE 3-continued

Primary screen- initial compounds.

| Structure | | IUPAC name | IC50 FYN (µM) | logP (consensus) | Compound ID. |
|---|---|---|---|---|---|
| 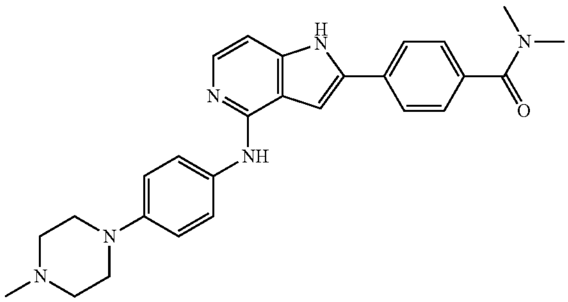 | 595 | N,N-dimethyl-4-[4-[4-(4-methylpiperazin-1-yl)anilino]-1H-pyrrolo[3,2-c]pyridin-2-yl]benzamide | 7.04339 | 3.71 | 838_2671_0263_0091 |
| 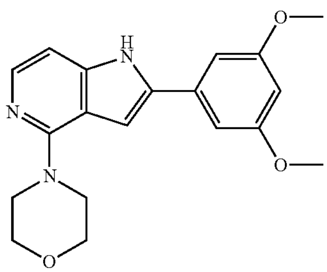 [SMILES: COc1cc(OC)cc(-c2cc3c(N4CCOCC4)nccc3[nH]2)c1] | 596 | 4-[2-(3,5-dimethoxyphenyl)-1H-pyrrolo[3,2-c]pyridin-4-yl]morpholine | 30 | 2.59 | 838_2728_0263_4009 |
| 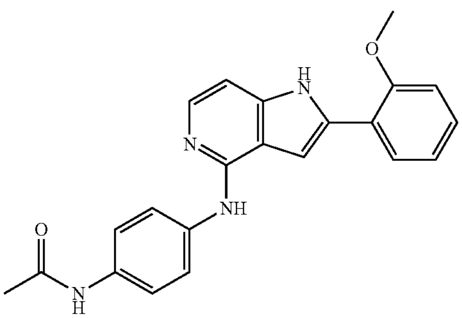 [SMILES: COc1ccccc1-c1cc2c(Nc3ccc(NC(C)=O)cc3)nccc2[nH]1] | 597 | N-[4-[[2-(2-methoxyphenyl)-1H-pyrrolo[3,2-c]pyridin-4-yl]amino]phenyl]acetamide | 30 | 3.54 | 838_2729_0263_0023 |
| 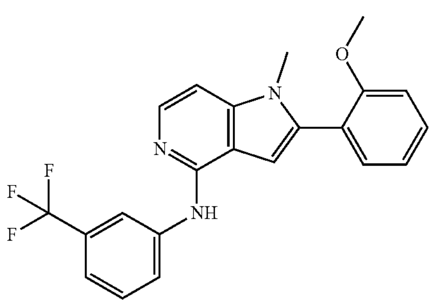 [SMILES: COc1ccccc1-c1cc2c(Nc3cccc(C(F)(F)F)c3)nccc2n1C] | 598 | 2-(2-methoxyphenyl)-1-methyl-N-[3-(trifluoromethyl)phenyl]pyrrolo[3,2-c]pyridin-4-amine | 30 | 5.40 | 838_2729_5837_0235 |
| 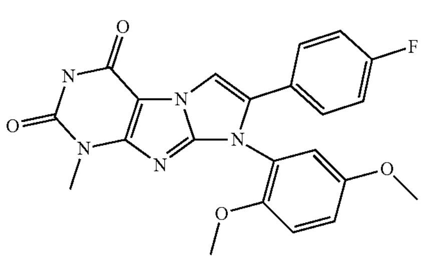 [SMILES: COc1ccc(OC)c(-n2c(-c3ccc(F)cc3)cn3c4c(=O)[nH]c(=O)n(C)c4nc23)c1] | 599 | 8-(2,5-dimethoxyphenyl)-7-(4-fluorophenyl)-1-methyl-3H-imidazo[1,2-g]purine-2,4-dione [Also listed as: 6-(2,5-dimethoxyphenyl)-7-(4-fluorophenyl)-4-methyl-purino[7,8-a]imidazole-1,3-dione: | 18.44433 | 2.44 | DT2012-0296118 |

TABLE 3-continued

Primary screen- initial compounds.

| Structure | | IUPAC name | IC50 FYN (μM) | logP (consensus) | Compound ID. |
|---|---|---|---|---|---|
| | 600 | methyl 2-amino-1-(3-hydroxyphenyl)pyrrolo[3,2-b]quinoxaline-3-carboxylate | 2.25787 | 3.64 | DT2012-0351552 |

TABLE 4

Secondary screen- initial candidate compounds re-synthesized and expanded.

| Structure | | IUPAC name | IC50 FYN (μM) | logP (consensus) | Compound ID. (prior ID No. if any) |
|---|---|---|---|---|---|
| 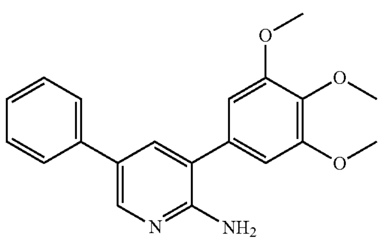 [SMILES: COc1cc(-c2cc(-c3ccccc3)cnc2N)cc(OC)c1OC] | 1 | 5-phenyl-3-(3,4,5-trimethoxyphenyl)-pyridin-2-amine | 1.3061932482 | 3.34 | BF000312489 (382_0087_0061) |
| 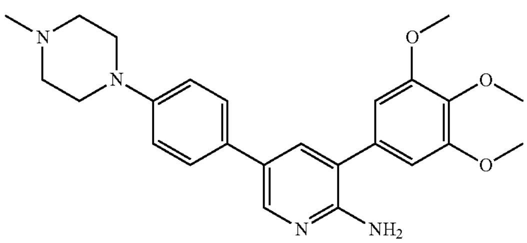 | 2 | 5-[4-(4-methylpiperazin-1-yl)phenyl]-3-(3,4,5-trimethoxyphenyl)-pyridin-2-amine | 0.232041699 | 3.30 | BF000312520 (382_0087_0218) |
| 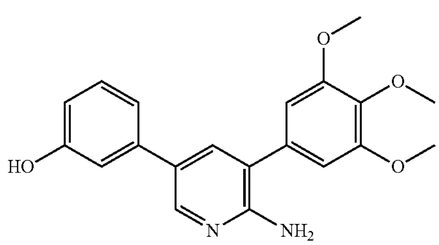 [SMILES: COc1cc(-c2cc(-c3cccc(O)c3)cnc2N)cc(OC)c1OC] | 3 | 3-[6-amino-5-(3,4,5-trimethoxyphenyl)-3-pyridyl]-phenol | 0.525870963 | 3.04 | BF000312527 (382_0087_0284) |
| 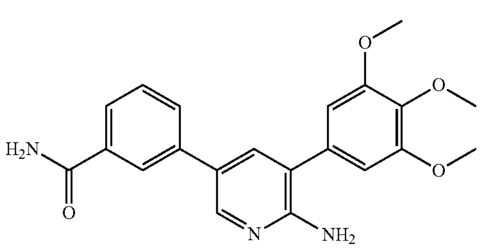 [SMILES: COc1cc(-c2cc(-c3cccc(C(N)=O)c3)cnc2N)cc(OC)c1OC] | 4 | 3-[6-amino-5-(3,4,5-trimethoxyphenyl)-3-pyridyl]-benzamide | 0.4942965 | 2.19 | BF000312539 (382_0087_0347) |

TABLE 4-continued

Secondary screen- initial candidate compounds re-synthesized and expanded.

| Structure | | IUPAC name | IC50 FYN (µM) | logP (consensus) | Compound ID. (prior ID No. if any) |
|---|---|---|---|---|---|
| 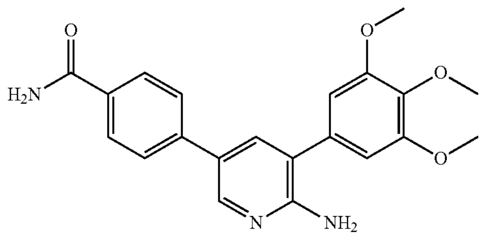 [SMILES: COc1cc(-c2cc(-c3ccc(C(N)=O)cc3)cnc2N)cc(OC)c1OC] | 5 | 4-[6-amino-5-(3,4,5-trimethoxyphenyl)-3-pyridyl]-benzamide | 0.45785952 | 2.19 | BF000312540 (382_0087_0346) |
| 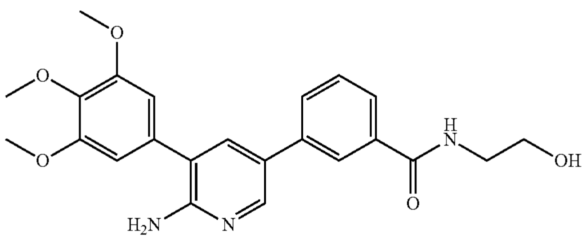 [SMILES: COc1cc(-c2cc(-c3cccc(C(=O)NCCO)c3)cnc2N)cc(OC)c1OC] | 6 | 3-[6-amino-5-(3,4,5-trimethoxyphenyl)-3-pyridyl]-N-(2-hydroxyethyl)-benzamide | 1.001189887 | 1.73 | BF000312542 (382_0087_0192) |
| 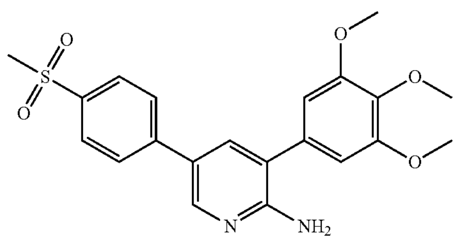 | 7 | 5-(4-methylsulfonylphenyl)-3-(3,4,5-trimethoxyphenyl)-pyridin-2-amine | 0.674160478 | 2.18 | BF000312544 |
| 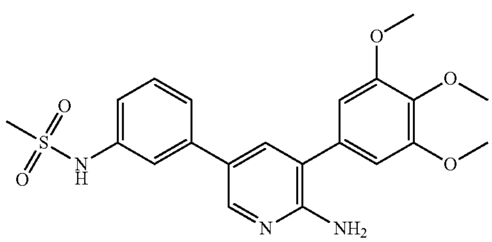 | 8 | N-[3-[6-amino-5-(3,4,5-trimethoxyphenyl)-3-pyridyl]-phenyl]-methanesulfonamide | 0.561599306 | 1.72 | BF000312545 (382_0087_6488) |
| 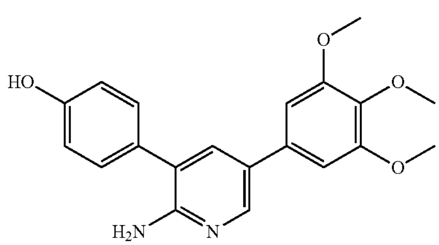 [SMILES: COc1cc(-c2cnc(N)c(-c3ccc(O)cc3)c2)cc(OC)c1OC] | 9 | 4-[2-amino-5-(3,4,5-trimethoxyphenyl)-3-pyridyl]-phenol | 0.2885 | 3.04 | BF000313556 (382_7249_0087) |
| 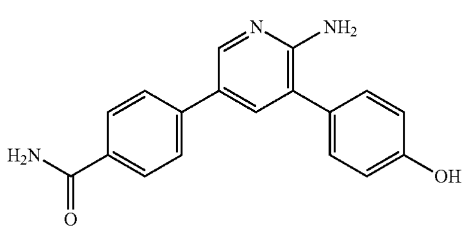 [SMILES: NC(=O)c1ccc(-c2cnc(N)c(-c3ccc(O)cc3)c2)cc1] | 10 | 4-[6-amino-5-(4-hydroxyphenyl)-3-pyridyl]-benzamide | 1.085653826 | 2.36 | BF000313559 |

TABLE 4-continued

Secondary screen- initial candidate compounds re-synthesized and expanded.

| Structure | | IUPAC name | IC50 FYN (μM) | logP (consensus) | Compound ID. (prior ID No. if any) |
|---|---|---|---|---|---|
| 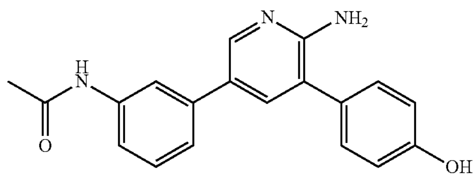 [SMILES: CC(=O)Nc1cccc(-c2cnc(N)c(-c3ccc(O)cc3)c2)c1] | 11 | N-[3-[6-amino-5-(4-hydroxy-phenyl)-3-pyridyl]-phenyl]-acetamide | 0.898083782 | 2.75 | BF000313562 (382_7249_0081) |
| 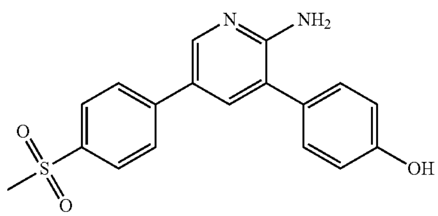 [SMILES: CS(=O)(=O)c1ccc(-c2cnc(N)c(-c3ccc(O)cc3)c2)cc1] | 12 | 4-[2-amino-5-(4-methyl-sulfonyl-phenyl)-3-pyridyl]-phenol | 1.551309576 | 2.35 | BF000313563 (382_7249_0174) |
| 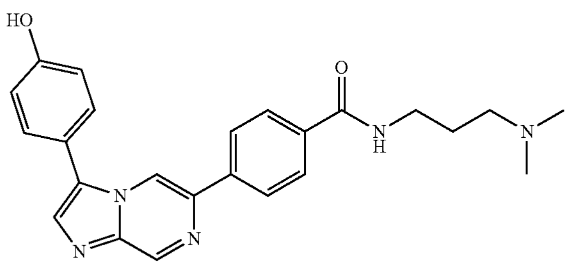 [SMILES: CN(C)CCCNC(=O)c1ccc(-c2cn3c(-c4ccc(O)cc4)cnc3cn2)cc1] | 13 | N-[3-(dimethyl-amino)-propyl]-4-[3-(4-hydroxy-phenyl)-imidazo[1,2-a]pyrazin-6-yl]-benzamide | 0.705417706 | 1.99 | BF000333874 |
| 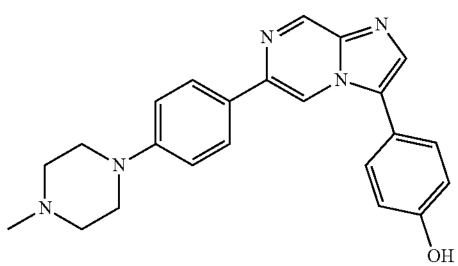 [SMILES: CN1CCN(c2ccc(-c3cn4c(-c5ccc(O)cc5)cnc4cn3)cc2)CC1] | 14 | 4-[6-[4-(4-methyl-piperazin-1-yl)phenyl]-imidazo[1,2-a]pyrazin-3-yl]phenol | 0.464568962 | 2.79 | BF000333878 (388_0080_0218) |
| 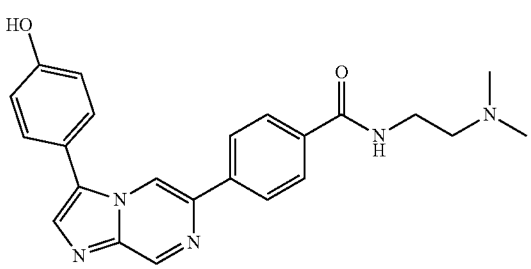 [SMILES: CN(C)CCNC(=O)c1ccc(-c2cn3c(-c4ccc(O)cc4)cnc3cn2)cc1] | 15 | N-[2-(dimethyl-amino)-ethyl]-4-[3-(4-hydroxy-phenyl)-imidazo[1,2-a]pyrazin-6-yl]-benzamide | 0.486180008 | 1.93 | BF000333881 |
| 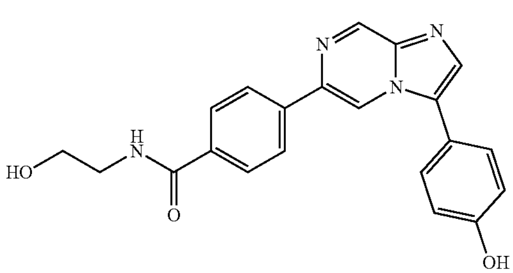 [SMILES: O=C(NCCO)c1ccc(-c2cn3c(-c4ccc(O)cc4)cnc3cn2)cc1] | 16 | N-(2-hydroxy-ethyl)-4-[3-(4-hydroxy-phenyl)-imidazo[1,2-a]pyrazin-6-yl]benzamide | 0.739736615 | 1.22 | BF000333882 (388_0080_0328) |

TABLE 4-continued

Secondary screen- initial candidate compounds re-synthesized and expanded.

| Structure | | IUPAC name | IC50 FYN (μM) | logP (consensus) | Compound ID. (prior ID No. if any) |
|---|---|---|---|---|---|
| 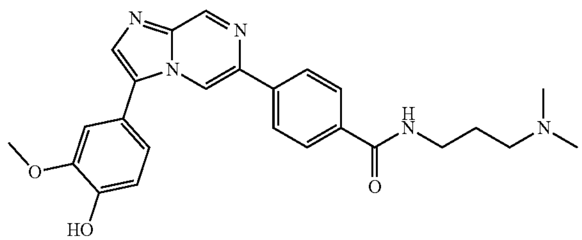 | 17 | N-[3-(dimethylamino)-propyl]-4-[3-(4-hydroxy-3-methoxyphenyl)-imidazo[1,2-a]pyrazin-6-yl]benzamide | 0.647432877 | 1.83 | BF000334019 (388_0314_0180) |
| 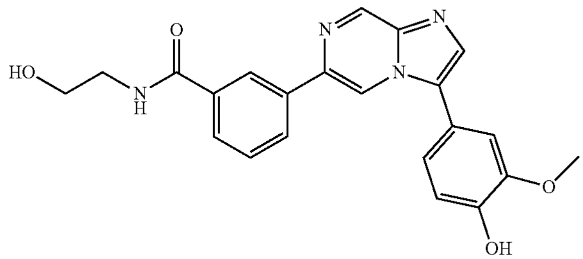 [SMILES: COc1cc(-c2cnc3cnc(-c4cccc(C(=O)NCCO)c4)cn23)ccc1O] | 18 | N-(2-hydroxyethyl)-3-[3-(4-hydroxy-3-methoxyphenyl)-imidazo[1,2-a]pyrazin-6-yl]benzamide | 1.275657607 | 1.07 | BF000334020 (388_0314_0192) |
| 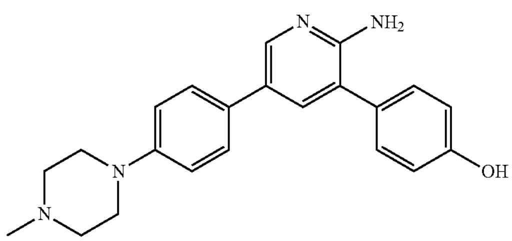 [SMILES: CN1CCN(c2ccc(-c3cnc(N)c(-c4ccc(O)cc4)c3)cc2)CC1] | 19 | 4-[2-amino-5-[4-(4-methylpiperazin-1-yl)phenyl]-3-pyridyl]-phenol | 0.520622627 | 3.47 | BF000710044 |
| 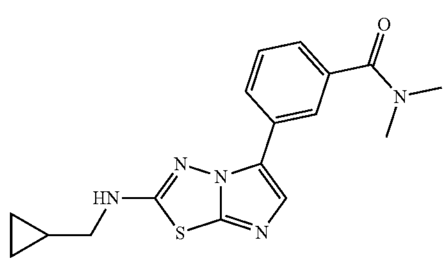 [SMILES: CN(C)C(=O)c1cccc(-c2cnc3sc(NCC4CC4)nn23)c1] | 20 | 3-[2-(cyclopropylmethylamino)-imidazo[2,1-b][1,3,4]-thiadiazol-5-yl]-N,N-dimethylbenzamide | 0.884088514 | 2.59 | BF000714798 (699_4051_0349) |
| 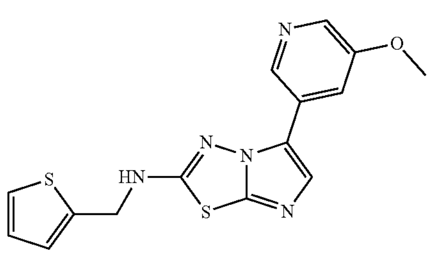 [SMILES: COc1cncc(-c2cnc3sc(NCc4cccs4)nn23)c1] | 21 | 5-(5-methoxy-3-pyridyl)-N-(2-thienylmethyl)-imidazo[2,1-b][1,3,4]-thiadiazol-2-amine | 0.437195357 | 2.77 | BF000714968 (699_0146_0196) |
| 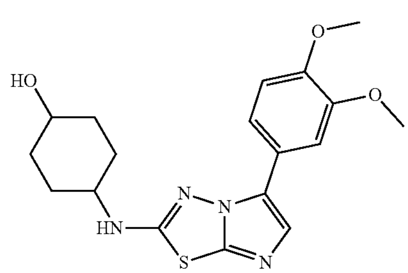 [SMILES: COc1ccc(-c2cnc3sc(NC4CCC(O)CC4)nn23)cc1OC] | 22 | 4-[[5-(3,4-dimethoxyphenyl)-imidazo[2,1-b][1,3,4]-thiadiazol-2-yl]amino]-cyclohexanol | 0.439583985 | 2.60 | BF000717406 (699_0240_0079) |

TABLE 4-continued

Secondary screen- initial candidate compounds re-synthesized and expanded.

| Structure | | IUPAC name | IC50 FYN (μM) | logP (consensus) | Compound ID. (prior ID No. if any) |
|---|---|---|---|---|---|
| 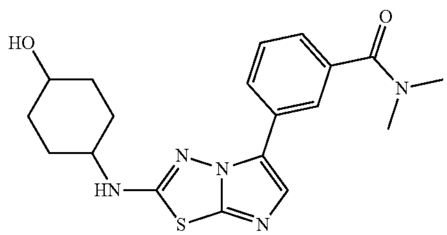 [SMILES: CN(C)C(=O)c1cccc(-c2cnc3sc(NC4CCC(O)CC4)nn23)c1] | 23 | 3-[2-[(4-hydroxy-cyclohexyl)-amino]-imidazo[2,1-b][1,3,4]-thiadiazol-5-yl]-N,N-dimethyl-benzamide | 0.288412517 | 2.22 | BF000717418 (699_0240_0349) |
| 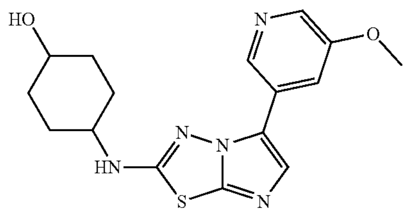 [SMILES: COc1cncc(-c2cnc3sc(NC4CCC(O)CC4)nn23)c1] | 24 | 4-[[5-(5-methoxy-3-pyridyl)-imidazo[2,1-b][1,3,4]-thiadiazol-2-yl]amino]-cyclohexanol | 0.300821259 | 1.54 | BF000802724 |
| 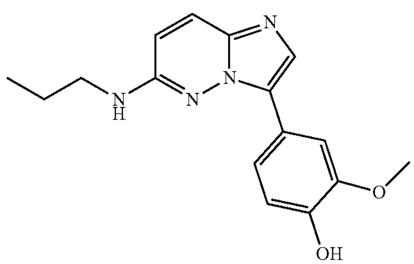 [SMILES: CCCNc1ccc2ncc(-c3ccc(O)c(OC)c3)n2n1] | 1 | 2-methoxy-4-[6-(propyl-amino)-imidazo[1,2-b]pyridazin-3-yl]phenol | 0.081593995 | 2.71 | BF000147080 |
| 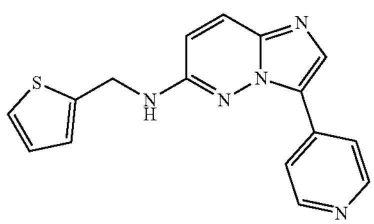 [SMILES: c1csc(CNc2ccc3ncc(-c4ccncc4)n3n2)c1] | 2 | 3-(4-pyridyl)-N-(2-thienyl-methyl)-[1,2-a]pyridazin-6-amine | 0.104821372 | 2.71 | BF000145941 |
| 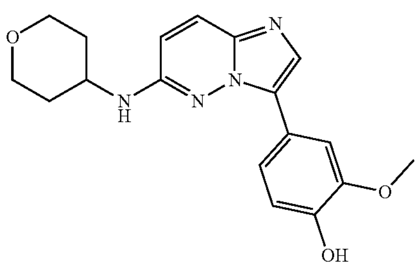 [SMILES: COc1cc(-c2cnc3ccc(NC4CCOCC4)nn23)ccc1O] | 3 | 2-methoxy-4-[6-(tetra-hydropyran-4-ylamino)-imidazo[1,2-b[pyridazin-3-yl]phenol | 0.112523997 | 1.79 | BF000147168 |
| 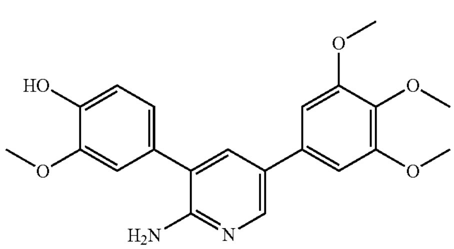 | 4 | 4-[2-amino-5-(3,4,5-trimethoxy-phenyl)-3-pyridyl]-2-methoxy-phenol | 0.115507056 | 2.88 | BF000313035 (382_0314_0087) |

TABLE 4-continued

Secondary screen- initial candidate compounds re-synthesized and expanded.

| Structure | | IUPAC name | IC50 FYN (μM) | logP (con-sensus) | Compound ID. (prior ID No. if any) |
|---|---|---|---|---|---|
| 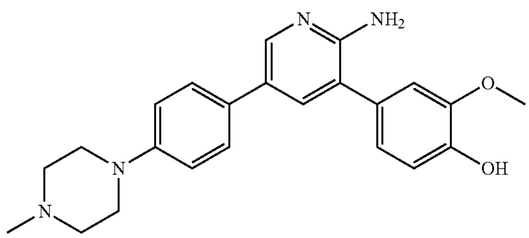 | 5 | 4-[2-amino-5-[4-(4-methylpiperazin-1-yl)phenyl]-3-pyridyl]-2-methoxy-phenol | 0.121074357 | 3.31 | BF000313028 |
| 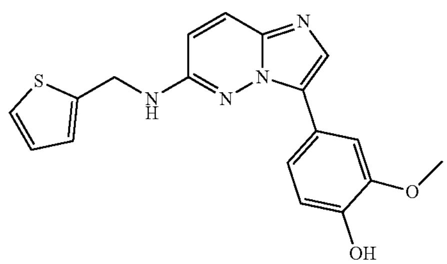 [SMILES: COc1cc(-c2cnc3ccc(NCc4cccs4)nn23)ccc1O] | 6 | 2-methoxy-4-[6-(2-thienyl-methyl-amino)-imidazo[1,2-b]pyridazin-3-yl]phenol | 0.166284575 | 3.46 | BF000145954 |
| 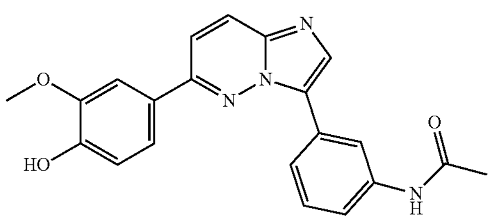 [SMILES: COc1cc(-c2ccc3ncc(-c4cccc(NC(C)=O)c4)n3n2)ccc1O] | 7 | N-(3-[6-(4-hydroxy-3-methoxy-phenyl)-imidazo[1,2-b]pyridazin-3-yl]phenyl]-acatamide | 0.166802816 | 3.03 | BF000726183 (828_0081_0314) |
| 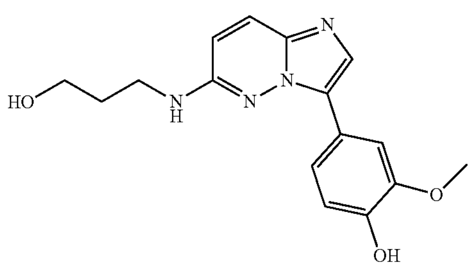 [SMILES: COc1cc(-c2cnc3ccc(NCCCO)nn23)ccc1O] | 8 | 4-[6-(3-hydroxy-propylamino)-imdazo[1,2-b]pyridazin-3-yl]-2-methoxy-phenol | 0.205976791 | 1.20 | BF000146250 (229_0248_0314) |
| 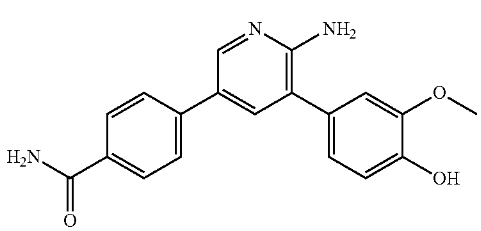 [SMILES: COc1cc(-c2cc(-c3ccc(C(N)=O)cc3)cnc2N)ccc1O] | 9 | 4-[6-amino-5-(4-hydroxy-3-methoxy-phenyl)-3-pyridyl]-benzamide | 0.214088697 | 2.20 | BF000313038 |
| 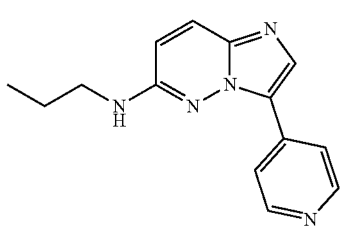 [SMILES: CCCNc1ccc2ncc(-c3ccncc3)n2n1] | 10 | N-propyl-3-(4-pyridyl)-imidazo[1,2-b]pyridazin-6-amine | 0.217345163 | 1.95 | BF000147056 |

TABLE 4-continued

Secondary screen- initial candidate compounds re-synthesized and expanded.

| Structure | | IUPAC name | IC50 FYN (μM) | logP (consensus) | Compound ID. (prior ID No. if any) |
|---|---|---|---|---|---|
| 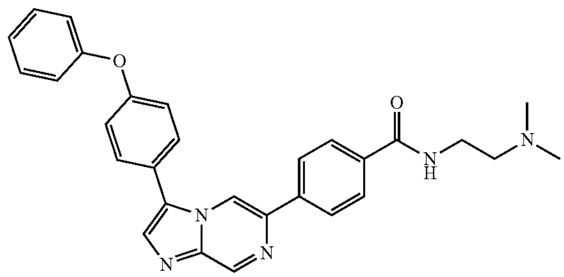 [SMILES: CN(C)CCNC(=O)c1ccc(-c2cn3c(-c4ccc(Oc5ccccc5)cc4)cnc3cn2)cc1] | 11 | N-[2-(dimethylamino)ethyl]-4-[3-(4-phenoxyphenyl)-imidazo[1,2-a]pyrazin-6-yl]-benzamide | 0.22160528 | 3.74 | BF000334031 |
| 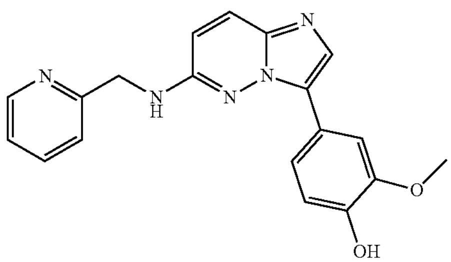 [SMILES: COc1cc(-c2cnc3ccc(NCc4ccccn4)nn23)ccc1O] | 12 | 2-methoxy-4-[6-(2-pyridylmethylamino)-imidazo[1,2-b]pyridazin-3-yl]phenol | 0.233047949 | 2.41 | BF000817095 |
| 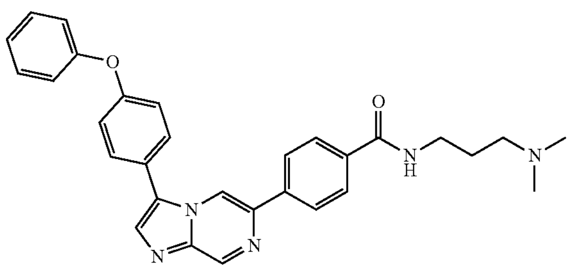 [SMILES: CN(C)CCCNC(=O)c1ccc(-c2cn3c(-c4ccc(Oc5ccccc5)cc4)cnc3cn2)cc1] | 13 | N-[3-(dimethylamino)-propyl]-4-[3-(4-phenoxyphenyl)imidazo[1,2-a]pyrazin-6-yl]benzamide | 0.247391087 | 3.80 | BF000816927 |
| 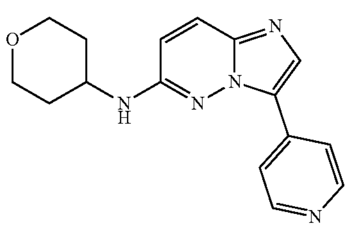 [SMILES: c1cc(-c2cnc3ccc(NC4CCOCC4)nn23)ccn1] | 14 | 3-(4-pyridyl)-N-tetrahydropyran-4-yl-imidazo[1,2-b]pyridazin-6-amine | 0.270083246 | 1.03 | BF000817099 |
| 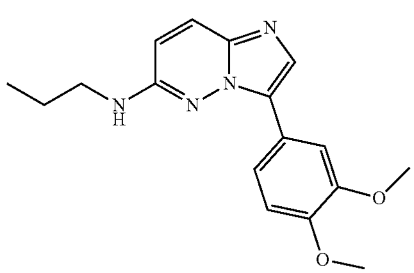 [SMILES: CCCNc1ccc2ncc(-c3ccc(OC)c(OC)c3)n2n1] | 15 | 3-(3,4-dimethoxyphenyl)-N-propyl-imidazo[1,2-b]pyridazin-6-amine | 0.285138703 | 2.85 | BF000147061 (229_0226_0079) |
| 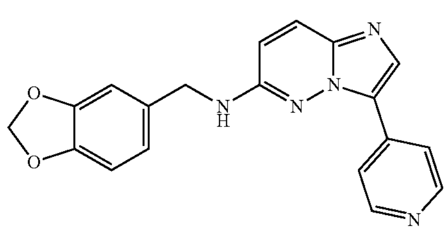 [SMILES: c1cc(-c2cnc3ccc(NCc4ccc5c(c4)OCO5)nn23)ccn1] | 16 | N-(1,3-benzodioxol-5-ylmethyl)-3-(4-pyridyl)-imidazo[1,2-b]pyridazin-6-amine | 0.297126173 | 2.42 | BF000146108 (229_0236_0069) |

TABLE 4-continued

Secondary screen- initial candidate compounds re-synthesized and expanded.

| Structure | | IUPAC name | IC50 FYN (μM) | logP (consensus) | Compound ID. (prior ID No. if any) |
|---|---|---|---|---|---|
| 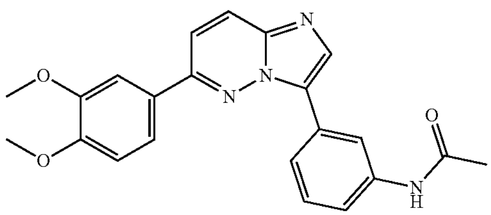 [SMILES: COc1ccc(-c2ccc3ncc(-c4cccc(NC(C)=O)c4)n3n2)cc1OC] | 17 | N-[3-[6-(3,4-dimethoxy-phenyl)-imidazo[1,2-a]pyridazin-3-yl]phenyl]-acatamide | 0.313364743 | 3.18 | BF000726345 (828_0081_0079) |
| 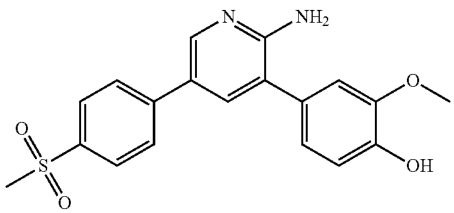 | 18 | 4-[2-amino-5-(4-methyl-sulfolyl-phenyl)-3-pyridyl]-2-methoxy-phenol | 0.315744691 | 2.19 | BF000313040 (382_0314_0174) |
| 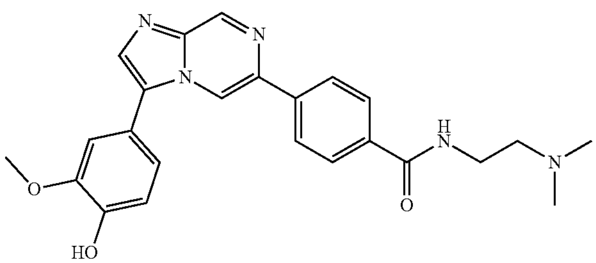 | 19 | N-[2-(dimethyl-amino)ethyl]-4-[3-(4-hydroxy-3-methoxy-phenyl)-imidazo[1,2-a]pyrazin-6-yl]benzamide | 0.336758519 | 1.77 | BF000334023 |
| 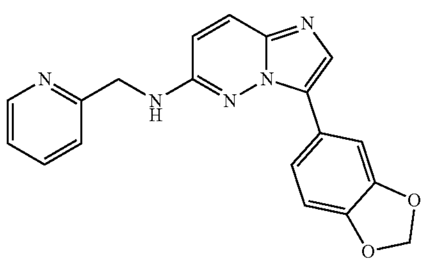 [SMILES: c1ccc(CNc2ccc3ncc(-c4ccc5c(c4)OCO5)n3n2)nc1] | 20 | 3-(1,3-benzodioxol-5-yl)-N-(2-pyridyl-methyl)-imidazo[1,2-b]pyridazin-6-amine | 0.354989794 | 2.50 | BF000146330 (229_4007_0068) |
| 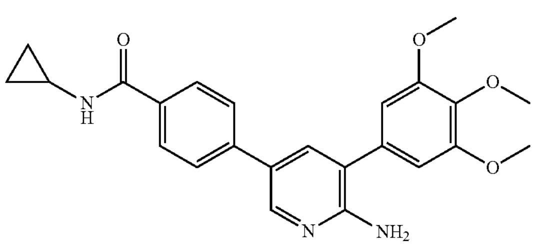 [SMILES: COc1cc(-c2cc(-c3ccc(C(=O)NC4CC4)cc3)cnc2N)cc(OC)c1OC] | 21 | 4-[6-amino-5-(3,4,5-trimethoxy-phenyl)-3-pyridyl]-N-cyclopropyl-benzamide | 0.376810127 | 2.88 | BF000312541 (382_0087_7489) |
| 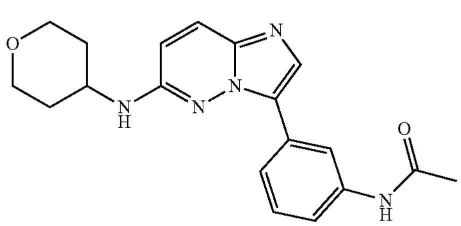 [SMILES: CC(=O)Nc1cccc(-c2cnc3ccc(NC4CCOCC4)nn23)c1] | 22 | N-[3-[6-(tetra-hydropyran-4-ylamino)-imidazo[1,2-b]pyridazin-3-yl)phenyl]-acetamide | 0.396885185 | 1.49 | BF000146155 (229_0242_0081) |

TABLE 4-continued

Secondary screen- initial candidate compounds re-synthesized and expanded.

| Structure | | IUPAC name | IC50 FYN (μM) | logP (consensus) | Compound ID. (prior ID No. if any) |
|---|---|---|---|---|---|
| 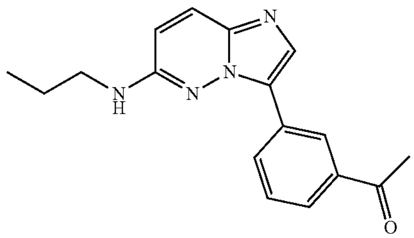 [SMILES: CCCNc1ccc2ncc(-c3cccc(C(C)=O)c3)n2n1] | 23 | 1-[3-[6-(propyl-amino)-imidazo[1,2-b]pyridazin-3-yl]phenyl]-ethanone | 0.405532058 | 2.72 | BF000147088 (229_0226_4145) |
| 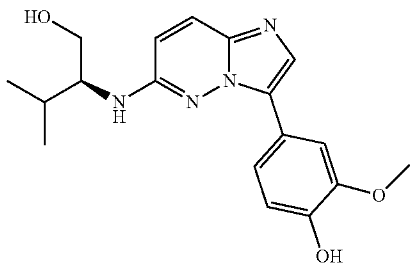 [SMILES: COc1cc(-c2cnc3ccc(N[C@H](CO)C(C)C)nn23)ccc1O] | 24 | 4-[6-[[(1S)-1-(hydroxy-methyl)-2-methyl-propyl]-amino]-imidazo[1,2-b]pyridazin-3-yl]-2-methoxy-phenol | 0.44318569 | 2.44 | BF000146319 |
| 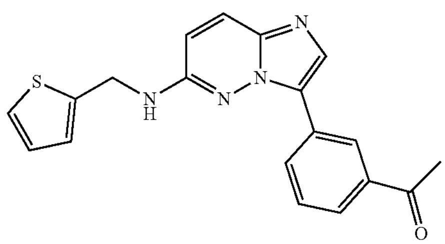 [SMILES: CC(=O)c1cccc(-c2cnc3ccc(NCc4cccs4)nn23)c1] | 25 | 1-[3-[6-(2-thienyl-methyl-amino)-imidazo[1,2-b]pyridazin-3-yl]phenyl)-ethanone | 0.450916544 | 3.48 | BF000145962 (229_0146_4145) |
| 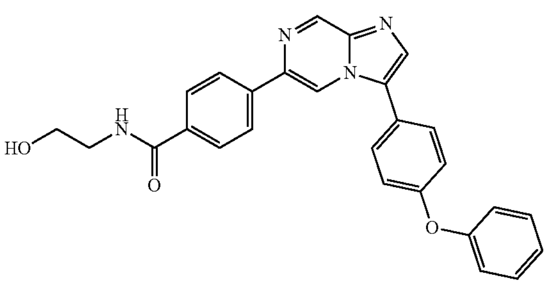 [SMILES: O=C(NCCO)c1ccc(-c2cn3c(-c4ccc(Oc5ccccc5)cc4)cnc3cn2)cc1] | 26 | N-(2-hydroxy-ethyl)-4-[3-(4-phenoxy-phenyl)-imidazo-[1,2-a]-pyrazin-6-yl]benzamide | 0.463504693 | 3.03 | BF000334032 (388_1029_0328) |
| 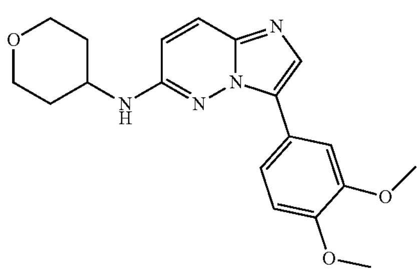 [SMILES: COc1ccc(-c2cnc3ccc(NC4CCOCC4)nn23)cc1OC] | 27 | 3-(3,4-dimethoxy-phenyl)-N-tetrahydro-pyran-4-yl-imidazo[1,2-b]pyridazin-6-amine | 0.479948935 | 1.93 | BF000146153 (229_0242_0079) |

TABLE 4-continued

Secondary screen- initial candidate compounds re-synthesized and expanded.

| Structure | | IUPAC name | IC50 FYN (µM) | logP (consensus) | Compound ID. (prior ID No. if any) |
|---|---|---|---|---|---|
| 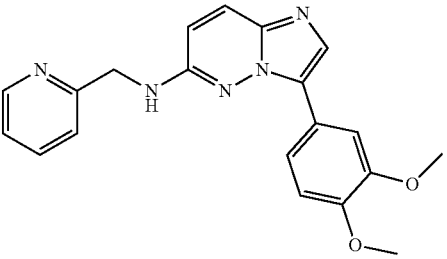 [SMILES: COc1ccc(-c2cnc3ccc(NCc4ccccn4)nn23)cc1OC] | 28 | 3-(3,4-dimethoxy-phenyl)-N-(2-pyridyl-methyl)-imidazo[1,2-b]pyridazin-6-amine | 0.494462769 | 2.56 | BF000147233 |
| 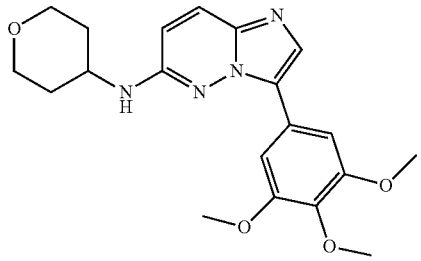 [SMILES: COc1cc(-c2cnc3ccc(NC4CCOCC4)nn23)cc(OC)c1OC] | 29 | N-tetrahydro-pyran-4-yl-3-(3,4,5-trimethoxy-phenyl)-imidazo[1,2-b]pyridazin-6-amine | 0.503383229 | 1.78 | BF000147394 (229_0242_0087) |
| 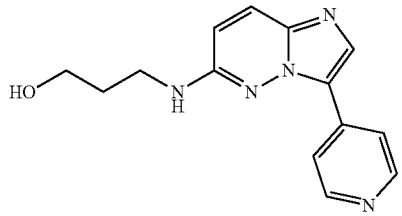 [SMILES: OCCCNc1ccc2ncc(-c3ccncc3)n2n1] | 30 | 3-[[3-(4-pyridyl)-imidazo[1,2-b]pyridazin-6-yl]amino]-propan-1-ol | 0.538085737 | 0.44 | BF000722253 |
| 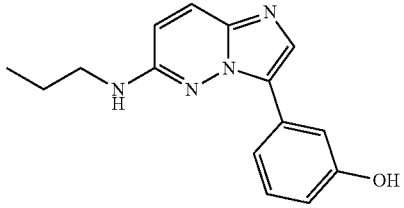 [SMILES: CCCNc1ccc2ncc(-c3cccc(O)c3)n2n1] | 31 | 3-[6-(propylamino)-imidazo[1,2-b]pyridazin-3-yl]phenol | 0.59230731 | 2.86 | BF000147075 (229_0226_0284) |
| 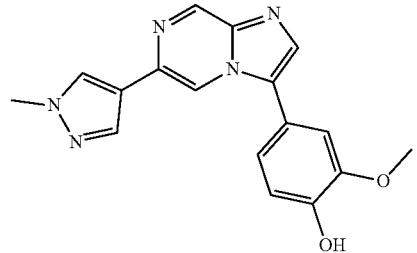 | 32 | 2-methoxy-4-[6-(1-methyl-pyrazol-4-yl)-imidazo[1,2-a]pyrazin-3-yl]phenol | 0.624331939 | 1.11 | BF000333452 (388_0314_8400) |
| 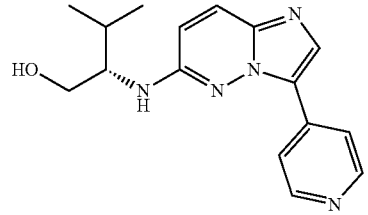 [SMILES: CC(C)[C@@H](CO)Nc1ccc2ncc(-c3ccncc3)n2n1] | 33 | (2S)-3-methyl-2-[[3-(4-pyridyl)-imidazo[1,2-b]pyridazin-6-yl]amino]-butan-1-ol | 0.630941398 | 1.68 | BF000817097 |

TABLE 4-continued

Secondary screen- initial candidate compounds re-synthesized and expanded.

| Structure | | IUPAC name | IC50 FYN (μM) | logP (consensus) | Compound ID. (prior ID No. if any) |
|---|---|---|---|---|---|
| 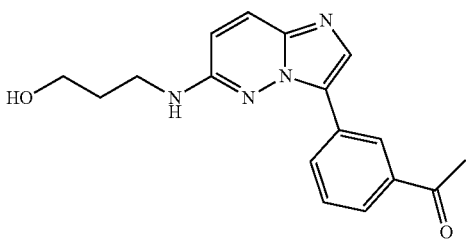 [SMILES: CC(=O)c1cccc(-c2cnc3ccc(NCCCO)nn23)c1] | 34 | 1-[3-[6-(3-hydroxy-propyl-amino)-imdazo[1,2-b]pyridazin-3-yl]phenyl]-ethanone | 0.64498853 | 1.21 | BF000817098 |
| 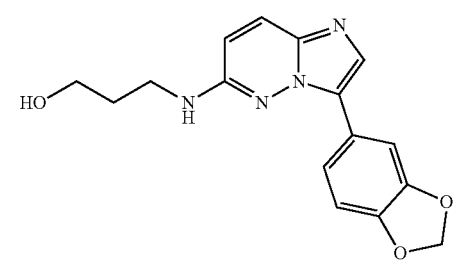 [SMILES: OCCCNc1ccc2ncc(-c3ccc4c(c3)OCO4)n2n1] | 35 | 3-[[3-(1,3-benzodioxol-5-yl)-imidazo[1,2-b]pyridazin-6-yl]amino]-propan-1-ol | 0.707789559 | 1.28 | BF000146218 (229_0248_0068) |
| 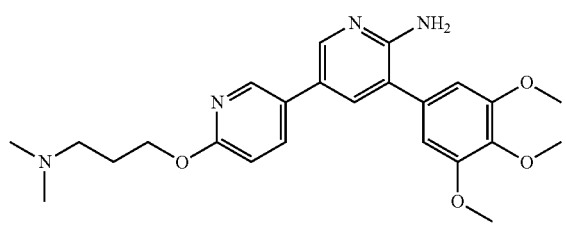 | 36 | 5-[6-(3-(dimethyl-amino)-propoxy]-3-pyridyl]-3-(3,4,5-trimethoxy-phenyl)-pyridin-2-amine | 0.709144298 | 2.64 | BF000312521 (382_0087_0002) |
| 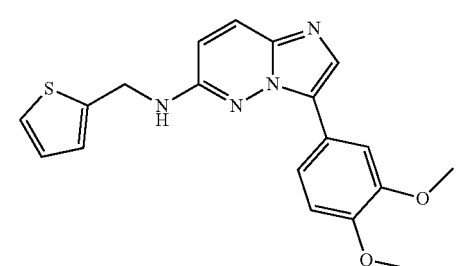 | 37 | 3-(3,4-dimetboxy-phenyl)-N-(2-thienyl-methyl)-imidazo[1,2-b]pyridazin-6-amine | 0.721406376 | 3.61 | BF000146992 |
| 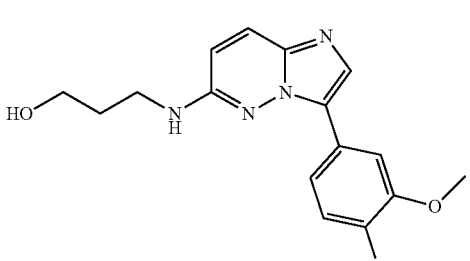 | 38 | 3-[[3-(3,4-dimethoxy-phenyl)-imidazo[1,2-b]pyridazin-6-yl]-amino]-propan-1-ol | 0.72516936 | 1.34 | BF000146224 |
| 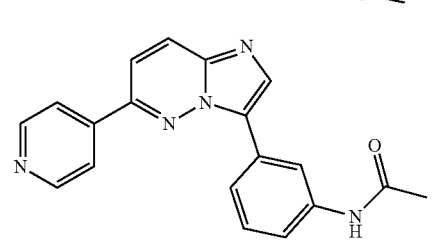 | 39 | N-[3-[6-(4-pyridyl)-imidazo[1,2-b]pyridazin-3-yl]phenyl]-acetamide | 0.740677454 | 2.27 | BF000817142 |

TABLE 4-continued

Secondary screen- initial candidate compounds re-synthesized and expanded.

| Structure | | IUPAC name | IC50 FYN (μM) | logP (consensus) | Compound ID. (prior ID No. if any) |
|---|---|---|---|---|---|
| 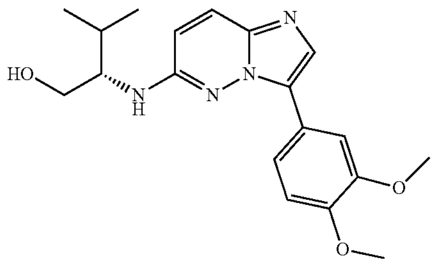 [SMILES: COc1ccc(-c2cnc3ccc(N[C@H](CO)C(C)C)nn23)cc1OC] | 40 | (2S)-2-[[3-(3,4-dimethoxyphenyl)-imidazo[1,2-b]pyridazin-yl]amino]-3-methyl-butan-1-ol | 0.742215008 | 2.59 | BF000147413 (229_0254_0079) |
| 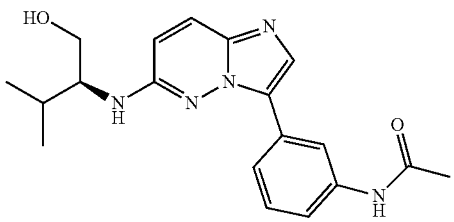 [SMILES: CC(=O)Nc1cccc(-c2cnc3ccc(N[C@H](CO)C(C)C)nn23)c1] | 41 | N-[3-[6-[[(1S)-1-(hydroxymethyl)-2-methyl-propyl]-amino]-imidazo[1,2-b]pyridazin-3-yl]-phenyl]acetamide | 0.791967537 | 2.14 | BF000146300 (229_0254_0081) |
| 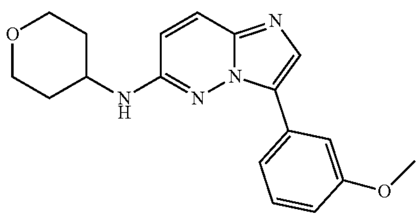 [SMILES: COc1cccc(-c2cnc3ccc(NC4CCOCC4)nn23)c1] | 42 | 3-(3-methoxyphenyl)-N-tetrahydropyran-4-yl-imidazo[1,2-b]pyridazin-6-amine | 0.828721524 | 2.09 | BF000146183 (229_0242_4140) |
| 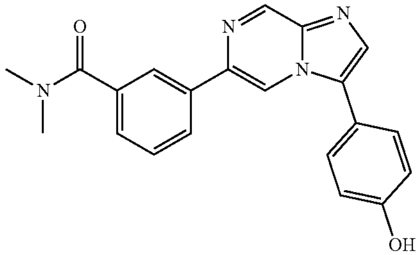 [SMILES: CN(C)C(=O)c1cccc(-c2cn3c(-c4ccc(O)cc4)cnc3cn2)c1] | 43 | 3-[3-(4-hydroxyphenyl)-imidazo[1,2-a]pyrazin-6-yl]-N,N-dimethyl-benzamide | 0.870676961 | 2.14 | BF000333343 (388_0080_0349) |
| 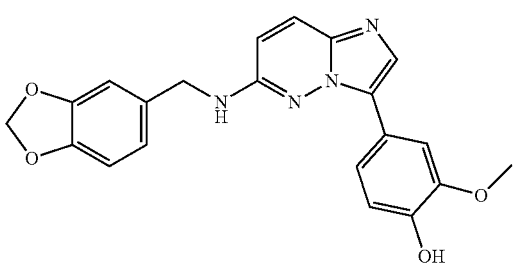 [SMILES: COc1cc(-c2cnc3ccc(NCc4ccc5c(c4)OCO5)nn23)ccc1O] | 44 | 4-[6-(1,3-benzodioxol-5-ylmethyl-amino)-imidazo[1,2-b]pyridazin-3-yl]-2-methoxy-phenol | 1.308570599 | 3.17 | BF000146126 |
| 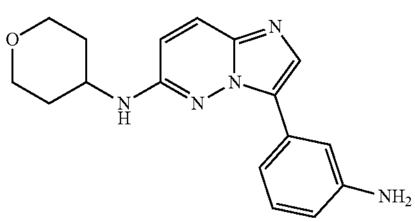 [SMILES: Nc1cccc(-c2cnc3ccc(NC4CCOCC4)nn23)c1] | 45 | 3-(3-aminophenyl)-N-tetrahydropyran-4-yl-imidazo[1,2-b]pyridazin-6-amine | 1.423322773 | 1.42 | BF000146142 (229_0242_0005) |

TABLE 4-continued

Secondary screen- initial candidate compounds re-synthesized and expanded.

| Structure | | IUPAC name | IC50 FYN (μM) | logP (consensus) | Compound ID. (prior ID No. if any) |
|---|---|---|---|---|---|
| 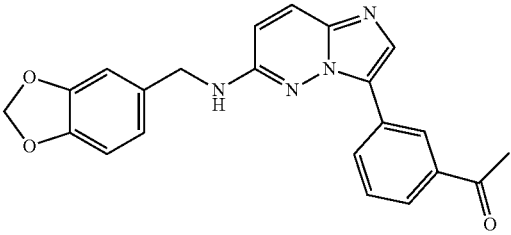 [SMILES: CC(=O)c1cccc(-c2cnc3ccc(NCc4ccc5c(c4)OCO5)nn23)c1] | 46 | 1-[3-[6-(1,3-benzodioxol-5-ylmethyl-amino)-imidazo[1,2-b]pyridazin-3-yl]phenyl]-ethanone | 3.189566346 | 3.19 | BF000147140 |
| 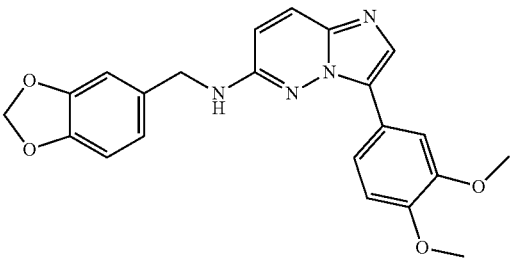 [SMILES: COc1ccc(-c2cnc3ccc(NCc4ccc5c(c4)OCO5)nn23)cc1OC] | 47 | N-(1,3-benzodioxol-5-ylmethyl)-3-[3,4-dimethoxy-phenyl)-imidazo[1,2-b]pyridazin-6-amine | 6.216010093 | 3.32 | BF000146114 |
| 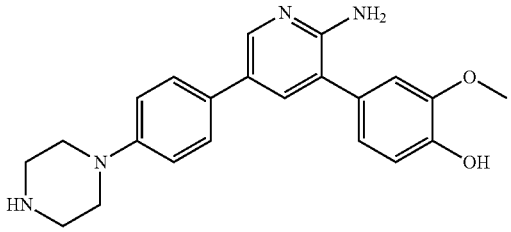 [SMILES: COc1cc(-c2cc(-c3ccc(N4CCNCC4)cc3)cnc2N)ccc1O] | | 4-[2-amino-5-(4-piperazin-1-ylphenyl)-3-pyridyl]-2-methoxy-phenol | 0.060908784 | 2.93 | BF000707279 |
| 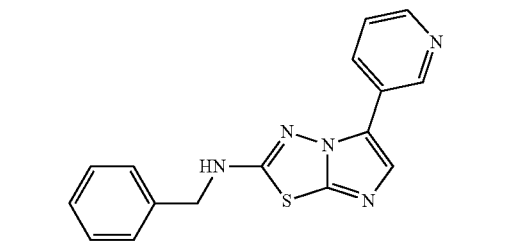 [SMILES: c1ccc(CNc2nn3c(-c4cccnc4)cnc3s2)cc1] | | N-benzyl-5-(3-pyridyl)-imidazo[2,1-b][1,3,4]-thiadiazol-2-amine | 0.633579663 | 3.01 | BF000714845 (699_0232_0071) |
| 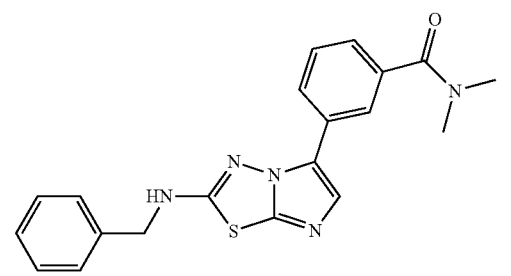 [SMILES: CN(C)C(=O)c1cccc(-c2cnc3sc(NCc4ccccc4)nn23)c1] | | 3-[2-(benzyl-amino)-imidazo[2,1-b][1,3,4]-thiadiazol-5-yl]-N,N-dimethyl-benzamide | 1.233285044 | 3.53 | BF000714847 (699_0232_0349) |
| 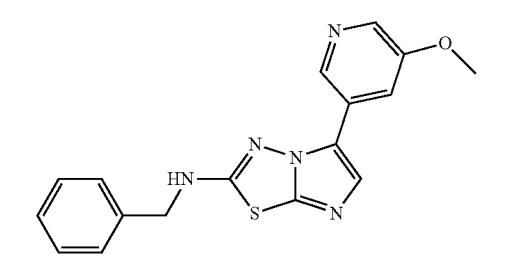 [SMILES: COc1cncc(-c2cnc3sc(NCc4ccccc4)nn23)c1] | | N-benzyl-5-(5-methoxy-3-pyridyl)-imidazo[2,1-b][1,3,4]-thiadiazol-2-amine | 0.217465905 | 2.86 | BF000714862 (699_0232_0196) |

TABLE 4-continued

Secondary screen- initial candidate compounds re-synthesized and expanded.

| Structure | IUPAC name | IC50 FYN (μM) | logP (con- sensus) | Compound ID. (prior ID No. if any) |
|---|---|---|---|---|
| 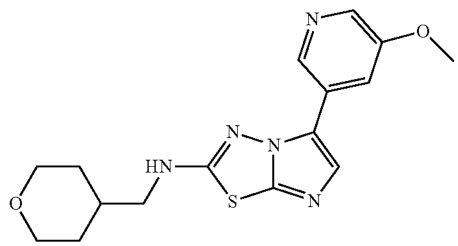 [SMILES: COc1cncc(-c2cnc3sc(NCC4CCOCC4)nn23)c1] | 5-(5-methoxy-3-pyridyl)-N-(tetra-hydropyran-4-ylmethyl)-imidazo[2,1-b][1,3,4]-thiadiazol-2-amine | 0.292588141 | 1.55 | BF000714923 (699_0243_0196) |
| 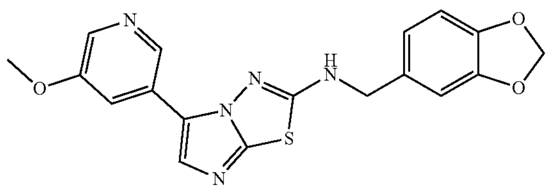 [SMILES: COc1cncc(-c2cnc3sc(NCc4ccc5c(c4)OCO5)nn23)c1] | N-(1,3-benzodioxol-5-ylmethyl)-5-(5-methoxy-3-pyridyl)-imidazo[2,1-b][1,3,4]-thiadiazol-2-amine | 0.289073347 | 2.48 | BF000714981 (699_0236_0196) |
| 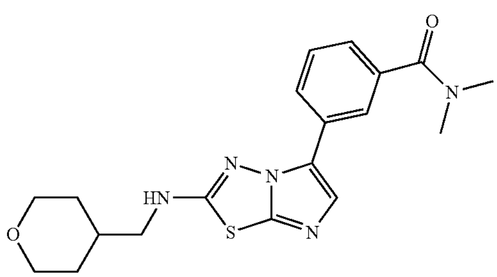 [SMILES: CN(C)C(=O)c1cccc(-c2cnc3sc(NCC4CCOCC4)nn23)c1] | N,N-dimethyl-3-[2-(tetra-hydropyran-4-ylmethyl-amino)-imidazo[2,1-b][1,3,4]-thiadiazol-5-yl]benzamide | 1.363919415 | 2.23 | BF000715802 (699_0243_0349) |
| 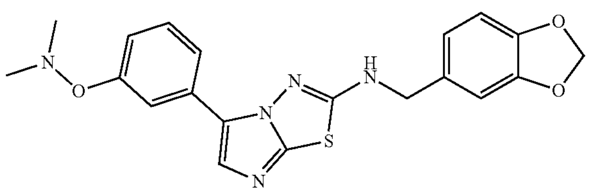 [SMILES: CN(C)Oc1cccc(-c2cnc3sc(NCc4ccc5c(c4)OCO5)nn23)c1] | 3-[2-(1,3-benzodioxol-5-ylmethyl-amino)-imidazo[2,1-b][1,3,4]-thiadiazol-5-yl]-N,N-dimethyl-benzamide | 1.925583132 | 3.15 | BF000717214 |
| 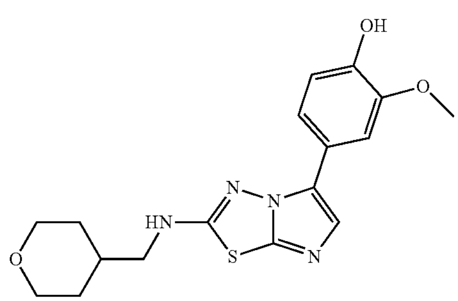 [SMILES: COc1cc(-c2cnc3sc(NCC4CCOCC4)nn23)ccc1O] | 2-methoxy-4-[2-(tetrahydro-pyran-4-ylmethyl-amino)-imidazo[2,1-b][1,3,4]-thiadiazol-5-yl]phenol | 0.710456332 | 2.47 | BF000717555 (699_0243_0314) |
| 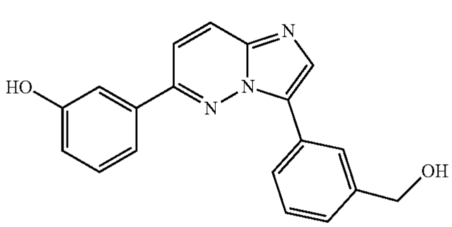 [SMILES: OCc1cccc(-c2cnc3ccc(-c4cccc(O)c4)nn23)c1] | 3-[3-[3-hydroxy-methyl)-phenyl]-imidazo[1,2-b]pyridazin-6-yl]phenol | 1.166257347 | 3.18 | BF000726195 (828_0291_0284) |

TABLE 4-continued

Secondary screen- initial candidate compounds re-synthesized and expanded.

| Structure | IUPAC name | IC50 FYN (μM) | logP (con-sensus) | Compound ID. (prior ID No. if any) |
|---|---|---|---|---|
| 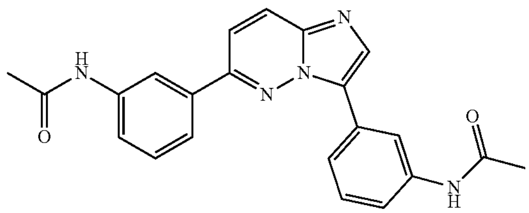 [SMILES: CC(=O)Nc1cccc(-c2ccc3ncc(-c4cccc(NC(C)=O)c4)n3n2)c1] | N-[3-[3-(3-acetamido-phenyl)-imidazo[1,2-b]pyridazin-6-yl]phenyl]-acetamide | 0.647620035 | 2.73 | BF000726346 (828_0081_0081) |
| 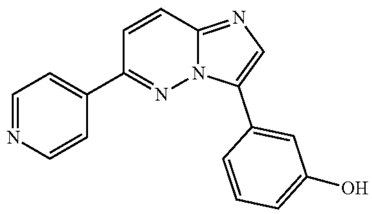 [SMILES: Oc1cccc(-c2cnc3ccc(-c4ccncc4)nn23)c1] | 3-[6-(4-pyridyl)-imidazo[1,2-b]pyridazin-3-yl]phenol | 0.342140497 | 2.73 | BF000726352 (828_0284_0069) |
| 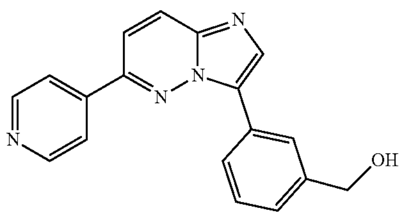 [SMILES: OCc1cccc(-c2cnc3ccc(-c4ccncc4)nn23)c1] | [3-[6-(4-pyridyl)-imidpzo[1,2-b]pyridazin-3-yl]phenyl]-methanol | 0.972914631 | 2.27 | BF000726364 |
| 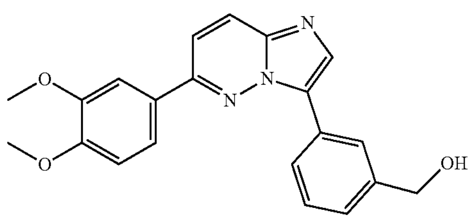 [SMILES: COc1ccc(-c2ccc3ncc(-c4cccc(CO)c4)n3n2)cc1OC] | [3-[6-(3,4-dimethoxy-phenyl)-imidazo[1,2-b]pyridazin-3-yl]phenyl]-methanol | 0.892824216 | 3.17 | BF000726366 (828_0291_0079) |
| 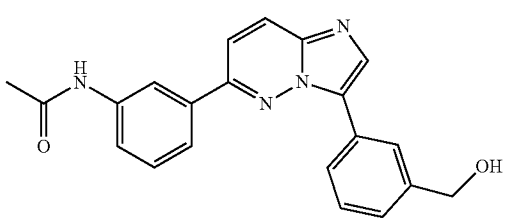 [SMILES: CC(=O)Nc1cccc(-c2ccc3ncc(-c4cccc(CO)c4)n3n2)c1] | N-[3-[3-[3-(hydroxy-methyl)phenyl]-imidazo[1,2-b]pyridazin-6-yl]phenyl]-acetamide | 1.516622765 | 2.72 | BF000726367 (828_0291_0081) |
| | 4-[6-(3,4-dimethoxy-phenyl)-imidazo[1,2-b]pyridazin-3-yl]-2-methoxy-phenol | 0.039407867 | 3.48 | BF000726453 (828_0314_0079) |

TABLE 4-continued

Secondary screen- initial candidate compounds re-synthesized and expanded.

| Structure | IUPAC name | IC50 FYN (μM) | logP (consensus) | Compound ID. (prior ID No. if any) |
|---|---|---|---|---|
| 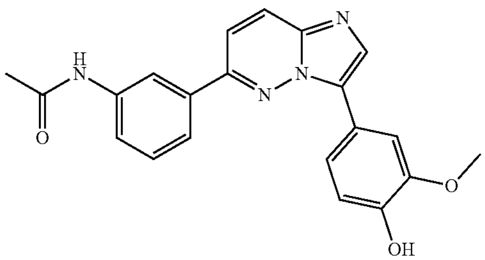 [SMILES: COc1cc(-c2cnc3ccc(-c4cccc(NC(C)=O)c4)nn23)ccc1O] | N-[3-[3-(4-hydroxy-3-methoxy-phenyl)-imidazo[1,2-b]pyridazin-6-yl]phenyl]-acetamide | 0.103548636 | 3.03 | BF000726454 (828_0314_0081) |
| 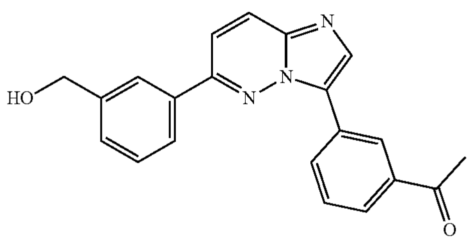 [SMILES: CC(=O)c1cccc(-c2cnc3ccc(-c4cccc(CO)c4)nn23)c1] | 1-[3-[6-[3-(hydroxy-methyl)-phenyl]-imidazo[1,2-b]pyridazin-3-yl]phenyl]-ethanone | 0.290543095 | 3.04 | BF000726471 (828_4145_0291) |
| 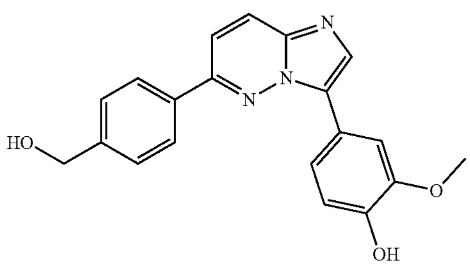 [SMILES: COc1cc(-c2cnc3ccc(-c4ccc(CO)cc4)nn23)ccc1O] | 4-[6-[4-(hydroxy-methyl)-phenyl]-imidazo[1,2-b]pyridazin-3-yl]-2-methoxy-phenol | 0.061804045 | 3.02 | BF000726486 828.0314_0285) |
| 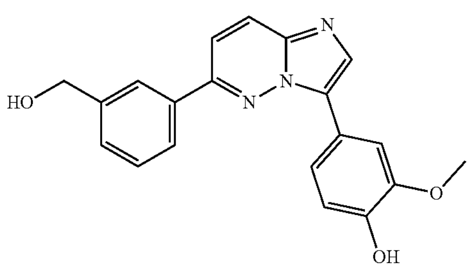 [SMILES: COc1cc(-c2cnc3ccc(-c4cccc(CO)c4)nn23)ccc1O] | 4-[6-[3-(hydroxy-methyl)-phenyl]-imidazo[1,2-b]pyridazin-3-yl]-2-methoxy-phenol | 0.062959987 | 3.02 | BF000726487 (828_0314_0291) |
| 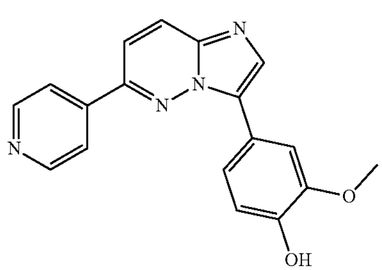 [SMILES: COc1cc(-c2cnc3ccc(-c4ccncc4)nn23)ccc1O] | 2-methoxy-4-[6-(4-pyridyl)-imidazo[1,2-b]pyridazin-3-yl]phenol | 0.079413853 | 2.57 | BF000817169 |
| 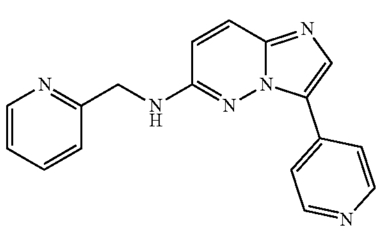 [SMILES: c1ccc(CNc2ccc3ncc(-c4ccncc4)n3n2)nc1] | 3-(4-pyridyl)-N-(2-pyridyl-methyl)-imidazo[1,2-b]pyridazin-6-amine | 0.170100794 | 1.66 | BF000817170 |

TABLE 4-continued

Secondary screen- initial candidate compounds re-synthesized and expanded.

| Structure | IUPAC name | IC50 FYN (μM) | logP (consensus) | Compound ID. (prior ID No. if any) |
|---|---|---|---|---|
| | 3,5-bis(3,4,5-trimethoxyphenyl)-pyridin-2-amine | 0.08540726 | 2.87 | BF000817175 |
| 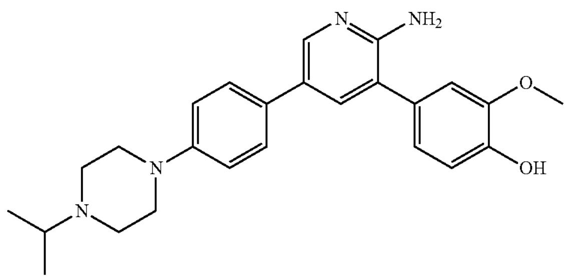 [SMILES: COc1cc(-c2cc(-c3ccc(N4CCN(C(C)C)CC4)cc3)cnc2N)ccc1O] | 4-[2-amino-5-[4-4-isopropyl-piperazin-1-yl)phenyl]-3-pyridyl]-2-methoxy-phenol | 0.078146017 | 4.08 | BF000817185 |
| 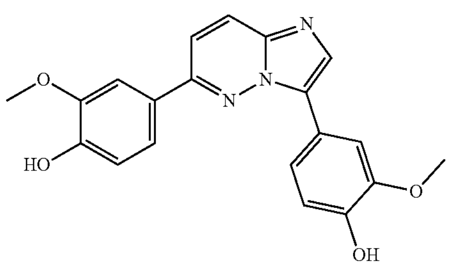 | 4-[3-(4-hydroxy-3-methoxy-phenyl)-imidazo[1,2-b]pyridazin-6-yl]-2-methoxy-phenol | 0.02944792 | 3.33 | BF000817186 |
| 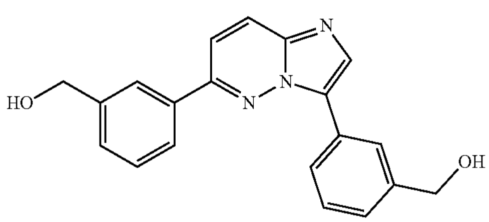 [SMILES: OCc1cccc(-c2ccc3ncc(-c4cccc(CO)c4)n3n2)c1] | [3-[3-[3-(hydroxy-methyl)-phenyl]-imidazo[1,2-b]pyridazin-6-yl]phenyl]-methanol | 0.828494158 | 2.72 | BF000817188 |
| 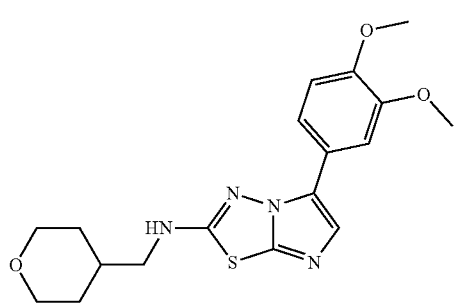 [SMILES: COc1ccc(-c2cnc3sc(NCC4CCOCC4)nn23)cc1OC] | 5-(3,4-dimethoxy-phenyl)-N-(tetra-hydropyran-4-ylmethyl)-imidazo[2,1-b][1,3,4]-thiadiazol-2-amine | 1.026007749 | 2.61 | BF000817208 |

TABLE 4-continued

Secondary screen- initial candidate compounds re-synthesized and expanded.

| Structure | IUPAC name | IC50 FYN (μM) | logP (consensus) | Compound ID. (prior ID No. if any) |
|---|---|---|---|---|
| 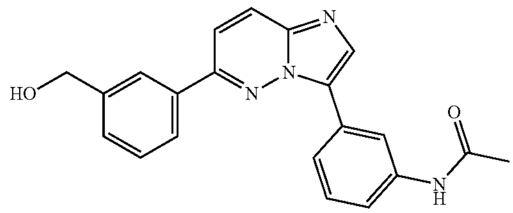 [SMILES: CC(=O)Nc1cccc(-c2cnc3ccc(-c4cccc(CO)c4)nn23)c1] | N-[3-[6-[3-(hydroxy-methyl)-phenyl]-imidazo[1,2-b]pyridazin-3-yl]phenyl]-acetamide | 0.435155145 | 2.72 | BF000817329 |
| 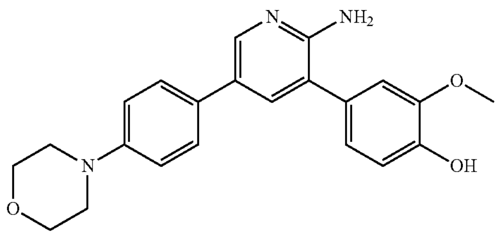 [SMILES: COc1cc(-c2cc(-c3ccc(N4CCOCC4)cc3)cnc2N)ccc1O] | 4-[2-amino-5-(4-morpholino-phenyl)-3-pyridyl]-2-methoxy-phenol | 0.212232208 | 3.24 | BF000817413 |
| 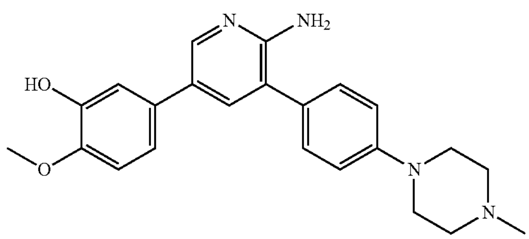 | 5-[6-amino-5-[4-(4-methyl-piperazin-1-yl)phenyl]-3-pyridyl]-2-methoxy-phenol | 9.65 | 3.31 | BF000817418 |

I claim:

1. A method of treating a condition associated with Fyn kinase activity, said method comprising administering a therapeutically effective amount of at least one compound, or pharmaceutically acceptable salt or solvate of the compound to a patient in need thereof, wherein the compound is selected from N-[3-(dimethyl-amino)-propyl]-4-[3-(4-hydroxy-phenyl)-imidazo[1,2-a]pyrazin-6-yl]-benzamide, N-[2-(dimethyl-amino)-ethyl]-4-[3-(4-hydroxy-phenyl)-imidazo[1,2-a]pyrazin-6-yl]-benzamide, N-(2-hydroxy-ethyl)-4-[3-(4-hydroxy-phenyl)-imidazo[1,2-a]pyrazin-6-yl]benzamide, N-[3-(dimethyl-amino)-propyl]-4-[3-(4-hydroxy-3-methoxy-phenyl)-imidazo[1,2-a]pyrazin-6-yl]benzamide, N-(2-hydroxy-ethyl)-3-[3-(4-hydroxy-3-methoxy-phenyl)-imidazo[1,2-a]pyrazin-6-yl]benzamide, N-[2-(dimethyl-amino)ethyl]-4-[3-(4-phenoxy-phenyl)-imidazo[1,2-a]pyrazin-6-yl]-benzamide, N-[3-(dimethyl-amino)-propyl]-4-[3-(4-phenoxy-phenyl) imidazo[1,2-a]pyrazin-6-yl]benzamide, N-[2-(dimethyl-amino)ethyl]-4-[3-(4-hydroxy-3-methoxy-phenyl)-imidazo[1,2-a]pyrazin-6-yl]benzamide, N-(2-hydroxy-ethyl)-4-[3-(4-phenoxy-phenyl)-imidazo-[1,2-a]-pyrazin-6-yl]benzamide, and 3-[3-(4-hydroxy-phenyl)-imidazo[1,2-a]pyrazin-6-yl]-N,N-dimethyl-benzamide, wherein the condition associated with Fyn kinase activity is selected from Type 1 diabetes, Type II diabetes, pre-diabetes, and obesity.

2. The method of claim 1 wherein the compound described in Table 4 of the description is N-[3-(dimethyl-amino)propyl]-4-[3-(4-phenoxyphenyl)imidazo[1,2-a]pyrazin-6-yl]benzamide.

3. The method of claim 1 wherein the compound described in Table 4 of the description is N-[2-(dimethyl-amino)ethyl]-4-[3-(4-phenoxyphenyl)imidazo [1,2-a] pyrazin-6-yl]benzamide.

4. A method of inhibiting the activity of Fyn kinase in a cell or a subject, comprising administering to the cell or subject an effective amount of a compound selected from N-[3-(dimethyl-amino)-propyl]-4-[3-(4-hydroxy-phenyl)-imidazo[1,2-a]pyrazin-6-yl]-benzamide, N-[2-(dimethyl-amino)-ethyl]-4-[3-(4-hydroxy-phenyl)-imidazo[1,2-a]pyrazin-6-yl]-benzamide, N-(2-hydroxy-ethyl)-4-[3-(4-hydroxy-phenyl)-imidazo[1,2-a]pyrazin-6-yl]benzamide, N-[3-(dimethyl-amino)-propyl]-4-[3-(4-hydroxy-3-methoxy-phenyl)-imidazo[1,2-a]pyrazin-6-yl]benzamide, N-(2-hydroxy-ethyl)-3-[3-(4-hydroxy-3-methoxy-phenyl)-imidazo [1,2-a]pyrazin-6-yl]benzamide, N-[2-(dimethyl-amino)ethyl]-4-[3-(4-phenoxy-phenyl)-imidazo[1,2-a]pyrazin-6-yl]-benzamide, N-[3-(dimethyl-amino)-propyl]-4-[3-(4-phenoxy-phenyl) imidazo[1,2-a]pyrazin-6-yl]benzamide, N-[2-(dimethyl-amino)ethyl]-4-[3-(4-hydroxy-3-methoxy-phenyl)-imidazo[1,2-a]pyrazin-6-yl]benzamide, N-(2-hydroxy-ethyl)-4-[3-(4-phenoxy-phenyl)-imidazo-[1,2-a]-pyrazin-6-yl]benzamide, and 3-[3-(4-hydroxy-phenyl)-imidazo[1,2-a]pyrazin-6-yl]-N,N-dimethyl-benzamide, or a pharmaceutically acceptable salt or solvate thereof.

5. The method of claim 4, wherein the subject has a disease selected from Type I diabetes, Type II diabetes, and obesity.

* * * * *